US012441722B2

(12) United States Patent
Zheng et al.

(10) Patent No.: US 12,441,722 B2
(45) Date of Patent: Oct. 14, 2025

(54) THERAPEUTIC AGENTS AND METHODS OF TREATMENT

(71) Applicant: University of Florida Research Foundation, Incorporated, Gainesville, FL (US)

(72) Inventors: Guangrong Zheng, Gainesville, FL (US); Daohong Zhou, Gainesville, FL (US); Xuan Zhang, Gainesville, FL (US); Wanyi Hu, Gainesville, FL (US); Xingui Liu, Gainesville, FL (US); Dongwen Lyu, Gainesville, FL (US); Yaxia Yuan, Gainesville, FL (US); Dinesh Thummuri, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 645 days.

(21) Appl. No.: 17/790,211

(22) PCT Filed: Jan. 15, 2021

(86) PCT No.: PCT/US2021/013602

§ 371 (c)(1),
(2) Date: Jun. 30, 2022

(87) PCT Pub. No.: WO2021/146536

PCT Pub. Date: Jul. 22, 2021

(65) Prior Publication Data

US 2023/0339929 A1 Oct. 26, 2023

Related U.S. Application Data

(60) Provisional application No. 62/961,330, filed on Jan. 15, 2020.

(51) Int. Cl.

| | |
|---|---|
| ***C07D 417/14*** | (2006.01) |
| ***A61K 31/4725*** | (2006.01) |
| ***A61K 45/06*** | (2006.01) |
| ***A61P 35/02*** | (2006.01) |

(52) U.S. Cl.

CPC ........ *C07D 417/14* (2013.01); *A61K 31/4725* (2013.01); *A61K 45/06* (2013.01); *A61P 35/02* (2018.01)

(58) Field of Classification Search

CPC .. C07D 417/14; A61K 31/4725; A61K 45/06; A61P 35/02; A61P 35/00

See application file for complete search history.

(56) References Cited

U.S. PATENT DOCUMENTS

| | | | |
|---|---|---|---|
| 2016/0272639 | A1 | 9/2016 | Arvinas |
| 2018/0362575 | A1 | 12/2018 | Mazitschek et al. |
| 2019/0135801 | A1 | 5/2019 | Zheng et al. |
| 2019/0343832 | A1 | 11/2019 | Laberge et al. |
| 2022/0117206 | A1 | 4/2022 | Pi et al. |
| 2022/0169628 | A1 | 6/2022 | Zheng et al. |

FOREIGN PATENT DOCUMENTS

| | | | | |
|---|---|---|---|---|
| KR | 10-2013-0056940 | A | 5/2013 | |
| WO | WO 2016/094509 | A1 | 6/2016 | |
| WO | WO 2017/024317 | A2 | 2/2017 | |
| WO | WO 2017/184995 | A1 | 10/2017 | |
| WO | WO 2017/197051 | A1 | 11/2017 | |
| WO | WO 2017/197055 | A1 | 11/2017 | |
| WO | WO-2017214322 | A1 * | 12/2017 | ......... A61K 47/6803 |
| WO | WO 2018/092064 | A1 | 5/2018 | |
| WO | WO 2018/106870 | A1 | 6/2018 | |
| WO | WO 2020/163823 | A2 | 8/2020 | |
| WO | WO 2021/146536 | A1 | 7/2021 | |
| WO | WO 2022/072094 | A1 | 4/2022 | |
| WO | WO 2023/064326 | A1 | 4/2023 | |
| WO | WO 2023/107606 | A1 | 6/2023 | |

OTHER PUBLICATIONS

International Search Report and Written Opinion for PCT/US2021/013602, mailed May 6, 2021.

Hu et al., Celastrol-Induced Nur77 Interaction with TRAF2 Alleviates Inflammation by Promoting Mitochondrial Ubiquitination and Autophagy. Mol Cell. Apr. 6, 2017;66(1):141-153.e6. doi: 10.1016/j.molcel.2017.03.008.

Leverson et al., Exploiting selective BCL-2 family inhibitors to dissect cell survival dependencies and define improved strategies for cancer therapy. Sci Transl Med. Mar. 18, 2015;7(279):279ra40. doi: 10.1126/scitranslmed.aaa4642.

Zhang et al., PROTACs are effective in addressing the platelet toxicity associated with BCL-XL inhibitors. Explor Target Antitumor Ther. 2020;1(4):259-272. doi: 10.37349/etat.2020.00017. Epub Aug. 31, 2020.

* cited by examiner

*Primary Examiner* — Joseph K McKane
*Assistant Examiner* — Ashli Ariana Chicks
(74) *Attorney, Agent, or Firm* — Wolf, Greenfield & Sacks, P.C.

(57) ABSTRACT

The invention is directed towards compounds (e.g., Formula (I) or a pharmaceutically acceptable salt, hydrate, solvate, or prodrug thereof), their mechanism of action, and methods of modulating proliferation activity, and methods of treating diseases and disorders using the compounds described herein (e.g., Formula (I), or a pharmaceutically acceptable salt, hydrate, solvate, or prodrug thereof).

22 Claims, 1 Drawing Sheet

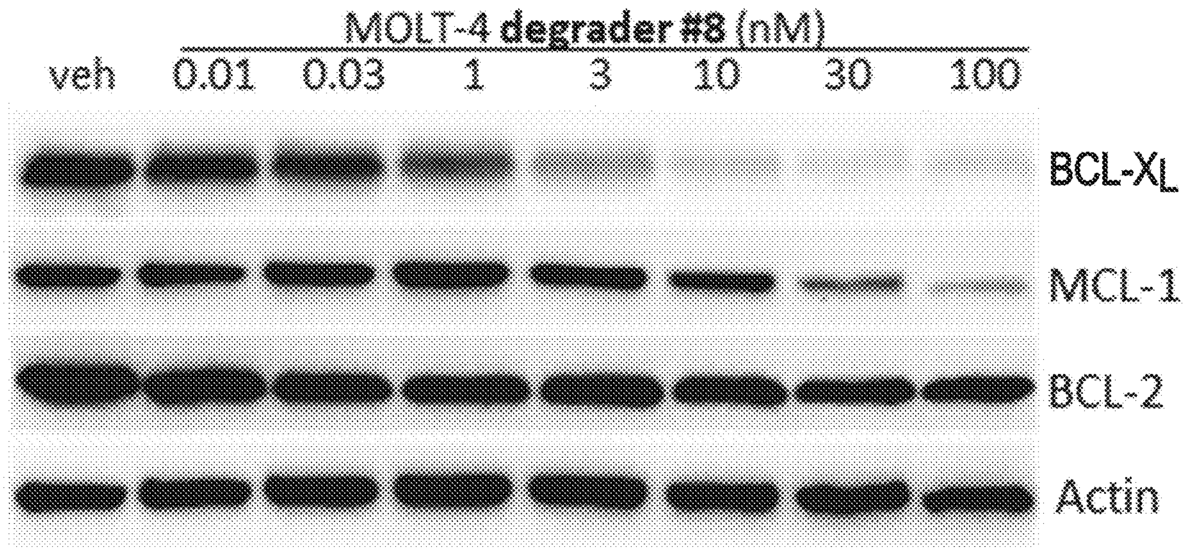
MOLT-4 degrader #8 (nM)
veh
0.01
0.03
1
3
10
30
100
BCL-XL
MCL-1
BCL-2
Actin

THERAPEUTIC AGENTS AND METHODS OF TREATMENT

RELATED APPLICATIONS

This application is a national stage filing under 35 U.S.C. § 371 of International Patent Application Serial No. PCT/US2021/013602, filed Jan. 15, 2021, which claims the benefit under 35 U.S.C. § 119(e) of the filing date of U.S. Provisional Application Ser. No. 62/961,330, filed Jan. 15, 2020, the entire contents of each of which are incorporated herein by reference in their entirety.

GOVERNMENT SUPPORT INFORMATION

This invention was made with government support under Grant Nos. CA223371, CA219836 and CA241191 awarded by the National Institutes of Health. The government has certain rights in the invention.

BACKGROUND

The B-cell lymphoma 2 (Bcl-2) protein family, consisting of pro- and anti-apoptotic members, plays a critical role in determining cell fate through regulation of the intrinsic apoptosis pathway. The anti-apoptotic Bcl-2 family proteins, such as Bcl-2, Bcl-xL, Bcl-w, and Mcl-1, are upregulated in many cancers and associated with tumor initiation, progression, and resistance to chemo- and targeted therapies. Thus, these anti-apoptotic Bcl-2 proteins are attractive targets for the development of novel anti-cancer agents (Lessene et al., *Nat Rev Drug Discov* 7: 989-1000, 2008; Vogler et al., *Cell Death Differ* 2009; 16: 360-367; Delbridge et al., *Nat Rev Cancer* 16: 99-109, 2016). Numerous Bcl-2 small molecule inhibitors have been reported (Bajwa et al., *Expert Opin Ther Patents* 22:37-55, 2012; Vogler, *Adv Med.* 1-14, 2014; Ashkenazi et al., 16: 273-284, 2017). The following are some of the Bcl-2 small molecule inhibitors that have been investigated at various stages of drug development: ABT-737 (US20070072860), navitoclax (ABT-263, WO2009155386), venetoclax (ABT-199, WO2010138588), obatoclax (GX 15-070, WO2004106328), (−)-gossypol (AT-101, WO2002097053), sabutoclax (BI-97C1, WO2010120943), TW-37 (WO2006023778), BM-1252 (APG-1252), and A-1155463 (VV02010080503).

Venetoclax, a selective Bcl-2 inhibitor, was approved by the FDA in 2016 for the treatment of chronic lymphocytic leukemia (CLL) with 17-p deletion. Venetoclax was designed to have high selectivity for Bcl-2 over Bcl-xL to avoid the on-target platelet toxicity (Souers et al., *Nat Med* 19: 202-208, 2013). Platelets depend on Bcl-xL to maintain their viability, therefore dose-limiting thrombocytopenia has been observed in animals and/or humans treated with ABT-737 (Schoenwaelder et al., *Blood* 118: 1663-1674, 2011), ABT-263 (Tse et al., *Cancer Res* 68: 3421-3428, 2008; Roberts et al., Bri J *Haematol* 170: 669-678, 2015), BM-1197 (Bai et al., *PLoS ONE* 9:e99404, 2014), A-1155463 (Tao et al., *ACS Med Chem Lett* 5:1088-1093, 2014), or A-1331852, due to their inhibition of Bcl-xL. However, many CLL patients are resistant to venetoclax (Roberts et al., *N Engl J Med* 374: 311-322, 2016) and upregulation of Bcl-xL by microenvironmental survival signals has been identified as the major component accountable for the resistance, consistent with the high efficacy of Bcl-2/Bcl-xL dual inhibitor ABT-263 in killing venetoclax resistant CLL cells (Oppermann et al., *Blood* 128: 934-947, 2016). In addition, Bcl-xL is generally more frequently overexpressed than Bcl-2 in solid tumors. Importantly, promising results have been documented from preclinical and clinical studies of ABT-263, as a single-agent or in combination with other antitumor agents, against several solid and hematologic malignancies (Delbridge et al., Nat Rev Cancer 16: 99-109, 2016). Thus, there is a need in the art to develop compounds that can retain the antitumor versatility and efficacy of the Bcl-xL inhibitors, while avoiding their on-target platelet toxicity.

BRIEF SUMMARY OF THE INVENTION

The invention is directed towards compounds (e.g., Formula (I)), their mechanism of action, and methods of modulating proliferation activity, and methods of treating diseases and disorders using the compounds described herein (e.g., Formula (I)). In another aspect, the disease or disorder is cancer. In another aspect, the cancer is a Bcl-xL-dependent cancer.

In another aspect, the invention is directed to a compound of Formula (I), or a pharmaceutically acceptable salt, hydrate, solvate, or prodrug thereof:

$$Y\text{-}L_2\text{-}R\text{-}L_1\text{-}Y_2 \qquad \text{Formula (I);}$$

wherein $L_1$ is independently

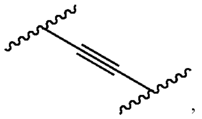,
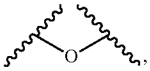,
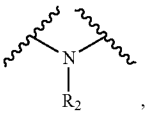,
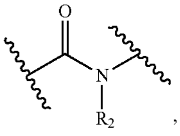,
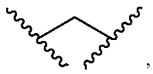,
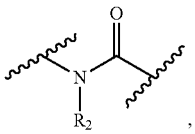,
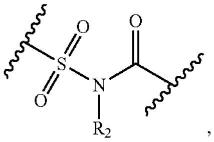,
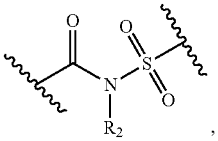, or absent;

- R is optionally substituted $C_{1-50}$ alkylene or optionally substituted $C_{1-50}$ heteroalkylene wherein:
  - optionally one or more backbone carbon atoms of each instance of the optionally substituted alkylene or optionally substituted heteroalkylene are independently replaced with —C(═O)O—, —OC(═O)—, —NHC(═O)—, —C(═O)NH—, optionally substituted cycloalkylene, optionally substituted heterocycloalkylene, optionally substituted arylene, or optionally substituted heteroarylene; and
  - optionally one or more backbone heteroatoms of each instance of the optionally substituted heteroalkylene are independently replaced with optionally substituted cycloalkylene, optionally substituted heterocycloalkylene, optionally substituted arylene, or optionally substituted heteroarylene;

L2 is independently
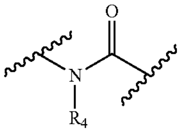,
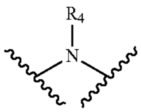,
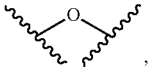,
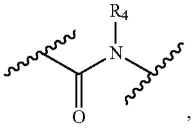,
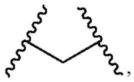,
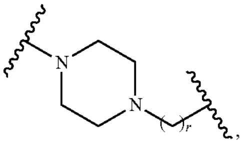,
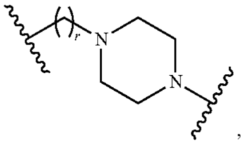,
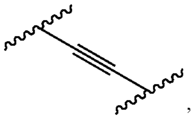, or
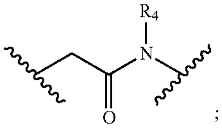;
Y is independently
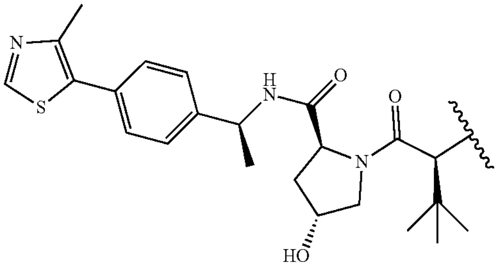,
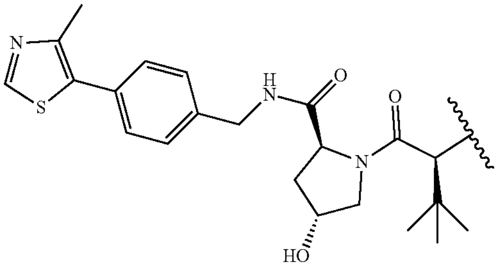,
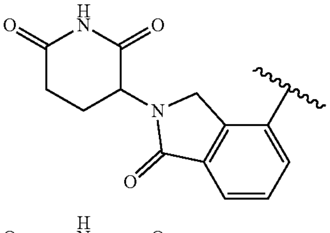,
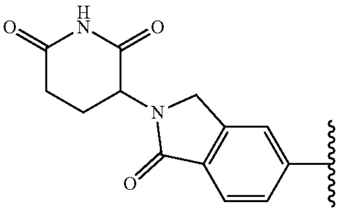,
-continued
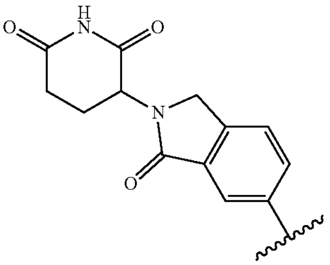,
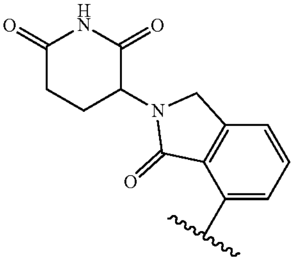,
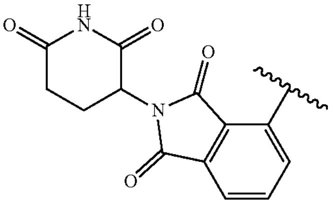,
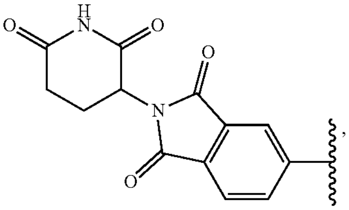,
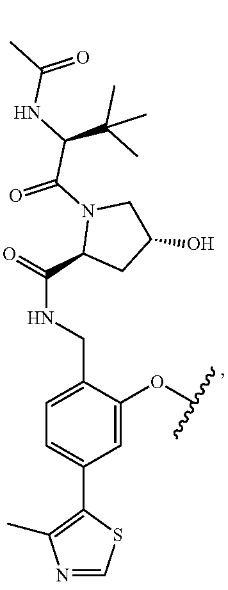,
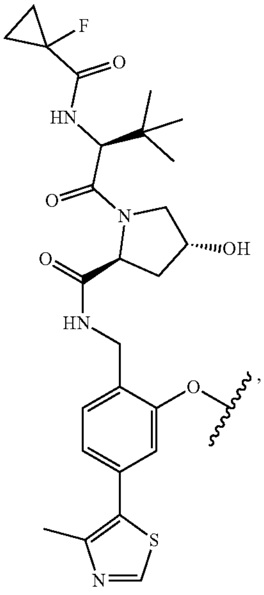, -continued
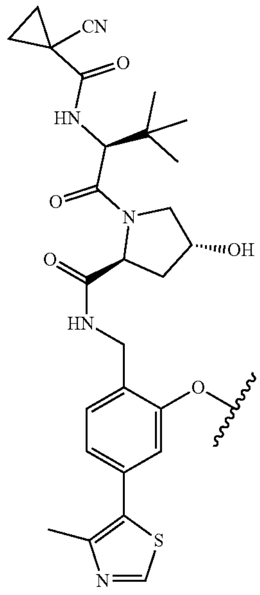
,
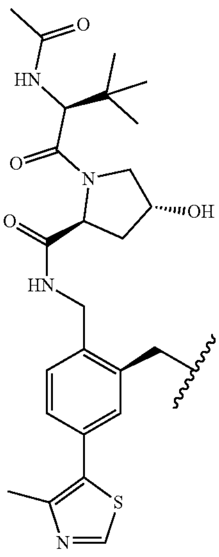
,
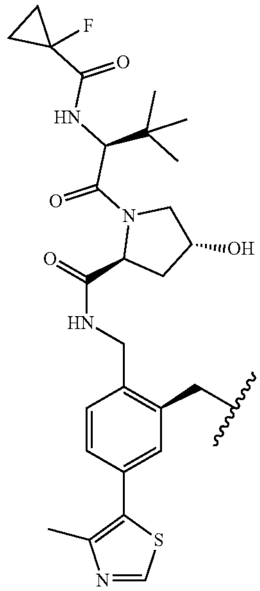
, or
-continued
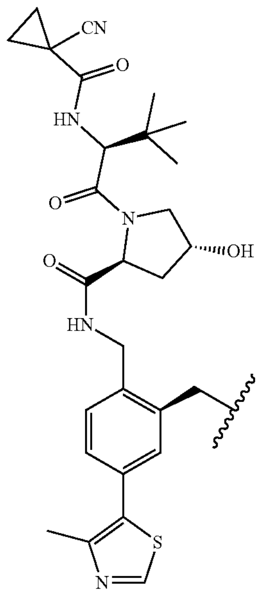
;
$Y_2$ is independently
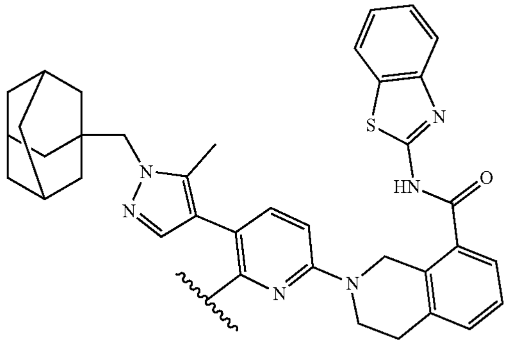
,
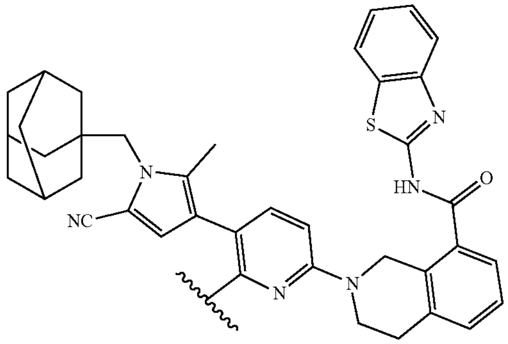
.

-continued
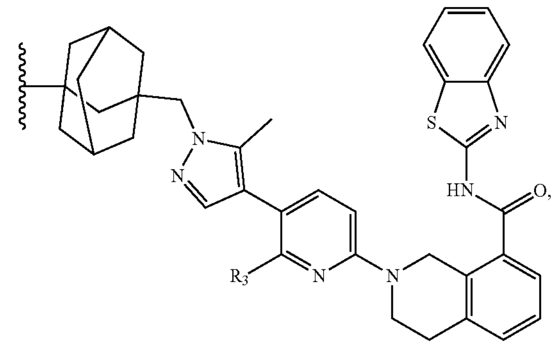
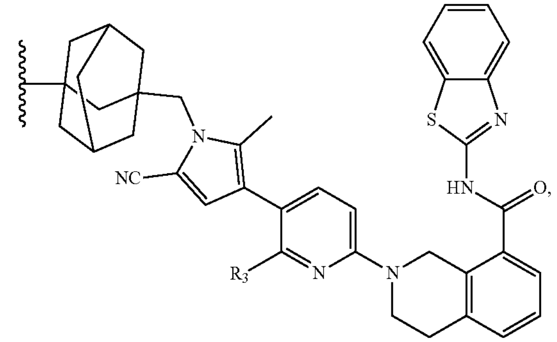
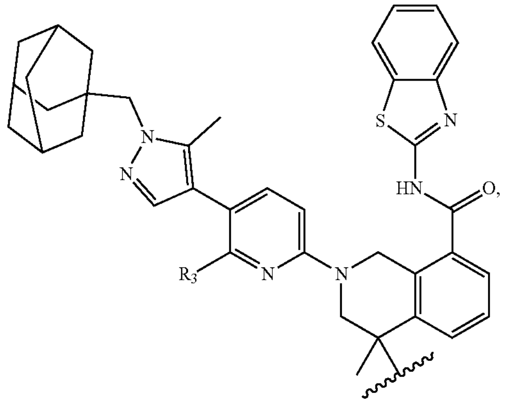
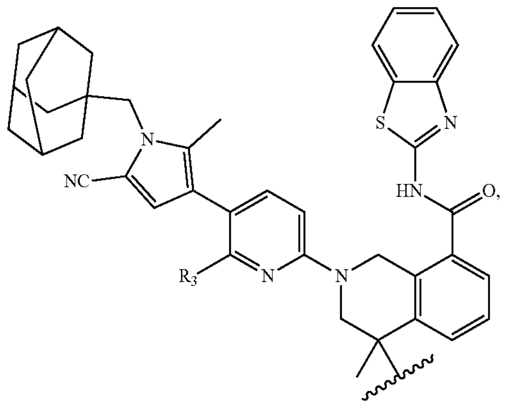
-continued
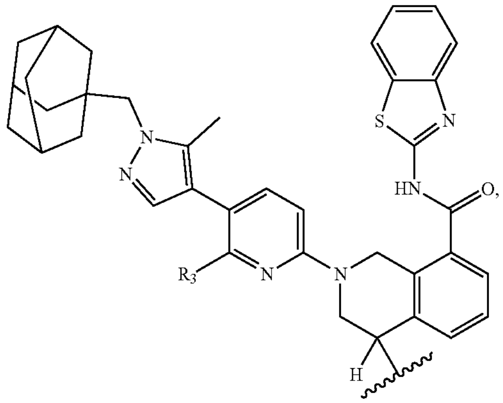
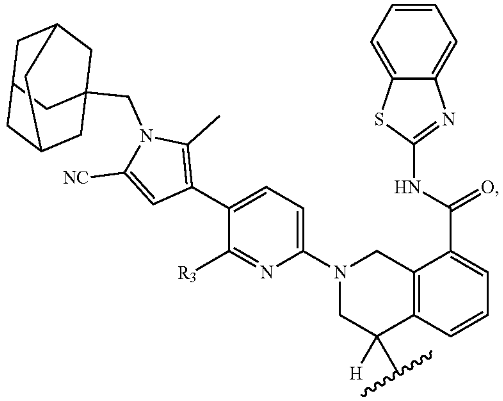
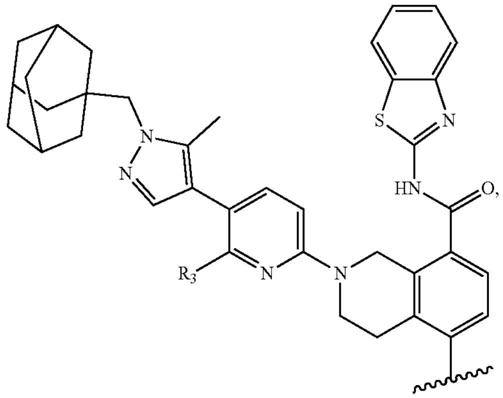
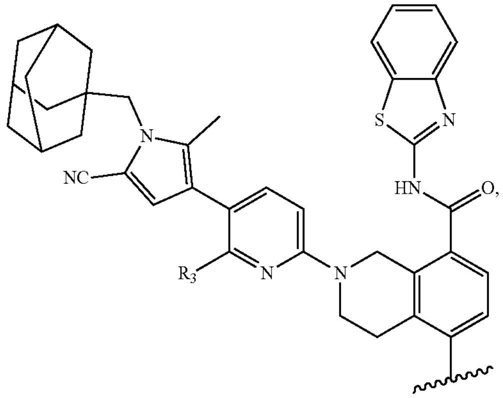

-continued

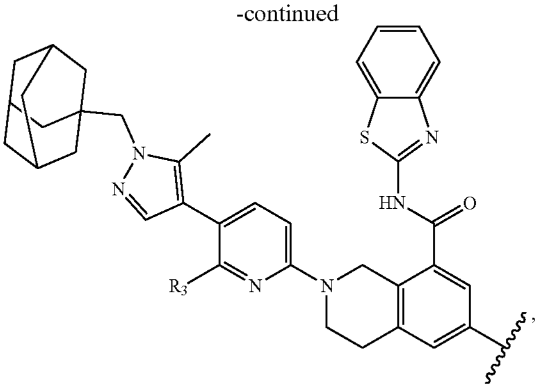

, or

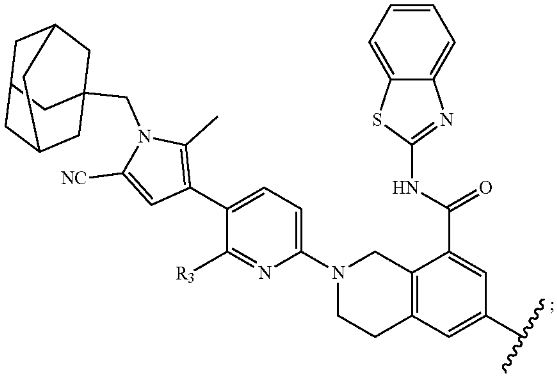

;

each $R_2$ is independently H, optionally substituted alkyl, or optionally substituted cycloalkyl;

each $R_3$ is hydrogen,

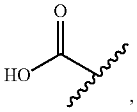

,

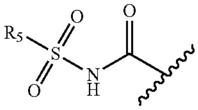

,

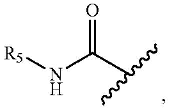

,

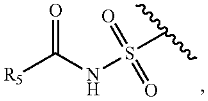

, or

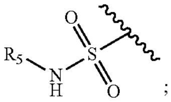

;

each $R_4$ is independently H, optionally substituted alkyl, or optionally substituted cycloalkyl;

each $R_5$ is independently H, optionally substituted alkyl, or optionally substituted cycloalkyl; and r is independently 0-10, inclusive.

In another aspect, the invention is directed to a compound of Formula (I), or a pharmaceutically acceptable salt, hydrate, solvate, or prodrug thereof:

$Y\text{-}L_2\text{-}R\text{-}L_1\text{-}Y_2$ Formula (I);

wherein $L_1$ is independently

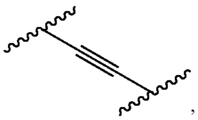

,

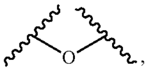

,

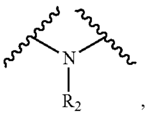

,

-continued

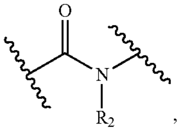

,

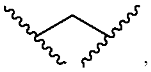

,

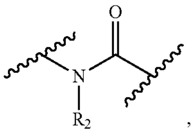

,

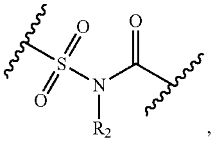

,

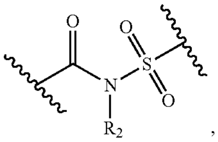

, or absent;

R is independently

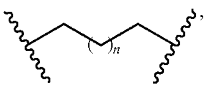

,

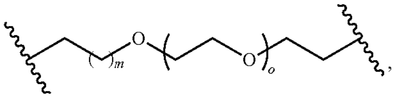

,

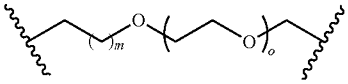

,

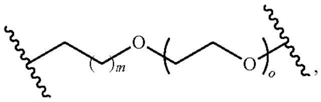

,

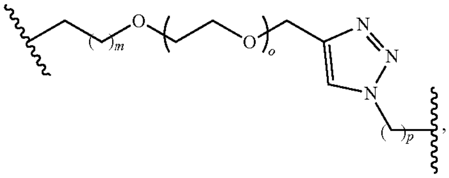

,

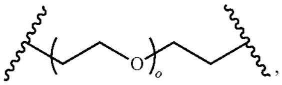

,

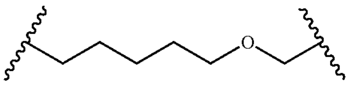

,

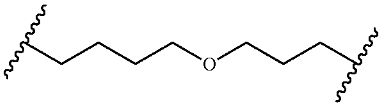

,

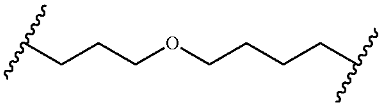

,

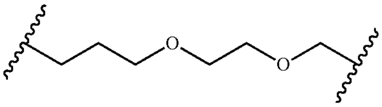

,

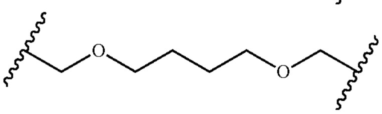

,

-continued
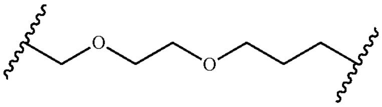,
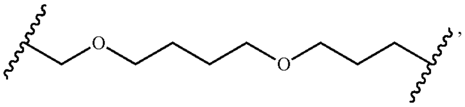, or
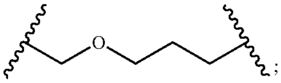;
$L_2$ is independently
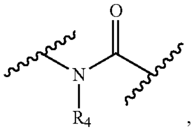, 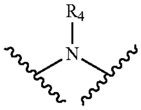, 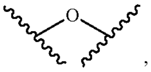,
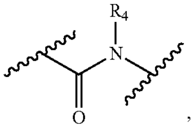, 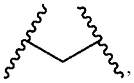,
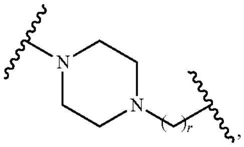, 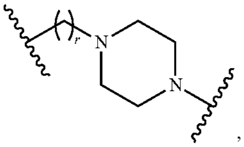,
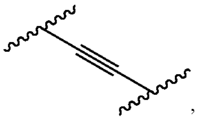, or 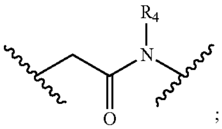;
Y is independently H
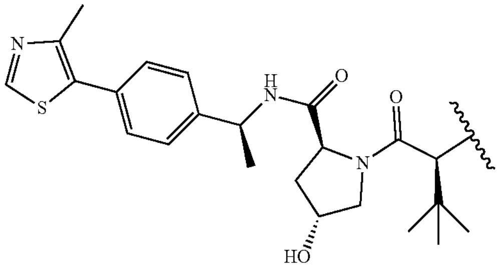,
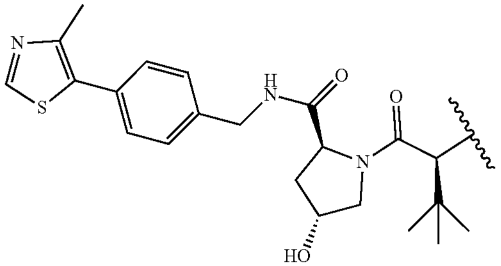,
-continued
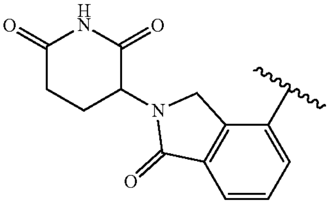,
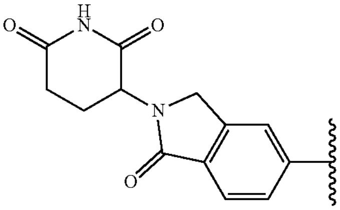,
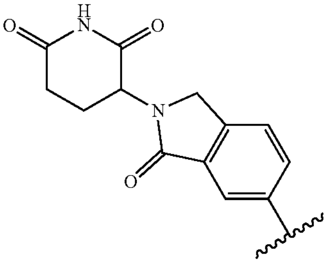,
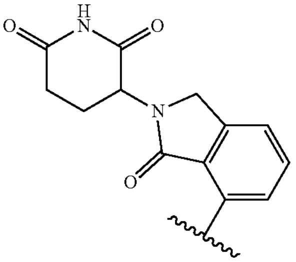,
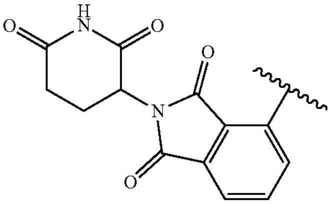,
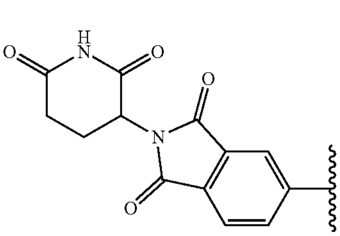, -continued
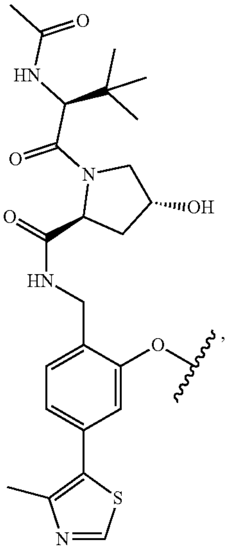
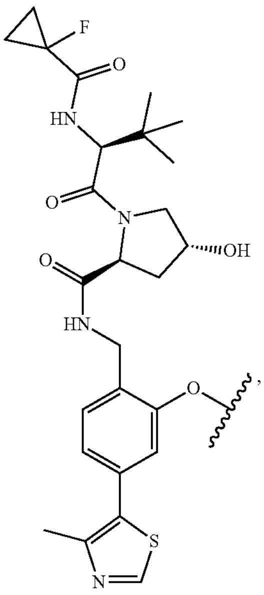
,
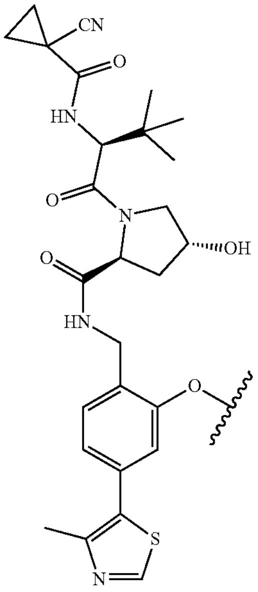
,
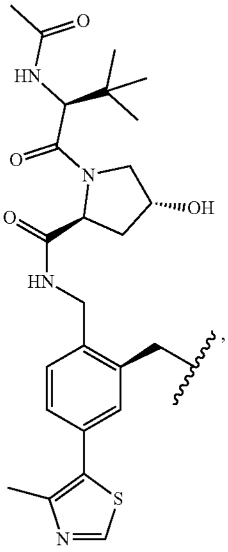
,
-continued
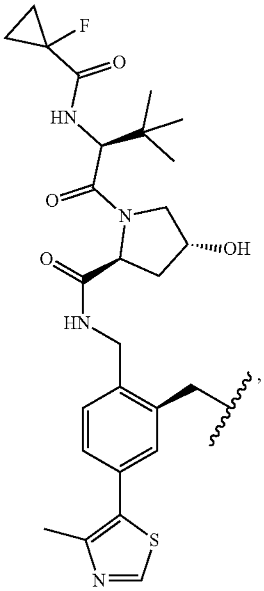
, or
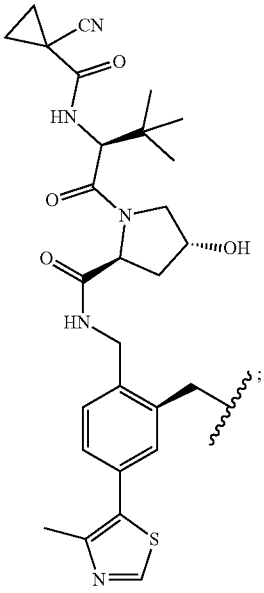
;
$Y_2$ is independently
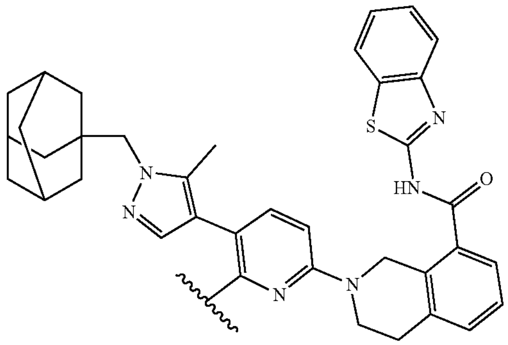
, -continued
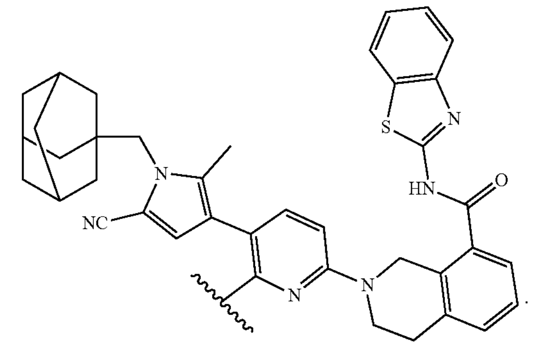
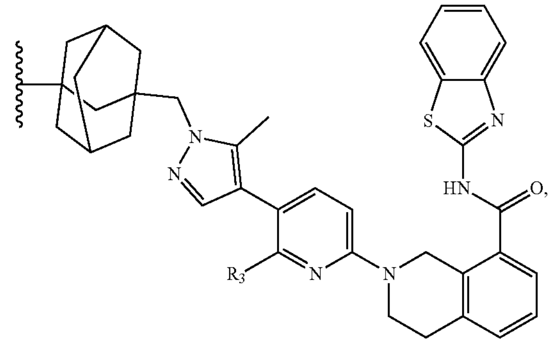
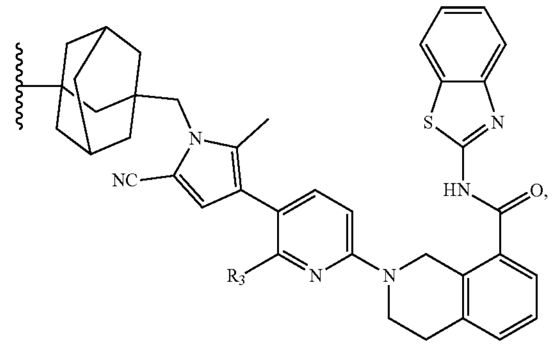
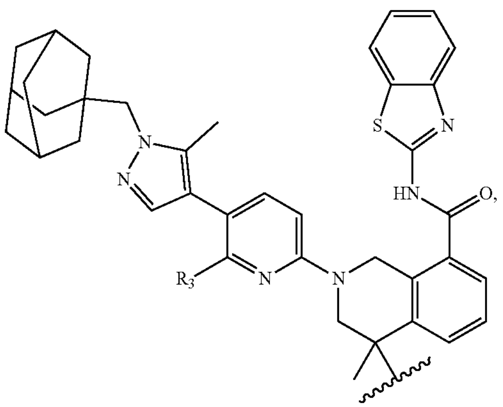
-continued
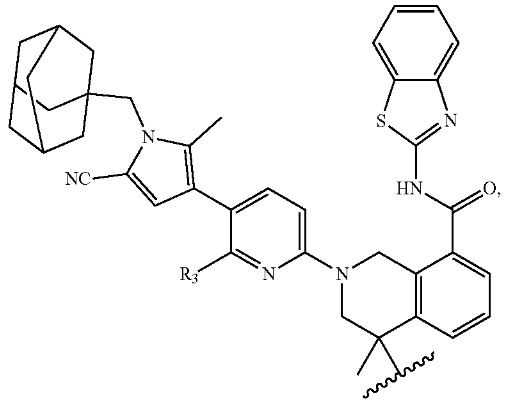
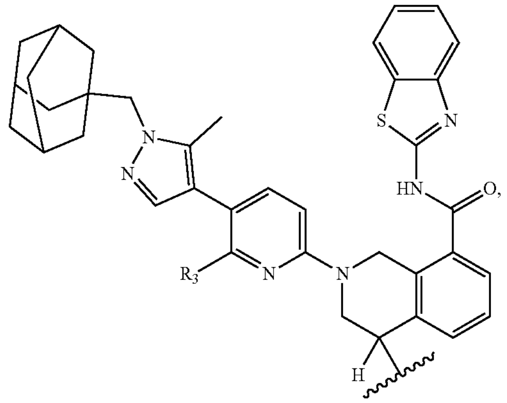
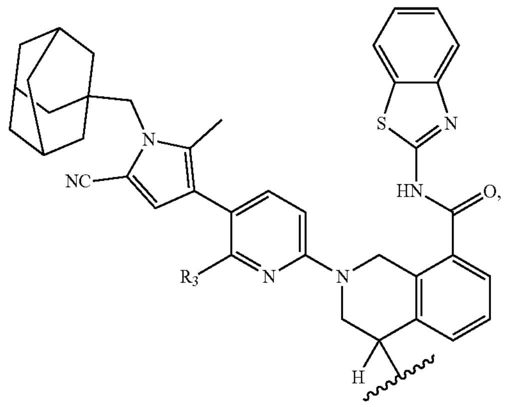
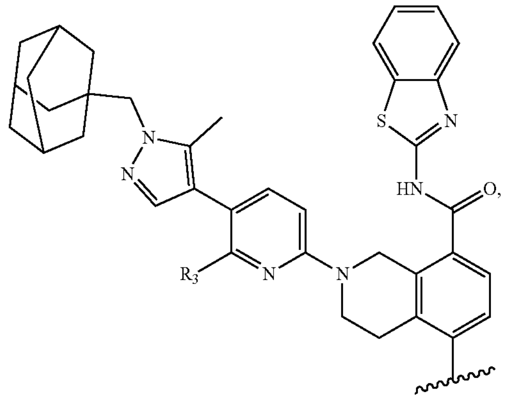

-continued

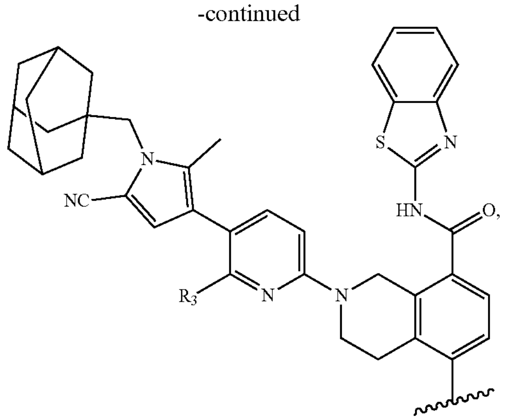

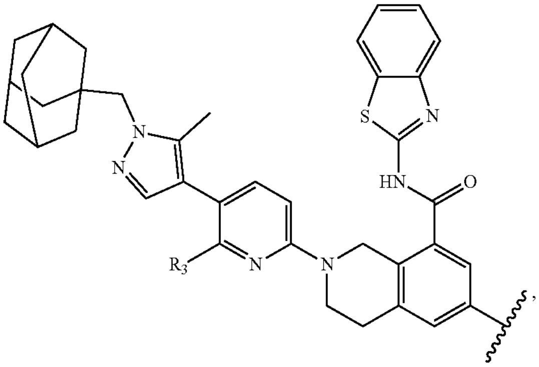

, or

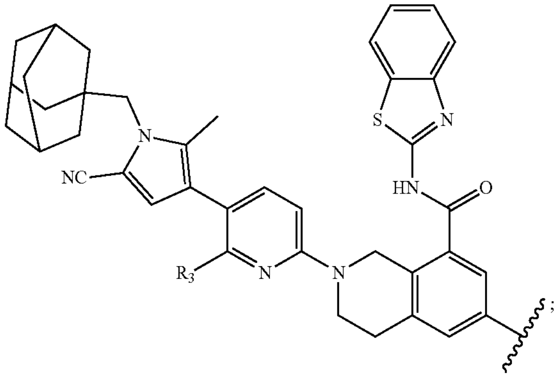

;

each $R_2$ is independently H, optionally substituted alkyl, or optionally substituted cycloalkyl;

each $R_3$ is

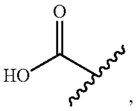

,

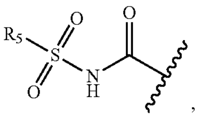

, or

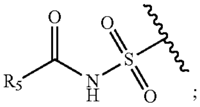

;

each $R_4$ is independently H, optionally substituted alkyl, or optionally substituted cycloalkyl;

each $R_5$ is independently H, optionally substituted alkyl, or optionally substituted cycloalkyl; and each m, n, o, p, and r is independently 0-10, inclusive.

In one aspect, R is

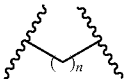

,

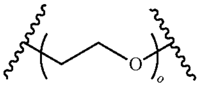

,

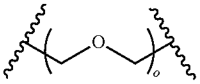

,

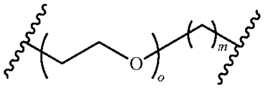

,

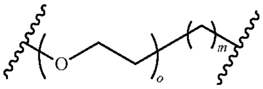

,

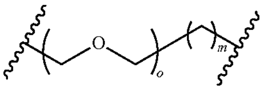

,

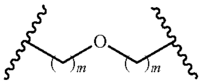

,

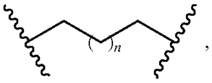

,

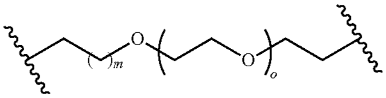

,

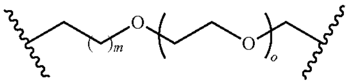

,

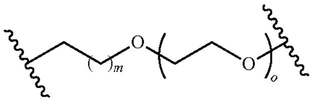

,

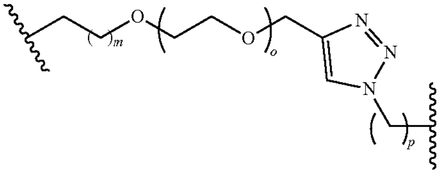

,

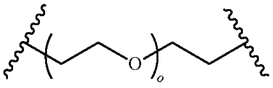

,

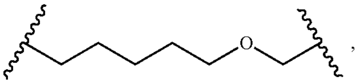

,

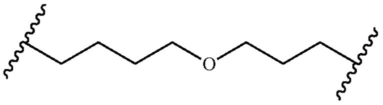

,

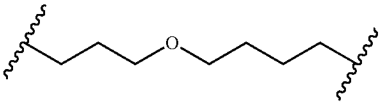

,

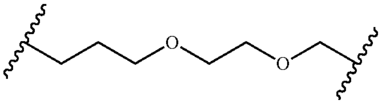

,

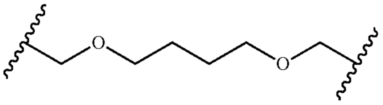

,

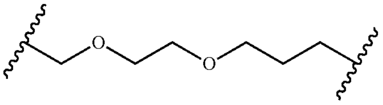

,

-continued
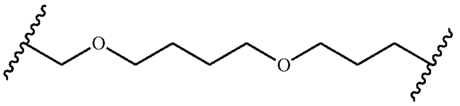
, or
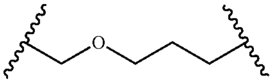
;
and each m, n, o, and p is independently 0-10, inclusive. In one aspect, R is
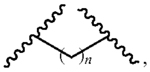
,
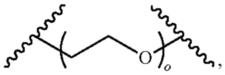
,
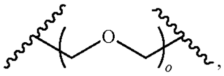
,
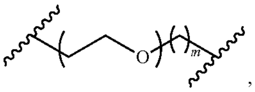
,
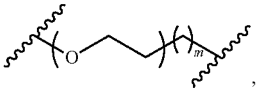
,
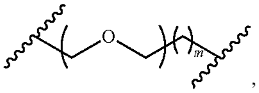
, or
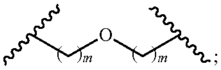
;
and each m, n, o, and p is independently 0-10, inclusive. In another aspect, R is
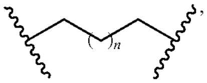
,
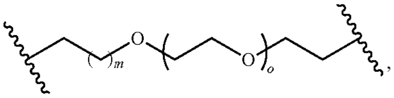
,
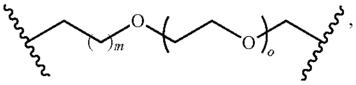
,
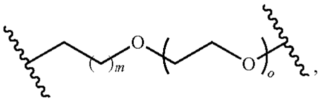
,
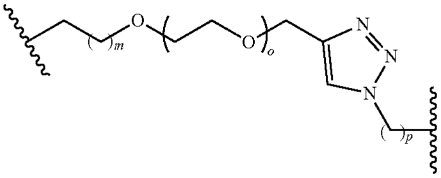
,
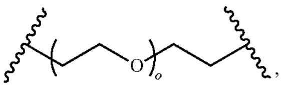
,
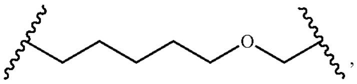
,
-continued
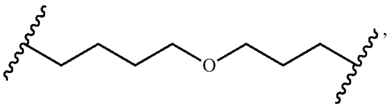
,
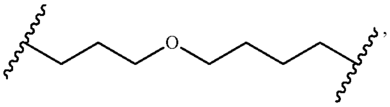
,
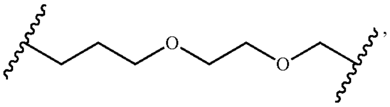
,
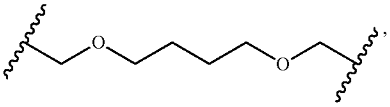
,
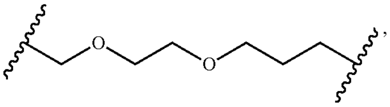
,
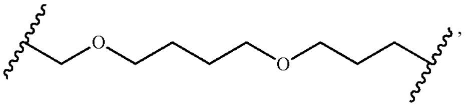
, or
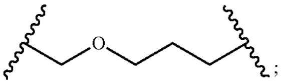
;
and each m, n, o, and p is independently 0-10, inclusive.
In another aspect, $Y_2$ is
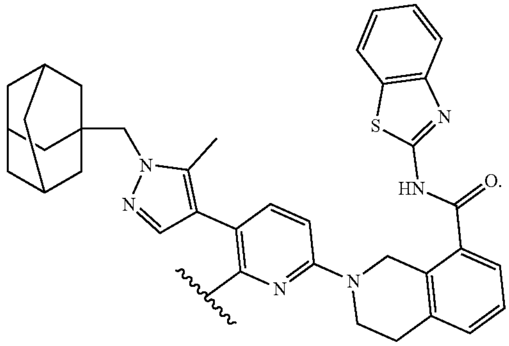 [SMILES: *c1nc(N2CCc3cccc(C(=O)Nc4nc5ccccc5s4)c3C2)ccc1-c1cnn(CC23CC4CC(CC(C4)C2)C3)c1C]
In another aspect, $L_1$ is
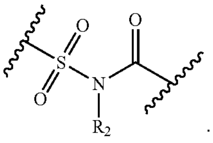
.

In another embodiment, $L_1$ is
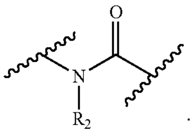
In another embodiment, $L_1$ is
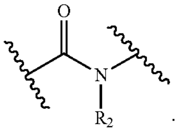
In another embodiment, $L_2$ is
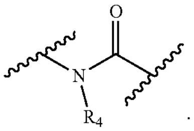
In another embodiment, $L_2$ is
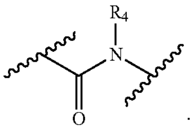
In another embodiment, $L_2$ is
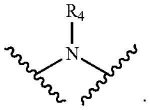
In another embodiment, $L_2$ is
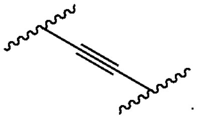 [SMILES: *C#C*]
In another embodiment, $L_2$ is
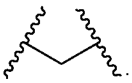 [SMILES: *C*]
In another aspect, $Y_2$ is
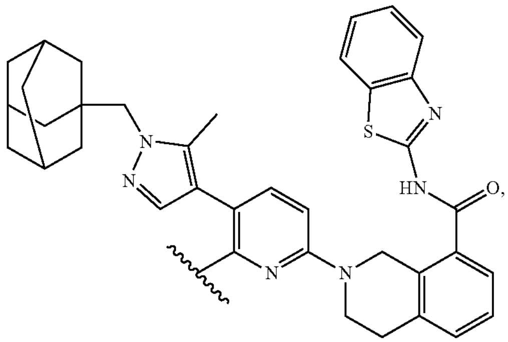 [SMILES: *c1nc(N2CCc3cccc(C(=O)Nc4nc5ccccc5s4)c3C2)ccc1-c1cnn(CC23CC4CC(CC(C4)C2)C3)c1C]
and $L_1$ is
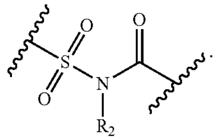
In another aspect, $Y_2$ is
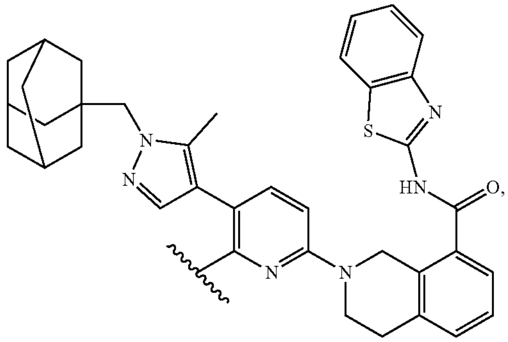 [SMILES: *c1nc(N2CCc3cccc(C(=O)Nc4nc5ccccc5s4)c3C2)ccc1-c1cnn(CC23CC4CC(CC(C4)C2)C3)c1C]
and $L_2$ is
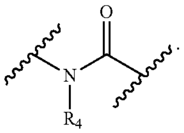

In another aspect, $Y_2$ is
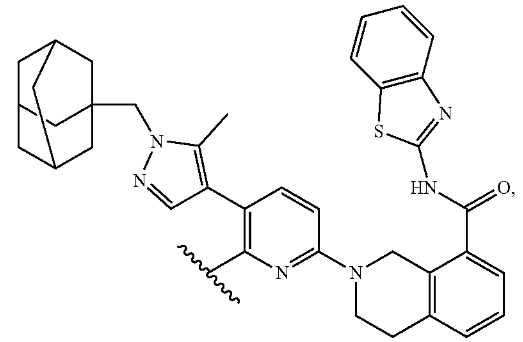 [SMILES: *c1nc(N2CCc3cccc(C(=O)Nc4nc5ccccc5s4)c3C2)ccc1-c1cnn(CC23CC4CC(CC(C4)C2)C3)c1C]
$L_1$ is
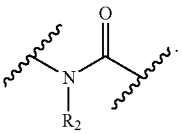
In another aspect, $Y_2$ is
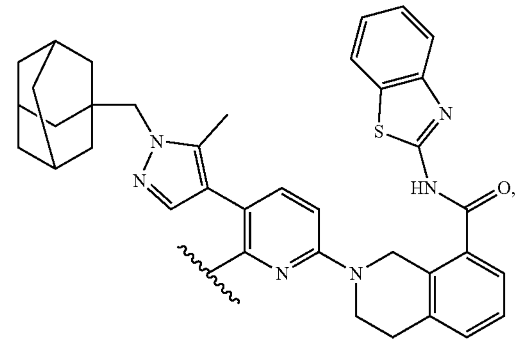 [SMILES: *c1nc(N2CCc3cccc(C(=O)Nc4nc5ccccc5s4)c3C2)ccc1-c1cnn(CC23CC4CC(CC(C4)C2)C3)c1C]
$L_1$ is
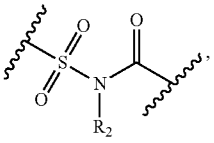
and $L_2$ is
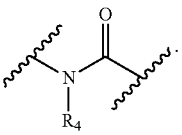
In any of the embodiments presented herein, $L_2$ is
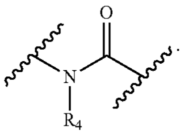
In any of the embodiments presented herein, Y is
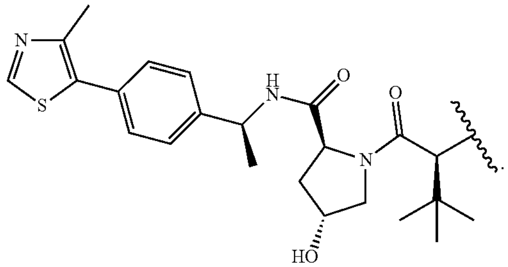 [SMILES: *[C@H](C(=O)N1C[C@H](O)C[C@H]1C(=O)N[C@@H](C)c1ccc(-c2scnc2C)cc1)C(C)(C)C]
In any of the embodiments presented herein, R is
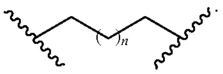
In some embodiments, R is
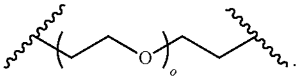
In some embodiments, R is
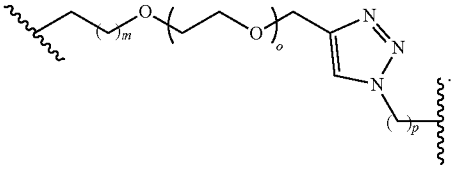
In some embodiments, R is
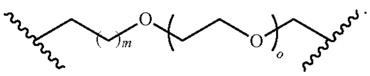
In some embodiments, R is
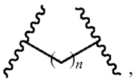,
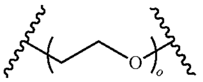,
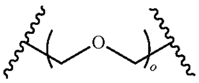,

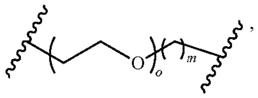

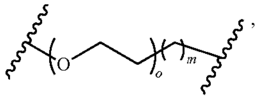

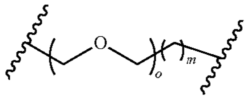
, or

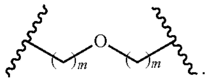

In some embodiments, R is

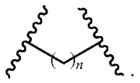

In some embodiments, R is

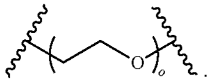

In some embodiments, R is

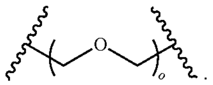

In some embodiments, R is

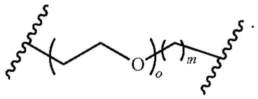

In some embodiments, R is

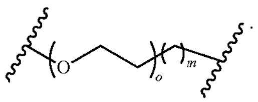

In some embodiments, R is

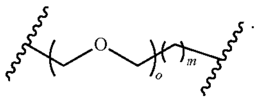

In some embodiments, R is

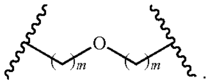

In another aspect, $Y_2$ is

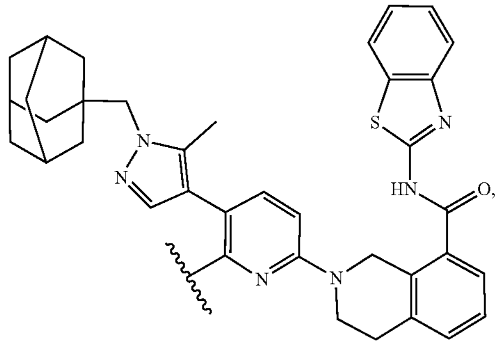 [SMILES: *c1nc(N2CCc3cccc(C(=O)Nc4nc5ccccc5s4)c3C2)ccc1-c1cnn(CC23CC4CC(CC(C4)C2)C3)c1C]

and R is

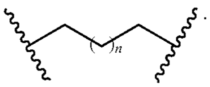

In any of the embodiments presented herein, n is 1-9, inclusive.

In any of the embodiments presented herein, n is 1-6, inclusive.

In any of the embodiments presented herein, $L_1$ is

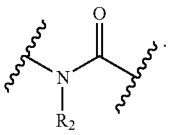

In another aspect, $Y_2$ is

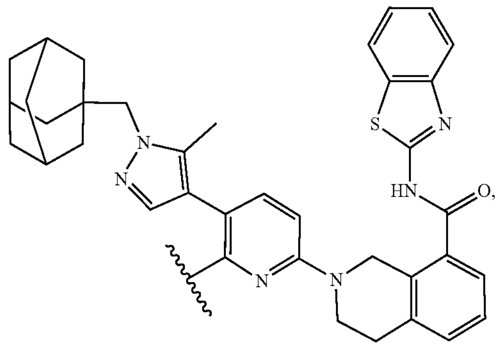 [SMILES: *c1nc(N2CCc3cccc(C(=O)Nc4nc5ccccc5s4)c3C2)ccc1-c1cnn(CC23CC4CC(CC(C4)C2)C3)c1C]

and $L_1$ is
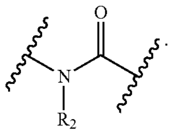
In any of the embodiments presented herein, Y is
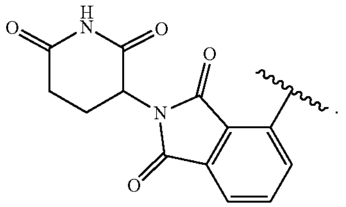 [SMILES: *c1cccc2c1C(=O)N(C1CCC(=O)NC1=O)C2=O]
In another aspect, $Y_2$ is
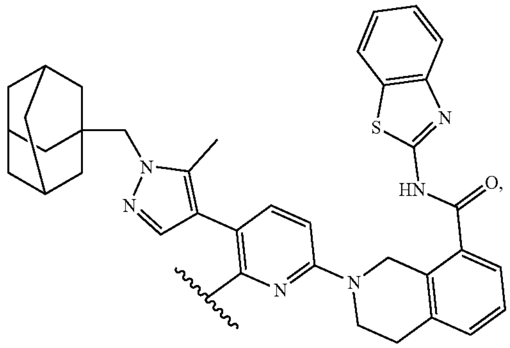 [SMILES: *c1nc(N2CCc3cccc(C(=O)Nc4nc5ccccc5s4)c3C2)ccc1-c1cnn(CC23CC4CC(CC(C4)C2)C3)c1C]
and Y is
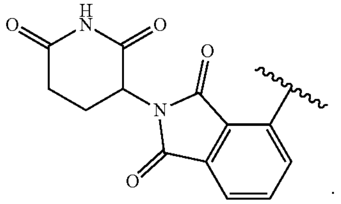 [SMILES: *c1cccc2c1C(=O)N(C1CCC(=O)NC1=O)C2=O]
In another aspect, $Y_2$ is
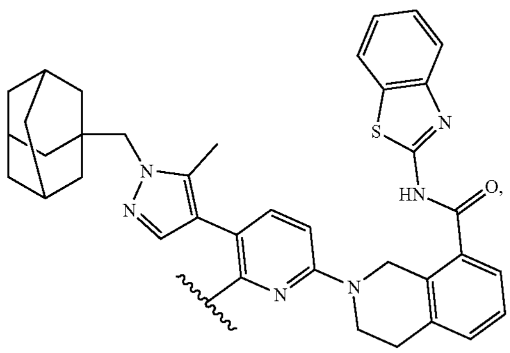 [SMILES: *c1nc(N2CCc3cccc(C(=O)Nc4nc5ccccc5s4)c3C2)ccc1-c1cnn(CC23CC4CC(CC(C4)C2)C3)c1C]
$L_2$ is
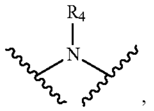
and Y is
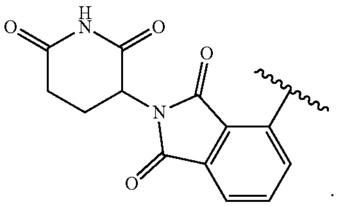 [SMILES: *c1cccc2c1C(=O)N(C1CCC(=O)NC1=O)C2=O]
In another aspect, $Y_2$ is
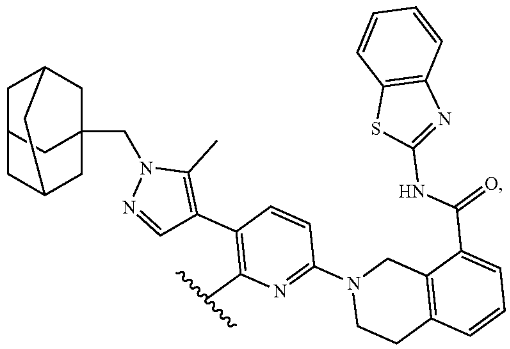 [SMILES: *c1nc(N2CCc3cccc(C(=O)Nc4nc5ccccc5s4)c3C2)ccc1-c1cnn(CC23CC4CC(CC(C4)C2)C3)c1C]
$L_1$ is
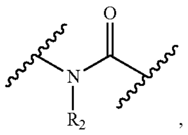
and Y is
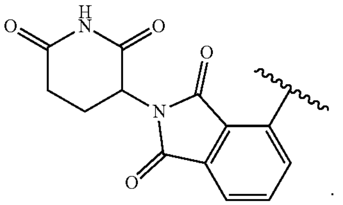 [SMILES: *c1cccc2c1C(=O)N(C1CCC(=O)NC1=O)C2=O]
In any of the embodiments presented herein, R is
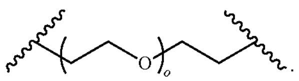

In another aspect, $Y_2$ is
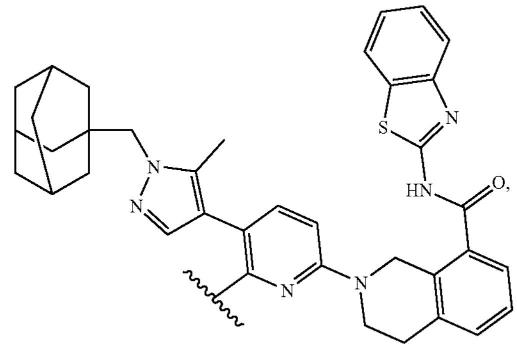 [SMILES: *c1nc(N2CCc3cccc(C(=O)Nc4nc5ccccc5s4)c3C2)ccc1-c1cnn(CC23CC4CC(CC(C4)C2)C3)c1C]
R is
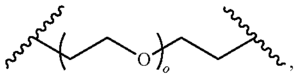
and $L_1$ is
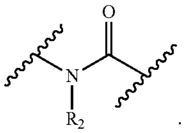
In another aspect, $Y_2$ is
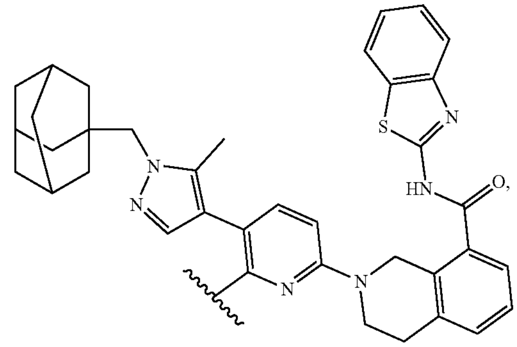
R is
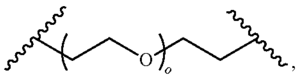
and $L_2$ is
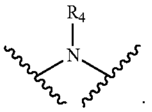
In another aspect, $Y_2$ is
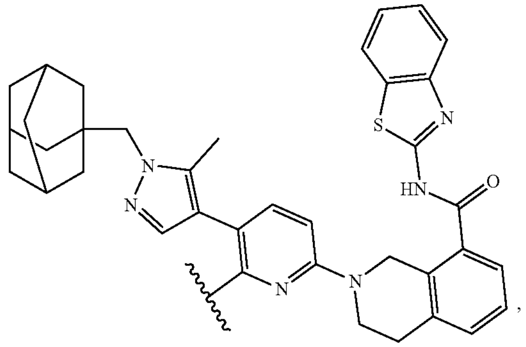 [SMILES: *c1nc(N2CCc3cccc(C(=O)Nc4nc5ccccc5s4)c3C2)ccc1-c1cnn(CC23CC4CC(CC(C4)C2)C3)c1C]
$L_2$ is
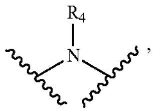
R is
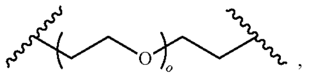
and Y is
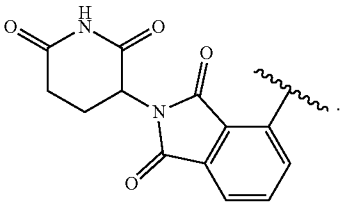 [SMILES: *c1cccc2c1C(=O)N(C1CCC(=O)NC1=O)C2=O]

In another aspect, $Y_2$ is

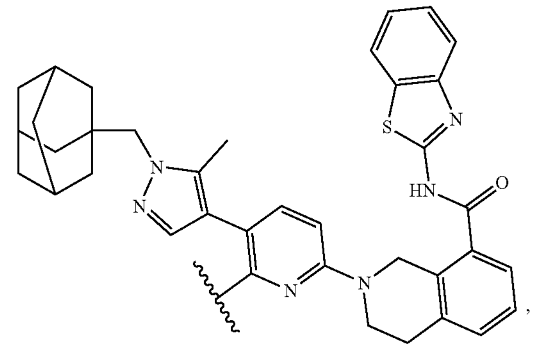 [SMILES: *c1nc(N2CCc3cccc(C(=O)Nc4nc5ccccc5s4)c3C2)ccc1-c1cnn(CC23CC4CC(CC(C4)C2)C3)c1C]

$L_1$ is

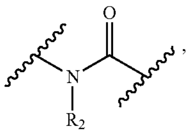

R is

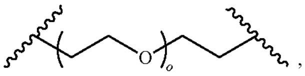

and Y is

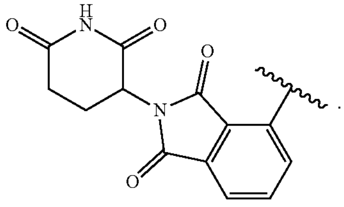

In any of the embodiments presented herein, R is

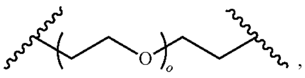

and o is 0-9, inclusive.

In any of the embodiments presented herein, R is

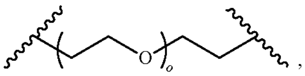

and o is 0-3, inclusive.

In any of the embodiments presented herein, R is

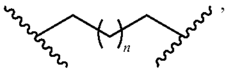

and n is 0-9, inclusive.

In any of the embodiments presented herein, R is

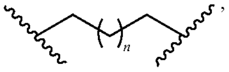

and n is 0-6, inclusive.

In any of the embodiments presented herein, R is

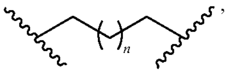

and n is 0-3, inclusive.

In any of the embodiments presented herein, R is

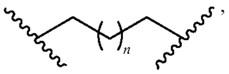

and n is 2, inclusive.

In any of the embodiments presented herein, Y is

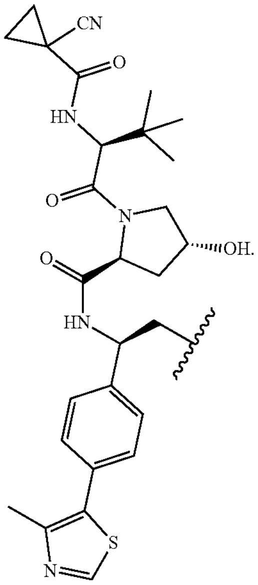 [SMILES: *C[C@H](NC(=O)[C@@H]1C[C@@H](O)CN1C(=O)[C@@H](NC(=O)C1(C#N)CC1)C(C)(C)C)c1ccc(-c2scnc2C)cc1]

In another aspect, $Y_2$ is
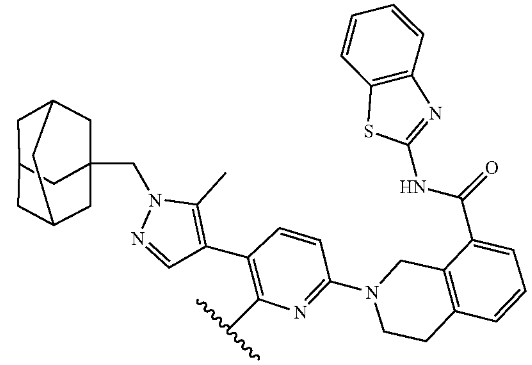
,
$L_1$ is
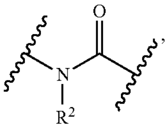
,
and Y is
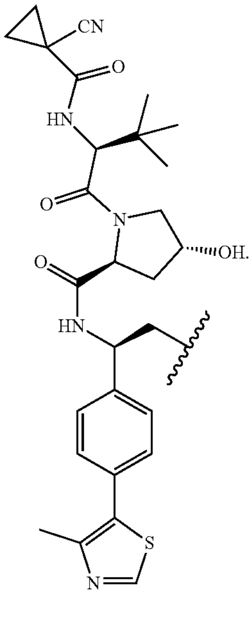 [SMILES: *C[C@H](NC(=O)[C@@H]1C[C@@H](O)CN1C(=O)[C@@H](NC(=O)C1(C#N)CC1)C(C)(C)C)c1ccc(-c2scnc2C)cc1]
In another aspect, $Y_2$ is,
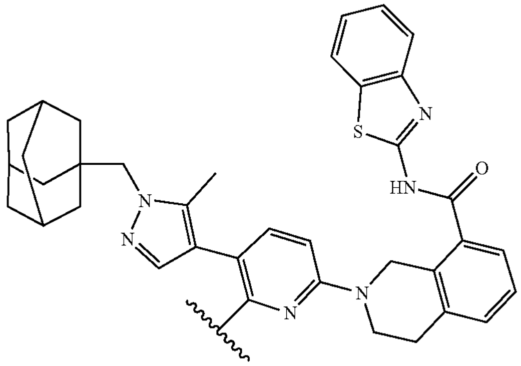
,
$L_1$ is
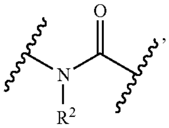
,
and $L_2$ is
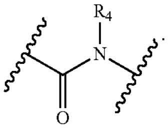
.
In another aspect, $Y_2$ is
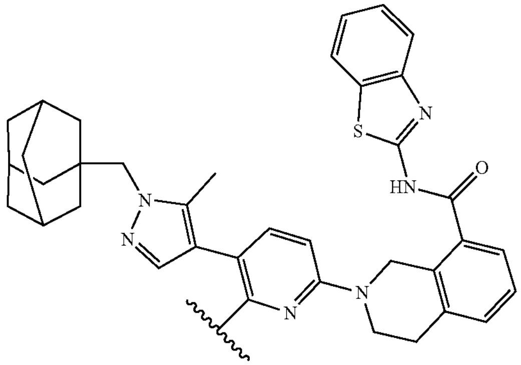
,
$L_1$ is
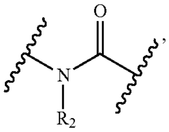
, $L_2$ is
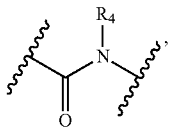
and Y is
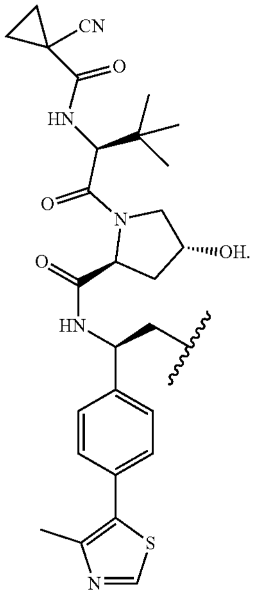 [SMILES: *C[C@H](NC(=O)[C@@H]1C[C@@H](O)CN1C(=O)[C@@H](NC(=O)C1(C#N)CC1)C(C)(C)C)c1ccc(-c2scnc2C)cc1]
In any of the embodiments presented herein, $L_1$ is
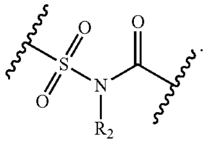
In another aspect, $L_2$ is
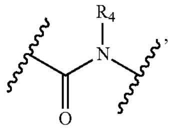
and $L_1$ is
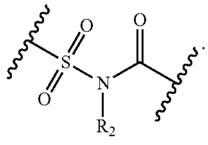
In another aspect, Y is
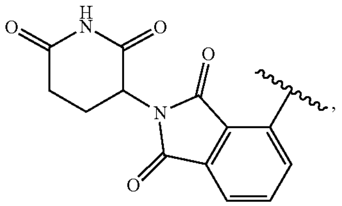
and $L_1$ is
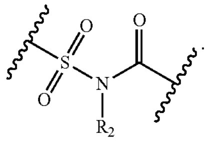
In another aspect, $L_2$ is
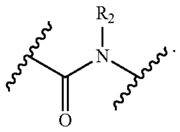
Y is
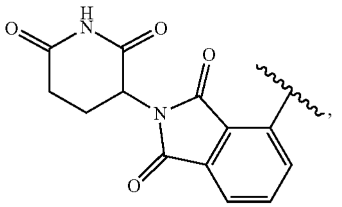 [SMILES: *c1cccc2c1C(=O)N(C1CCC(=O)NC1=O)C2=O]
and $L_1$ is
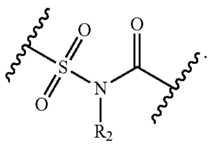

In another aspect, $Y_2$ is
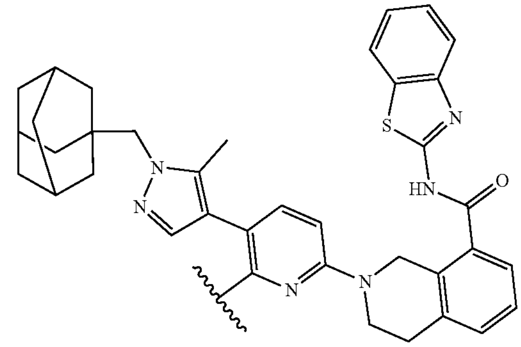
or
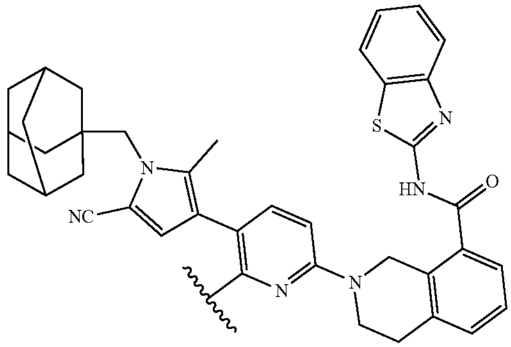
,
and $L_1$ is
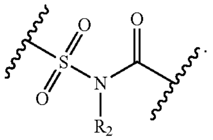
In another aspect, $Y_2$ is
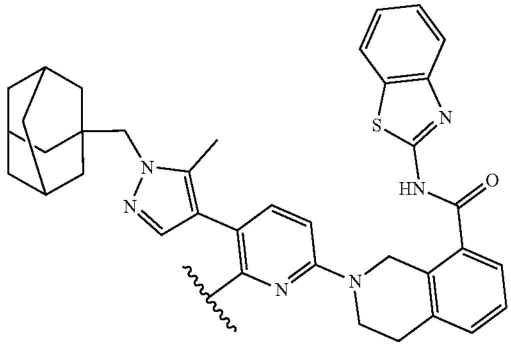
or
-continued
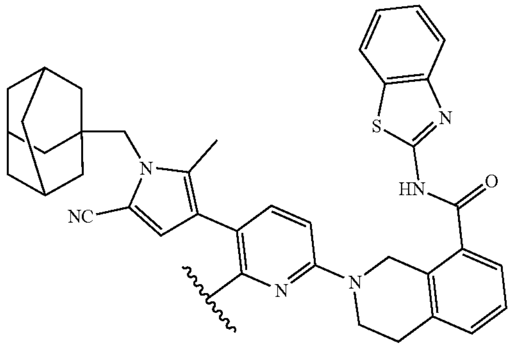
,
$L_2$ is
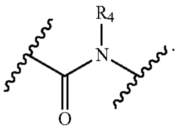
and $L_1$ is
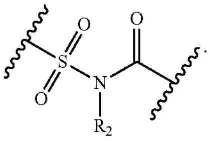
In another aspect, $Y_2$ is
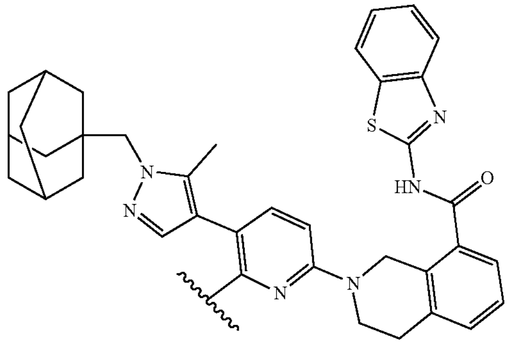
or
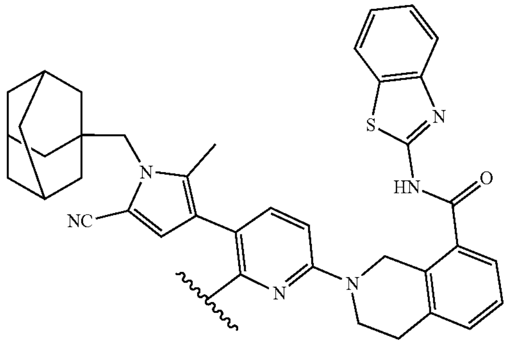
, Y is
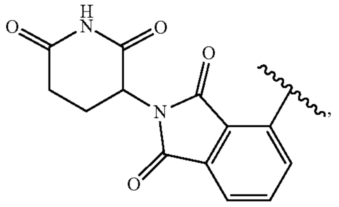 [SMILES: *c1cccc2c1C(=O)N(C1CCC(=O)NC1=O)C2=O]
and $L_1$ is
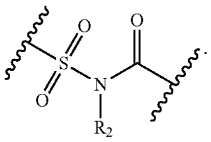
In another aspect, $Y_2$ is
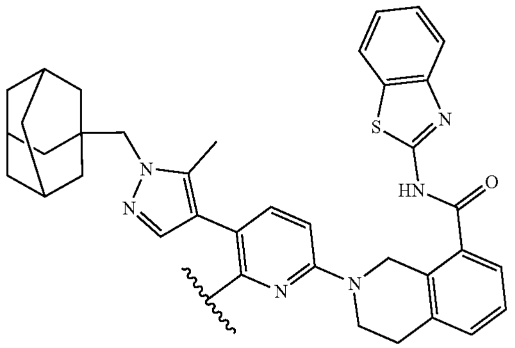
or
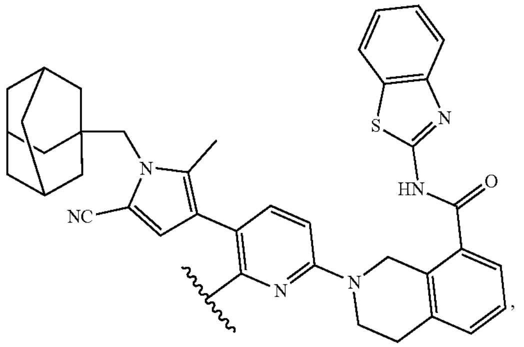
$L_2$ is
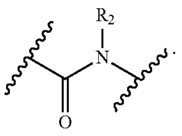
Y is
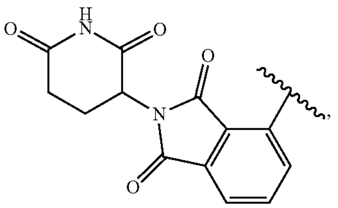 [SMILES: *c1cccc2c1C(=O)N(C1CCC(=O)NC1=O)C2=O]
and $L_1$ is
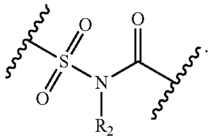
In another aspect, $Y_2$ is
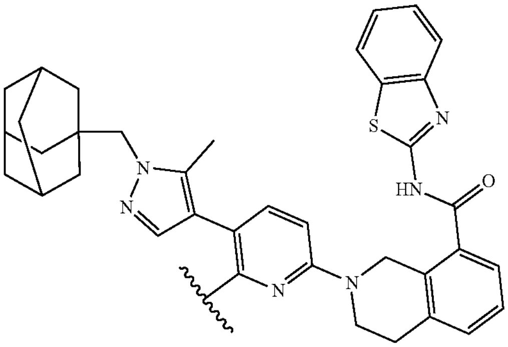
or
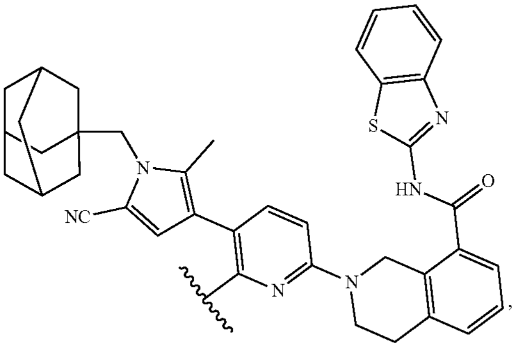
R is
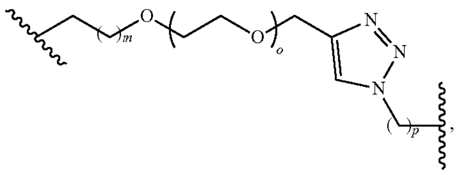

and $L_1$ is
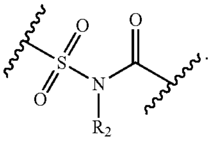
In another aspect, m is 1. In another aspect, o is 1. In another aspect, p is 1. In another aspect, m is 1, o is 1, and p is 1.
In another aspect, $Y_2$ is
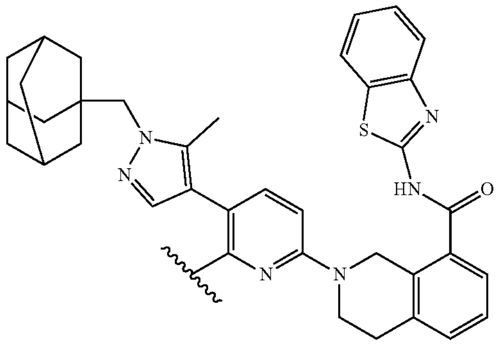
or
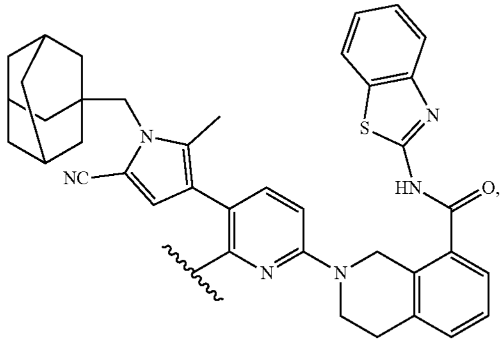
$L_2$ is
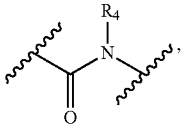
R is
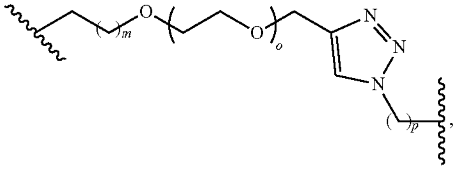
and $L_1$ is
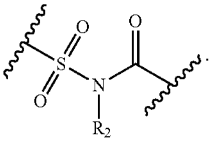
In another aspect, m is 1. In another aspect, o is 1. In another aspect, p is 1. In another aspect, m is 1, o is 1, and p is 1.
In another aspect, $Y_2$ is
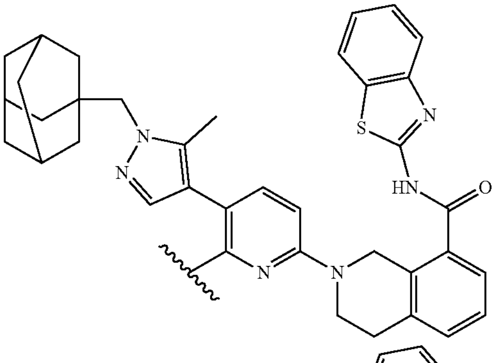
or
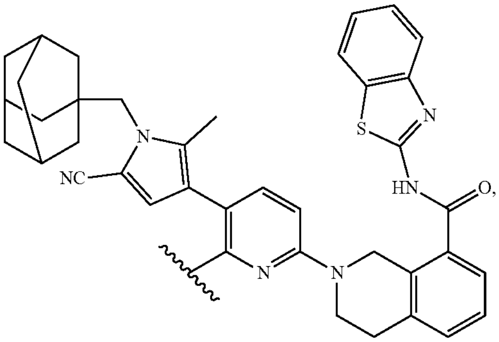
Y is
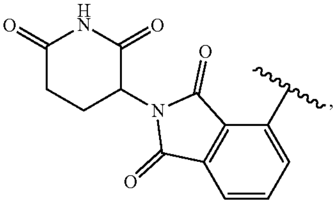 [SMILES: *c1cccc2c1C(=O)N(C1CCC(=O)NC1=O)C2=O]
R is
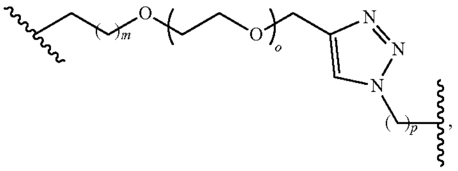

and $L_1$ is
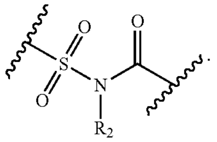
In another aspect, m is 1. In another aspect, o is 1. In another aspect, p is 1. In another aspect, m is 1, o is 1, and p is 1.
In another aspect, $Y_2$ is
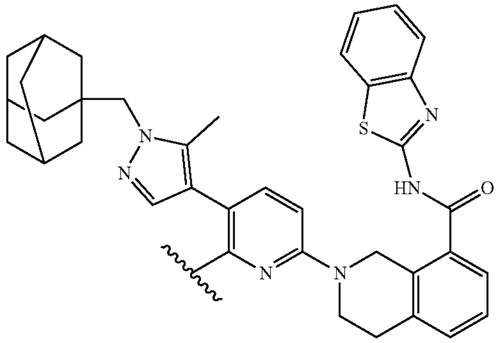
or
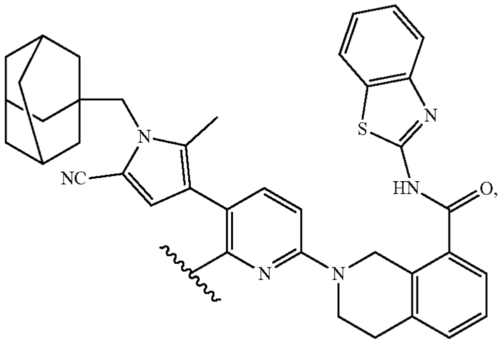
$L_2$ is
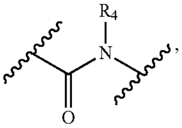
Y is
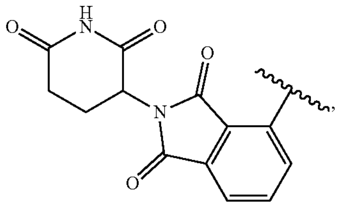 [SMILES: *c1cccc2c1C(=O)N(C1CCC(=O)NC1=O)C2=O]
R is
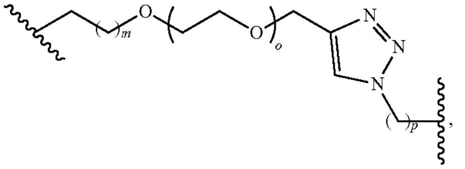
and $L_1$ is
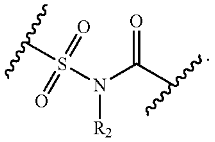
In another aspect, m is 1. In another aspect, o is 1. In another aspect, p is 1. In another aspect, m is 1, o is 1, and p is 1.
In another aspect, $Y_2$ is
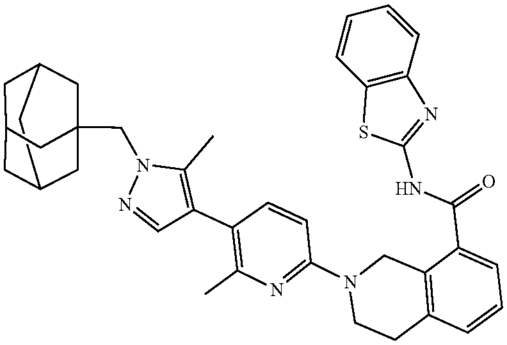
or
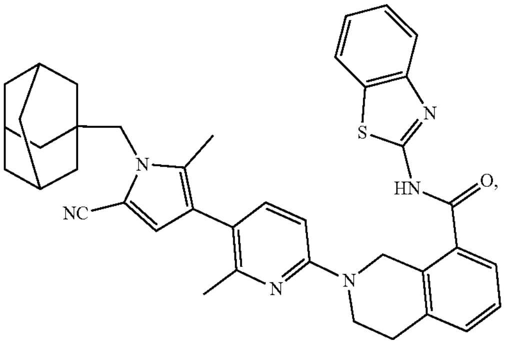
R is
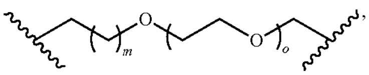

and $L_1$ is
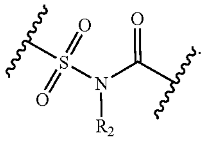
In another aspect, m is 1. In another aspect, o is 1. In another aspect, m is 1, and o is 1.
In another aspect, $Y_2$ is
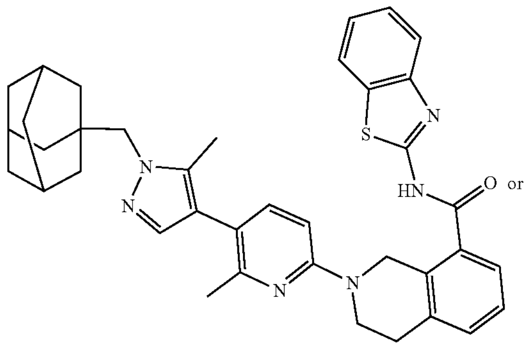
or
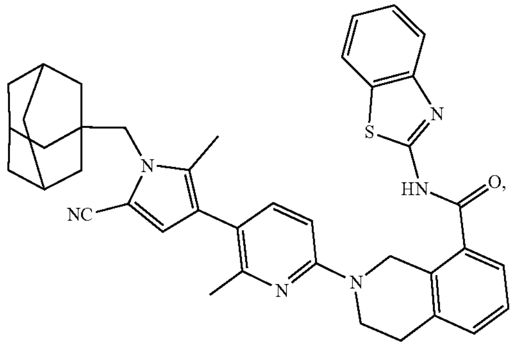
$L_2$ is
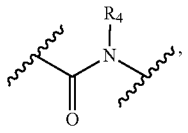
R is
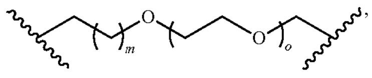
and $L_1$ is
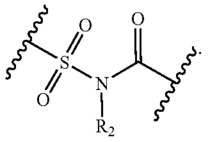
In another aspect, m is 1. In another aspect, o is 1. In another aspect, m is 1, and o is 1.
In another aspect, $Y_2$ is
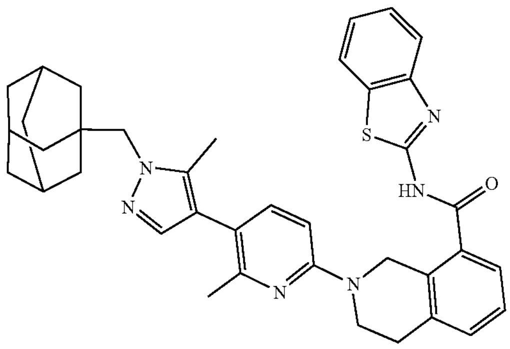
or
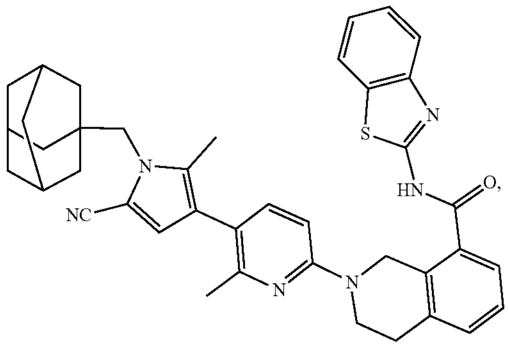
Y is
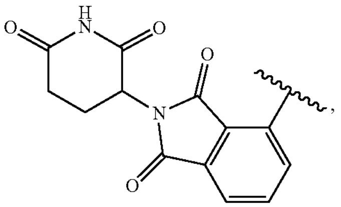 [SMILES: *c1cccc2c1C(=O)N(C1CCC(=O)NC1=O)C2=O]
R is
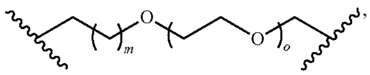

and $L_1$ is
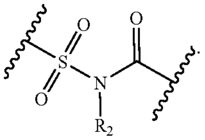
In another aspect, m is 1. In another aspect, o is 1. In another aspect, m is 1, and o is 1.
In another aspect, $Y_2$ is
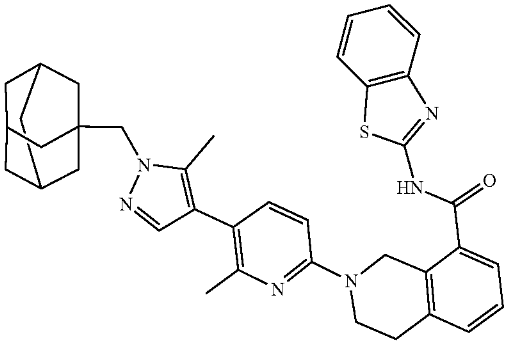
or
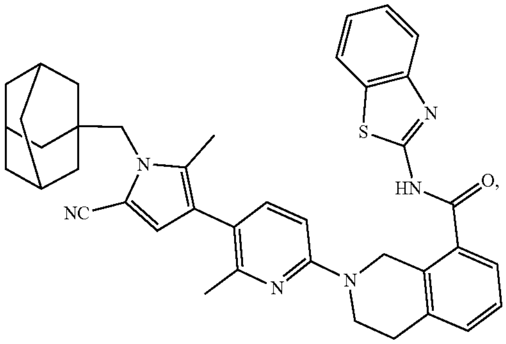
$L_2$ is
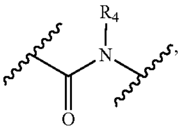
Y is
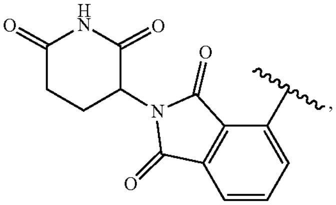 [SMILES: *c1cccc2c1C(=O)N(C1CCC(=O)NC1=O)C2=O]
R is
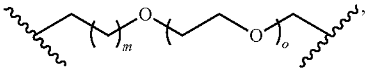
and $L_1$ is
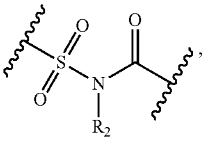
In another aspect, m is 1. In another aspect, o is 1. In another aspect, m is 1, and o is 1.
In another aspect, $L_2$ is
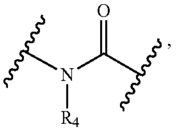
and Y is
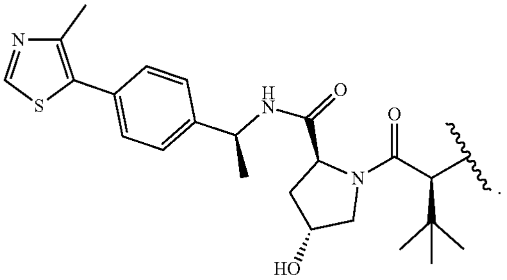 [SMILES: *[C@H](C(=O)N1C[C@H](O)C[C@H]1C(=O)N[C@@H](C)c1ccc(-c2scnc2C)cc1)C(C)(C)C]
In another aspect, $L_2$ is
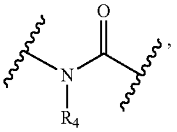
R is
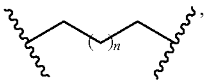

and Y is
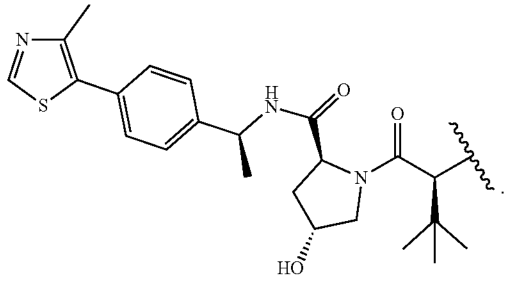 [SMILES: *[C@H](C(=O)N1C[C@H](O)C[C@H]1C(=O)N[C@@H](C)c1ccc(-c2scnc2C)cc1)C(C)(C)C]
In another aspect, n is 1-6, inclusive. In another aspect, n is 5.
In another aspect, $L_2$ is
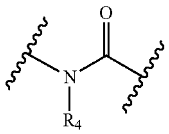
,
and $Y_2$ is
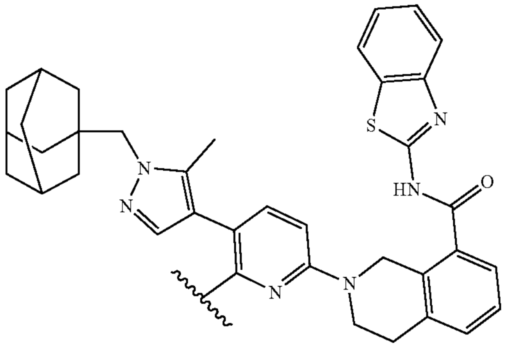
or
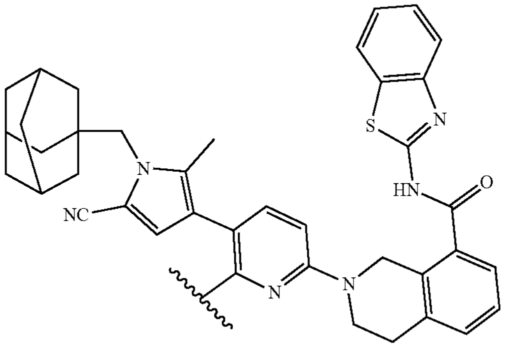
.
In another aspect, $L_2$ is
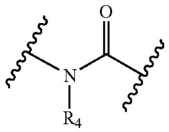
,
$Y_2$ is
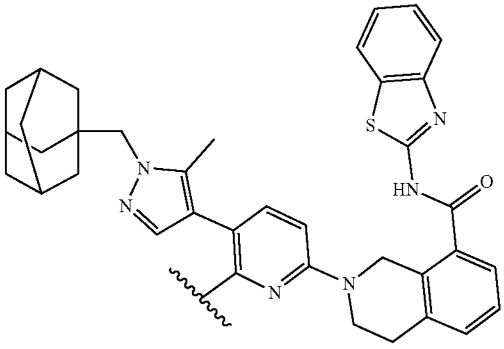
or
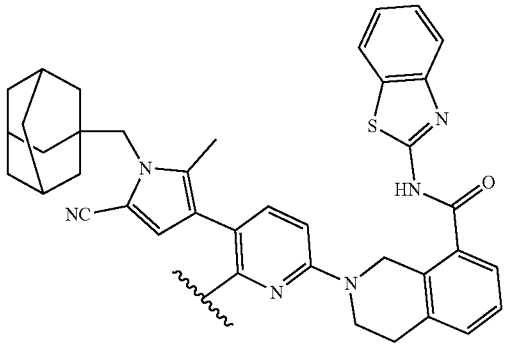
,
and Y is
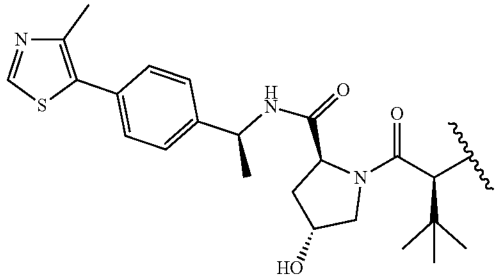
.
In another aspect, $L_2$ is
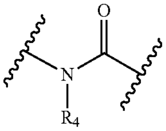
,
R is
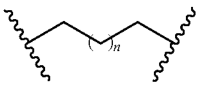
, $Y_2$ is
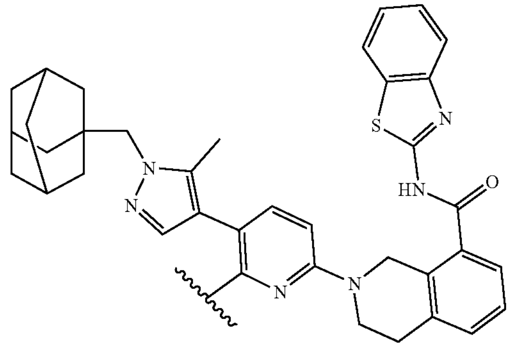
or
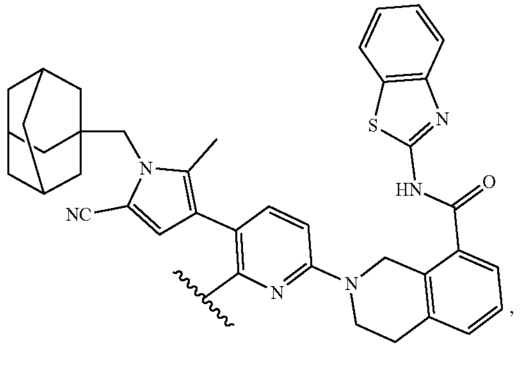
and Y is
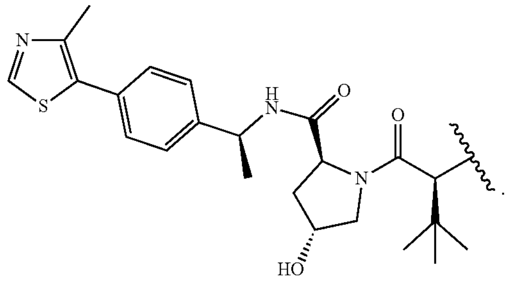 [SMILES: *[C@H](C(=O)N1C[C@H](O)C[C@H]1C(=O)N[C@@H](C)c1ccc(-c2scnc2C)cc1)C(C)(C)C]
In another aspect, n is 1-6, inclusive. In another aspect, n is 5.
In another aspect, $L_2$ is
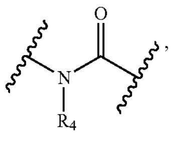
and $L_1$ is
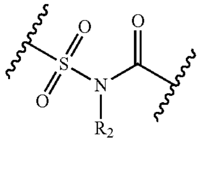
or
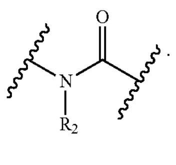
In another aspect, $L_2$ is
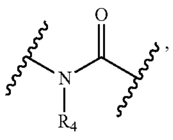
$L_1$ is
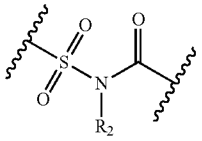
or
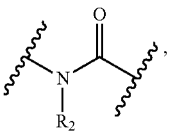
and $Y_2$
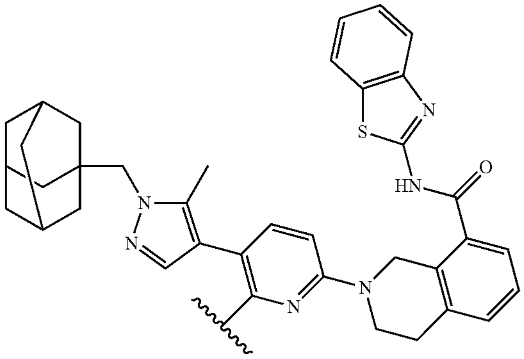
or
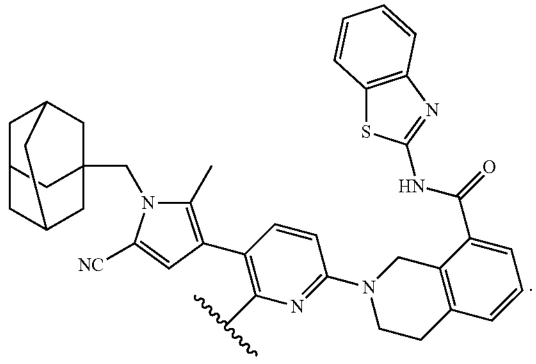
In another aspect, $L_2$ is
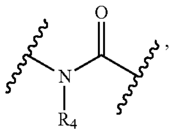

$Y_2$ is
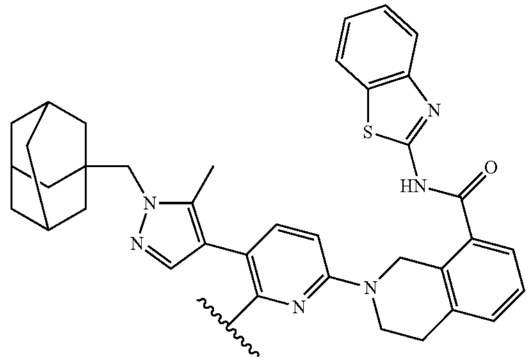
or
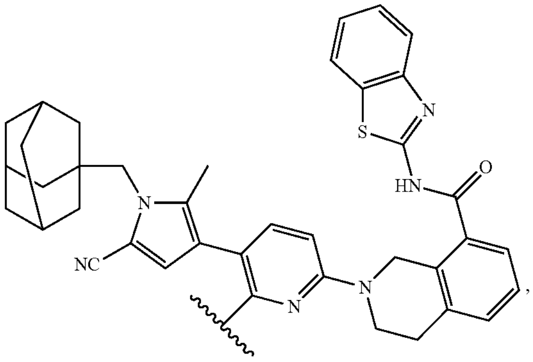
$L_1$ is
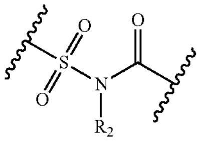
or
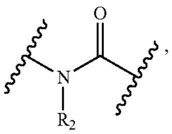
and Y is
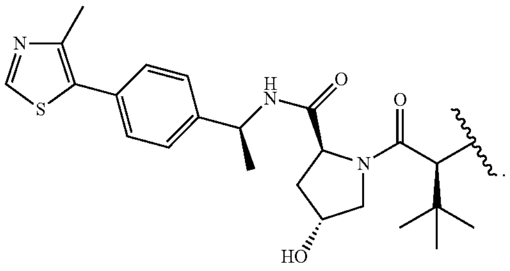 [SMILES: *[C@H](C(=O)N1C[C@H](O)C[C@H]1C(=O)N[C@@H](C)c1ccc(-c2scnc2C)cc1)C(C)(C)C]
In another aspect, $L_2$ is
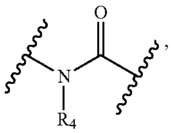
R is
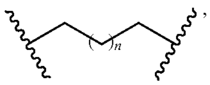
$Y_2$ is
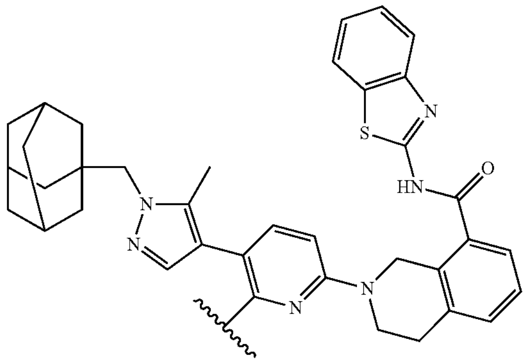
or
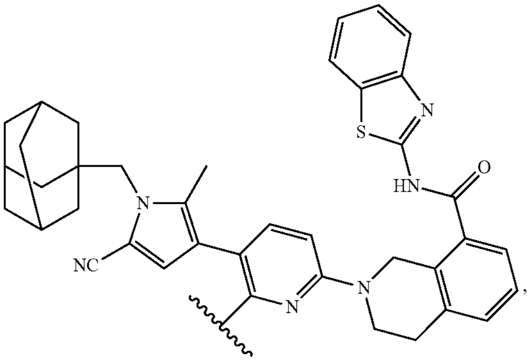
$L_1$ is
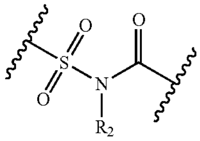
or
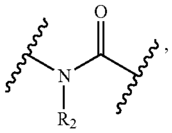
and Y is
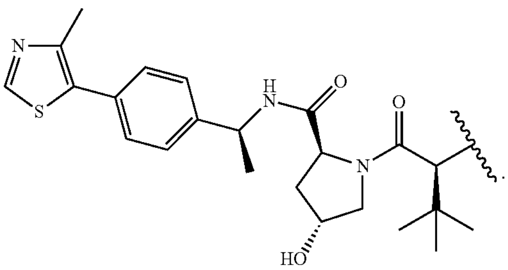 [SMILES: *[C@H](C(=O)N1C[C@H](O)C[C@H]1C(=O)N[C@@H](C)c1ccc(-c2scnc2C)cc1)C(C)(C)C]
In another aspect, n is 1-6, inclusive. In another aspect, n is 5.

In another aspect, the compound is:
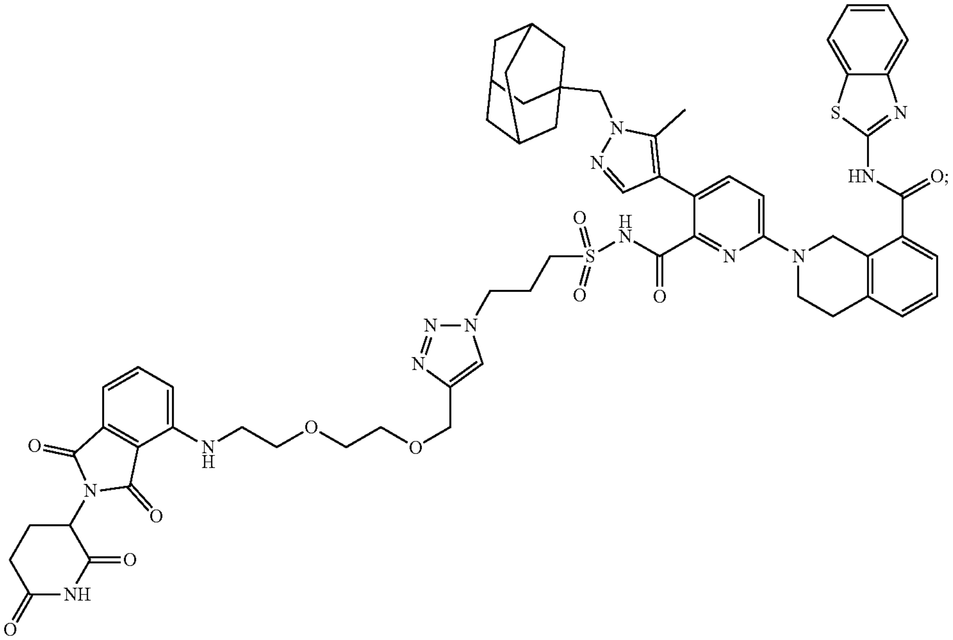
;
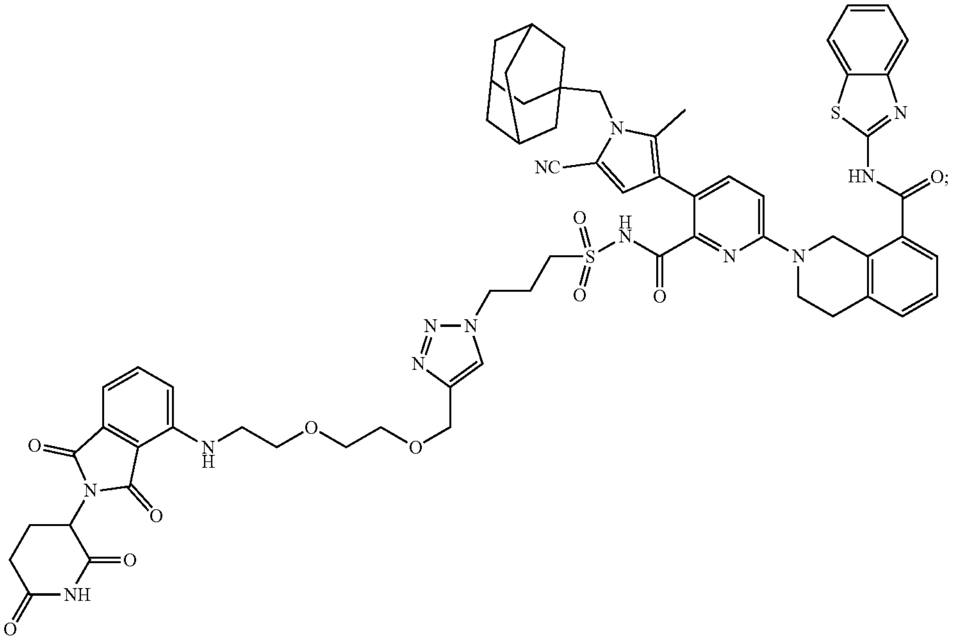
;
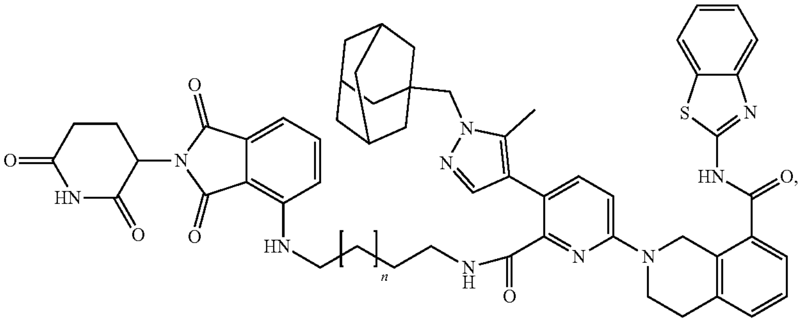
,
n = 1

-continued
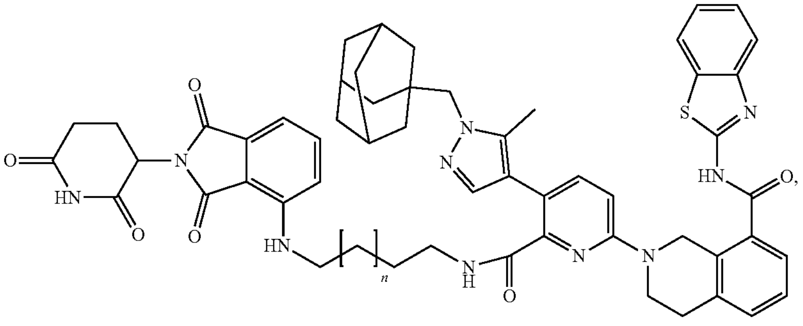
n = 3
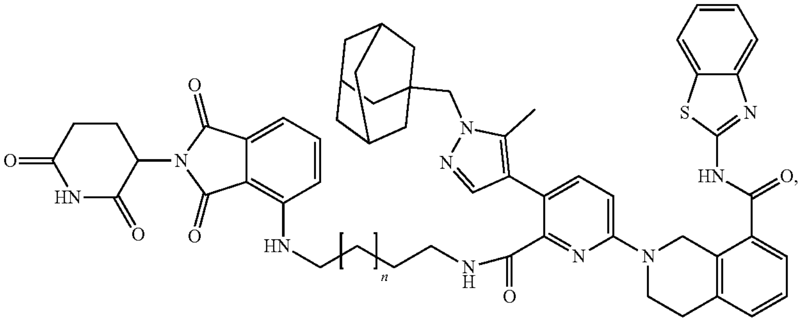
n = 5
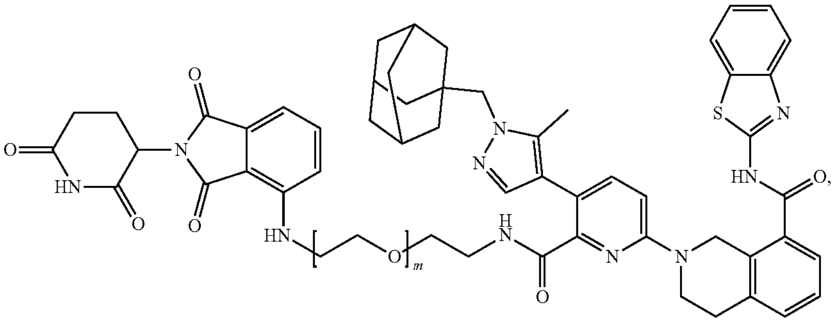
m = 1
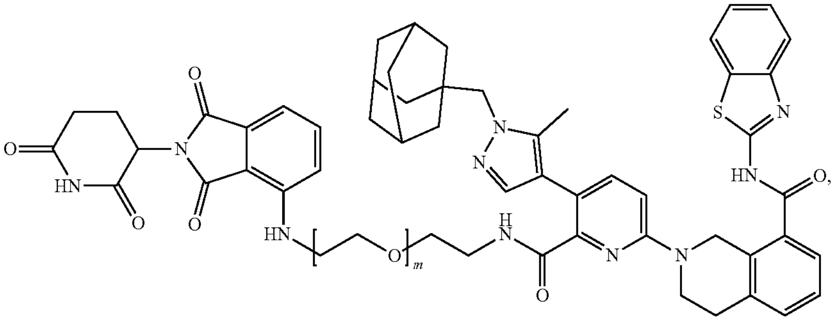
m = 2

-continued
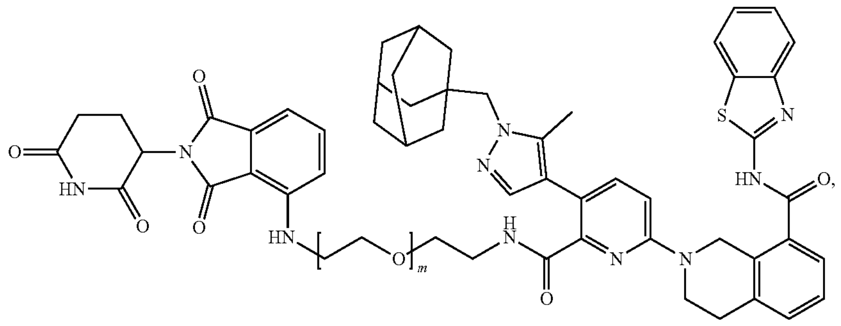
m = 3
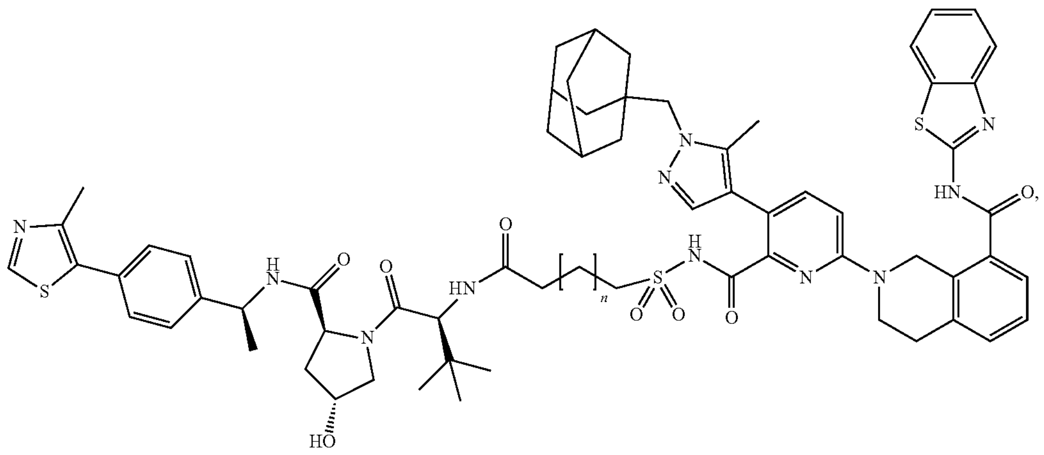
n = 1
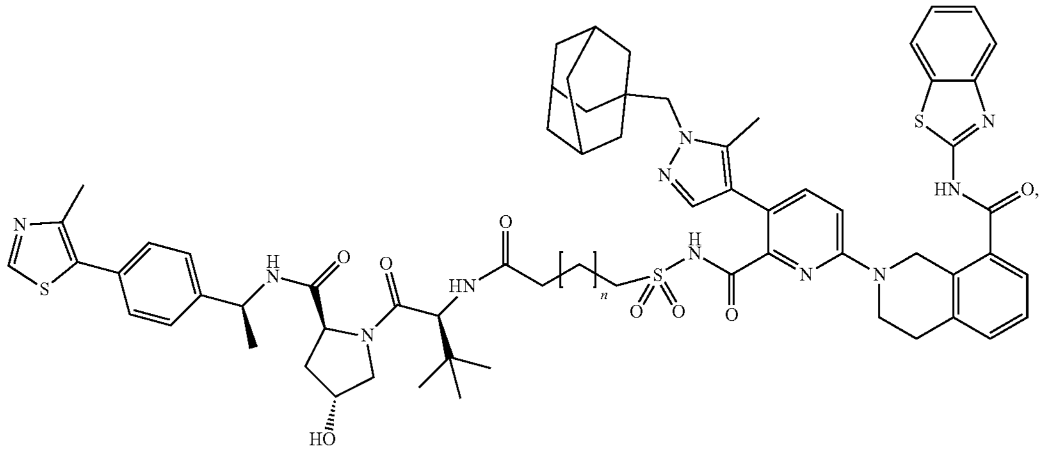
n = 2

-continued
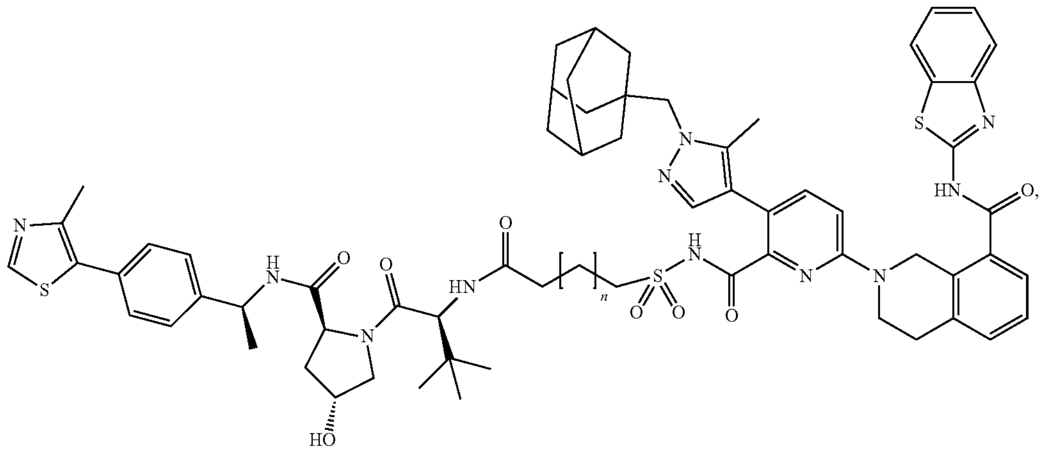
n = 3
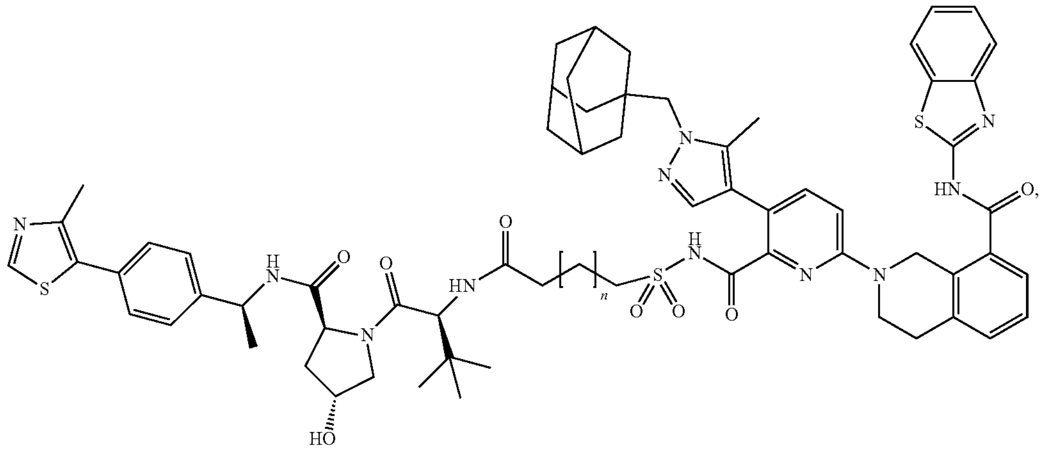
n = 4
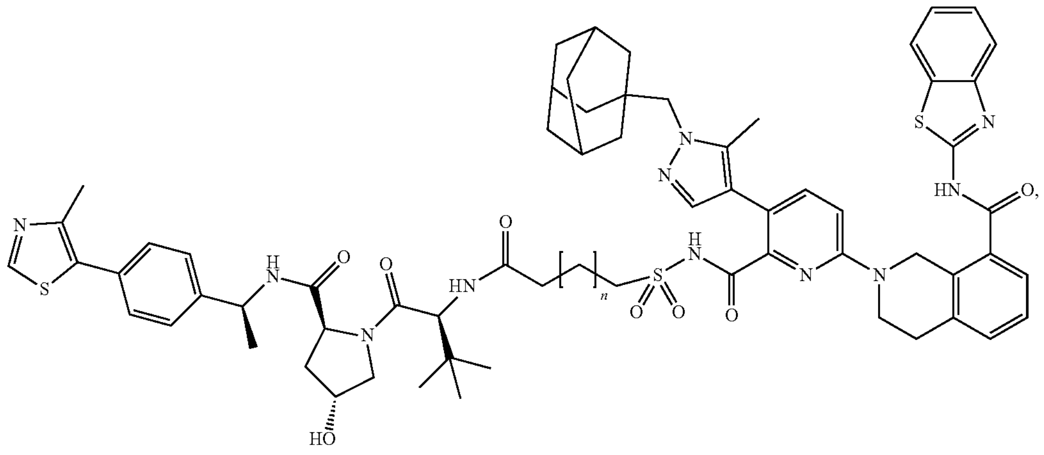
n = 5

-continued
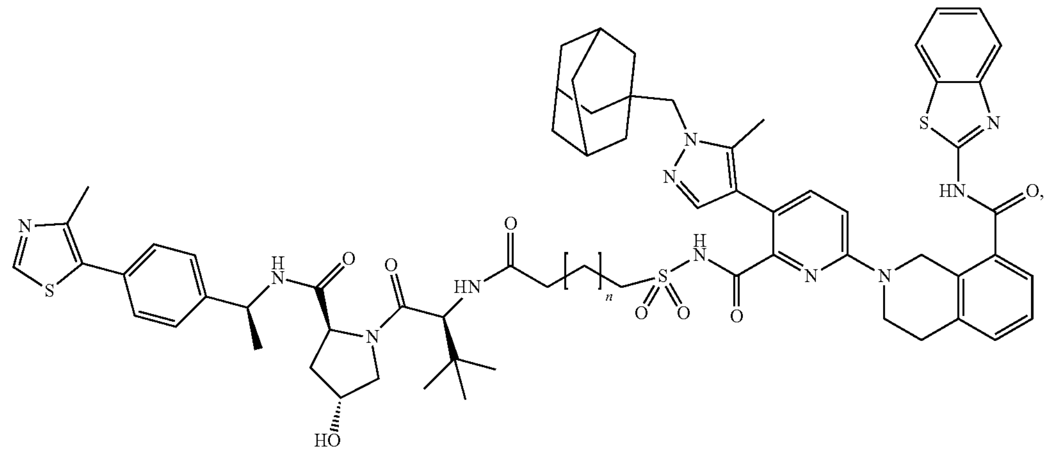
n = 6
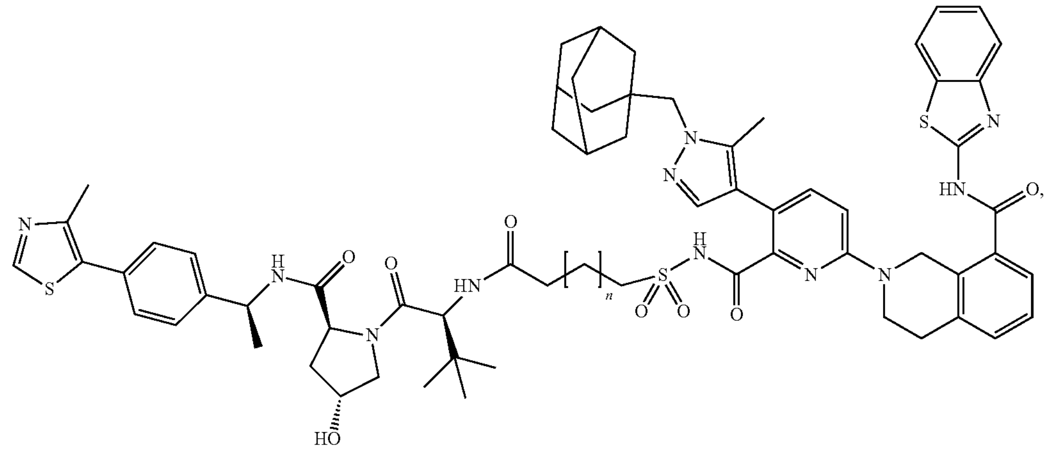
n = 7
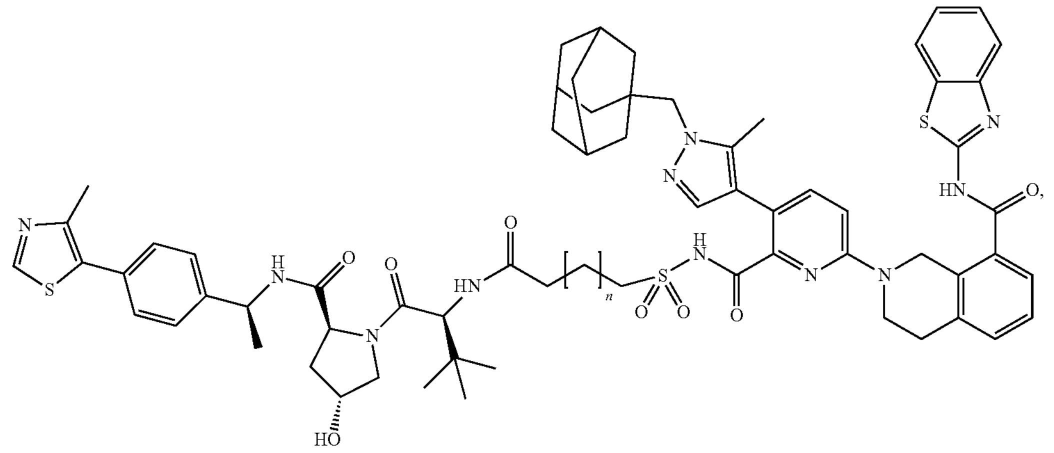
n = 8

-continued
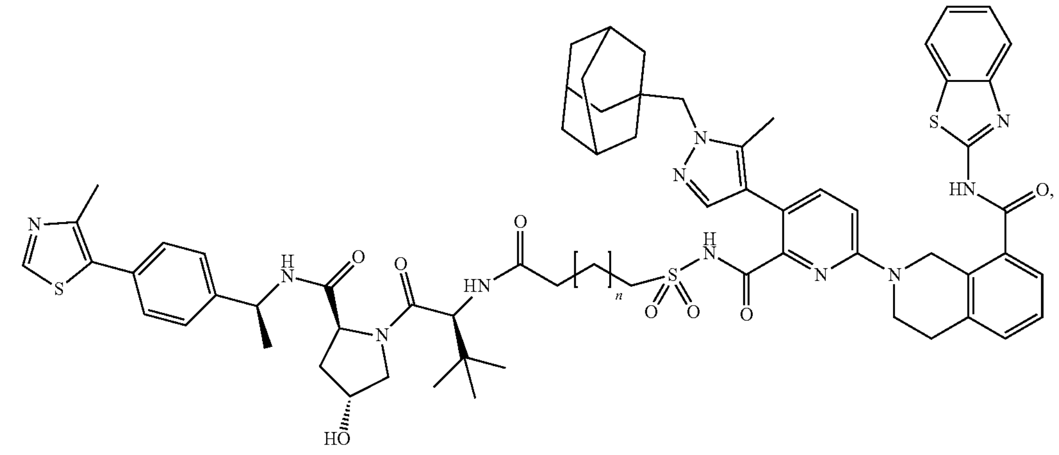
n = 9
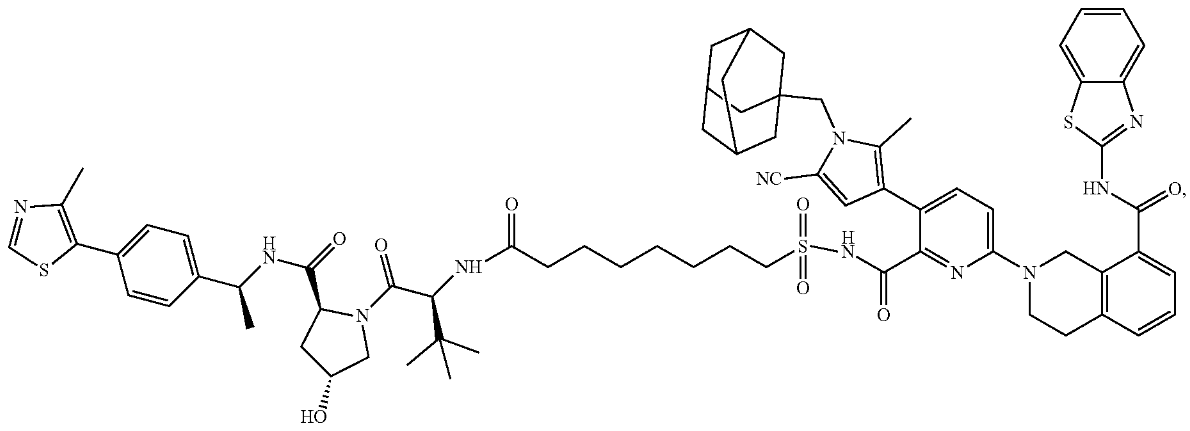
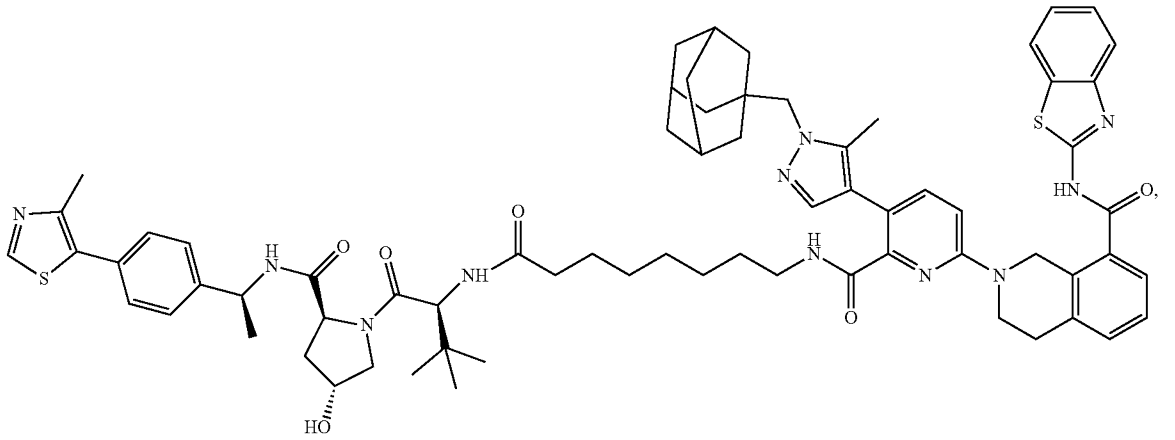

-continued
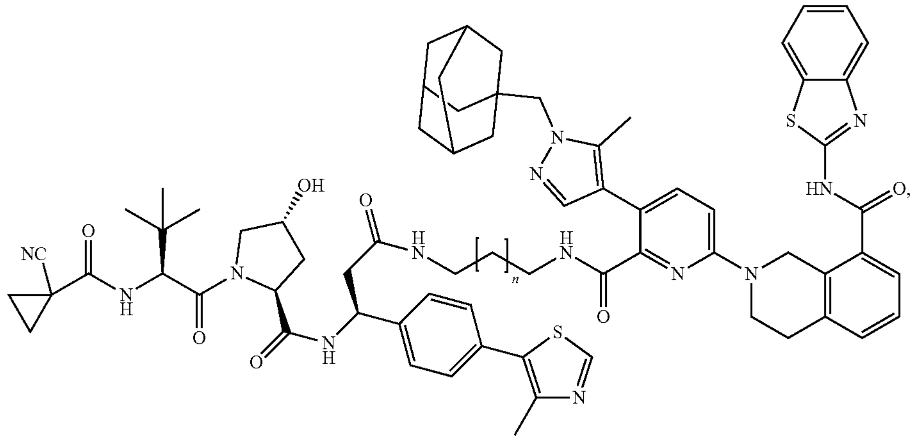
n = 0
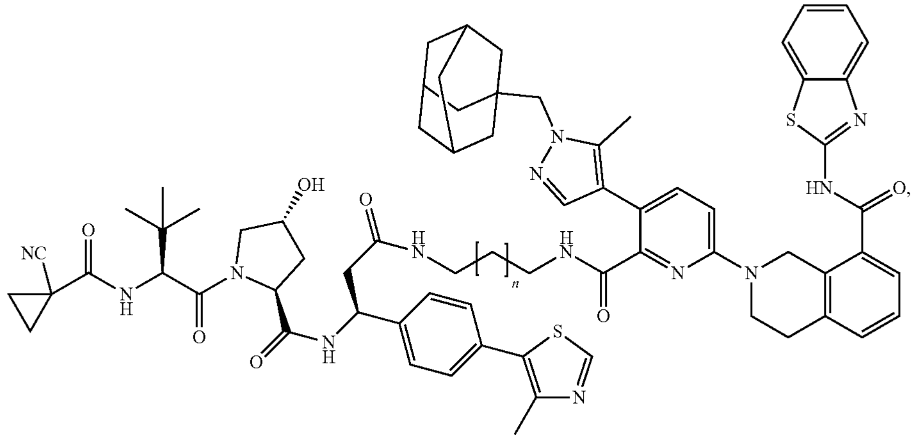
n = 1
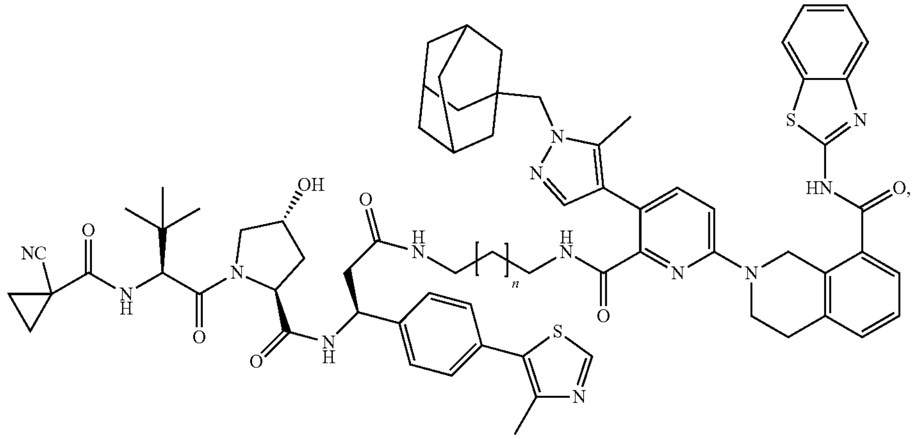
n = 2

-continued
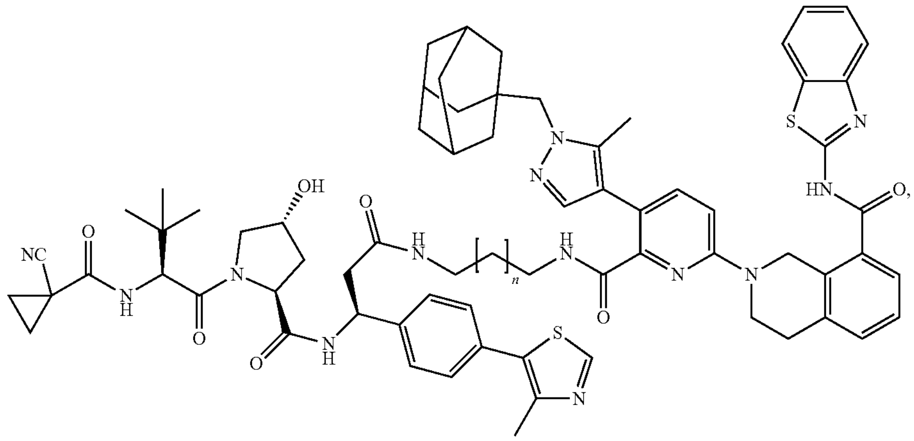
n = 3
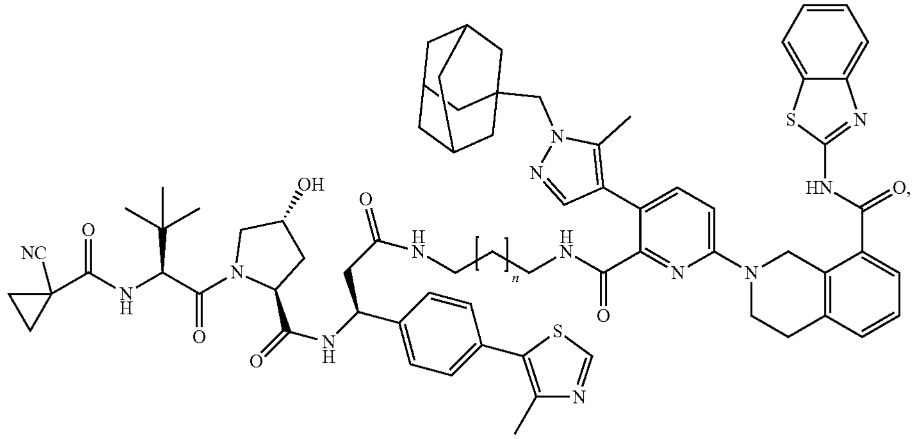
n = 4
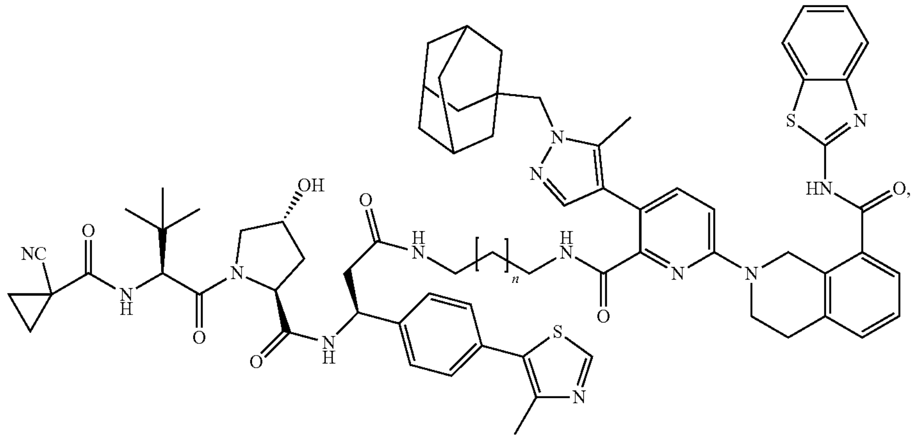
n = 6

-continued
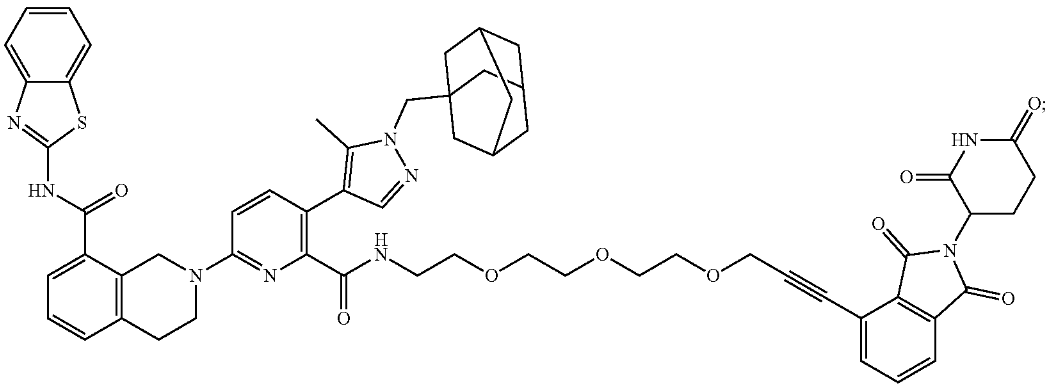
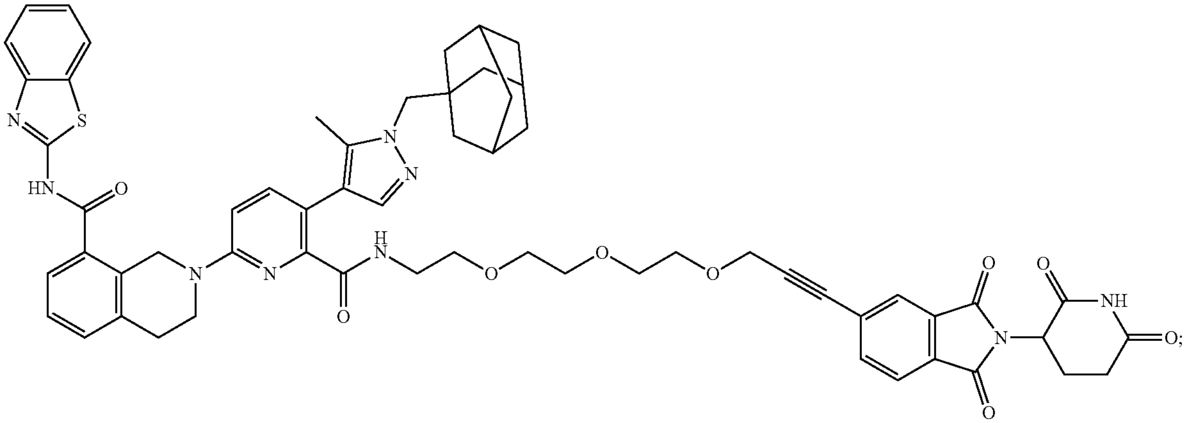
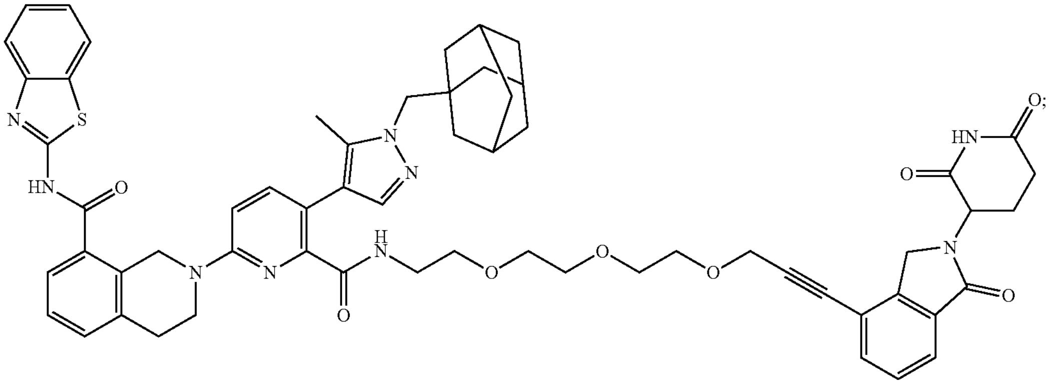
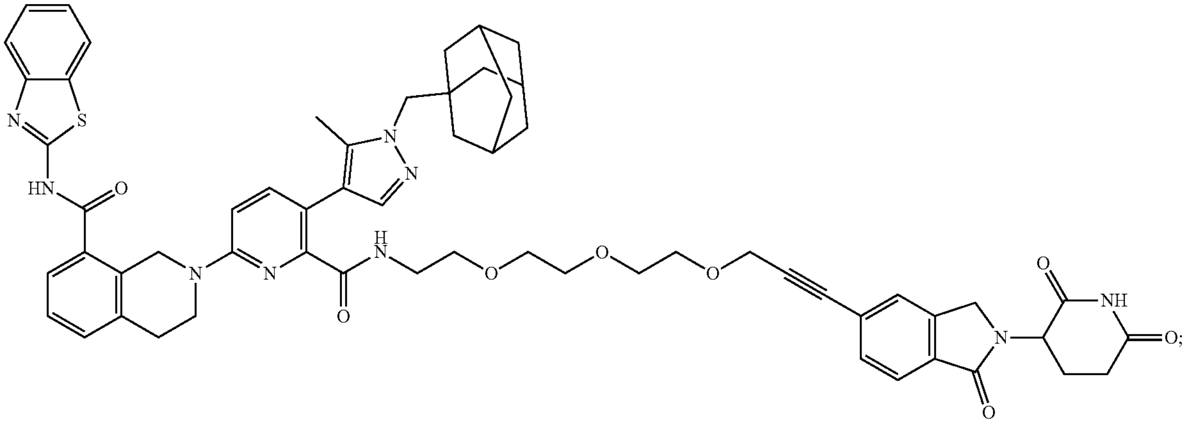

-continued
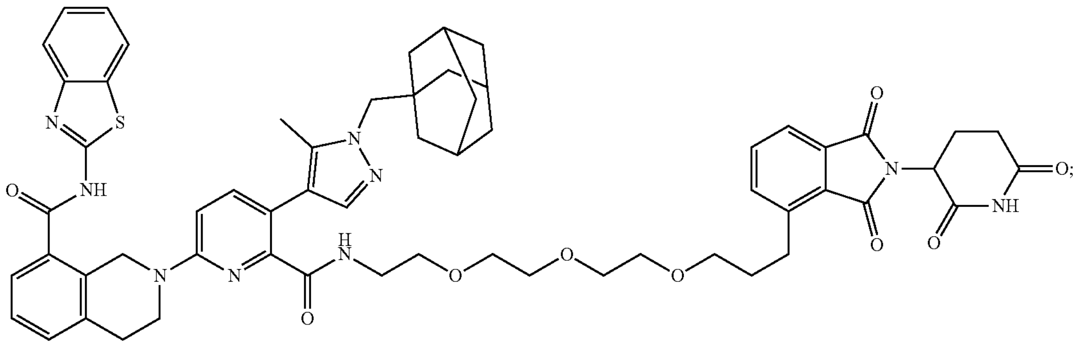
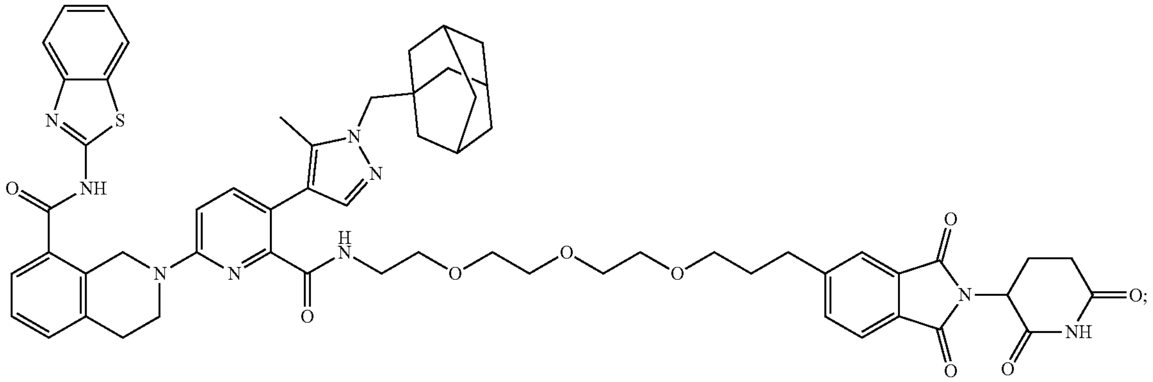
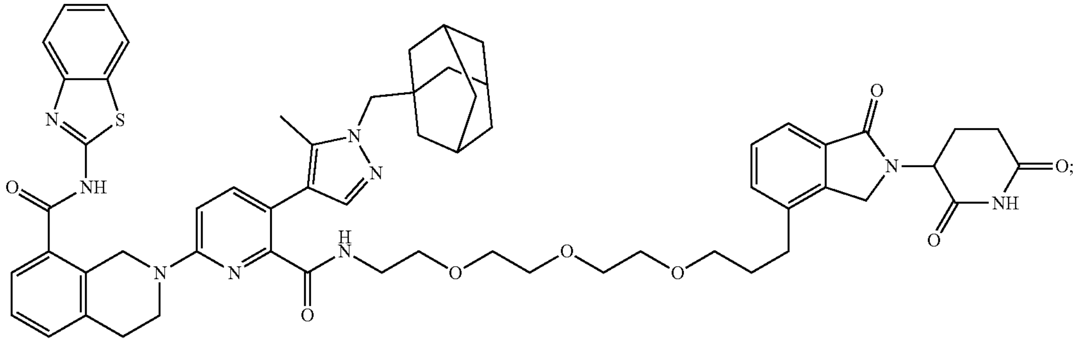
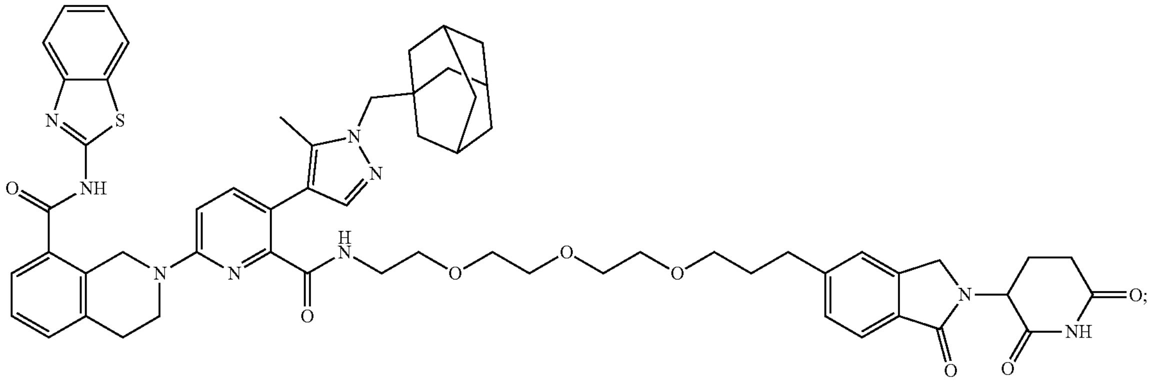

-continued
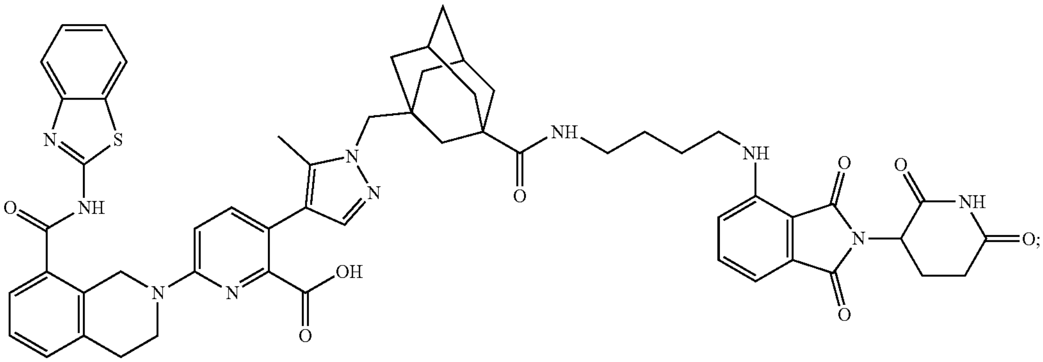
;
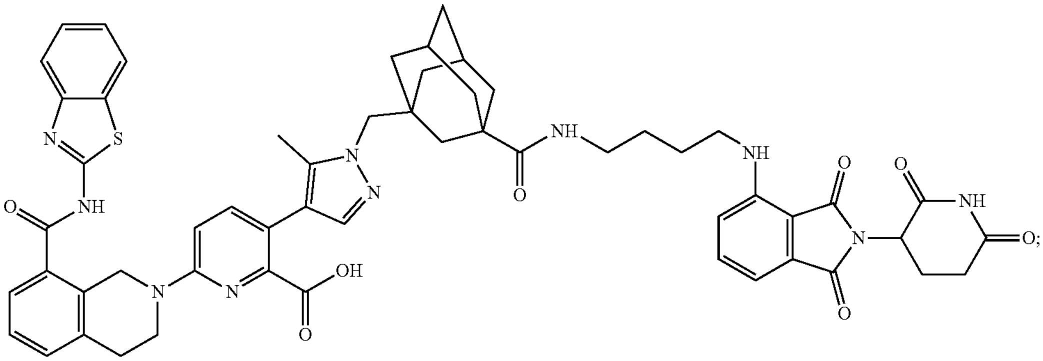
;
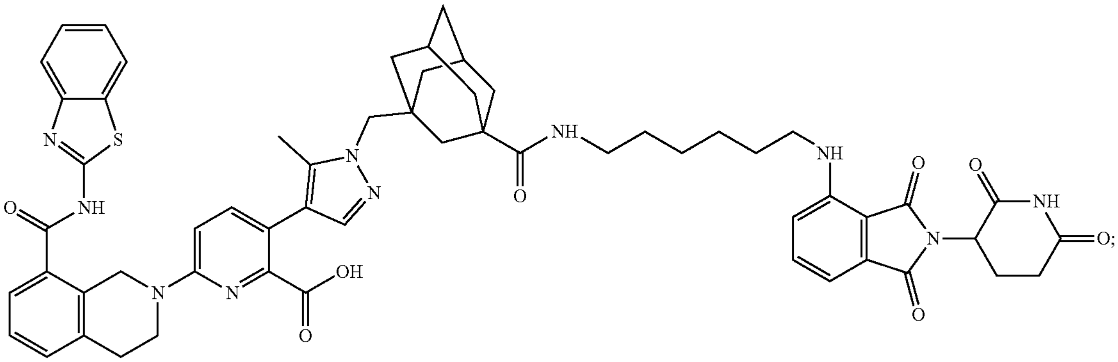
;
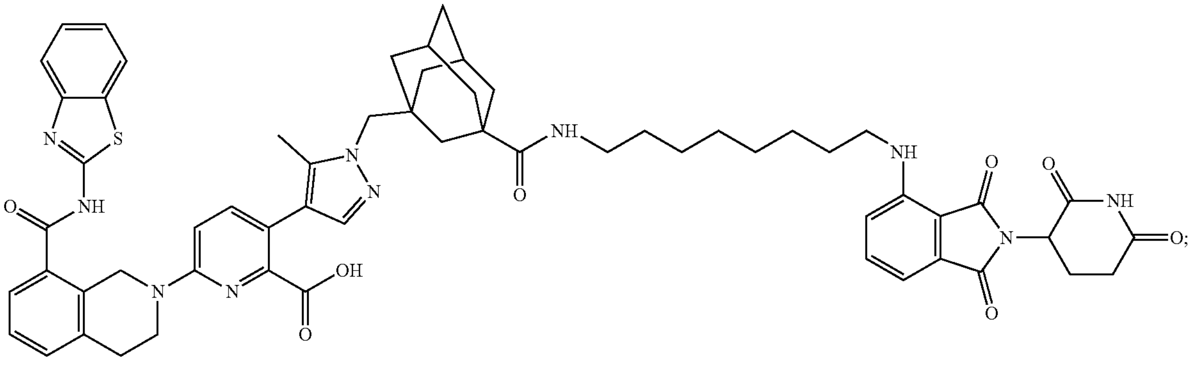
;

-continued
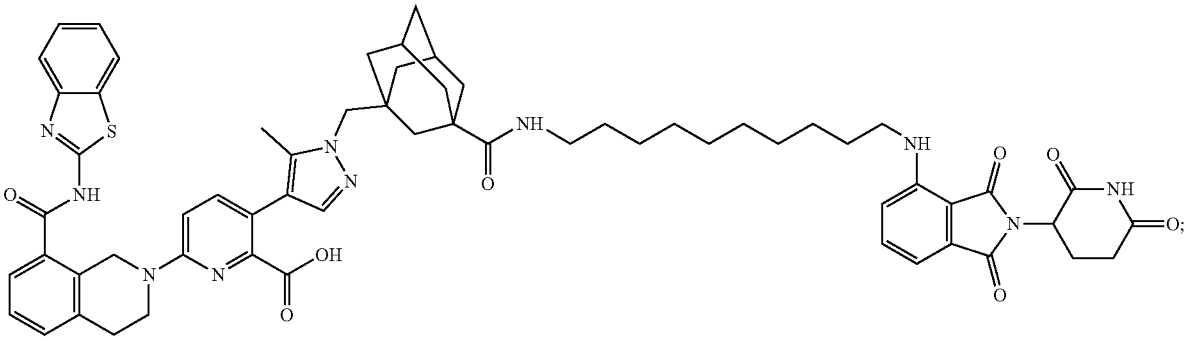
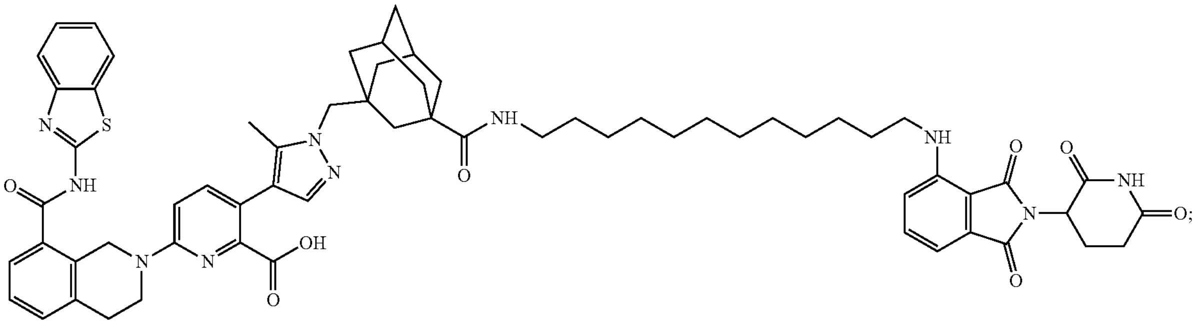
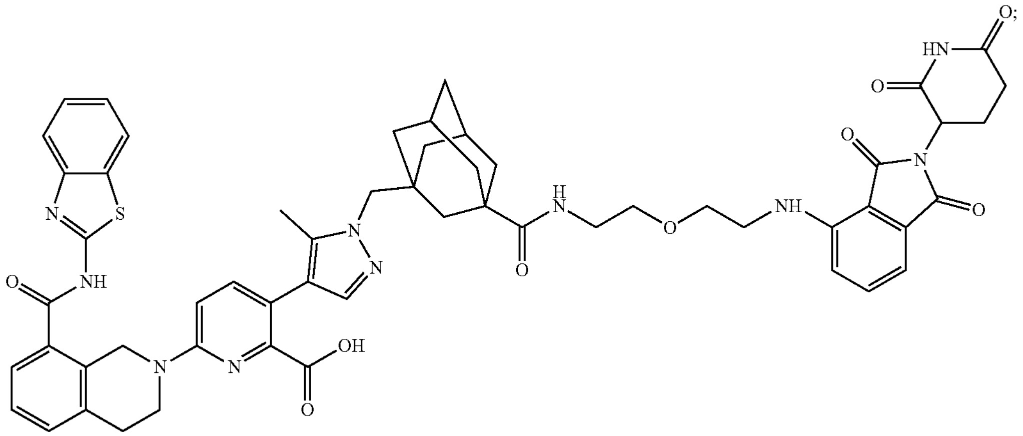
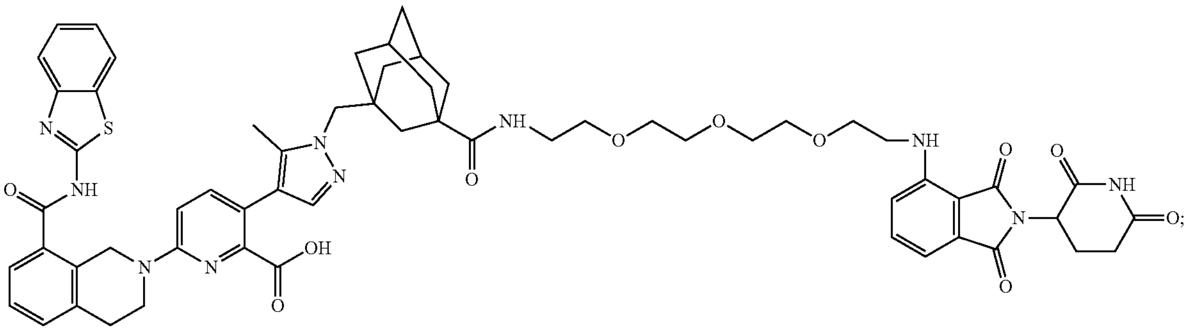

-continued

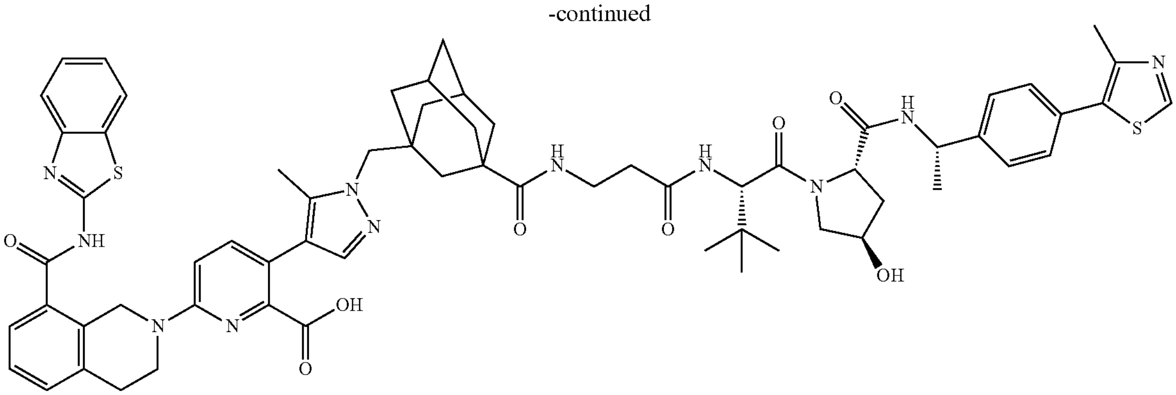

;

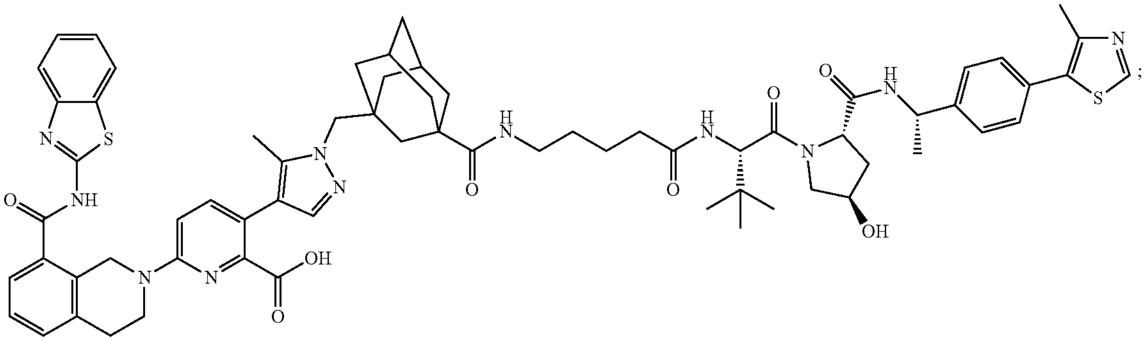

; or

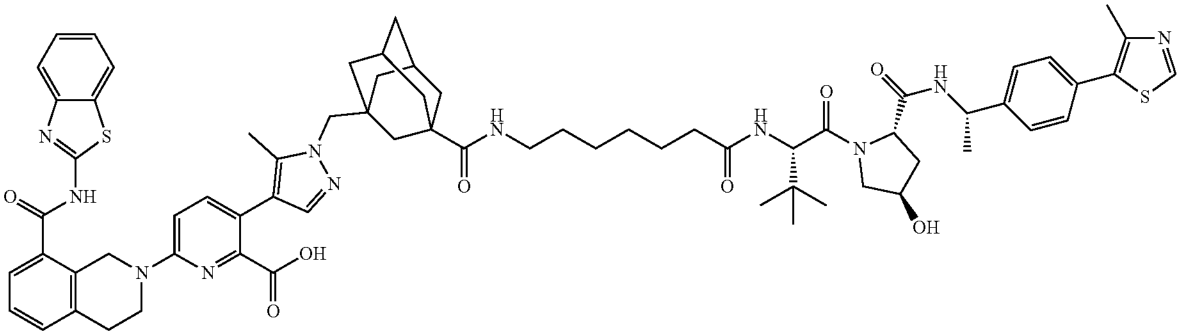

;

In another aspect, the invention provides a pharmaceutical composition comprising a compound described herein (e.g., Formula (I)), or a pharmaceutically acceptable salt, hydrate, solvate, or prodrug thereof, and a pharmaceutically acceptable carrier. In another aspect, the pharmaceutical composition further comprises an additional agent. In another aspect, the additional agent is an anti-cancer agent. In another aspect, the anti-cancer agent is an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

In another aspect, the invention provides a method of degrading Bcl-2 proteins, the method comprising administering an effective amount of a compound described herein (e.g., Formula (I)), or a pharmaceutically acceptable salt, hydrate, solvate, or prodrug thereof. In another aspect, the compound is administered in vitro. In another aspect, the compound is administered in vivo. In another aspect, the method further comprises administering the compound to a subject.

In another aspect, the invention provides a method of treating a disease or disorder in a subject in need thereof, the method comprising administering an effective amount of a compound described herein (e.g., Formula (I)), or a pharmaceutically acceptable salt, hydrate, solvate, or prodrug thereof. In another aspect, the disease is cancer. In another aspect, the cancer is a solid tumor. In another aspect, the cancer is chronic lymphocyctic leukemia. In another aspect, the subject is a mammal. In another aspect, the subject is a human.

In another aspect, the invention provides a method of treating a subject suffering from or susceptible to a disease or disorder, the method comprising administering an effective amount of a compound described herein (e.g., Formula (I)), or a pharmaceutically acceptable salt, hydrate, solvate, or prodrug thereof. In another aspect, the disease is cancer. In another aspect, the cancer is a solid tumor. In another aspect, the cancer is chronic lymphocyctic leukemia. In another aspect, the subject is a mammal. In another aspect, the subject is a human.

In another aspect, the invention provides a method of treating a Bcl-2-dependent (e.g., mediated) cancer in a subject in need thereof, the method comprising administering an effective amount of a compound described herein (e.g., Formula (I)), or a pharmaceutically acceptable salt, hydrate, solvate, or prodrug thereof, wherein the platelet toxicity of the compound is less than other Bcl-2 inhibitors.

In another aspect, the Bcl-2-dependent (e.g., mediated) cancer is chronic lymphocyctic leukemia. In another aspect, the other Bcl-2 inhibitor is ABT-737, navitoclax (ABT-263), venetoclax (ABT-199), obatoclax (GX 15-070), (−)-gossypol (AT-101), sabutoclax (BI-97C1), TW-37, BM-1252 (APG-1252), A-1155463, or A-1331852. In another aspect, the other Bcl-2 inhibitor is venetoclax or ABT-263.

In another aspect, the invention provides a method of treating a subject suffering from or susceptible to a Bcl-2-dependent (e.g., mediated) cancer, the method comprising administering an effective amount of a compound described herein (e.g., Formula (I)), or a pharmaceutically acceptable salt, hydrate, solvate, or prodrug thereof, wherein the platelet toxicity of the compound is less than other Bcl-2 inhibitors. In another aspect, the Bcl-2-dependent (e.g., mediated) cancer is chronic lymphocyctic leukemia. In another aspect, the other Bcl-2 inhibitor is ABT-737, navitoclax (ABT-263), venetoclax (ABT-199), obatoclax (GX 15-070), (−)-gossypol (AT-101), sabutoclax (BI-97C1), TW-37, BM-1252 (APG-1252), orA-1155463. In another aspect, the other Bcl-2 inhibitor is venetoclax or ABT-263.

In another aspect, the invention provides a method of treating a Bcl-2-dependent (e.g., mediated) cancer in a subject in need thereof, the method comprising administering an effective amount of a compound described herein (e.g., Formula (I)), or a pharmaceutically acceptable salt, hydrate, solvate, or prodrug thereof, such that ratio of human platelet toxicity ($IC_{50}$) to anticancer activity ($IC_{50}$) of the compound is greater than one. In another aspect, wherein the Bcl-2-dependent (e.g., mediated) cancer is chronic lymphocyctic leukemia. In another aspect, wherein the anticancer activity is measured in MOLT-4 cells. In another aspect, wherein the ratio is greater than 2.5. In another aspect, wherein the ratio is greater than 5. In another aspect, wherein the ratio is greater than 10. In another aspect, wherein the ratio is greater than 20. In another aspect, wherein the ratio is greater than 40.

In another aspect, the invention provides a method of treating a subject suffering from or susceptible to a Bcl-2-dependent (e.g., mediated) cancer, the method comprising administering an effective amount of a compound described herein (e.g., Formula (I)), or a pharmaceutically acceptable salt, hydrate, solvate, or prodrug thereof, such that ratio of human platelet toxicity ($IC_{50}$) to anticancer activity ($IC_{50}$) of the compound is greater than one. In another aspect, wherein the Bcl-2-dependent (e.g., mediated) cancer is chronic lymphocyctic leukemia. In another aspect, wherein the anticancer activity is measured in MOLT-4 cells. In another aspect, wherein the ratio is greater than 2.5. In another aspect, wherein the ratio is greater than 5. In another aspect, wherein the ratio is greater than 10. In another aspect, wherein the ratio is greater than 20. In another aspect, wherein the ratio is greater than 40.

Compounds of the present invention are bivalent compounds that are able to promote the degradation of the anti-apoptotic Bcl-2 family of proteins. These bivalent compounds connect a Bcl-2 small molecule inhibitor or ligand to an E3 ligase binding moiety, such as von Hippel-Lindau (VHL) E3 ligase binding moiety (such as HIF-1α-derived (R)-hydroxyproline containing VHL E3 ligase ligands) or cereblon (CRBN) E3 ligase binding moiety (thalidomide derivatives such as pomalidomide). VHL is part of the cullin-2 (CUL2) containing E3 ubiquitin ligase complex elongin BC-CUL2-VHL (known as CRL2VHL) responsible for degradation of the transcription factor HIF-1α. (R)-Hydroxyproline containing VHL E3 ligase ligands derived from HIF-1α have been identified with high affinity. CRBN is part of the cullin-4 (CUL4) containing E3 ubiquitin ligase complex CUL4-RBXl-DDB1-CRBN (known as CRL4CRBN). Thalidomide and its derivatives, such as lenalidomide and pomalidomide, interact specifically with this CRBN complex and induce degradation of essential IKAROS transcription factors. CC-122, a non-phthalimide analogue of thalidomide, also interacts with CRBN E3 ligase complex but induces the degradation of lymphoid transcription factor Aiolos. The bivalent compounds can actively recruit anti-apoptotic Bcl-2 family of proteins to an E3 ubiquitin ligase, such as CRBN or VHL E3 ligase, resulting in their degradation by ubiquitin proteasome system.

Platelets depend on Bcl-xL protein for survival. Thus, inhibition of Bcl-xL protein in platelets causes thrombocytopenia which limits the use of Bcl-xL inhibitors as cancer therapeutic agents. Given the well-documented importance of Bcl-xL in solid tumors and its contribution to drug resistance, strategies devised to minimize the on-target platelet toxicity associated with the inhibition of Bcl-xL could boost the therapeutic applications of drugs like ABT-263, a dual Bcl-2/Bcl-xL inhibitor, in cancer. The compounds in the present invention were designed to recruit an E3 ligase, such as CRBN or VHL E3 ligase, that is minimally expressed in platelets for the targeted degradation of Bcl-xL.

Thus, the compounds described herein (e.g., Formula (I)) have reduced platelet toxicity compared with their corresponding Bcl-2/Bcl-xL inhibitors. Accordingly, the present disclosure provides compositions and methods for selectively degrading anti-apoptotic Bcl-2 family of proteins.

BRIEF DESCRIPTION OF THE DRAWING

The FIGURE is a western blot showing protein degradation in MOLT4 cells incubated with various concentrations of degrader #8.

DETAILED DESCRIPTION

Definitions

In order that the invention may be more readily understood, certain terms are first defined here for convenience.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, the bond is a single bond, the dashed line is a single bond or absent, and the bond or is a single or double bond.

When a range of values ("range") is listed, it encompasses each value and sub-range within the range. A range is inclusive of the values at the two ends of the range unless otherwise provided. For example "$C_{1-6}$ alkyl" encompasses, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety. For example, alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

The term "unsaturated bond" refers to a double or triple bond.

The term "unsaturated" or "partially unsaturated" refers to a moiety that includes at least one double or triple bond.

The term "saturated" or "fully saturated" refers to a moiety that does not contain a double or triple bond, e.g., the moiety only contains single bonds.

As used herein, the term "treating" a disorder encompasses ameliorating, mitigating and/or managing the disorder and/or conditions that may cause the disorder. The terms "treating" and "treatment" refer to a method of alleviating or abating a disease and/or its attendant symptoms. In accordance with the present invention, "treating" includes blocking, inhibiting, attenuating, modulating, reversing the effects of and reducing the occurrence of e.g., the harmful effects of a disorder.

As used herein, "inhibiting" encompasses reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 μM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "1" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)$CF_3$), sulfonates (e.g., mesyl, tosyl), acetamides (e.g., —NHC(O)Me), carbamates (e.g., N(Me) C(O)Ot-Bu), phosphonates (e.g., —OP(O)$(OEt)_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, arylamino-substituted aryl, arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy. In some embodiments, the substituent is selected from the group consisting of alkyl, cycloalkyl, heterocycloalkyl, aryl, heteroaryl, halogen, haloalkyl, cyano, nitro, alkoxy, hydroxyl, hydroxylalkyl, oxo (i.e., carbonyl), carboxyl, formyl, amino, aminoalkyl, amido (e.g., —C(═O)$NH_2$ or —NHC(═O)).

"Bcl-2" as used herein alone or as part of a group references to a member of the Bcl-2 family of proteins comprise the following Bcl-xL, MCL-1, Bcl-W, BFL-1/A1, Bcl-B, BAX, BAK, and BOK.

Compounds of the Invention

Compounds delineated herein (i.e., Formula I) include salt, hydrate and solvates thereof. They include all compounds delineated in schemes herein, whether intermediate or final compounds in a process.

Compounds of the invention can be obtained from natural sources or made or modified made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2nd Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. All hydrate and solvate forms of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In another aspect, the invention provides a method of degrading Bcl-2 proteins, the method comprising administering an effective amount of a compound described herein (e.g., Formula (I)), or a pharmaceutically acceptable salt, hydrate, solvate, or prodrug thereof. In another aspect, the compound is administered in vitro. In another aspect, the compound is administered in vivo. In another aspect, the method further comprises administering the compound to a subject.

In another aspect, the invention provides a method of treating a disease or disorder in a subject in need thereof, the method comprising administering an effective amount of a compound described herein (e.g., Formula (I)), or a pharmaceutically acceptable salt, hydrate, solvate, or prodrug thereof. In another aspect, the disease is cancer. In another aspect, the cancer is a solid tumor. In another aspect, the cancer is chronic lymphocyctic leukemia. In another aspect, the subject is a mammal. In another aspect, the subject is a human.

In another aspect, the invention provides a method of treating a subject suffering from or susceptible to a disease or disorder, the method comprising administering an effective amount of a compound described herein (e.g., Formula (I)), or a pharmaceutically acceptable salt, hydrate, solvate, or prodrug thereof. In another aspect, the disease is cancer. In another aspect, the cancer is a solid tumor. In another aspect, the cancer is chronic lymphocyctic leukemia. In another aspect, the subject is a mammal. In another aspect, the subject is a human.

In another aspect, the invention provides a method of treating a Bcl-2 dependent (e.g., mediated) cancer in a subject in need thereof, the method comprising administering an effective amount of a compound described herein (e.g., Formula (I)), or a pharmaceutically acceptable salt, hydrate, solvate, or prodrug thereof, such that platelet toxicity is reduced relative to other Bcl-2 inhibitors. In another aspect, the Bcl-2 dependent (e.g., mediated) cancer is chronic lymphocyctic leukemia. In another aspect, the other Bcl-2 inhibitor is ABT-737, navitoclax (ABT-263), venetoclax (ABT-199), obatoclax (GX 15-070), (−)-gossypol (AT-101), sabutoclax (BI-97$C_1$), TW-37, BM-1252 (APG-1252), A-1155463, or A-1331852. In another aspect, the other Bcl-2 inhibitor is venetoclax or ABT-263. A Bcl-2 dependent cancer is a cancer (or cancer cell) that depends on Bcl-2 for survival. A Bcl-2 mediated cancer is a cancer (or cancer cell) that is mediated by Bcl-2.

In another aspect, the invention provides a method of treating a subject suffering from or susceptible to a Bcl-xL-dependent cancer, the method comprising administering an effective amount of a compound described herein (e.g., Formula (I)), or a pharmaceutically acceptable salt, hydrate, solvate, or prodrug thereof, such that platelet toxicity is reduced relative to other Bcl-xL specific or Bcl-2/Bcl-xL dual inhibitors. In another aspect, the other Bcl-2 inhibitor is ABT-737, navitoclax (ABT-263), venetoclax (ABT-199), obatoclax (GX 15-070), (−)-gossypol (AT-101), sabutoclax (BI-97C1), TW-37, BM-1252 (APG-1252), A-1155463, or A-1331852. In another aspect, the other Bcl-2 inhibitor is venetoclax or ABT-263.

In another aspect, the invention provides a method of treating a Bcl-2-dependent cancer in a subject in need thereof, the method comprising administering an effective amount of a compound described herein (e.g., Formula (I)), or a pharmaceutically acceptable salt, hydrate, solvate, or prodrug thereof, such that ratio of human platelet toxicity ($IC_{50}$) to anticancer activity ($IC_{50}$) is less than that of other Bcl-2 inhibitors. In another aspect, wherein the other Bcl-2 inhibitor is venetoclax or ABT-263. In another aspect, wherein the anticancer activity is measured in MOLT-4 cells. In another aspect, wherein the ratio is greater than 1. In another aspect, wherein the ratio is greater than 10. In another aspect, wherein the ratio is greater than 20. In another aspect, wherein the ratio is greater than 40.

In another aspect, the invention provides a method of treating a subject suffering from or susceptible to a Bcl-xL-dependent cancer, the method comprising administering an effective amount of a compound described herein (e.g., Formula (I)), or a pharmaceutically acceptable salt, hydrate, solvate, or prodrug thereof, such that ratio of human platelet toxicity ($IC_{50}$) to anticancer activity ($IC_{50}$) is less than that of other Bcl-2 inhibitors. In another aspect, wherein the other Bcl-2 inhibitor is venetoclax or ABT-263. In another aspect, wherein the anticancer activity is measured in MOLT-4 cells. In another aspect, wherein the ratio is greater than 1. In another aspect, wherein the ratio is greater than 10. In another aspect, wherein the ratio is greater than 20. In another aspect, wherein the ratio is greater than 40.

The present disclosure encompasses a method of selectively killing one or more cancer cells in a sample, the method comprising contacting a composition comprising an effective amount of a compound of Formula (I), or a pharmaceutically acceptable salt, hydrate, solvate, or prodrug thereof, with the sample. In another aspect, the present disclosure encompasses a method of selectively killing one or more cancer cells in a subject in need thereof, the method comprising administering to the subject a composition comprising a therapeutically effective amount of a compound of Formula (I) or a pharmaceutically acceptable salt, hydrate, solvate, or prodrug thereof.

By selectively killing one or more cancer cells is meant a composition of the invention does not appreciably kill non-cancer cells at the same concentration. In one embodiment, a composition of the invention has reduced platelet toxicity and retained or improved toxicity in cancer cells when compared to similar BCL-2 inhibitors. Accordingly, the median lethal dose or LD50 of the inhibitor in non-cancer cells may be about 5 to about 50 times higher than the LD50 of the inhibitor in cancer cells. As used herein, the LD50 is the concentration of inhibitor required to kill half the cells in the cell sample. For example, the LD50 of the inhibitor in non-cancer cells may be greater than about 5, about 6, about 7, about 8, about 9 or about 10 times higher than the LD50 of the inhibitor in cancer cells. Alternatively, the LD50 of the inhibitor in non-cancer cells may be greater than about 10, about 15, about 20, about 25, about 30, about 35, about 40, about 45, or about 50 times higher than the LD50 of the inhibitor in cancer cells. Additionally, the LD50 of the inhibitor in non-cancer cells may be greater than 50 times higher than the LD50 of the inhibitor in cancer cells. In a specific embodiment, the LD50 of the inhibitor in non-cancer cells is greater than 10 times higher than the LD500 of the inhibitor in cancer cells. In another specific embodiment, the LD50 of the inhibitor in non-cancer cells is greater than 20 times higher than the LD50 of the inhibitor in cancer cells.

Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, choriocarcinoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, glioblastoma, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenstrom), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In certain embodiments, a cancer is selected from the group consisting of synovial sarcoma, Burkitt lymphoma, Hodgkin lymphoma, multiple myeloma, neuroblastoma, glioblastoma, small cell lung cancer, pancreatic cancer, hepatocellular (liver) cancer, endometrial cancer, ovarian cancer, cervical cancer, breast cancer, prostate cancer, bladder cancer, melanoma, rhabdomyosarcoma, osteosarcoma/malignant fibrous histiocytoma of bone, choriocarcinoma, kidney cancer (renal cell cancer), thyroid cancer, and leukemias (acute lymphoblastic, acute myeloid, chronic lymphocytic, and chronic myelogenous).

Pharmaceutical Compositions

In one aspect, the invention provides a pharmaceutical composition comprising the compound of any of the formulae herein (e.g., Formula (I) or a pharmaceutically acceptable salt, hydrate, solvate, or prodrug thereof), and a pharmaceutically acceptable carrier.

In another embodiment, the invention provides a pharmaceutical composition wherein the compound of any of the formulae herein is a compound of Formula I, or a pharmaceutically acceptable salt, hydrate, solvate, or prodrug thereof, and a pharmaceutically acceptable carrier. In another aspect, the composition further comprises an additional agent. In another aspect, the additional agent is an anti-cancer agent. In another aspect, the anticancer agent is alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcetabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors include, but are not limited to, amsacrine, etoposide (VP-16), irinotecan, mitoxantrone, RFS 2000, teniposide, and topotecan.

Non-limiting examples of suitable anti-hormonal agents such as aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib.

Angiogeneisis inhibitors such as angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide; and growth inhibitory polypeptides such as bortazomib, erythropoietin, interleukins (e.g., IL-1, IL-2, IL-3, IL-6), leukemia inhibitory factor, interferons, romidepsin, thrombopoietin, TNF-$\alpha$, CD30 ligand, 4-1BB ligand, andApo-1 ligand.

Non-limiting examples of photodynamic therapeutic agents include aminolevulinic acid, methyl aminolevulinate, retinoids (alitretinon, tamibarotene, tretinoin), and temoporfin.

Other antineoplastic agents include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

In one aspect, the invention provides a kit comprising an effective amount of a compound of any of the formulae herein (e.g., Formula (I) or a pharmaceutically acceptable salt, hydrate, solvate, or prodrug thereof), in unit dosage form, together with instructions for administering the compound to a subject suffering from or susceptible to cancer. In another aspect, the cancer is a solid tumor. In another aspect, the cancer is chronic lymphocyctic leukemia.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein, or a pharmaceutically acceptable salt, hydrate, solvate, or prodrug thereof, and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound (e.g., apratoxin) employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *theobroma*; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and *echinacea*, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

Compound Preparation
Example 1: Preparation of 2-(5-(1-(adamantan-1-ylmethyl)-5-methyl-1H-pyrazol-4-yl)-6-(((3-(4-((2-(2-((2-(2,6-dioxopiperidin-3-yl)-1,3-dioxoisoindolin-4-yl)amino)ethoxy)ethoxy)methyl)-1H-1,2,3-triazol-1-yl)propyl)sulfonyl)carbamoyl)pyridin-2-yl)-N-(benzo[d]thiazol-2-yl)-1,2,3,4-tetrahydroisoquinoline-8-carboxamide (degrader #1)
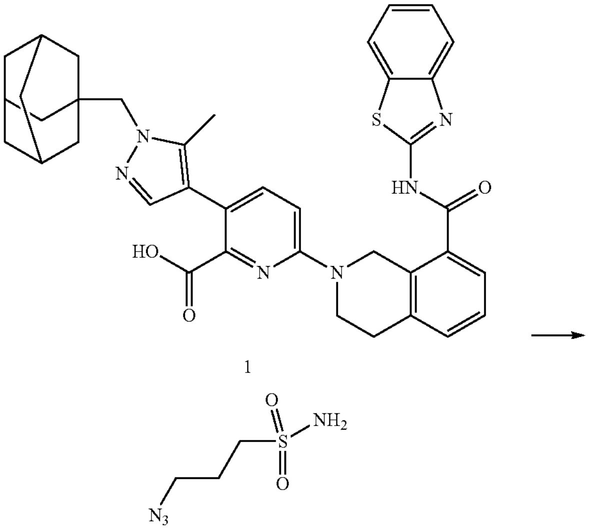
1
2
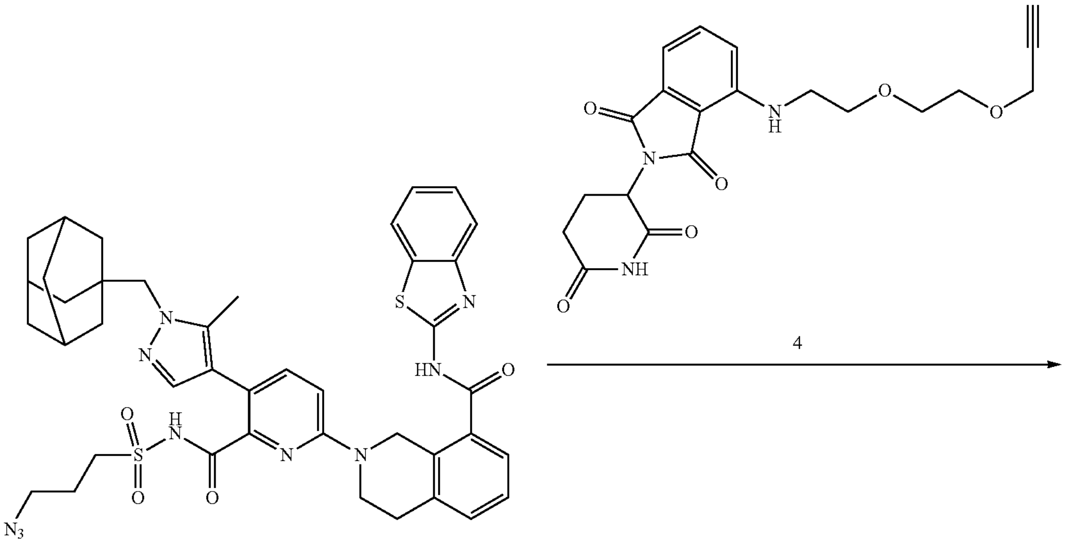
4
3

-continued

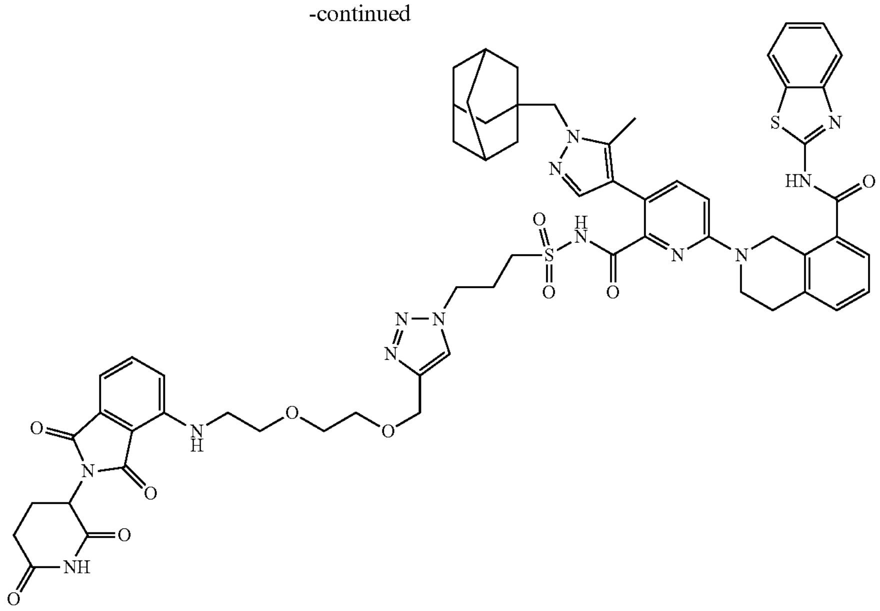

degrader #1

Preparation of 2-(5-(1-(adamantan-1-ylmethyl)-5-methyl-1H-pyrazol-4-yl)-6-(((3-azidopropyl)sulfonyl)carbamoyl)pyridin-2-yl)-N-(benzo[d]thiazol-2-yl)-1,2,3,4-tetrahydroisoquinoline-8-carboxamide (3). A mixture of compound 1 (40 mg, 0.061 mmol), 2 (20 mg, 0.122 mmol), EDC (23.5 mg, 0.122 mmol), DMAP (13.7 mg, 0.122 mmol) was stirred in DCM (5 mL) for 16 h. The mixture was concentrated under vacuum and the residue was purified by silica gel flash column chromatography using EtOAc and hexanes as eluents to afford the title compound (30 mg, yield 61%). $^1$H NMR (600 MHz, Chloroform-d) δ 10.24 (br s, 1H), 7.88 (dd, J=7.7, 1.4 Hz, 11H), 7.65 (d, J=7.6 Hz, 1H), 7.57-7.49 (m, 2H), 7.45-7.30 (m, 5H), 7.09 (d, J=8.8 Hz, 1H), 5.12 (s, 2H), 3.97-3.89 (m, 2H), 3.75 (s, 2H), 3.61-3.51 (m, 2H), 3.45 (t, J=6.6 Hz, 2H), 3.09 (t, J=6.0 Hz, 2H), 2.15-2.06 (m, 5H), 2.04-1.97 (m, 3H), 1.75-1.62 (m, 12H) ppm.

Preparation of 2-(5-(1-(adamantan-1-ylmethyl)-5-methyl-1H-pyrazol-4-yl)-6-(((3-(4-((2-(2-((2-(2,6-dioxopiperidin-3-yl)-1,3-dioxoisoindolin-4-yl)amino)ethoxy)ethoxy)methyl)-1H-1,2,3-triazol-1-yl)propyl)sulfonyl)carbamoyl)pyridin-2-yl)-N-(benzo[d]thiazol-2-yl)-1,2,3,4-tetrahydroisoquinoline-8-carboxamide (degrader #1). To a mixture of compound 3 (15 mg, 0.019 mmol), compound 4 (15 mg, 0.038 mmol) in $^t$BuOH-THF (2 mL, 1:1, v/v) under argon was added $CuSO_4{\cdot}5H_2O$ (0.93 mg, 0.0038 mmol) and sodium ascorbate (0.75 mg, 0.0038 mmol) in 0.3 mL water. The mixture was stirred at 55° C. for 2 h and extracted with DCM. The organic phase was washed with brine, dried over $Na_2SO_4$, filtered and evaporated to dryness. The crude product was purified by silica gel flash column chromatography using DCM and MeOH as eluents to afford the title compound (9.3 mg, yield 42%). $^1$H NMR (600 MHz, Chloroform-d) δ 11.46 (s, 11H), 10.25 (br s, 11H), 8.06 (d, J=8.1 Hz, 11H), 7.85 (dd, J=7.9, 1.1 Hz, 11H), 7.65 (dd, J=7.8, 1.2 Hz, 11H), 7.57-7.37 (m, 5H), 7.36-7.31 (m, 11H), 7.24 (d, J=7.6 Hz, 1H), 7.17-7.11 (m, 2H), 7.06 (d, J=8.9 Hz, 1H), 6.94 (d, J=8.6 Hz, 1H), 6.52 (t, J=5.6 Hz, 11H), 5.22-5.01 (m, 2H), 4.95 (dd, J=12.4, 5.3 Hz, 1H), 4.67-4.56 (m, 2H), 4.41-4.29 (m, 2H), 3.97-3.81 (m, 2H), 3.77-3.62 (m, 8H), 3.52-3.31 (m, 4H), 3.08-2.97 (m, 2H), 2.93-2.72 (m, 3H), 2.38-2.30 (m, 2H), 2.16-1.97 (m, 7H), 1.72-1.62 (m, 12H) ppm.

Example 2: Preparation of 2-(5-(1-(adamantan-1-ylmethyl)-5-cyano-2-methyl-1H-pyrrol-3-yl)-6-(((3-(4-((2-(2-((2-(2,6-dioxopiperidin-3-yl)-1,3-dioxoisoindolin-4-yl)amino)ethoxy)ethoxy)methyl)-1H-1,2,3-triazol-1-yl)propyl)sulfonyl)carbamoyl)pyridin-2-yl)-N-(benzo[d]thiazol-2-yl)-1,2,3,4-tetrahydroisoquinoline-8-carboxamide (degrader #2)
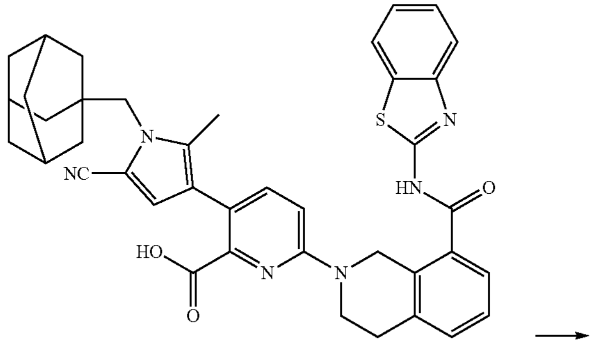
5
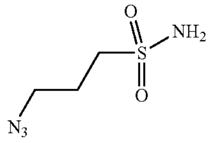
2
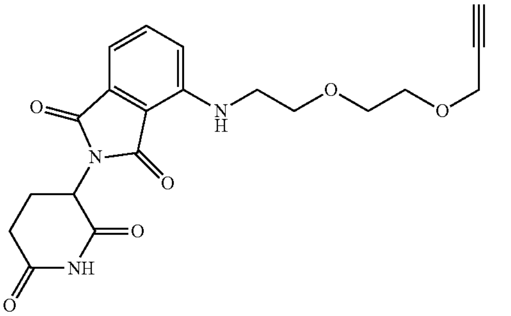
4
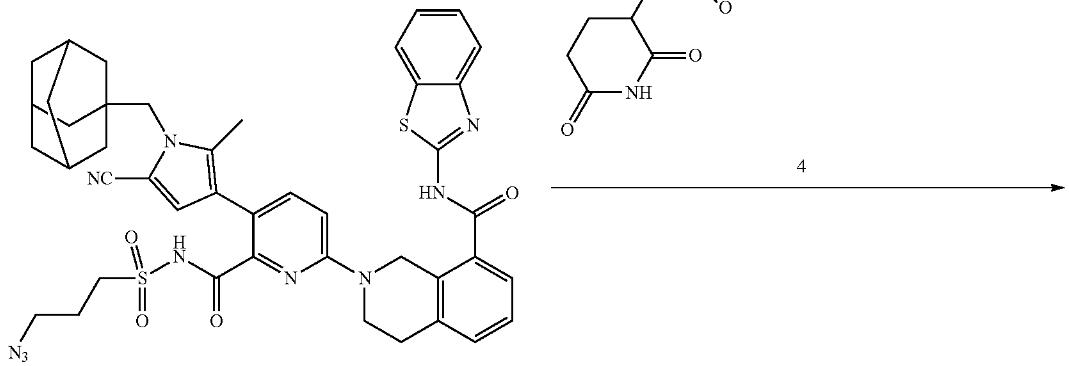
6

-continued
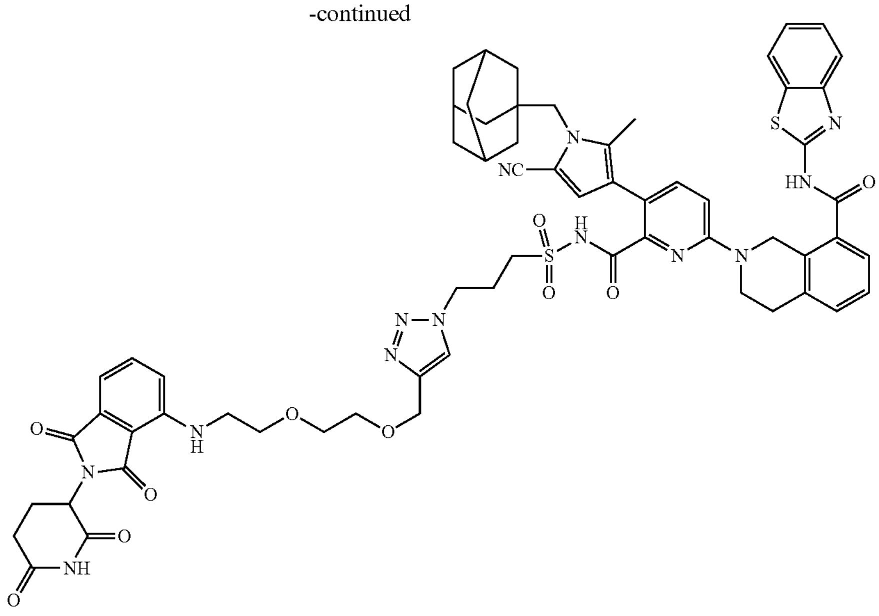
degrader #2
The title compound was obtained using same synthetic route as described in Example 1, except using compound 5 and 2 as the starting materials. $^1$H NMR (600 MHz, Chloroform-d) δ 11.62 (s, 1H), 11.47 (br s, 1H), 10.18 (br s, 1H), 8.13 (d, J=8.1 Hz, 1H), 7.87 (dd, J=7.9, 1.3 Hz, 1H), 7.66 (d, J=7.6 Hz, 1H), 7.58-7.52 (m, 1H), 7.51-7.42 (m, 3H), 7.37-7.32 (m, 1H), 7.24 (d, J=7.6 Hz, 1H), 7.18-7.10 (m, 2H), 7.06 (d, J=8.8 Hz, 1H), 6.95 (d, J=8.5 Hz, 1H), 6.74 (s, 1H), 6.56-6.48 (m, 1H), 5.24-5.06 (m, 2H), 5.00-4.92 (m, 1H), 4.63-4.54 (m, 2H), 4.40-4.27 (m, 2H), 4.00-3.91 (m, 1H), 3.91-3.83 (m, 1H), 3.76-3.61 (m, 8H), 3.50-3.44 (m, 2H), 3.39-3.33 (m, 2H), 3.07-3.00 (m, 2H), 2.94-2.73 (m, 3H), 2.38-2.29 (m, 2H), 2.21-2.12 (m, 4H), 2.03 (s, 3H), 1.74-1.64 (m, 12H) ppm.
Example 3: Preparation of Degraders #3-#8
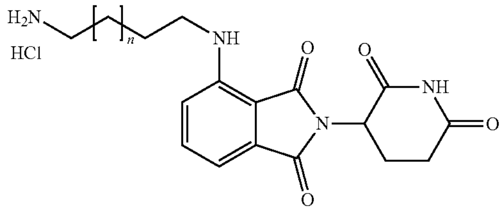
7a, n = 1
7b, n = 3
7c, n = 5
or
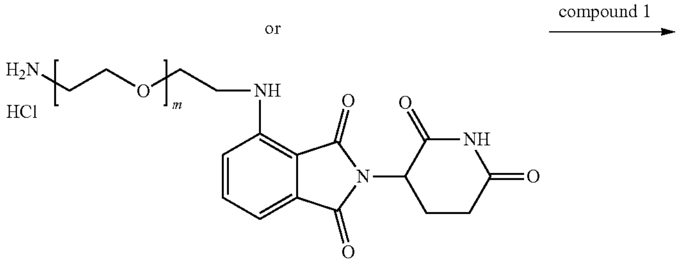
7d, m = 1
7e, m = 2
7f, m = 3

-continued

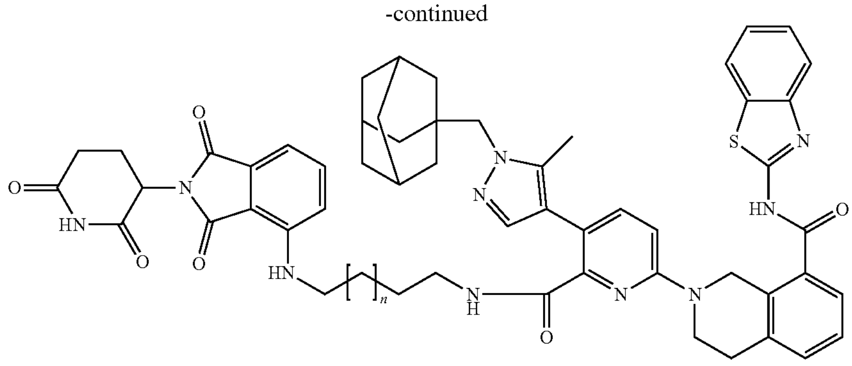

degrader #3, n = 1
degrader #4, n = 3
degrader #5, n = 5

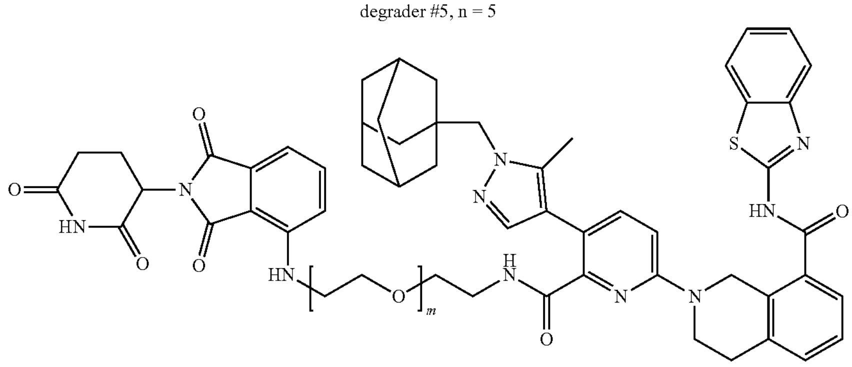

degrader #6, m = 1
degrader #7, m = 2
degrader #8, m = 3

Preparation of 2-(5-(1-(adamantan-1-ylmethyl)-5-methyl-1H-pyrazol-4-yl)-6-((4-((2-(2,6-dioxopiperidin-3-yl)-1,3-dioxoisoindolin-4-yl)amino)butyl)carbamoyl)pyridin-2-yl)-N-(benzo[d]thiazol-2-yl)-1,2,3,4-tetrahydroisoquinoline-8-carboxamide (degrader #3). Compound 1 (20 mg, 0.03 mmol), 7a (13.8 mg, 0.036 mmol), HATU (12.0 mg, 0.032 mmol) and TEA (27 μL, 0.19 mmol) in DCM (3 mL) was stirred at room temperature for 1 h. The mixture was diluted with and extracted with DCM. The organic phase was washed with water, brine, dried over $Na_2SO_4$, filtered, and evaporated to dryness. The residue was purified by silica gel flash column chromatography using DCM and methanol as eluents to afford the title compound (20.8 mg, yield 70%). $^1H$ NMR (600 MHz, Chloroform-d) δ 10.97 (br s, 1H), 9.91 (br s, 1H), 8.19 (s, 1H), 7.91-7.77 (m, 2H), 7.54-7.29 (m, 6H), 7.22-6.94 (m, 3H), 6.88 (d, J=8.7 Hz, 1H), 6.70 (s, 1H), 6.11 (s, 1H), 5.26-5.07 (m, 2H), 4.98-4.81 (m, 1H), 3.86-3.67 (m, 4H), 3.50-3.38 (m, 2H), 3.19-3.11 (m, 2H), 3.02-2.93 (m, 2H), 2.90-2.68 (m, 3H), 2.11-2.05 (m, 4H), 2.02-1.97 (m, 3H), 1.74-1.64 (m, 16H) ppm. LC-MS (ESI): m/z 985.6 $[M+H]^+$.

Preparation of 2-(5-(1-(adamantan-1-ylmethyl)-5-methyl-1H-pyrazol-4-yl)-6-((6-((2-(2,6-dioxopiperidin-3-yl)-1,3-dioxoisoindolin-4-yl)amino)hexyl)carbamoyl)pyridin-2-yl)-N-(benzo[d]thiazol-2-yl)-1,2,3,4-tetrahydroisoquinoline-8-carboxamide (degrader #4). Starting from 7b and 1, 18.9 mg degrader #4 was obtained using the above-mentioned method for degrader #3. Yield 62%. $^1H$ NMR (600 MHz, Chloroform-d) δ 11.22 (br s, 1H), 10.52 (br s, 1H), 8.00 (t, J=6.0 Hz, 1H), 7.93 (d, J=8.1 Hz, 1H), 7.84 (d, J=7.6 Hz, 1H), 7.52-7.39 (m, 5H), 7.36-7.31 (m, 1H), 7.14 (d, J=7.7 Hz, 1H), 7.10 (d, J=7.1 Hz, 11H), 6.94-6.88 (m, 2H), 6.84 (d, J=8.6 Hz, 1H), 6.21 (t, J=5.7 Hz, 1H), 5.28 (d, J=17.0 Hz, 1H), 4.99 (d, J=17.1 Hz, 1H), 4.92 (dd, J=12.3, 5.4 Hz, 1H), 3.92-3.79 (m, 2H), 3.73 (s, 2H), 3.45-3.28 (m, 2H), 3.25-3.12 (m, 2H), 3.02-2.93 (m, 2H), 2.87-2.74 (m, 3H), 2.18-2.13 (m, 1H), 2.09 (s, 3H), 2.02-1.97 (m, 3H), 1.74-1.63 (m, 12H), 1.57-1.49 (m, 4H), 1.37-1.31 (m, 4H) ppm. LC-MS (ESI): m/z 1013.5 $[M+H]^+$.

Preparation of 2-(5-(1-(adamantan-1-ylmethyl)-5-methyl-1H-pyrazol-4-yl)-6-((8-((2-(2,6-dioxopiperidin-3-yl)-1,3-dioxoisoindolin-4-yl)amino)octyl)carbamoyl)pyridin-2-yl)-N-(benzo[d]thiazol-2-yl)-1,2,3,4-tetrahydroisoquinoline-8-carboxamide (degrader #5). Starting from 7c and 1, 19.1 mg degrader #5 was obtained using the above-mentioned method for degrader #3. Yield 61%. $^1H$ NMR (600 MHz, Chloroform-d) δ 11.33 (s, 1H), 10.99 (s, 1H), 8.02 (d, J=8.1 Hz, 1H), 7.97 (t, J=6.0 Hz, 1H), 7.85 (d, J=7.8 Hz, 1H), 7.55 (dd, J=8.5, 7.1 Hz, 1H), 7.53-7.39 (m, 4H), 7.38-7.32 (m, 1H), 7.13 (d, J=7.1 Hz, 1H), 7.10 (d, J=7.5 Hz, 1H), 6.91 (dd, J=8.6, 4.0 Hz, 2H), 6.80 (t, J=7.6 Hz, 11H), 6.25 (t, J=5.6 Hz, 11H), 5.35 (d, J=17.1 Hz, 11H), 4.98-4.83 (m, 2H), 3.99-3.79 (m, 2H), 3.73 (s, 2H), 3.47-3.27 (m, 2H), 3.28-3.21 (m, 2H), 3.05-2.93 (m, 2H), 2.92-2.74 (m, 3H), 2.22-2.13 (m, 11H), 2.09 (s, 3H), 2.02-1.97 (m, 3H), 1.75-1.63 (m, 12H), 1.61-1.49 (m, 4H), 1.37-1.33 (m, 2H), 1.26-1.17 (m, 6H) ppm. LC-MS (ESI): m/z 1041.5 $[M+H]^+$.

Preparation of 2-(5-(1-(adamantan-1-ylmethyl)-5-methyl-1H-pyrazol-4-yl)-6-((2-(2-((2-(2,6-dioxopiperidin-3-yl)-1,3-dioxoisoindolin-4-yl)amino)ethoxy)ethyl)carbamoyl)pyridin-2-yl)-N-(benzo[d]thiazol-2-yl)-1,2,3,4-tetrahydroisoquinoline-8-carboxamide (degrader #6).

Starting from 7d and 1, 25.2 mg degrader #6 was obtained using the above-mentioned method for degrader #3. Yield 84%. $^1$H NMR (600 MHz, Chloroform-d) δ 11.52 (br s, 1H), 11.27 (br s, 1H), 8.25-8.13 (m, 1H), 8.02 (d, J=8.1 Hz, 1H), 7.85 (dd, J=7.9, 1.0 Hz, 11H), 7.52 (t, J=7.8 Hz, 1H), 7.47-7.30 (m, 5H), 7.09-7.01 (m, 2H), 6.92 (dd, J=14.7, 8.1 Hz, 2H), 6.76 (d, J=8.7 Hz, 1H), 6.60-6.48 (m, 1H), 4.94-4.79 (m, 2H), 4.72-4.60 (m, 1H), 3.93-3.83 (m, 1H), 3.80-3.54 (m, 9H), 3.51-3.33 (m, 2H), 2.91-2.55 (m, 5H), 2.10 (s, 3H), 2.03-1.94 (m, 4H), 1.73-1.59 (m, 12H) ppm. LC-MS (ESI): m/z 1001.6 $[M+H]^+$.

Preparation of 2-(5-(1-(adamantan-1-ylmethyl)-5-methyl-1H-pyrazol-4-yl)-6-((2-(2-(2-((2-(2,6-dioxopiperidin-3-yl)-1,3-dioxoisoindolin-4-yl)amino)ethoxy)ethoxy)ethyl)carbamoyl)pyridin-2-yl)-N-(benzo[d]thiazol-2-yl)-1,2,3,4-tetrahydroisoquinoline-8-carboxamide (degrader #7). Starting from 7e and 1, 23.1 mg degrader #7 was obtained using the above-mentioned method for degrader #3. Yield 74%. $^1$H NMR (600 MHz, Chloroform-d) δ 11.50 (br s, 1H), 11.26 (br s, 1H), 8.16-8.10 (m, 11H), 8.05 (d, J=8.0 Hz, 11H), 7.86 (d, J=7.8 Hz, 1H), 7.57-7.39 (m, 5H), 7.38-7.33 (m, 1H), 7.11 (d, J=7.1 Hz, 1H), 7.03 (d, J=7.6 Hz, 1H), 6.97-6.82 (m, 3H), 6.50-6.41 (m, 1H), 5.05-4.90 (m, 2H), 4.86 (dd, J=12.6, 5.5 Hz, 1H), 4.00-3.90 (m, 1H), 3.88-3.81 (m, 1H), 3.78-3.68 (m, 4H), 3.68-3.51 (m, 8H), 3.48-3.36 (m, 2H), 3.01-2.91 (m, 2H), 2.90-2.66 (m, 3H), 2.16-2.07 (m, 4H), 2.01-1.97 (m, 3H), 1.72-1.60 (m, 12H) ppm. LC-MS (ESI): m/z 1045.3 $[M+H]^+$.

Preparation of 2-(5-(1-(adamantan-1-ylmethyl)-5-methyl-1H-pyrazol-4-yl)-6-((2-(2-(2-(2-((2-(2,6-dioxopiperidin-3-yl)-1,3-dioxoisoindolin-4-yl)amino)ethoxy)ethoxy)ethoxy)ethyl)carbamoyl)pyridin-2-yl)-N-(benzo[d]thiazol-2-yl)-1,2,3,4-tetrahydroisoquinoline-8-carboxamide (degrader #8). Starting from 7f and 1, 18.2 mg degrader #8 was obtained using the above-mentioned method for degrader #3. Yield 56%. $^1$H NMR (600 MHz, Chloroform-d) δ 11.79-11.13 (m, 2H), 8.12 (d, J=8.0 Hz, 1H), 8.07-7.98 (m, 1H), 7.86 (dd, J=8.0, 1.1 Hz, 1H), 7.60-7.33 (m, 6H), 7.17-7.09 (m, 2H), 7.00-6.86 (m, 3H), 6.41 (t, J=5.5 Hz, 11H), 5.13-5.01 (m, 2H), 4.94 (dd, J=12.3, 5.4 Hz, 1H), 4.00-3.86 (m, 2H), 3.77-3.36 (m, 18H), 3.00 (t, J=6.1 Hz, 2H), 2.93-2.72 (m, 3H), 2.18-2.12 (m, 1H), 2.09 (s, 3H), 2.02-1.96 (m, 3H), 1.73-1.63 (m, 12H) ppm. LC-MS (ESI): m/z 1089.5 $[M+H]^+$.

Example 4: Preparation of Degraders #9-#17

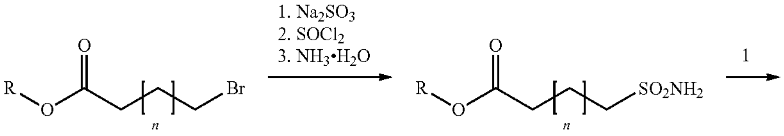

8a, n = 1, R = Bn
8b, n = 2, R = Me
8c, n = 3, R = Me
8d, n = 4, R = Me
8e, n = 5, R = Et
8f, n = 6, R = Me
8g, n = 7, R = Me
8h, n = 8, R = Me
8i, n = 9, R = Me 9a, n = 1, R = Bn
9b, n = 2, R = Me
9c, n = 3, R = Me
9d, n = 4, R = Me
9e, n = 5, R = Et
9f, n = 6, R = Me
9g, n = 7, R = Me
9h, n = 8, R = Me
9i, n = 9, R = Me

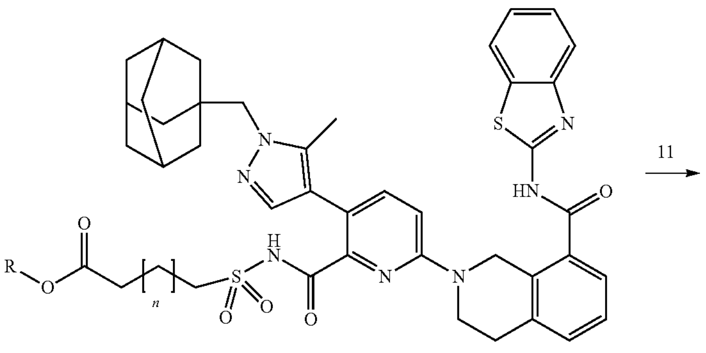

10a, n = 1, R = Bn
10b, n = 2, R = Me
10c, n = 3, R = Me
10d, n = 4, R = Me
10e, n = 5, R = Et
10f, n = 6, R = Me
10g, n = 7, R = Me
10h, n = 8, R = Me
10i, n = 9, R = Me

-continued

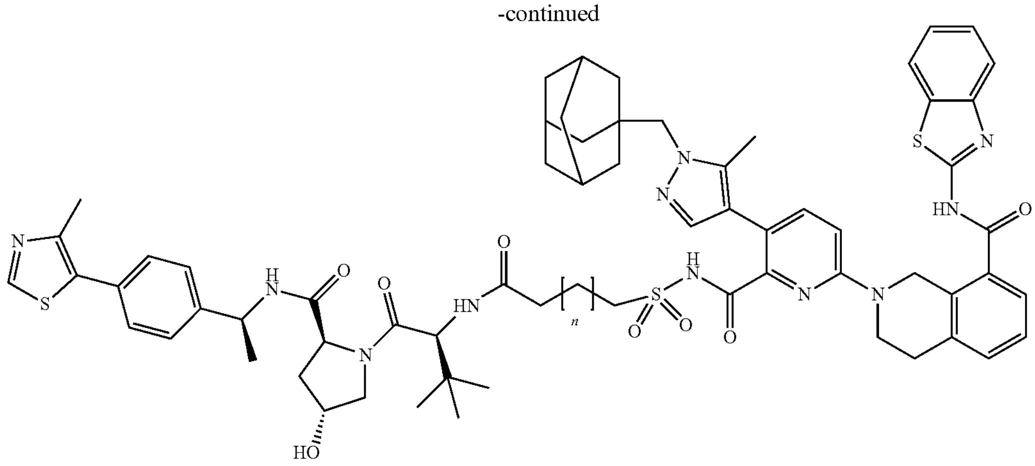

degrader #9, n = 1 degrader #14, n = 6
degrader #10, n = 2 degrader #15, n = 7
degrader #11, n = 3 degrader #16, n = 8
degrader #12, n = 4 degrader #17, n = 9
degrader #13, n = 5

11

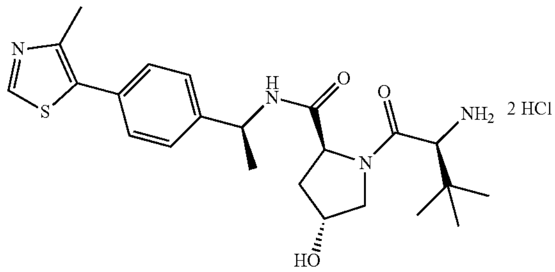

General procedure for sulfonamide synthesis: Preparation of methyl 6-sulfamoylhexanoate (9c). A mixture of compound 8c (2.0 g, 9.6 mmol), $Na_2SO_3$ (1.57 g, 12.4 mmol) in water (10 mL) was refluxed overnight. The solvent was removed under reduced pressure and the residue was dissolved in THF (20 mL) and DMF (1 mL). The mixture was cooled to 0° C. and $SOCl_2$ (6 mL, 83 mmol) was added dropwise into the solution. Then it was heated to 70° C. and stirred for 1 h. The solvent was removed under reduced pressure and acetonitrile (20 mL) was added to the residue. The resulting suspension was added into ammonium hydroxide (15 mL) at 0° C. After 20 min, the reaction mixture was diluted with EtOAc and poured into water. The organic phase was washed with water×1, brine×1, dried over $Na_2SO_4$, filtered, and evaporated to dryness. The residue was purified by silica gel flash column chromatography using EtOAc and hexanes as eluents to afford the title compound (1.25 g, yield 63%). $^1H$ NMR (600 MHz, Chloroform-d) δ 4.96 (s, 2H), 3.69 (s, 3H), 3.22-3.09 (m, 2H), 2.36 (t, J=7.3 Hz, 2H), 1.95-1.84 (m, 2H), 1.75-1.64 (m, 2H), 1.56-1.44 (m, 2H) ppm.

Preparation of benzyl 4-sulfamoylbutanoate (9a). Starting from 8a, compound 9a was obtained using the above-mentioned method for 9c. Yield 41%. $^1H$ NMR (600 MHz, Chloroform-d) δ 7.43-7.33 (m, 5H), 5.16 (s, 2H), 4.65 (s, 2H), 3.26-3.18 (m, 2H), 2.61 (t, J=7.0 Hz, 2H), 2.27-2.18 (m, 2H) ppm.

Preparation of methyl 5-sulfamoylpentanoate (9b). Starting from 8b, compound 9b was obtained using the above-mentioned method for 9c. Yield 64%. $^1H$ NMR (600 MHz, Chloroform-d) δ 4.69 (s, 2H), 3.71 (s, 3H), 3.23-3.10 (m, 2H), 2.41 (t, J=7.2 Hz, 2H), 2.02-1.89 (m, 2H), 1.88-1.78 (m, 2H) ppm.

Preparation of methyl 7-sulfamoylheptanoate (9d). Starting from 8d, compound 9d was obtained using the above-mentioned method for 9c. Yield 49%. $^1H$ NMR (600 MHz, Chloroform-d) δ 4.58 (s, 2H), 3.69 (s, 3H), 3.18-3.09 (m, 2H), 2.34 (t, J=7.4 Hz, 2H), 1.96-1.84 (m, 2H), 1.73-1.62 (m, 2H), 1.54-1.46 (m, 2H), 1.44-1.35 (m, 2H) ppm.

Preparation of ethyl 8-sulfamoyloctanoate (9e). Starting from 8e, compound 9e was obtained using the above-mentioned method for 9c. Yield 70%. $^1H$ NMR (600 MHz, Chloroform-d) δ 4.85 (s, 2H), 4.18-4.10 (m, 2H), 3.17-3.09 (m, 2H), 2.31 (t, J=7.5 Hz, 2H), 1.93-1.83 (m, 2H), 1.68-1.59 (m, 2H), 1.51-1.43 (m, 2H), 1.41-1.32 (m, 4H), 1.27 (t, J=7.1 Hz, 3H) ppm.

Preparation of methyl 9-sulfamoylnonanoate (9f). Starting from 8f, compound 9f was obtained using the above-mentioned method for 9c. Yield 21%. $^1H$ NMR (600 MHz, Chloroform-d) δ 4.55 (s, 2H), 3.69 (s, 3H), 3.19-3.09 (m, 2H), 2.33 (t, J=7.5 Hz, 2H), 1.93-1.84 (m, 2H), 1.71-1.61 (m, 2H), 1.51-1.43 (m, 2H), 1.40-1.29 (m, 6H) ppm.

Preparation of methyl 10-sulfamoyldecanoate (92). Starting from 8g, compound 9g was obtained using the above-mentioned method for 9c. Yield 31%. $^1H$ NMR (600 MHz, Chloroform-d) δ 4.53 (s, 2H), 3.69 (s, 3H), 3.19-3.07 (m, 2H), 2.33 (t, J=7.5 Hz, 2H), 1.94-1.82 (m, 2H), 1.69-1.60 (m, 2H), 1.50-1.42 (m, 2H), 1.40-1.27 (m, 8H) ppm.

Preparation of methyl 11-sulfamoylundecanoate (9h). Starting from 8h, compound 9h was obtained using the above-mentioned method for 9c. Yield 34%. $^1H$ NMR (600

MHz, Chloroform-d) δ 4.52 (s, 2H), 3.69 (s, 3H), 3.17-3.09 (m, 2H), 2.33 (t, J=7.5 Hz, 2H), 1.92-1.84 (m, 2H), 1.67-1.60 (m, 2H), 1.50-1.42 (m, 2H), 1.38-1.27 (m, 10H) ppm.

Preparation of methyl 12-sulfamoyldodecanoate (9i). Starting from 8i, compound 9i was obtained using the above-mentioned method for 9c. Yield 20%. $^1$H NMR (600 MHz, Chloroform-d) δ 4.56 (s, 2H), 3.69 (s, 3H), 3.18-3.07 (m, 211), 2.33 (t, J=7.5 Hz, 211), 1.93-1.84 (m, 2H), 1.68-1.61 (m, 2H), 1.50-1.42 (m, 2H), 1.39-1.26 (m, 12H) ppm.

General procedure for the preparation of degraders #9-#17: Preparation of methyl 6-(N-(3-(1-(adamantan-1-ylmethyl)-5-methyl-1H-pyrazol-4-yl)-6-(8-(benzo[d]thiazol-2-ylcarbamoyl)-3,4-dihydroisoquinolin-2(1H)-yl)picolinoyl)sulfamoyl)hexanoate (10c). A mixture of 9c (22 mg, 0.105 mmol), 1 (35 mg, 0.053 mmol), EDC (20.4 mg, 0.106 mmol) and DMAP (11.9 mg, 0.106 mmol) in DCM (5 mL) was stirred at room temperature overnight. The reaction mixture was diluted with EtOAc and poured into water. The organic phase was washed with 1N HCl (aq)×1, water×1, brine×1, dried over $Na_2SO_4$, filtered and evaporated to dryness. The residue was purified by silica gel flash column chromatography using EtOAc and hexanes as eluents to afford the title compound (40 mg, yield 89%). $^1$H NMR (600 MHz, Chloroform-d) δ 10.08 (br s, 1H), 7.90 (d, J=7.7 Hz, 1H), 7.79 (d, J=8.1 Hz, 11H), 7.64 (d, J=7.5 Hz, 11H), 7.54 (d, J=8.7 Hz, 11H), 7.50-7.35 (m, 5H), 7.13-7.09 (m, 11H), 5.11 (s, 2H), 3.98 (t, J=6.1 Hz, 2H), 3.75 (s, 2H), 3.66 (s, 3H), 3.48-3.44 (m, 2H), 3.10 (t, J=6.0 Hz, 2H), 2.28 (t, J=7.4 Hz, 2H), 2.09 (s, 3H), 2.01 (s, 3H), 1.90-1.83 (m, 2H), 1.75-1.63 (m, 14H), 1.46-1.40 (m, 2H) ppm.

Preparation of 2-(5-(1-(adamantan-1-ylmethyl)-5-methyl-1H-pyrazol-4-yl)-6-(((6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexyl)sulfonyl)carbamoyl)pyridin-2-yl)-N-(benzo[d]thiazol-2-yl)-1,2,3,4-tetrahydroisoquinoline-8-carboxamide (degrader #11). Compound 10c (40 mg, 0.047 mmol) and LiOH monohydrate (20 mg, 0.48 mmol) in a mixture of THF (1 mL), MeOH (1 mL) and water (0.3 mL) was stirred at 50° C. for 2 h. The reaction was cooled to room temperature and the pH was adjusted with 1N HCl (aq) till 4-5. The solution was extracted with EtOAc and the organic phase was washed with water×1, brine×1, dried over $Na_2SO_4$, filtered, and evaporated to dryness. The crude acid intermediate (21 mg, 0.028 mmol) was dissolved in DCM (3 mL) and mixed with compound 11 (13 mg, 0.025 mmol), HATU (10 mg, 0.026 mmol) and trimethylamine (50 μL, 0.36 mmol). The reaction mixture was stirred at room temperature for 1 h and poured into water followed by extraction with DCM. The organic phase was washed with water×1, brine×1, dried over $Na_2SO_4$, filtered and evaporated to dryness. The residue was purified by silica gel flash column chromatography using DCM and methanol as eluents to afford the title compound (17.8 mg, yield 30%). $^1$H NMR (600 MHz, Chloroform-d) δ 11.06 (br s, 1H), 10.12 (br s, 1H), 8.69 (s, 1H), 7.90 (d, J=7.8 Hz, 1H), 7.63 (d, J=8.0 Hz, 1H), 7.58-7.48 (m, 2H), 7.45-7.39 (m, 6H), 7.38-7.30 (m, 3H), 7.23-7.15 (m, 1H), 7.08 (t, J=7.6 Hz, 1H), 7.02 (d, J=8.8 Hz, 1H), 5.16-5.03 (m, 3H), 4.63 (d, J=9.0 Hz, 1H), 4.52-4.43 (m, 2H), 4.12 (d, J=11.5 Hz, 1H), 3.92-3.79 (m, 2H), 3.72 (s, 2H), 3.56 (dd, J=11.4, 3.5 Hz, 1H), 3.50-3.36 (m, 2H), 3.26-3.18 (m, 1H), 3.12-3.01 (m, 2H), 2.53-2.45 (m, 4H), 2.09-1.86 (m, 13H), 1.73-1.60 (m, 12H), 1.53-1.36 (m, 5H), 1.10 (s, 9H) ppm.

Preparation of 2-(5-(1-(adamantan-1-ylmethyl)-5-methyl-1H-pyrazol-4-yl)-6-(((4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-4-oxobutyl)sulfonyl)carbamoyl)pyridin-2-yl)-N-(benzo[d]thiazol-2-yl)-1,2,3,4-tetrahydroisoquinoline-8-carboxamide (degrader #9). Starting from 9a and 1, compound degrader #9 was obtained using the above-mentioned method for degrader #11. $^1$H NMR (600 MHz, Chloroform-d) δ 10.86 (br s, 1H), 10.05 (br s, 1H), 8.69 (s, 1H), 7.91 (d, J=7.9 Hz, 2H), 7.72 (d, J=8.1 Hz, 1H), 7.53-7.32 (m, 9H), 7.28-7.21 (m, 2H), 7.07-6.96 (m, 2H), 5.24-5.07 (m, 2H), 4.96 (d, J=17.3 Hz, 1H), 4.66 (d, J=9.1 Hz, 1H), 4.49-4.36 (m, 2H), 4.11 (d, J=11.5 Hz, 1H), 4.03-3.95 (m, 1H), 3.80-3.66 (m, 3H), 3.55 (dd, J=11.5, 3.5 Hz, 1H), 3.48-3.41 (m, 1H), 3.22-3.06 (m, 2H), 3.04-2.96 (m, 1H), 2.57-2.46 (m, 4H), 2.41-2.33 (m, 11H), 2.27-2.18 (m, 1H), 2.07-1.92 (m, 9H), 1.71-1.63 (m, 12H), 1.49 (d, J=6.9 Hz, 3H), 1.11 (s, 9H) ppm.

Preparation of 2-(5-(1-(adamantan-1-ylmethyl)-5-methyl-1H-pyrazol-4-yl)-6-(((5-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)sulfonyl)carbamoyl)pyridin-2-yl)-N-(benzo[d]thiazol-2-yl)-1,2,3,4-tetrahydroisoquinoline-8-carboxamide (degrader #10). Starting from 9b and 1, compound degrader #10 was obtained using the above-mentioned method for degrader #11. $^1$H NMR (600 MHz, Chloroform-d) δ 11.17 (br s, 1H), 10.23 (br s, 1H), 8.68 (s, 1H), 7.80 (d, J=7.4 Hz, 1H), 7.58 (d, J=7.6 Hz, 1H), 7.50-7.42 (m, 3H), 7.41-7.29 (m, 8H), 7.18 (t, J=7.6 Hz, 1H), 6.98 (d, J=8.8 Hz, 1H), 6.72-6.60 (m, 1H), 5.12-5.01 (m, 2H), 4.95-4.85 (m, 1H), 4.59-4.50 (m, 2H), 4.42 (s, 1H), 3.98 (d, J=11.3 Hz, 1H), 3.78-3.67 (m, 4H), 3.55-3.47 (m, 2H), 3.46-3.33 (m, 2H), 3.05-2.95 (m, 2H), 2.50 (s, 3H), 2.44-2.36 (m, 1H), 2.14-1.89 (m, 13H), 1.76-1.61 (m, 12H), 1.45 (d, J=7.0 Hz, 3H), 0.98 (s, 9H) ppm.

Preparation of 2-(5-(1-(adamantan-1-ylmethyl)-5-methvl-1H-pyrazol-4-yl)-6-(((7-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptyl)sulfonyl)carbamol)pyridin-2-yl)-N-(benzo[d]thiazol-2-yl)-1,2,3,4-tetrahydroisoquinoline-8-carboxamide (degrader #12). Starting from 9d and 1, compound degrader #12 was obtained using the above-mentioned method for degrader #11. $^1$H NMR (600 MHz, Chloroform-d) δ 10.78 (br s, 1H), 10.11 (br s, 1H), 8.69 (s, 1H), 7.88 (d, J=7.8 Hz, 1H), 7.66 (d, J=8.0 Hz, 1H), 7.58 (d, J=7.6 Hz, 1H), 7.52 (d, J=8.8 Hz, 1H), 7.46-7.32 (m, 9H), 7.21 (t, J=7.6 Hz, 1H), 7.05 (d, J=8.8 Hz, 1H), 6.59 (d, J=8.8 Hz, 1H), 5.17-4.99 (m, 3H), 4.62-4.52 (m, 2H), 4.47 (s, 1H), 4.10 (d, J=11.4 Hz, 1H), 3.95-3.83 (m, 2H), 3.73 (s, 2H), 3.57 (dd, J=11.3, 3.5 Hz, 1H), 3.51-3.42 (m, 1H), 3.42-3.23 (m, 2H), 3.11-3.03 (m, 2H), 2.52 (s, 3H), 2.49-2.42 (m, 1H), 2.12-1.93 (m, 11H), 1.70-1.58 (m, 14H), 1.51-1.41 (m, 5H), 1.34-1.29 (m, 2H), 1.07 (s, 9H) ppm.

Preparation of 2-(5-(1-(adamantan-1-ylmethyl)-5-methyl-1H-pyrazol-4-yl)-6-(((8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctyl)sulfonyl)carbamoyl)pyridin-2-yl)-N-(benzo[d]thiazol-2-yl)-1,2,3,4-tetrahydroisoquinoline-8-carboxamide (degrader #13). Starting from 9e and 1, compound degrader #13 was obtained using the above-mentioned method for degrader #11. $^1$H NMR (600 MHz, Chloroform-d) δ 10.76 (br s, 1H), 10.11 (br s, 1H), 8.69 (s, 1H), 7.94-7.87 (m, 1H), 7.74 (d, J=8.0 Hz, 1H), 7.61 (d, J=7.6 Hz, 1H), 7.53 (d, J=8.7 Hz, 1H), 7.48-7.44 (m, 1H), 7.43-7.33 (m, 9H), 7.06 (d, J=8.8 Hz, 1H), 6.74 (d, J=8.8 Hz, 1H), 5.21 (d, J=17.2 Hz, 1H), 5.14-5.08 (m, 1H), 5.01 (d, J=17.2 Hz, 1H), 4.68 (t, J=8.0 Hz, 1H), 4.62 (d, J=9.0 Hz, 1H), 4.52 (s, 1H), 4.19-4.16 (m, 1H), 3.97-3.86 (m, 2H), 3.73 (s, 2H), 3.60 (dd, J=11.5, 3.4 Hz, 1H), 3.48-3.41 (m, 1H), 3.37-3.32 (m, 1H), 3.26-3.02 (m, 3H), 2.52-2.46 (m, 4H), 2.11-1.94 (m, 11H), 1.80-1.65 (m, 14H), 1.50-1.44 (m, 5H), 1.14-1.06 (m, 13H) ppm.

Preparation of 2-(5-(1-(adamantan-1-ylmethyl)-5-methyl-1H-pyrazol-4-yl)-6-(((9-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-9-oxononyl)sulfonyl)carbamoyl)pyridin-2-yl)-N-(benzo[d]thiazol-2-yl)-1,2,3,4-tetrahydroisoquinoline-8-carboxamide (degrader #14). Starting from 9f and 1, compound degrader #14 was obtained using the above-mentioned method for degrader #11. $^1$H NMR (600 MHz, Chloroform-d) δ 10.89 (br s, 1H), 10.14 (br s, 1H), 8.69 (s, 1H), 7.94-7.85 (m, 1H), 7.69 (d, J=8.0 Hz, 1H), 7.62-7.49 (m, 2H), 7.47-7.33 (m, 9H), 7.25 (t, J=7.6 Hz, 1H), 7.05 (d, J=8.8 Hz, 1H), 6.69 (d, J=8.8 Hz, 1H), 5.17-5.01 (m, 3H), 4.64-4.57 (m, 2H), 4.52 (s, 1H), 4.22-4.14 (m, 1H), 3.93-3.85 (m, 2H), 3.74 (s, 2H), 3.60 (dd, J=11.4, 3.5 Hz, 1H), 3.51-3.19 (m, 3H), 3.06 (t, J=6.1 Hz, 2H), 2.56-2.49 (m, 4H), 2.11-1.97 (m, 9H), 1.81-1.64 (m, 14H), 1.50-1.42 (m, 5H), 1.33-1.29 (m, 2H), 1.17-1.05 (m, 15H) ppm.

Preparation of 2-(5-(1-(adamantan-1-ylmethyl)-5-methyl-1H-pyrazol-4-yl)-6-(((10-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-10-oxodecyl)sulfonyl)carbamoyl)pyridin-2-yl)-N-(benzo[d]thiazol-2-yl)-1,2,3,4-tetrahydroisoquinoline-8-carboxamide (degrader #15). Starting from 9g and 1, compound degrader #15 was obtained using the above-mentioned method for degrader #11. $^1$H NMR (600 MHz, Chloroform-d) δ 11.14 (br s, 1H), 10.16 (br s, 1H), 8.69 (s, 1H), 7.87 (d, J=7.8 Hz, 1H), 7.63-7.50 (m, 3H), 7.43-7.32 (m, 9H), 7.27-7.23 (m, 1H), 7.05 (d, J=8.8 Hz, 1H), 6.64 (d, J=8.8 Hz, 1H), 5.21-4.95 (m, 3H), 4.71-4.57 (m, 2H), 4.52 (s, 1H), 4.15 (d, J=11.4 Hz, 1H), 3.94-3.83 (m, 2H), 3.73 (s, 2H), 3.60 (dd, J=11.4, 3.5 Hz, 1H), 3.49-3.36 (m, 2H), 3.11-3.00 (m, 2H), 2.54-2.46 (m, 4H), 2.10-1.98 (m, 9H), 1.83-1.78 (m, 2H), 1.73-1.61 (m, 12H), 1.50-1.44 (m, 5H), 1.34-1.30 (m, 2H), 1.20-1.09 (m, 8H), 1.07 (s, 9H) ppm.

Preparation of 2-(5-(1-(adamantan-1-ylmethyl)-5-methyl-1H-pyrazol-4-yl)-6-(((11-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-11-oxoundecyl)sulfonyl)carbamoyl)pyridin-2-yl)-N-(benzo[d]thiazol-2-yl)-1,2,3,4-tetrahydroisoquinoline-8-carboxamide (degrader #16). Starting from 9 h and 1, compound degrader #16 was obtained using the above-mentioned method for degrader #11. $^1$H NMR (600 MHz, Chloroform-d) δ 11.14 (br s, 1H), 10.16 (br s, 1H), 8.69 (s, 1H), 7.88 (dd, J=7.8, 1.3 Hz, 1H), 7.58 (t, J=6.9 Hz, 2H), 7.52 (d, J=8.8 Hz, 1H), 7.44-7.31 (m, 9H), 7.27-7.24 (m, 1H), 7.04 (d, J=8.8 Hz, 1H), 6.69 (d, J=9.0 Hz, 1H), 5.20 (d, J=17.2 Hz, 1H), 5.12-5.05 (m, 1H), 4.95 (d, J=17.2 Hz, 1H), 4.71-4.60 (m, 2H), 4.55-4.48 (m, 1H), 4.21-4.12 (m, 1H), 3.95-3.82 (m, J=6.0 Hz, 2H), 3.73 (s, 2H), 3.61 (dd, J=11.4, 3.5 Hz, 1H), 3.49-3.36 (m, 2H), 3.12-2.98 (m, 2H), 2.57-2.48 (m, 4H), 2.12-2.03 (m, 6H), 2.03-1.97 (m, 3H), 1.85-1.79 (m, 2H), 1.73-1.61 (m, 12H), 1.52-1.45 (m, 5H), 1.39-1.33 (m, 2H), 1.21-1.09 (m, 10H), 1.08 (s, 9H) ppm.

Preparation of 2-(5-(1-(adamantan-1-ylmethyl)-5-methyl-1H-pyrazol-4-yl)-6-(((12-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-12-oxododecyl)sulfonyl)carbamoyl)pyridin-2-yl)-N-(benzo[d]thiazol-2-yl)-1,2,3,4-tetrahydroisoquinoline-8-carboxamide (degrader #17). Starting from 9i and 1, compound degrader #17 was obtained using the above-mentioned method for degrader #11. $^1$H NMR (600 MHz, Chloroform-d) δ 11.11 (br s, 1H), 10.16 (br s, 1H), 8.69 (s, 1H), 7.87 (dd, J=7.8, 1.4 Hz, 1H), 7.59 (d, J=7.6 Hz, 1H), 7.55-7.50 (m, 2H), 7.42-7.31 (m, 9H), 7.26 (t, J=7.6 Hz, 1H), 7.05 (d, J=8.8 Hz, 1H), 6.55 (d, J=8.8 Hz, 1H), 5.17-4.97 (m, 3H), 4.67 (t, J=7.9 Hz, 1H), 4.61 (d, J=8.8 Hz, 1H), 4.57-4.49 (m, 1H), 4.20-4.10 (m, 1H), 3.95-3.85 (m, 2H), 3.73 (s, 2H), 3.63-3.40 (m, 4H), 3.11-3.01 (m, 2H), 2.57-2.47 (m, 4H), 2.14-1.99 (m, 9H), 1.85-1.81 (m, 2H), 1.73-1.61 (m, 12H), 1.53-1.46 (m, 5H), 1.39-1.34 (m, 2H), 1.23-1.11 (m, 12H), 1.07 (s, 9H) ppm.

Example 5: Preparation of 2-(5-(1-(adamantan-1-ylmethyl)-5-cyano-2-methyl-1H-pyrrol-3-yl)-6-(((8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctyl)sulfonyl)carbamoyl)pyridin-2-yl)-N-(benzo[d]thiazol-2-yl)-1,2,3,4-tetrahydroisoquinoline-8-carboxamide (degrader #18)

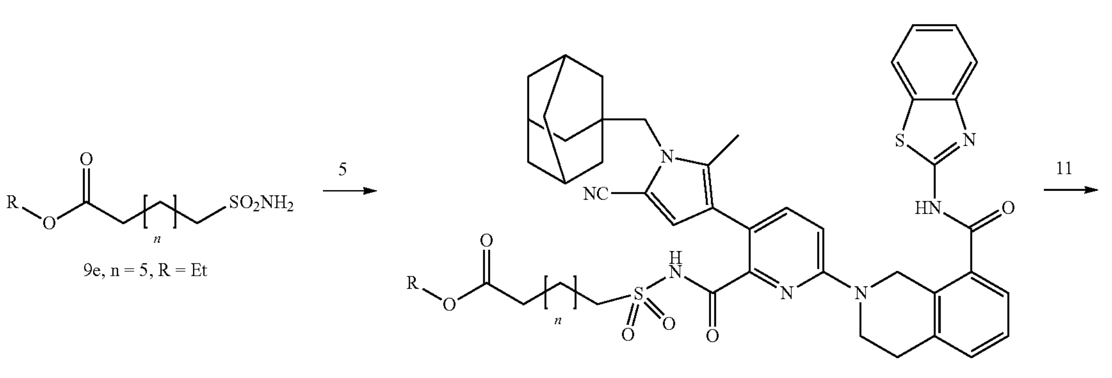

9e, n = 5, R = Et 12, n = 5, R = Et

-continued

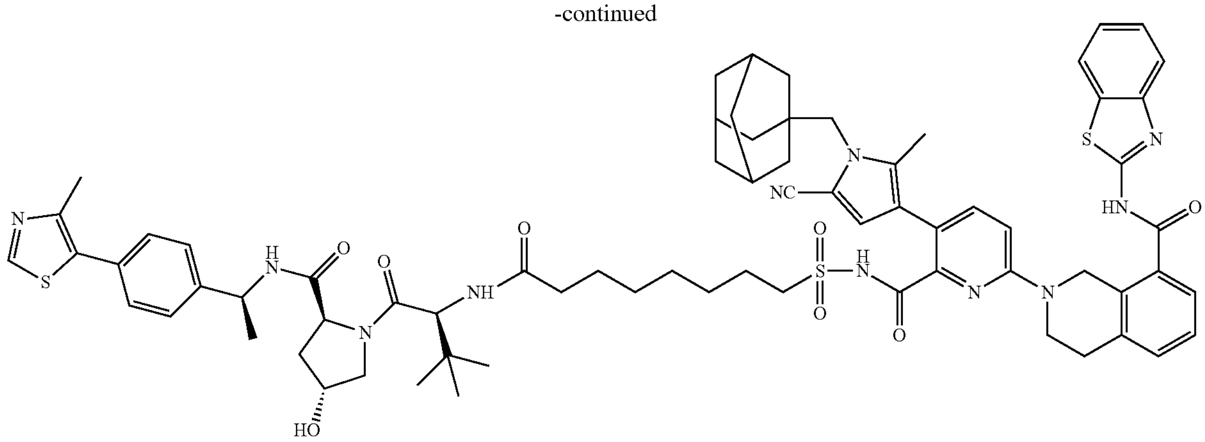

degrader #18

Starting from 9e and 5, compound degrader #18 was obtained using the above-mentioned method for degrader #11. $^1$H NMR (600 MHz, Chloroform-d) δ 10.16 (br s, 1H), 8.69 (s, 1H), 7.88 (dd, J=7.9, 1.3 Hz, 1H), 7.66-7.55 (m, 2H), 7.48 (d, J=8.8 Hz, 11H), 7.43-7.32 (m, 8H), 7.26 (t, J=7.6 Hz, 11H), 7.04 (d, J=8.8 Hz, 1H), 6.77-6.70 (m, 2H), 5.25-4.96 (m, 3H), 4.66 (t, J=8.1 Hz, 11H), 4.59 (d, J=8.9 Hz, 1H), 4.54-4.48 (m, 1H), 4.14-4.11 (m, 1H), 3.95-3.82 (m, 2H), 3.71 (s, 2H), 3.60 (dd, J=11.5, 3.5 Hz, 1H), 3.48-3.40 (m, 1H), 3.38-3.30 (m, 1H), 3.10-3.00 (m, 2H), 2.51-2.42 (m, 4H), 2.09-1.96 (m, 111H), 1.78-1.62 (m, 14H), 1.51-1.43 (m, 5H), 1.17-1.04 (m, 13H) ppm.

Example 6: Preparation of 2-(5-(1-(adamantan-1-ylmethyl)-5-methyl-1H-pyrazol-4-yl)-6-((8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctyl)carbamoyl)pyridin-2-yl)-N-(benzo[d]thiazol-2-yl)-1,2,3,4-tetrahydroisoquinoline-8-carboxamide (degrader #19)

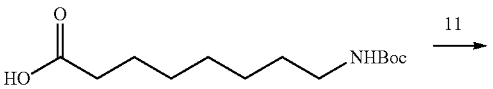

13

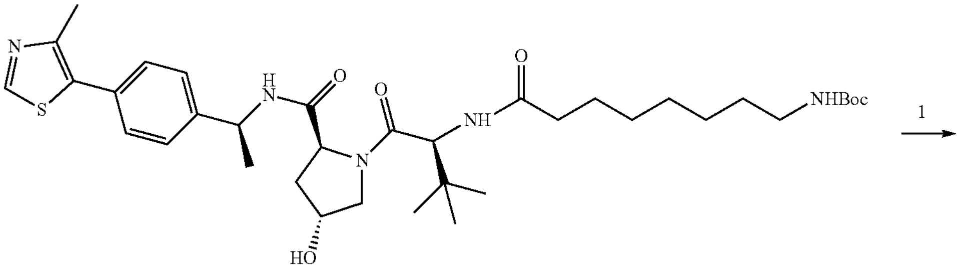

14

-continued

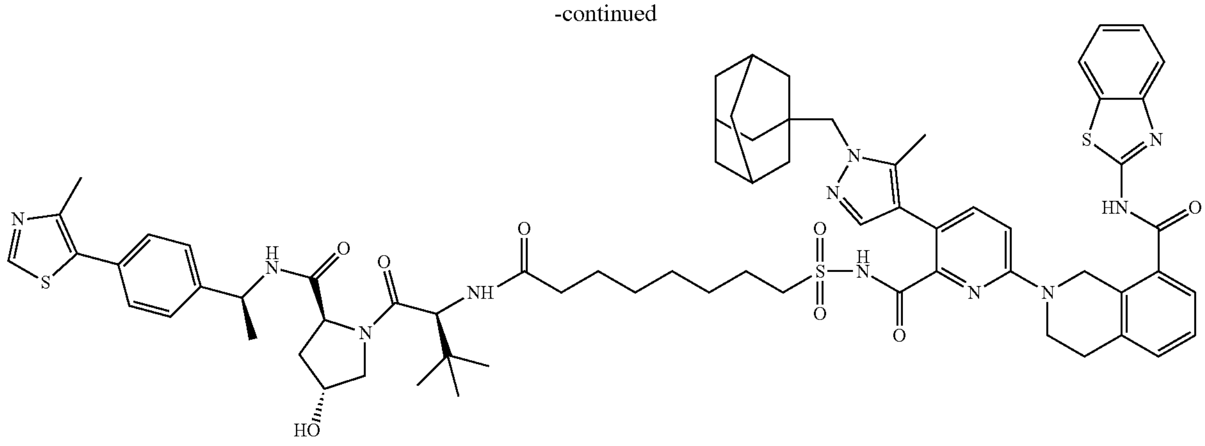

degrader #19

Preparation of tert-butyl (8-(((S)-1-((2S,4R)-4-hydroxy-2-(((S)-1-(4-(4-methylthiazol-5-yl)phenyl)ethyl)carbamoyl) pyrrolidin-1-yl)-3,3-dimethyl-1-oxobutan-2-yl)amino)-8-oxooctyl)carbamate (14). A mixture of 13 (50 mg, 0.19 mmol), 11 (100 mg, 0.19 mmol), HATU (77 mg, 0.20 mmol) and TEA (135 μL, 0.97 mmol) in DCM (5 mL) was stirred at room temperature for 1 h. The mixture was poured into water and extracted with DCM. The organic phase was washed with water×1, brine×1, dried over $Na_2SO_4$, filtered, and evaporated to dryness. The residue was purified by silica gel flash column chromatography using DCM and methanol as eluents to afford the title compound (70 mg, yield 53%). 1H NMR (600 MHz, Chloroform-d) δ 8.70 (s, 1H), 7.50-7.46 (m, 1H), 7.45-7.36 (m, 4H), 6.17-6.04 (m, 1H), 5.15-5.04 (m, 1H), 4.77 (t, J=7.9 Hz, 1H), 4.63-4.51 (m, 3H), 4.20-4.16 (m, 1H), 3.65-3.57 (m, 1H), 3.23-3.16 (m, 2H), 3.14-3.05 (m, 2H), 2.86 (s, 1H), 2.64-2.52 (m, 4H), 2.27-2.20 (m, 2H), 2.14-2.08 (m, 11H), 1.49-1.41 (m, 14H), 1.35-1.29 (m, 6H), 1.07 (s, 9H) ppm.

Preparation of 2-(5-(1-(adamantan-1-ylmethyl)-5-methyl-1H-pyrazol-4-yl)-6-((8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctyl)carbamoyl)pyridin-2-yl)-N-(benzo[d]thiazol-2-yl)-1,2,3,4-tetrahydroisoquinoline-8-carboxamide (degrader #19). A mixture of compound 14 (35 mg, 0.05 mmol) and an HCl solution (4N in 1,4-dixone, 1.0 mL) in DCM (5 mL) and MeOH (1 mL) was stirred at room temperature for 2 h. The solvent was removed under reduced pressure and the residue was dissolved in DCM (5 mL). Then it was treated with compound 1 (20 mg, 0.03 mmol), HATU (12 mg, 0.03 mmol) and TEA (21 μL, 0.29 mmol) and the resulting mixture was stirred at room temperature for 1 h. The reaction mixture was poured into water and extracted with DCM. The organic phase was washed with water×1, brine×1, dried over $Na_2SO_4$, filtered, and evaporated to dryness. The residue was purified by silica gel flash column chromatography using DCM and methanol as eluents to afford the title compound (14.2 mg, yield 39%). $^1H$ NMR (600 MHz, Chloroform-d) δ 11.34 (br s, 1H), 8.69 (s, 1H), 7.93-7.82 (m, 2H), 7.56-7.50 (m, 2H), 7.45-7.29 (m, 10H), 7.15 (t, J=7.6 Hz, 1H), 6.89 (d, J=8.7 Hz, 1H), 6.78 (d, J=8.9 Hz, 1H), 5.25-5.12 (m, 2H), 5.08 (p, J=7.1 Hz, 1H), 4.60 (d, J=8.9 Hz, 1H), 4.54 (t, J=8.0 Hz, 1H), 4.48-4.40 (m, 1H), 4.12-4.07 (m, 1H), 3.92-3.79 (m, 2H), 3.71 (s, 2H), 3.56 (dd, J=11.3, 3.6 Hz, 1H), 3.39-3.20 (m, 2H), 3.05 (t, J=6.1 Hz, 2H), 2.51 (s, 3H), 2.47-2.40 (m, 1H), 2.11-1.99 (m, 9H), 1.72-1.59 (m, 12H), 1.49-1.41 (m, 7H), 1.19-1.01 (m, 15H) ppm.

Example 7: Preparation of Degraders #20-#25

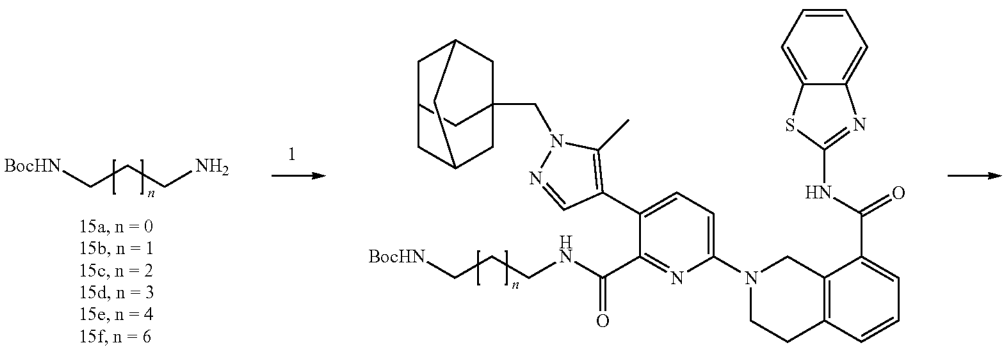

15a, n = 0
15b, n = 1
15c, n = 2
15d, n = 3
15e, n = 4
15f, n = 6

16a, n = 0
16b, n = 1
16c, n = 2
16d, n = 3
16e, n = 4
16f, n = 6

-continued

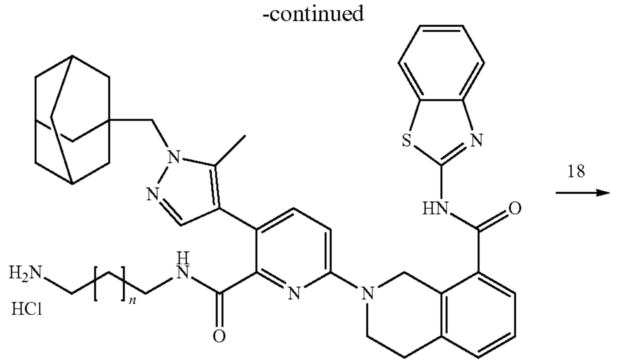

17a, n = 0
17b, n = 1
17c, n = 2
17d, n = 3
17e, n = 4
17f, n = 6

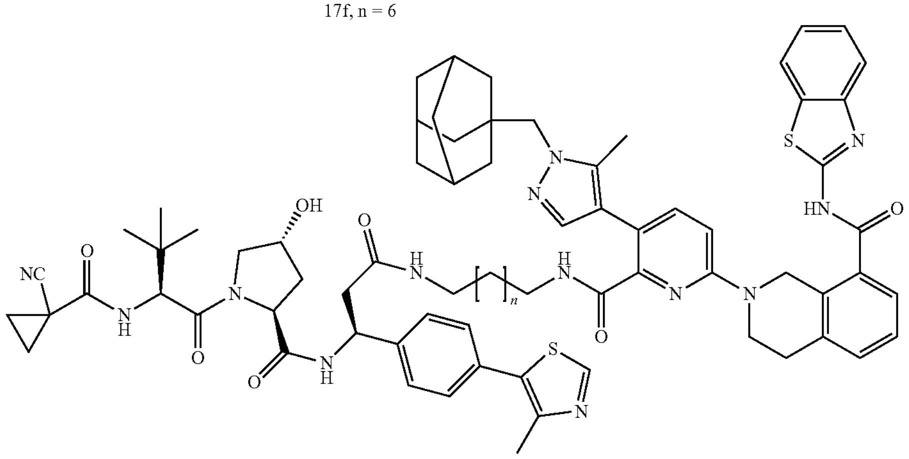

degrader #20, n = 0
degrader #21, n = 1
degrader #22, n = 2
degrader #23, n = 3
degrader #24, n = 4
degrader #25, n = 6

18

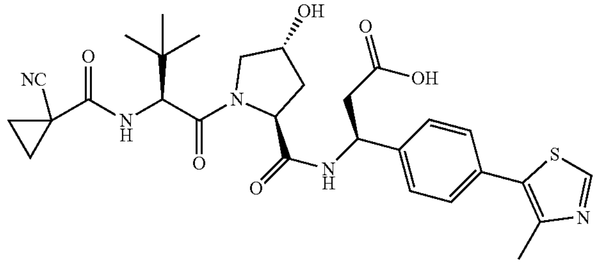

Preparation of tert-butyl (3-(3-(1-(adamantan-1-ylmethyl)-5-methyl-1H-pyrazol-4-yl)-6-(8-(benzo[d]thiazol-2-ylcarbamoyl)-3,4-dihydroisoquinolin-2(1H)-yl)picolinamido)propyl)carbamate (16b). A mixture of 1 (15 mg, 0.023 mmol), 15b (6.2 mg, 0.036 mmol), HATU (9.5 mg, 0.025 mmol), and TEA (100 μL, 0.72 mmol) in DCM (2 mL) was stirred at room temperature for 1 h. The mixture was poured into water and extracted with DCM. The organic phase was washed with water×1, brine×1, dried over $Na_2SO_4$, filtered, and evaporated to dryness. The residue was purified by silica gel flash column chromatography using EtOAc and hexanes as eluents to afford the title compound (10.1 mg, yield 54%). $^1$H NMR (600 MHz, Chloroform-d) δ 8.19-8.12 (m, 1H), 7.92-7.87 (m, 1H), 7.58 (dd, J=7.7, 1.3 Hz, 1H), 7.50 (d, J=7.7 Hz, 1H), 7.46 (d, J=8.6 Hz, 1H), 7.41-7.33 (m, 4H), 7.28-7.24 (m, 1H), 6.92 (d, J=8.7 Hz, 1H), 5.23-5.12 (m, 3H), 4.01-3.92 (m, 2H), 3.73 (s, 2H), 3.47-3.40 (m, 2H), 3.21-3.04 (m, 4H), 2.09 (s, 3H), 2.01 (s, 3H), 1.76-1.62 (m, 14H), 1.41 (s, 9H) ppm.

Preparation of 2-(5-(1-(adamantan-1-ylmethyl)-5-methyl-1H-pyrazol-4-yl)-6-((3-((S)-3-((2S,4R)-1-((S)-2-(1-cyanocyclopropane-1-carboxamido)-3,3-dimethylbutanoyl)-4-hydroxypyrrolidine-2-carboxamido)-3-(4-(4-methylthiazol-5-yl)phenyl)propanamido)propyl)carbamoyl)pyridin-2-yl)-N-(benzo[d]thiazol-2-yl)-1,2,3,4-tetrahydroisoquinoline-8-carboxamide (degrader #21). A mixture of compound 16b (10.1 mg, 0.012 mmol), TFA (200 uL) in DCM (2 mL) was stirred at room overnight. The solvent was removed under reduced pressure and the crude 17b was dissolved in DCM (3 mL). Then it was mixed with 18 (9.3 mg, 0.016 mmol), HATU (5.2 mg, 0.014 mmol) and TEA (50 μL, 0.36 mmol). The resulting mixture was stirred at room temperature for 1 h. Then it was poured into water and extracted with DCM. The organic phase was washed with water×1, brine×1, dried over $Na_2SO_4$, filtered, and evaporated to dryness. The residue was purified by silica gel flash column chromatography using EtOAc, DCM, and hexanes as eluents to afford the title compound (7.9 mg, yield 51%). $^1$H NMR (600 MHz, Chloroform-d) δ 8.66-8.58 (m, 2H), 8.05-7.97 (m, 1H), 7.89 (d, J=7.9 Hz, 1H), 7.70-7.64 (m, 1H), 7.61-7.52 (m, 2H), 7.43-7.29 (m, 7H), 7.28-7.15 (m, 5H), 6.91 (d, J=8.7 Hz, 1H), 5.37-5.31 (m, 1H), 5.25 (d, J=17.4 Hz, 1H), 5.08 (d, J=17.1 Hz, 1H), 4.87-4.80 (m, 1H), 4.63-4.54 (m, 2H), 3.94-3.59 (m, 8H), 3.11-3.00 (m, 4H), 2.89-2.83 (m, 1H), 2.57 (dd, J=13.5, 5.6 Hz, 1H), 2.32 (s, 3H), 2.18-2.13 (m, 2H), 2.05 (s, 3H), 1.96-1.92 (m, 3H), 1.82-1.52 (m, 16H), 1.49-1.41 (m, 2H), 1.05 (s, 9H) ppm.

Preparation of 2-(5-(1-(adamantan-1-ylmethyl)-5-methyl-1H-pyrazol-4-yl)-6-((2-((S)-3-((2S,4R)-1-((S)-2-(1-cyanocyclopropane-1-carboxamido)-3,3-dimethylbutanoyl)-4-hydroxypyrrolidine-2-carboxamido)-3-(4-(4-methylthiazol-5-yl)phenyl)propanamido)ethyl)carbamoyl)pyridin-2-yl)-N-(benzo[d]thiazol-2-yl)-1,2,3,4-tetrahydroisoquinoline-8-carboxamide (degrader #20). Starting from 15a and 1, compound degrader #20 was obtained using the above-mentioned method for degrader #21. $^1$H NMR (600 MHz, Chloroform-d) δ 8.56 (s, 1H), 8.43-8.35 (m, 1H), 8.25 (d, J=9.2 Hz, 1H), 7.95-7.85 (m, 2H), 7.80 (d, J=8.1 Hz, 1H), 7.56-7.50 (m, 2H), 7.49-7.43 (m, 1H), 7.40-7.29 (m, 5H), 7.27-7.25 (m, 1H), 7.16 (d, J=8.0 Hz, 2H), 6.86 (d, J=8.7 Hz, 1H), 6.81 (d, J=7.9 Hz, 2H), 5.33-5.28 (m, 2H), 5.03 (t, J=8.6 Hz, 1H), 4.83 (d, J=16.9 Hz, 1H), 4.68-4.63 (m, 1H), 4.57 (d, J=8.6 Hz, 1H), 4.13-4.05 (m, 1H), 4.03-3.92 (m, 2H), 3.89-3.75 (m, 3H), 3.71-3.61 (m, 2H), 3.27 (dd, J=27.4, 14.0 Hz, 2H), 3.16-2.98 (m, 2H), 2.92 (dd, J=13.6, 4.4 Hz, 1H), 2.54 (dd, J=13.5, 4.3 Hz, 1H), 2.24-2.17 (m, 5H), 2.01-1.93 (m, 6H), 1.71-1.62 (m, 14H), 1.52-1.44 (m, 2H), 1.07 (s, 9H) ppm.

Preparation of 2-(5-(1-(adamantan-1-ylmethyl)-5-methyl-1H-pyrazol-4-yl)-6-((4-((S)-3-((2S,4R)-1-((S)-2-(1-cyanocyclopropane-1-carboxamido)-3,3-dimethylbutanoyl)-4-hydroxypyrrolidine-2-carboxamido)-3-(4-(4-methylthiazol-5-yl)phenyl)propanamido)butyl)carbamoyl)pyridin-2-yl)-N-(benzo[d]thiazol-2-yl)-1,2,3,4-tetrahydroisoquinoline-8-carboxamide (degrader #22). Starting from 15c and 1, compound degrader #22 was obtained using the above-mentioned method for degrader #21. $^1$H NMR (600 MHz, Chloroform-d) δ 8.46 (s, 1H), 8.18 (d, J=7.7 Hz, 1H), 7.92-7.86 (m, 2H), 7.66-7.59 (m, 1H), 7.59-7.53 (m, 1H), 7.42-7.32 (m, 8H), 7.26-7.23 (m, 1H), 7.16-7.09 (m, 3H), 6.84 (d, J=8.7 Hz, 1H), 5.32-5.25 (m, 1H), 5.16-5.09 (m, 1H), 4.99 (d, J=16.9 Hz, 1H), 4.78-4.72 (m, 1H), 4.55 (d, J=8.7 Hz, 1H), 4.47 (s, 1H), 3.82-3.66 (m, 6H), 3.48-3.33 (m, 2H), 3.11-3.01 (m, 4H), 2.92 (dd, J=14.3, 4.8 Hz, 1H), 2.73 (dd, J=14.3, 5.7 Hz, 1H), 2.35 (s, 3H), 2.19 (s, 2H), 2.10 (s, 3H), 2.02-1.91 (m, 5H), 1.73-1.59 (m, 12H), 1.53-1.44 (m, 6H), 1.05 (s, 9H) ppm.

Preparation of 2-(5-(1-(adamantan-1-ylmethyl)-5-methyl-1H-pyrazol-4-yl)-6-((5-((S)-3-((2S,4R)-1-((S)-2-(1-cyanocyclopropane-1-carboxamido)-3,3-dimethylbutanoyl)-4-hydroxypyrrolidine-2-carboxamido)-3-(4-(4-methylthiazol-5-yl)phenyl)propanamido)pentyl)carbamoyl)pyridin-2-yl)-N-(benzo[d]thiazol-2-yl)-1,2,3,4-tetrahydroisoquinoline-8-carboxamide (degrader #23). Starting from 15d and 1, compound degrader #23 was obtained using the above-mentioned method for degrader #21. $^1$H NMR (600 MHz, Chloroform-d) δ 8.61 (s, 1H), 8.37-8.25 (m, 1H), 7.88-7.80 (m, 2H), 7.60 (d, J=7.5 Hz, 2H), 7.46-7.30 (m, 5H), 7.27-7.19 (m, 5H), 7.16 (d, J=7.6 Hz, 1H), 7.08 (s, 1H), 6.89 (d, J=8.7 Hz, 1H), 5.35-5.27 (m, 1H), 5.24-5.10 (m, 2H), 4.70 (t, J=8.3 Hz, 1H), 4.57 (d, J=8.8 Hz, 1H), 4.49-4.41 (m, 1H), 3.91-3.77 (m, 3H), 3.73-3.63 (m, 3H), 3.27-3.23 (m, 2H), 3.06-3.00 (m, 4H), 2.56 (s, 2H), 2.45 (s, 3H), 2.20-2.03 (m, 5H), 1.96 (s, 3H), 1.71-1.55 (m, 14H), 1.46-1.35 (m, 6H), 1.17-1.09 (m, 2H), 0.99 (s, 9H) ppm.

Preparation of 2-(5-(1-(adamantan-1-ylmethyl)-5-methyl-1H-pyrazol-4-yl)-6-((6-((S)-3-((2S,4R)-1-((S)-2-(1-cyanocyclopropane-1-carboxamido)-3,3-dimethylbutanoyl)-4-hydroxypyrrolidine-2-carboxamido)-3-(4-(4-methylthiazol-5-yl)phenyl)propanamido)hexyl)carbamoyl)pyridin-2-yl)-N-(benzo[d]thiazol-2l)-1,2,3,4-tetrahydroisoquinoline-8-carboxamide (degrader #24). Starting from 15e and 1, compound degrader #24 was obtained using the above-mentioned method for degrader #21. $^1$H NMR (600 MHz, Chloroform-d) δ 10.96 (br s, 1H), 8.62 (s, 1H), 8.02 (d, J=7.9 Hz, 1H), 7.86 (dd, J=7.8, 1.4 Hz, 1H), 7.78 (t, J=6.3 Hz, 1H), 7.62-7.55 (m, 2H), 7.44 (d, J=8.7 Hz, 1H), 7.40-7.29 (m, 9H), 7.28-7.24 (m, 1H), 7.09 (d, J=8.6 Hz, 1H), 6.90 (d, J=8.7 Hz, 1H), 6.76-6.70 (m, 1H), 5.32-5.13 (m, 3H), 4.63 (t, J=8.1 Hz, 1H), 4.53 (d, J=8.6 Hz, 1H), 4.46-4.39 (m, 1H), 3.91-3.86 (m, 2H), 3.82 (d, J=11.0 Hz, 1H), 3.70 (s, 2H), 3.63 (dd, J=11.2, 4.0 Hz, 1H), 3.34-3.15 (m, 3H), 3.10-3.03 (m, 3H), 2.67 (d, J=5.8 Hz, 2H), 2.48 (s, 3H), 2.14-2.07 (m, 5H), 2.00-1.96 (m, 3H), 1.76-1.60 (m, 16H), 1.49-1.44 (m, 4H), 1.36-1.32 (m, 2H), 1.18-1.16 (m, 2H), 1.05 (s, 9H) ppm.

Preparation of 2-(5-(1-(adamantan-1-ylmethyl)-5-methyl-1H-pyrazol-4-yl)-6-((8-((S)-3-((2S,4R)-1-((S)-2-(1-cyanocyclopropane-1-carboxamido)-3,3-dimethylbutanoyl)-4-hydroxypyrrolidine-2-carboxamido)-3-(4-(4-methylthiazol-5-yl)phenyl)propanamido)octyl)carbamoyl)pyridin-2-yl)-N-(benzo[d]thiazol-2-yl)-1,2,3,4-tetrahydroisoquninoline-8-carboxamide (degrader #25). Starting from 15f and 1, compound degrader #25 was obtained using the above-mentioned method for degrader #21. $^1$H NMR (600 MHz, Chloroform-d) δ 11.05 (br s, 1H), 8.63 (s, 1H), 8.02-7.95 (m, 1H), 7.89-7.80 (m, 2H), 7.63-7.56 (m, 1H), 7.55-7.50 (m, 1H), 7.48-7.43 (m, 1H), 7.40-7.31 (m, 8H), 7.27-7.25 (m, 1H), 7.10 (d, J=8.6 Hz, 1H), 6.94-6.88 (m, 1H), 6.54-6.45 (m, 1H), 5.35-5.31 (m, 1H), 5.20 (s, 2H), 4.63 (t, J=8.2 Hz, 1H), 4.54 (d, J=8.6 Hz, 1H), 4.50-4.46 (m, 1H), 3.91-3.87 (m, 2H), 3.75-3.63 (m, 4H), 3.30-3.22 (m, 2H), 3.18-3.05 (m, 4H), 2.79-2.69 (m, 2H), 2.49-2.46 (m, 3H), 2.21-2.15 (m, 2H), 2.09 (s, 3H), 1.98 (s, 3H), 1.73-1.46 (m, 18H), 1.38-1.31 (m, 2H), 1.16-1.03 (m, 17H) ppm.

Example 8: Preparation of Degraders #26-#33

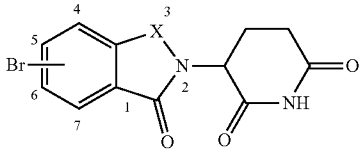

20a, 4-position, X = carbonyl
20b, 5-position, X = carbonyl
20c, 4-position, X = methylene
20d, 5-position, X = methylene

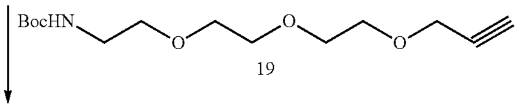

19

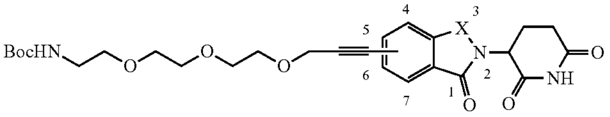

21a, 4-position, X = carbonyl
21b, 5-position, X = carbonyl
21c, 4-position, X = methylene
21d, 5-position, X = methylene

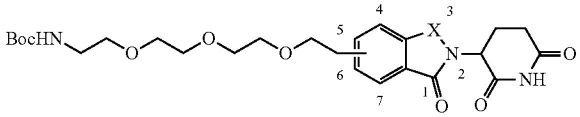

22a, 4-position, X = carbonyl
22b, 5-position, X = carbonyl
22c, 4-position, X = methylene
22d, 5-position, X = methylene

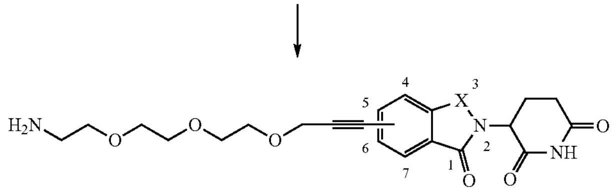

23a, 4-position, X = carbonyl
23b, 5-position, X = carbonyl
23c, 4-position, X = methylene
23d, 5-position, X = methylene

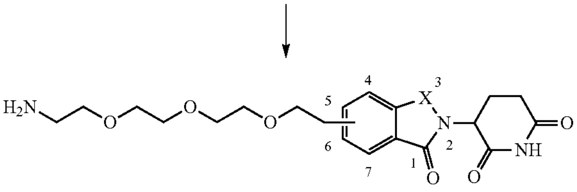

24a, 4-position, X = carbonyl
24b, 5-position, X = carbonyl
24c, 4-position, X = methylene
24d, 5-position, X = methylene

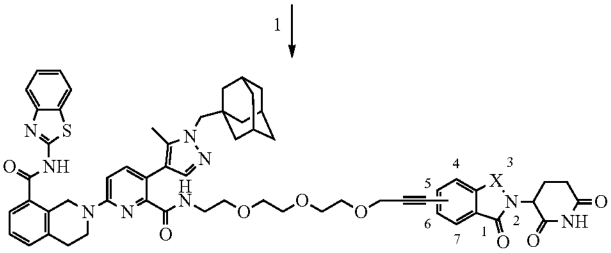

degrader #26, 4-position, X = carbonyl
degrader #27, 5-position, X = carbonyl
degrader #28, 4-position, X = methylene
degrader #29, 5-position, X = methylene

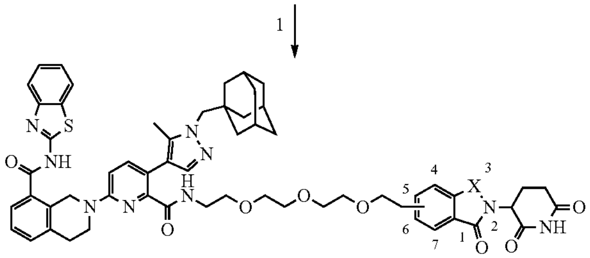

degrader #30, 4-position, X = carbonyl
degrader #31, 5-position, X = carbonyl
degrader #32, 4-position, X = methylene
degrader #33, 5-position, X = methylene General method for the preparation of compounds 21a-d. A mixture of 19 (1.2 equiv.), 20 (1.0 equiv.), $Pd(PPh_3)_4$ (0.1 equiv.), CuI (0.2 equiv.), and $Et_3N$ (4.8 equiv.) in DMSO was heated under microwave irradiation at 120° C. for 30 min. The reaction was cooled to room temperature, poured into water and extracted with EtOAc. The organic layer was washed with water×2, brine×1, dried over anhydrous $Na_2SO_4$, filtered, and evaporated to dryness. The crude product was purified by flash column chromatography using EtOAc and DCM as eluents to afford the title compound.

Preparation of tert-Butyl (2-(2-(2-((3-(2-(2,6-dioxopiperidin-3-yl)-1,3-dioxoisoindolin-4-yl)prop-2-yn-1-yl)oxy)ethoxy)ethoxy)ethyl)carbamate (21a). Following general method, compound 21a was obtained from 19 and 20a. Yield 80%, 15 $^1H$ NMR (600 MHz, $CDCl_3$) δ 8.18 (s, 1H), 7.88-7.84 (in, 1H), 7.80-7.77 (m, 1H), 7.73 (t, J 7.6 Hz, 1H), 5.07 (s, 1H), 5.01 (dd, J=12.5, 5.4 Hz, 1H), 4.55 (s, 2H), 3.91-3.86 (m, 2H), 3.79-3.75 (m, 2H), 3.71-3.66 (m, 4H), 3.59-3.54 (m, 2H), 3.39-3.30 (m, 2H), 2.98-2.75 (m, 3H), 2.21-2.14 (m, 1H), 1.46 (s, 9H) ppm. LC-MS (ESI): m/z 566.2 $[M+Na]^+$.

Preparation of tert-Butyl (2-(2-(2-((3-(2-(2,6-dioxopiperidin-3-yl)-1,3-dioxoisoindolin-5-yl)prop-2-yn-1-yl)oxy)ethoxy)ethoxy)ethyl)carbamate (21b). Following general method, compound 21b was obtained from 19 and 20b. Yield 76%. $^1$H NMR (600 MHz, $CDCl_3$) δ 7.99 (s, 1H), 7.93-7.89 (m, 1H), 7.86-7.83 (m, 1H), 7.81-7.78 (m, 1H), 5.05-4.94 (m, 2H), 4.48 (s, 2H), 3.82-3.77 (m, 2H), 3.75-3.71 (m, 2H), 3.69-3.62 (m, 4H), 3.55 (t, J=5.1 Hz, 2H), 3.37-3.28 (m, 2H), 2.96-2.72 (m, 3H), 2.18-2.13 (m, 1H), 1.44 (s, 9H) ppm. LC-MS (ESI): m/z 566.2 $[M+Na]^+$.

Preparation of tert-Butyl (2-(2-(2-((3-(2-(2,6-dioxopiperidin-3-yl)-1-oxoisoindolin-4-yl)prop-2-yn-1-yl)oxy)ethoxy)ethoxy)ethyl)carbamate (21c). Following general method, compound 21c was obtained from 19 and 20c. Yield 85%. $^1$H NMR (600 MHz, $CDCl_3$) δ 8.20 (s, 1H), 7.86 (dd, J=7.7, 1.1 Hz, 1H), 7.63 (dd, J=7.6, 1.0 Hz, 11H), 7.47 (t, J=7.6 Hz, 1H), 5.24 (dd, J=13.3, 5.1 Hz, 11H), 5.04 (s, 11H), 4.57-4.34 (m, 4H), 3.79-3.75 (m, 2H), 3.73-3.70 (m, 2H), 3.67-3.63 (m, 4H), 3.56-3.52 (m, 2H), 3.34-3.28 (m, 2H), 2.96-2.80 (m, 2H), 2.46-2.35 (m, 1H), 2.28-2.19 (m, 1H), 1.44 (s, 9H) ppm. LC-MS (ESI): m/z 552.3 $[M+Na]^+$.

Preparation of tert-Butyl (2-(2-(2-((3-(2-(2,6-dioxopiperidin-3-yl)-1-oxoisoindolin-5-yl)prop-2-yn-1-yl)oxy)ethoxy)ethoxy)ethyl)carbamate (21d). Following general method, compound 21d was obtained from 19 and 20d. Yield 71%. $^1$H NMR (600 MHz, $CDCl_3$) δ 7.91 (s, 1H), 7.86-7.81 (m, 1H), 7.58-7.53 (m, 2H), 5.21 (dd, J=13.3, 5.1 Hz, 1H), 5.02 (s, 1H), 4.53-4.30 (m, 4H), 3.82-3.78 (m, 2H), 3.74-3.72 (m, 2H), 3.68-3.63 (m, 4H), 3.58-3.53 (m, 2H), 3.36-3.27 (m, 2H), 2.98-2.80 (m, 2H), 2.42-2.33 (m, 1H), 2.27-2.19 (m, 1H), 1.44 (s, 9H) ppm. LC-MS (ESI): m/z 552.2 $[M+Na]^+$.

General method for the preparation of compounds 22a-d. A mixture of 21 (1.0 equiv.) and 10% Pd/C (10% w/w) in EtOAc-methanol (5/1, v/v) was stirred at room temperature under $H_2$ atmosphere overnight. The solid was removed by filtration, and the filtrate was evaporated to dryness to afford the designed compound.

Preparation of tert-Butyl (2-(2-(2-(3-(2-(2,6-dioxopiperidin-3-yl)-1,3-dioxoisoindolin-4-yl)propoxy)ethoxy)ethoxy)ethyl)carbamate (22a). Following general method, compound 22a was obtained from 21a. Yield 100%. $^1$H NMR (600 MHz, $CDCl_3$) δ 8.20-8.05 (m, 1H), 7.76-7.73 (m, 1H), 7.70-7.63 (m, 1H), 7.60-7.56 (m, 1H), 5.11-4.96 (m, 2H), 3.68-3.55 (m, 12H), 3.39-3.13 (m, 4H), 2.97-2.73 (m, 3H), 2.21-2.14 (m, 1H), 2.03-1.95 (m, 2H), 1.47-1.45 (m, 9H) ppm. LC-MS (ESI): m/z 570.3 $[M+Na]^+$.

Preparation of tert-Butyl (2-(2-(2-(3-(2-(2,6-dioxopiperidin-3-yl)-1,3-dioxoisoindolin-5-yl)propoxy)ethoxy)ethoxy)ethyl)carbamate (22b). Following general method, compound 22b was obtained from 21b. Yield 100%. $^1$H NMR (600 MHz, $CDCl_3$) δ 8.02 (s, 1H), 7.84-7.79 (m, 1H), 7.76-7.74 (m, 1H), 7.63-7.60 (m, 1H), 5.09-4.95 (m, 2H), 3.69-3.55 (m, 10H), 3.50 (t, J=6.2 Hz, 2H), 3.40-3.29 (m, 2H), 2.97-2.73 (m, 5H), 2.19-2.14 (m, 1H), 2.02-1.93 (m, 2H), 1.47-1.45 (m, 9H) ppm. LC-MS (ESI): m/z 570.3 $[M+Na]^+$.

Preparation of tert-Butyl (2-(2-(2-(3-(2-(2,6-dioxopiperidin-3-yl)-1-oxoisoindolin-4-yl)propoxy)ethoxy)ethoxy)ethyl)carbamate (22c). Following general method, compound 22c was obtained from 21c. Yield 100%. $^1$H NMR (600 MHz, $CDCl_3$) δ 8.68-8.46 (m, 1H), 7.77-7.71 (m, 1H), 7.46-7.37 (m, 2H), 5.29-5.23 (m, 1H), 5.19-5.09 (m, 1H), 4.52-4.29 (m, 2H), 3.66-3.30 (m, 14H), 2.96-2.58 (m, 4H), 2.45-2.17 (m, 2H), 1.98-1.64 (m, 2H), 1.45-1.41 (m, 9H) ppm. LC-MS (ESI): m/z 556.3 $[M+Na]^+$.

Preparation of tert-Butyl (2-(2-(2-(3-(2-(2,6-dioxopiperidin-3-yl)-1-oxoisoindolin-5-yl)propoxy)ethoxy)ethoxy)ethyl)carbamate (22d). Following general method, compound 22d was obtained from 21d. Yield 100%. $^1$H NMR (600 MHz, $CDCl_3$) δ 8.38-8.32 (m, 11H), 7.82-7.77 (m, 11H), 7.34-7.29 (m, 2H), 5.23 (dd, J=13.3, 5.1 Hz, 11H), 5.16-5.03 (m, 1H), 4.52-4.26 (m, 2H), 3.76-3.48 (m, 12H), 3.36-3.26 (m, 2H), 2.95-2.66 (m, 4H), 2.42-2.28 (m, 1H), 2.25-2.19 (m, 1H), 1.97-1.66 (m, 2H), 1.45-1.43 (m, 9H) ppm. LC-MS (ESI): m/z 556.2 $[M+Na]^+$.

General method for the preparation of compounds 23a-d and 24a-d. A mixture of 21/22 (1.0 equiv.) and TFA (30 equiv.) in DCM was stirred at room temperature overnight. The reaction mixture was concentrated under reduced pressure. The residue was washed with $Et_2O$ and the solid was collected by filtration to afford the title compound, which is used directly in the next step.

Preparation of 4-(3-(2-(2-(2-Aminoethoxy)ethoxy)ethoxy)prop-1-yn-1-yl)-2-(2,6-dioxopiperidin-3-yl)isoindoline-1,3-dione (23a). Following general method, compound 23a was obtained from 21a. Yield 88%. $^1$H NMR (600 MHz, $CDCl_3$) δ 8.54 (s, 1H), 7.91-7.86 (m, 1H), 7.80-7.73 (m, 2H), 5.02 (dd, J=12.2, 5.5 Hz, 1H), 4.52 (s, 2H), 3.86-3.76 (m, 8H), 3.70-3.68 (m, 2H), 3.32-3.25 (m, 2H), 2.98-2.73 (m, 3H), 2.25-2.18 (m, 1H) ppm. LC-MS (ESI): m/z 444.1 $[M+H]^+$.

Preparation of 5-(3-(2-(2-(2-Aminoethoxy)ethoxy)ethoxy)prop-1-yn-1-yl)-2-(2,6-dioxopiperidin-3-yl)isoindoline-1,3-dione (23b). Following general method, compound 23b was obtained from 21b. Yield 90%. $^1$H NMR (600 MHz, $CDCl_3$) δ 8.23 (s, 1H), 7.94-7.89 (m, 1H), 7.86-7.82 (m, 1H), 7.81-7.78 (m, 1H), 4.99 (dd, J=12.6, 5.4 Hz, 1H), 4.46 (s, 2H), 3.85-3.78 (m, 4H), 3.76-3.72 (m, 4H), 3.70-3.67 (m, 2H), 3.28-3.19 (m, 2H), 2.98-2.72 (m, 3H), 2.21-2.13 (m, 1H) ppm. LC-MS (ESI): m/z 444.2 $[M+H]^+$.

Preparation of 3-(4-(3-(2-(2-(2-Aminoethoxy)ethoxy)ethoxy)prop-1-yn-1-yl)-1-oxoisoindolin-2-yl)piperidine-2,6-dione (23c). Following general method, compound 23c was obtained from 21c. Yield 82%. $^1$H NMR (600 MHz, $CDCl_3$) δ 8.92 (s, 1H), 7.87-7.84 (m, 1H), 7.65-7.62 (m, 1H), 7.48 (t, J=7.7 Hz, 1H), 5.25-5.23 (m, 1H), 4.53-4.40 (m, 4H), 3.77-3.66 (m, 10H), 3.25-3.18 (m, 2H), 2.95-2.79 (m, 2H), 2.49-2.39 (m, 1H), 2.21-2.18 (m, 1H) ppm. LC-MS (ESI): m/z 430.2 $[M+H]^+$.

Preparation of 3-(5-(3-(2-(2-(2-Aminoethoxy)ethoxy)ethoxy)prop-1-yn-1-yl)-1-oxoisoindolin-2-yl)piperidine-2,6-dione (23d). Following general method, compound 23d was obtained from 21d. Yield 92%. $^1$H NMR (600 MHz, $CD_3OD$) δ7.82-7.78 (m, 1H), 7.68 (s, 1H), 7.63-7.59 (m, 1H), 5.17 (dd, J=13.4, 5.2 Hz, 1H), 4.58-4.45 (m, 4H), 3.84-3.80 (m, 2H), 3.75-3.70 (m, 8H), 3.17-3.10 (m, 2H), 2.98-2.89 (m, 1H), 2.86-2.79 (m, 1H), 2.56-2.47 (m, 1H), 2.24-2.16 (m, 1H) ppm. LC-MS (ESI): m/z 430.2 $[M+H]^+$.

Preparation of 4-(3-(2-(2-(2-Aminoethoxy)ethoxy)ethoxy)propyl)-2-(2,6-dioxopiperidin-3-yl)isoindoline-1,3-dione (24a). Following general method, compound 24a was obtained from 22a. Yield 92%. $^1$H NMR (600 MHz, $CDCl_3$) δ 8.85 (s, 1H), 7.78-7.75 (m, 1H), 7.70-7.67 (m, 1H), 7.56 (dd, J=7.6, 1.0 Hz, 1H), 5.05-5.00 (m, 1H), 3.87-3.80 (m, 2H), 3.77-3.57 (m, 10H), 3.30-3.16 (m, 3H), 3.12-3.03 (m, 1H), 2.97-2.73 (m, 3H), 2.22-2.17 (m, 1H), 2.02-1.87 (m, 2H) ppm. LC-MS (ESI): m/z 448.2 $[M+H]^+$.

Preparation of 5-(3-(2-(2-(2-Aminoethoxy)ethoxy)ethoxy)propyl)-2-(2,6-dioxopiperidin-3-yl)isoindoline-1,3-dione (24b). Following general method, compound 24b was obtained from 22b. Yield 95%. $^1$H NMR (600 MHz, $CDCl_3$) δ 8.59 (s, 1H), 7.80-7.77 (m, 1H), 7.73-7.70 (m, 1H), 7.59-7.56 (m, 1H), 5.01-4.95 (m, 1H), 3.80-3.26 (m, 14H), 2.95-2.71 (m, 5H), 2.18-2.12 (m, 1H), 1.98-1.68 (m, 2H) ppm. LC-MS (ESI): m/z 448.2 $[M+H]^+$.

Preparation of 3-(4-(3-(2-(2-(2-Aminoethoxy)ethoxy)ethoxy)propyl)-1-oxoisoindolin-2-yl)piperidine-2,6-dione (24c). Following general method, compound 24c was obtained from 22c. Yield 84%. $^1$H NMR (600 MHz, $CDCl_3$) δ 9.22 (s, 1H), 7.78-7.65 (m, 1H), 7.48-7.36 (m, 2H), 5.29-5.20 (m, 1H), 4.54-4.28 (m, 2H), 3.84-3.41 (m, 12H), 3.25-3.12 (m, 2H), 2.98-2.59 (m, 4H), 2.48-2.18 (m, 2H), 1.99-1.65 (m, 2H) ppm. LC-MS (ESI): m/z 434.2 $[M+H]^+$.

Preparation of 3-(5-(3-(2-(2-(2-Aminoethoxy)ethoxy)ethoxy)propyl)-1-oxoisoindolin-2-yl)piperidine-2,6-dione (24d). Following general method, compound 24d was obtained from 22d. Yield 90%. $^1$H NMR (600 MHz, $CDCl_3$) δ 8.42-7.98 (m, 1H), 7.82-7.75 (m, 1H), 7.34-7.28 (m, 2H), 5.29-5.18 (m, 1H), 4.56-4.32 (m, 2H), 3.82-3.12 (m, 14H), 2.95-2.67 (m, 4H), 2.44-2.20 (m, 2H), 1.97-1.64 (m, 2H) ppm. LC-MS (ESI): m/z 434.0 $[M+H]^+$.

General method for the preparation of degraders #26-#33. A mixture of 1 (1.0 equiv.), amine 23/24 (1.0 equiv.), HATU (1.05 equiv.), and $Et_3N$ (5.0 equiv.) in DCM was stirred at room temperature for 1 h. The mixture was poured into water and extracted with DCM. The organic layer was washed with $NH_4Cl$ (aq.)×1, brine×1, dried over anhydrous $Na_2SO_4$, filtered and concentrated under vacuum. The crude product was purified by flash column chromatography to afford the desired compound.

Preparation of 2-(5-(1-(adamantan-1-ylmethyl)-5-methyl-1H-pyrazol-4-yl)-6-((2-(2-(2-((3-(2-(2,6-dioxopiperidin-3-yl)-1,3-dioxoisoindolin-4-yl)prop-2-yn-1-yl)oxy)ethoxy)ethoxy)ethyl)carbamoyl)pyridin-2-yl)-N-(benzo[d]thiazol-2-yl)-1,2,3,4-tetrahydroisocuinoline-8-carboxamide (degrader #26). Following general method, degrader #26 was obtained from 1 and 23a (22.1 mg, yield 89%). $^1$H NMR (600 MHz, $CDCl_3$) δ 8.10-7.98 (m, 2H), 7.87-7.80 (m, 2H), 7.76-7.65 (m, 2H), 7.56-7.51 (m, 1H), 7.46-7.36 (m, 3H), 7.35-7.30 (m, 1H), 7.14 (d, J=7.7 Hz, 1H), 6.96 (t, J=7.6 Hz, 1H), 6.85 (d, J=8.7 Hz, 1H), 5.08-4.97 (m, 3H), 4.43-4.32 (m, 2H), 3.90-3.83 (m, 2H), 3.80-3.62 (m, 6H), 3.59-3.45 (m, 8H), 2.99 (t, J=6.1 Hz, 2H), 2.92-2.69 (m, 3H), 2.18-2.13 (m, 1H), 2.05 (s, 3H), 2.00-1.94 (m, 3H), 1.70-1.57 (m, 12H) ppm. LC-MS (ESI): m/z 1084.4 $[M+H]^+$.

Preparation of 2-(5-(1-(adamantan-1-ylmethyl)-5-methyl-1H-pyrazol-4-yl)-6-((2-(2-(2-((3-(2-(2,6-dioxopiperidin-3-yl)-1,3-dioxoisoindolin-5-yl)prop-2-yn-1-yl)oxy)ethoxy)ethoxy)ethyl)carbamoyl)pyridin-2-yl)-N-(benzo[d]thiazol-2-yl)-1,2,3,4-tetrahydroisocuinoline-8-carboxamnide (degrader #27). Following general method, degrader #27 was obtained from 1 and 23b (11.5 mg, yield 46%). $^1$H NMR (600 MHz, $CDCl_3$) δ 8.17-8.10 (m, 2H), 7.87-7.84 (m, 11H), 7.83-7.79 (m, 2H), 7.73 (s, 11H), 7.52-7.45 (m, 2H), 7.43 (d, J=8.6 Hz, 11H), 7.40 (s, 1H), 7.36-7.33 (m, 1H), 7.03-6.98 (m, 1H), 6.93 (d, J=8.7 Hz, 1H), 6.74 (t, J=7.6 Hz, 1H), 5.07-4.98 (m, 2H), 4.93-4.85 (m, 1H), 4.50 (s, 2H), 4.08-3.99 (m, 2H), 3.83-3.67 (m, 10H), 3.65-3.55 (m, 4H), 3.01-2.81 (m, 5H), 2.25-2.19 (m, 1H), 2.08 (s, 3H), 2.00-1.97 (m, 3H), 1.70-1.61 (m, 12H) ppm. LC-MS (ESI): m/z 1084.6 [M+H]).

Preparation of 2-(5-(1-(adamantan-1-ylmethyl)-5-methyl-1H-pyrazol-4-yl)-6-((2-(2-(2-((3-(2-(2,6-dioxopiperidin-3-yl)-1-oxoisoindolin-4-yl)prop-2-yn-1-yl)oxy)ethoxy)ethoxy)ethyl)carbamoyl)pyridin-2-yl)-N-(benzo[d]thiazol-2-yl)-1,2,3,4-tetrahydroisoguinoline-8-carboxamide (degrader #28). Following general method, degrader #28 was obtained from 1 and 23c (22.0 mg, yield 89%). $^1$H NMR (600 MHz, $CDCl_3$) δ 8.10 (d, J=8.1 Hz, 1H), 7.98 (t, J=5.6 Hz, 1H), 7.89 (dd, J=7.6, 1.0 Hz, 1H), 7.86-7.82 (m, 1H), 7.66 (dd, J=7.7, 1.0 Hz, 1H), 7.58 (dd, J=7.8, 1.2 Hz, 1H), 7.52 (t, J=7.6 Hz, 1H), 7.50-7.45 (m, 1H), 7.42 (d, J=8.6 Hz, 1H), 7.38 (s, 1H), 7.37-7.32 (m, 1H), 7.07 (dd, J=7.7, 1.2 Hz, 1H), 6.89 (d, J=8.7 Hz, 1H), 6.74 (t, J=7.7 Hz, 1H), 5.28 (dd, J=13.5, 5.2 Hz, 1H), 5.17-4.88 (m, 2H), 4.39-4.24 (m, 4H), 4.06-3.98 (m, 1H), 3.89-3.81 (m, 1H), 3.71-3.50 (m, 14H), 3.01 (t, J=6.0 Hz, 2H), 2.95-2.81 (m, 2H), 2.46-2.35 (m, 1H), 2.25-2.19 (m, 1H), 2.07 (s, 3H), 2.00-1.95 (m, 3H), 1.70-1.60 (m, 12H) ppm. LC-MS (ESI): m/z 1070.5 $[M+H]^+$.

Preparation of 2-(5-(1-(adamantan-1-ylmethyl)-5-methyl-1H-pyrazol-4-yl)-6-((2-(2-(2-((3-(2-(2,6-dioxopiperidin-3-yl)-1-oxoisoindolin-5-yl)prop-2-yn-1-yl)oxy)ethoxy)ethoxy)ethyl)carbamoyl)pyridin-2-yl)-N-(benzo[d]thiazol-2-yl)-1,2,3,4-tetrahydroisoguinoline-8-carboxamide (degrader #29). Following general method, degrader #29 was obtained from 1 and 23d (17.3 mg, yield 70%). $^1$H NMR (600 MHz, $CDCl_3$) δ 8.13 (t, J=5.8 Hz, 1H), 8.10 (d, J=8.1 Hz, 1H), 7.87-7.83 (m, 2H), 7.62-7.58 (m, 1H), 7.53-7.45 (m, 2H), 7.44-7.32 (m, 4H), 7.00 (d, J=7.5 Hz, 1H), 6.91 (d, J=8.7 Hz, 1H), 6.60 (t, J=7.7 Hz, 1H), 5.27 (dd, J=13.6, 5.3 Hz, 1H), 5.09-4.77 (m, 2H), 4.48 (s, 2H), 4.24-4.02 (m, 3H), 4.00-3.91 (m, 1H), 3.83-3.77 (m, 4H), 3.73-3.67 (m, 6H), 3.64-3.55 (m, 4H), 3.02-2.85 (m, 4H), 2.41-2.23 (m, 2H), 2.08 (s, 3H), 2.00-1.97 (m, 3H), 1.70-1.61 (m, 12H) ppm. LC-MS (ESI): m/z 1070.4 $[M+H]^+$.

Preparation of 2-(5-(1-(adamantan-1-ylmethyl)-5-methyl-1H-pyrazol-4-yl)-6-((2-(2-(2-(3-(2-(2,6-dioxopiperidin-3-yl)-1,3-dioxoisoindolin-4-yl)propoxy)ethoxy)ethoxy)ethyl)carbamoyl)pyridin-2-yl)-N-(benzo[d]thiazol-2-yl)-1,2,3,4-tetrahydroisociuinoline-8-carboxamide (degrader #30). Following general method, degrader #30 was obtained from 1 and 24a (16.6 mg, yield 66%). $^1$H NMR (600 MHz, $CDCl_3$) δ 8.13 (d, J=8.1 Hz, 1H), 8.10-8.06 (m, 1H), 7.86-7.83 (m, 1H), 7.78-7.74 (m, 1H), 7.70 (t, J=7.5 Hz, 1H), 7.61-7.58 (m, 1H), 7.52-7.46 (m, 2H), 7.44-7.38 (m, 2H), 7.36-7.32 (m, 1H), 7.00-6.97 (m, 1H), 6.90 (d, J=8.7 Hz, 1H), 6.61 (t, J=7.6 Hz, 1H), 5.04-4.93 (m, 3H), 4.04-3.92 (m, 2H), 3.71 (s, 2H), 3.63-3.49 (m, 12H), 3.42-3.36 (m, 2H), 3.09-2.86 (m, 6H), 2.80-2.73 (m, 1H), 2.21-2.15 (m, 1H), 2.08 (s, 3H), 2.00-1.97 (m, 3H), 1.86-1.76 (m, 2H), 1.71-1.62 (m, 12H) ppm. LC-MS (ESI): m/z 1088.7 $[M+H]^+$.

Preparation of 2-(5-(1-(adamantan-1-ylmethyl)-5-methyl-1H-pyrazol-4-yl)-6-((2-(2-(2-(3-(2-(2,6-dioxopiperidin-3-yl)-1,3-dioxoisoindolin-5-yl)propoxy)ethoxy)ethoxy)ethyl)carbamoyl)pyridin-2-yl)-N-(benzo[d]thiazol-2-yl)-1,2,3,4-tetrahydroisociuinoline-8-carboxamide (degrader #31). Following general method, degrader #31 was obtained from 1 and 24b (14.2 mg, yield 57%). $^1$H NMR (600 MHz, $CDCl_3$) δ 8.16 (t, J=5.7 Hz, 1H), 8.11 (d, J=8.1 Hz, 1H), 7.86-7.83 (m, 1H), 7.76 (d, J=7.5 Hz, 1H), 7.63 (d, J=1.4 Hz, 1H), 7.60-7.57 (m, 1H), 7.52-7.44 (m, 2H), 7.42 (d, J=8.7 Hz, 1H), 7.39 (s, 1H), 7.35-7.32 (m, 1H), 7.03-6.99 (m, 1H), 6.92 (d, J=8.7 Hz, 1H), 6.83 (t, J=7.6 Hz, 1H), 5.01 (dd, J=12.8, 5.3 Hz, 1H), 4.97 (s, 2H), 4.04-3.94 (m, 2H), 3.72-3.54 (m, 14H), 3.51-3.45 (m, 2H), 3.00-2.76 (m, 7H), 2.22-2.15 (m, 1H), 2.08 (s, 3H), 2.02-1.95 (m, 5H), 1.70-1.61 (m, 12H) ppm. LC-MS (ESI): m/z 1088.5 $[M+H]^+$.

Preparation of 2-(5-(1-(adamantan-1-ylmethyl)-5-methyl-1H-pyrazol-4-yl)-6-((2-(2-(2-(3-(2-(2,6-dioxopiperidin-3-yl)-1-oxoisoindolin-4-yl)propoxy)ethoxy)ethoxylethyl)carbamoyl)pyridin-2-yl)-N-(benzo[d]thiazol-2-yl)-1,2,3,4-tetrah droisoquinoline-8-carboxamide (degrader #32).

Following general method, degrader #32 was obtained from 1 and 24c (23.0 mg, yield 93%). $^{1}H$ NMR (600 MHz, $CDCl_3$) δ 8.13 (d, J=8.1 Hz, 1H), 8.02-7.95 (m, 1H), 7.86-7.82 (m, 1H), 7.80-7.76 (m, 1H), 7.60-7.56 (m, 1H), 7.50-7.40 (m, 4H), 7.38-7.32 (m, 2H), 7.06 (d, J=7.6 Hz, 1H), 6.87 (d, J=8.7 Hz, 1H), 6.81-6.76 (m, 1H), 5.28 (dd, J=13.4, 5.1 Hz, 1H), 5.18-4.91 (m, 2H), 4.30-4.17 (m, 2H), 3.98-3.92 (m, 1H), 3.74-3.44 (m, 13H), 3.37-3.20 (m, 4H), 3.07-2.82 (m, 4H), 2.64-2.54 (m, 2H), 2.45-2.34 (m, 1H), 2.25-2.18 (m, 1H), 2.07 (s, 3H), 1.99-1.96 (m, 3H), 1.85-1.75 (m, 2H), 1.70-1.61 (m, 12H) ppm. LC-MS (ESI): m/z 1074.9 [M+H]+.

Preparation of 2-(5-(1-(adamantan-1-ylmethyl)-5-methyl-1H-pyrazol-4-yl)-6-((2-(2-(2-(3-(2-(2,6-dioxopiperidin-3-yl)-1-oxoisoindolin-5-yl)propoxy)ethoxy)ethoxy)ethyl)carbamoyl)pyridin-2-yl)-N-(benzo[d]thiazol-2-yl) 1,2,3,4-tetrahydroisociuinoline-8-carboxamide (degrader #33). Following general method, degrader #33 was obtained from 1 and 24d (11.2 mg, yield 45%). $^{1}H$ NMR (600 MHz, $CDCl_3$) δ 8.19-8.13 (m, 2H), 7.87-7.80 (m, 2H), 7.56 (dd, J=7.7, 1.3 Hz, 1H), 7.52-7.47 (m, 1H), 7.44-7.32 (m, 4H), 7.19 (s, 1H), 6.97 (d, J=7.6 Hz, 1H), 6.91 (d, J=8.7 Hz, 1H), 6.69 (t, J=7.6 Hz, 1H), 5.27 (dd, J=13.5, 5.2 Hz, 1H), 5.06-4.83 (m, 2H), 4.26-4.17 (m, 2H), 4.10-4.04 (m, 1H), 3.95-3.89 (m, 1H), 3.73-3.69 (m, 6H), 3.67-3.64 (m, 2H), 3.63-3.59 (m, 4H), 3.57-3.49 (m, 4H), 2.99-2.81 (m, 6H), 2.42-2.34 (m, 1H), 2.27-2.22 (m, 1H), 2.08 (s, 3H), 2.01-1.95 (m, 5H), 1.70-1.61 (m, 12H) ppm. LC-MS (ESI): m/z 1074.6 [M+H]+.

Example 9: Preparation of Degraders #34-#43

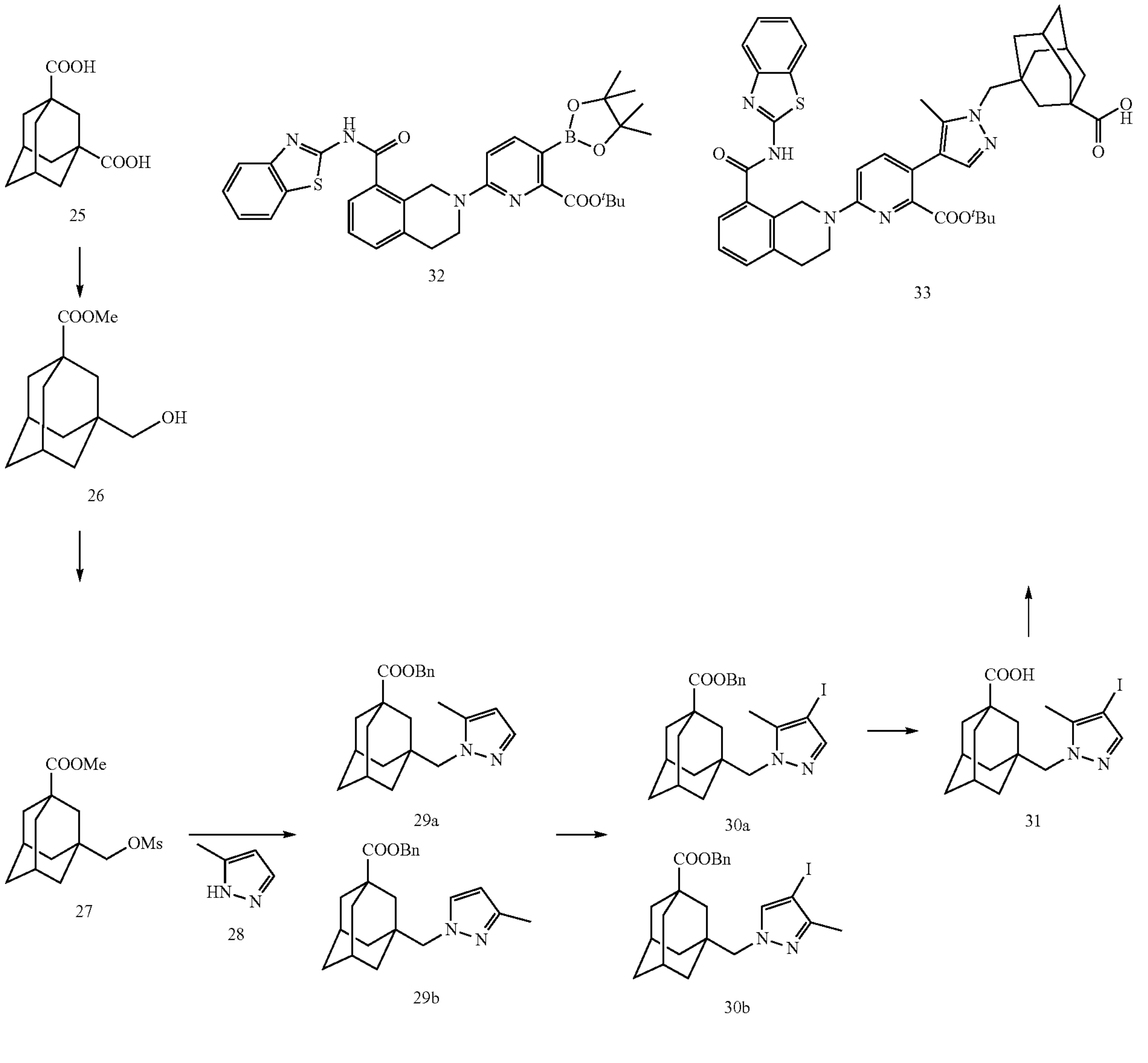

25 32 33 26 27 28 29a 29b 30a 30b 31

Preparation of methyl (1s,3r,5R,7S)-3-(hydroxymethyl) adamantane-1-carboxylate (26). To a mixture of 25 (20 g, 89.2 mmol) in THF (200 mL) was added borane dimethyl sulfide complex (10 mL, 105.3 mmol) at 0° C. The resulting solution was stirred at 0° C. for 1 h and then at room temperature overnight. It was quenched by the addition of saturated $NH_4Cl$ (aq) and diluted with water. Subsequently, the mixture was extracted with EtOAc and the organic layer was washed with water×1, brine×1, dried over anhydrous $Na_2SO_4$, filtered, and evaporated to dryness. The residue was dissolved in MeOH (150 mL) and conc. $H_2SO_4$ (10 mL) was slowly added into the solution. The resulting mixture was refluxed for 2 h and cooled to room temperature. It was diluted with water and extracted with EtOAc. The organic layer was washed with water×1, brine×1, dried over anhydrous $Na_2SO_4$, filtered, and evaporated to dryness. The crude product was purified by flash column chromatography using EtOAc and hexanes as eluents to afford the title compound (4.75 g, 24% yield). $^1$H NMR (600 MHz, $CDCl_3$) δ 3.66 (s, 3H), 3.26 (s, 2H), 2.15-2.12 (m, 2H), 1.91-1.79 (m, 4H), 1.71-1.62 (m, 4H), 1.53-1.47 (m, 4H) ppm. LC-MS (ESI): m/z 225.1 $[M+H]^+$.

Preparation of methyl (1s,3r,5R,7S)-3-(((methylsulfonyl)oxy)methyl)adamantane-1-carboxylate (27). To a mixture of 26 (4.75 g, 21.1 mmol) and $EtN_3$ (5.75 mL, 41.3 mmol) in DCM (100 mL) was added MsCl (1.85 mL, 23.4 mmol) at 0° C. Then the mixture was stirred at room temperature for 3 h. It was poured into water and extracted with EtOAc. The organic layer was washed with water×1, brine×1, dried over anhydrous $Na_2SO_4$, filtered, and evaporated to dryness. The crude product was purified by flash column chromatography using EtOAc and hexanes as eluents to afford the title compound (6.0 g, 93% yield). $^1$H NMR (600 MHz, $CDCl_3$) δ 3.83 (s, 2H), 3.66 (s, 3H), 3.01 (s, 3H), 2.17-2.14 (m, 2H), 1.92-1.88 (m, 2H), 1.83-1.78 (m, 2H), 1.74-1.63 (m, 4H), 1.56-1.55 (m, 4H) ppm. LC-MS (ESI): m/z 344.2 $[M+H+ACN]^+$.

Preparation of benzyl (1s,3r,5R,7S)-3-((5-methyl-1H-pyrazol-1-yl)methyl)adamantane-1-carboxylate (29a) and benzyl (1s,3r,5R,7S)-3-((3-methyl-1H-pyrazol-1-yl)mnethyl)adamantane-1-carboxylate (29b). A mixture of 27 (400 mg, 1.32 mmol), 28 (220 mg, 2.68 mmol), $^t$BuOK (280 mg, 2.5 mmol), and KI (22 mg, 0.13 mmol) in DMSO (9 mL) was heated under microwave irradiation at 160° C. for 1 h. The reaction was cooled to room temperature, and $Na_2CO_3$ (421 mg, 3.97 mmol) and BnBr (463 μL, 3.90 mmol) was added into the solution. The resulting mixture was stirred at room temperature overnight. Then it was poured into water and extracted with EtOAc. The organic layer was washed with water×2, brine×1, dried over anhydrous $Na_2SO_4$, filtered, and evaporated to dryness. The crude product was purified by flash column chromatography using EtOAc and hexanes as eluents to afford the title compound as a mixture (291 mg, 61% yield), which was used directly in the next step. LC-MS (ESI): m/z 365.1 $[M+H]^+$.

Preparation of benzyl (1s,3r,5R,7S)-3-((4-iodo-5-methyl-1H-pyrazol-1-yl)methyl)adamantane-1-carboxylate (30a) and benzyl (1s,3r,5R,7S)-3-((4-iodo-3-methyl-1H-pyrazol-1-yl)methyl)adamantane-1-carboxylate (30b). A mixture of 29 (290 mg, 0.80 mmol) and NIS (215 mg, 0.96 mmol) in DCM (20 mL) at 0° C. for 1 h and then rt for 2 h. The reaction mixture was poured into water and extracted with EtOAc. The organic layer was washed with 10% $Na_2S_2O_3$ (aq)×1, brine×1, dried over anhydrous $Na_2SO_4$, filtered, and evaporated to dryness. The crude product was purified by flash column chromatography using toluene and $Et_2O$ as eluents to afford compounds 30a (80 mg, 20% yield) and 30b (18 mg, 5% yield). $^1$H NMR and LC-MS data for compound 30a. $^1$H NMR (600 MHz, $CDCl_3$) δ 7.46 (s, 1H), 7.42-7.32 (m, 5H), 5.12 (s, 2H), 3.85 (s, 2H), 2.29 (s, 3H), 2.16-2.11 (m, 2H), 1.93-1.88 (m, 2H), 1.85-1.80 (m, 2H), 1.73 (s, 2H), 1.70-1.64 (m, 1H), 1.60-1.52 (m, 5H). LC-MS (ESI): m/z 491.2 $[M+H]^+$. $^1$H NMR and LC-MS data for compound 30b. $^1$H NMR (600 MHz, $CDCl_3$) δ 7.41-7.35 (m, 2H), 7.34-7.30 (m, 3H), 7.25 (s, 1H), 5.10 (s, 2H), 3.76 (s, 2H), 2.23 (s, 3H), 2.12 (s, 2H), 1.88 (d, J=12.5 Hz, 2H), 1.79 (d, J=12.5 Hz, 2H), 1.69-1.62 (m, 4H), 1.50-1.44 (m, 4H) ppm. LC-MS (ESI): m/z 491.1 $[M+H]^+$.

Preparation of (1s,3r,5R,7S)-3-((4-iodo-5-methyl-1H-pyrazol-1-yl)methyl)adamantane-1-carboxylic acid (31). A mixture of 30a (330 mg, 0.67 mmol) and LiOH monohydrate (170 mg, 4.05 mmol) in THF (2 mL), MeOH (2 mL), and water (1 mL) were stirred at 45° C. for 3 h. The reaction mixture was cooled to room temperature and the pH was adjusted to 5-6 by the addition of 1N HCl (aq). The resulting solution was poured into water and extracted with EtOAc. The organic layer was washed with water×1, brine×1, dried over anhydrous $Na_2SO_4$, filtered, and evaporated to dryness. The crude product was purified by flash column chromatography using EtOAc and hexanes as eluents to afford the title compound (265 mg, 99% yield). $^1$H NMR (600 MHz, $CDCl_3$) δ 7.48 (s, 1H), 3.84 (s, 2H), 2.29 (s, 3H), 2.17-2.11 (m, 2H), 1.90-1.84 (m, 2H), 1.83-1.78 (m, 2H), 1.75 (s, 2H), 1.69-1.58 (m, 211), 1.57-1.49 (m, 4H) ppm. LC-MS (ESI): m/z 401.0 $[M+H]^+$.

Preparation of (1r,3r)-3-((4-(6-(8-(benzo[d]thiazol-2-ylcarbamoyl)-3,4-dihydroisoquinolin-2(1H)-yl)-2-(tert-butoxycarbonyl)pyridin-3-yl)-5-methyl-1H-pyrazol-1-yl)methyl)adamantane-1-carboxylic acid (33). A mixture of 32 (40 mg, 0.065 mmol), $Pd(PPh_3)_4$ (8.0 mg, 0.007 mmol) and, $Cs_2CO_3$ (60 mg, 0.185 mmol) in DMF (1.0 mL), 1,4-dioxane (0.7 mL), and $H_2O$ (0.4 mL) was heated under microwave irradiation at 140° C. for 20 min. The reaction was cooled to room temperature, poured into water and extracted with EtOAc. The organic layer was washed with water×2, brine×1, dried over anhydrous $Na_2SO_4$, filtered, and evaporated to dryness. The crude product was purified by flash column chromatography using EtOAc and hexanes as eluents to afford the title compound (32 mg, 65% yield). $^1$H NMR (600 MHz, $CDCl_3$) δ 7.86-7.79 (m, 1H), 7.68-7.60 (m, 2H), 7.45-7.37 (m, 2H), 7.36-7.26 (m, 3H), 7.26-7.23 (m, 1H), 6.80 (d, J=8.8 Hz, 1H), 5.02 (s, 2H), 4.03 (t, J=5.9 Hz, 2H), 3.80-3.77 (m, 2H), 3.02 (t, J=6.0 Hz, 2H), 2.15-2.09 (m, 5H), 1.88-1.80 (m, 4H), 1.76 (s, 2H), 1.65-1.54 (m, 6H), 1.31 (s, 9H) ppm. LC-MS (ESI): m/z 759.2 $[M+H]^+$.

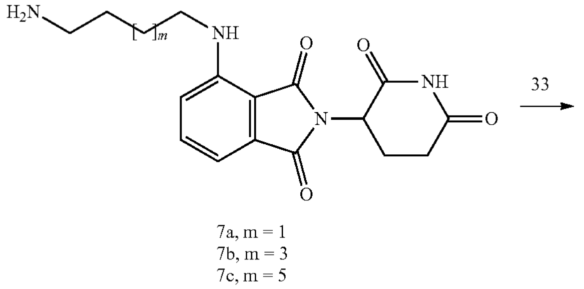

7a, m = 1
7b, m = 3
7c, m = 5
7d, m = 7
7e, m = 9

-continued
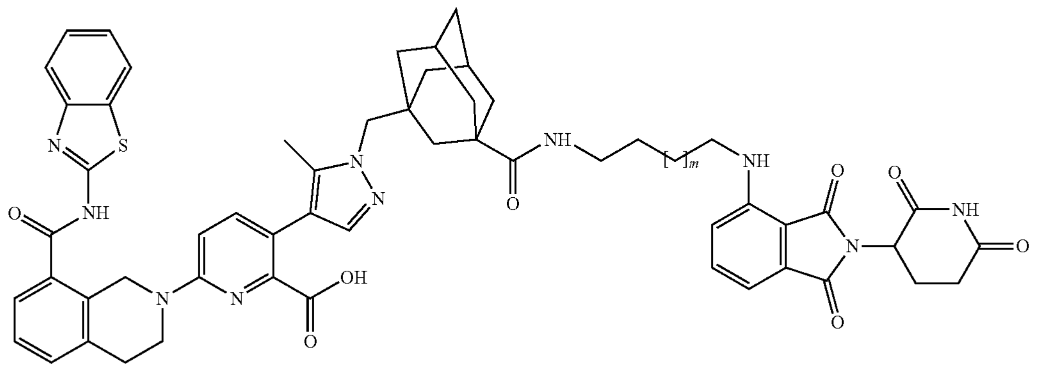
degrader #34, m = 1
degrader #35, m = 3
degrader #36, m = 5
degrader #37, m = 7
degrader #38, m = 9
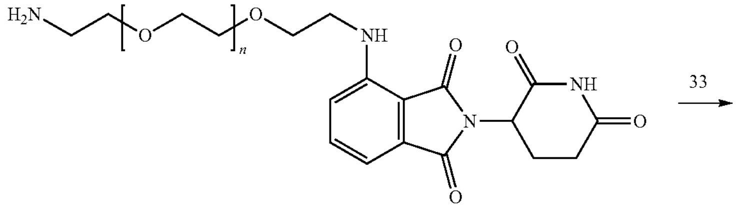
7d, n = 1
7f, n = 3
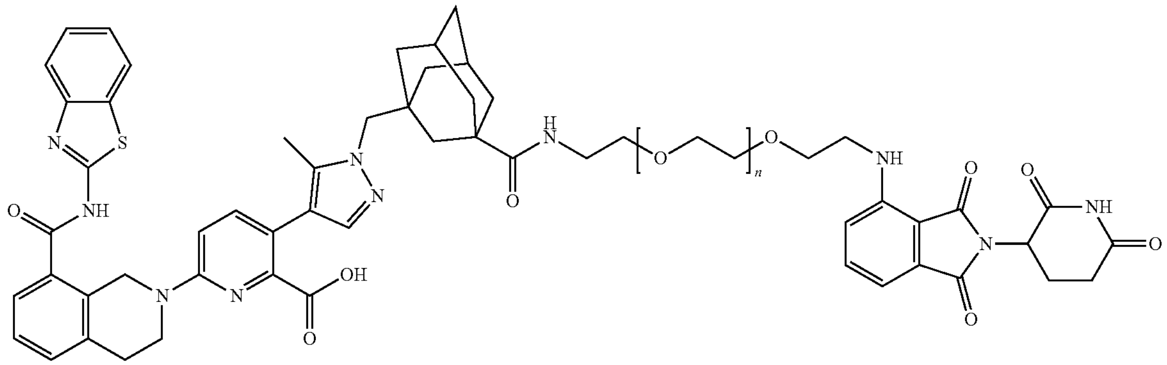
degrader #39, n = 0
degrader #40, n = 2
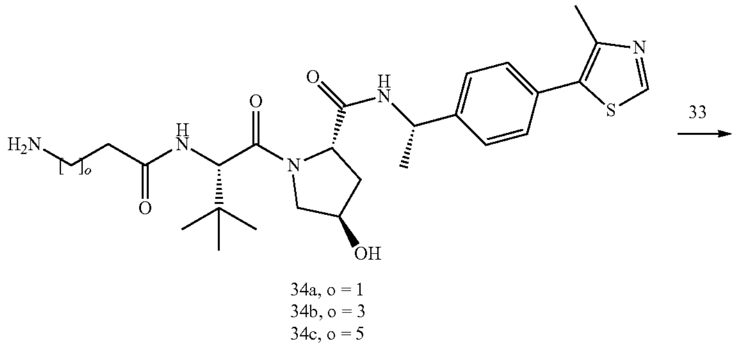
34a, o = 1
34b, o = 3
34c, o = 5

-continued

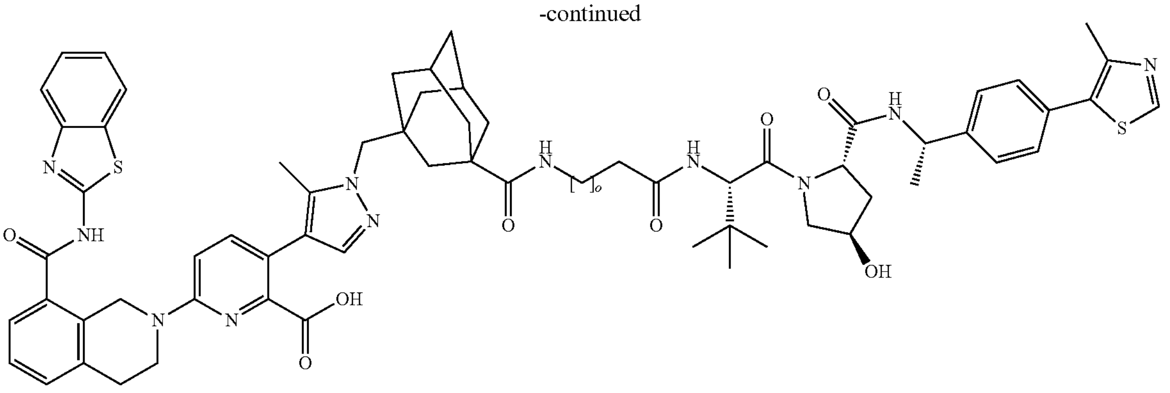

degrader #41, o = 1
degrader #42, o = 3
degrader #43, o = 5

General method for the preparation of degraders #34-#43. A mixture of 33 (1.0 equiv.), amine 7/34 (1.0 equiv.), HATU (1.05 equiv.), and $Et_3N$ (5.0 equiv.) in DCM was stirred at room temperature for 1 h. The mixture was poured into water and extracted with DCM. The organic layer was washed with $NH_4Cl$ (aq.)×1, brine×1, dried over anhydrous $Na_2SO_4$, filtered and concentrated under vacuum. The crude product was purified by flash column chromatography to afford the desired compound.

Preparation of 6-(8-(benzo[d]thiazol-2-ylcarbamoyl)-3,4-dihydroisoquinolin-2(1H)-yl)-3-(1-(((1r,3r)-3-((4-((2-(2,6-dioxopiperidin-3-yl)-1,3-dioxoisoindolin-4-yl)amino)butyl) carbamoyl)adamantan-1-yl)methyl)-5-methyl-1H-pyrazol-4-yl)picolinic acid (degrader #34). Following general method B, degrader #34 was obtained from 7a and 33 (8.5 mg, yield 41%). $^1$H NMR (600 MHz, $CDCl_3$) δ 8.74 (s, 11H), 7.83 (d, J=7.9 Hz, 1H), 7.71 (d, J=8.2 Hz, 1H), 7.64-7.54 (m, 2H), 7.44-7.38 (m, 3H), 7.35-7.29 (m, 4H), 7.06 (d, J=8.8 Hz, 1H), 7.00 (d, J=7.0 Hz, 1H), 6.71-6.64 (m, 1H), 6.56 (d, J=8.7 Hz, 1H), 6.06-5.99 (m, 1H), 5.31-5.15 (m, 2H), 4.77-4.65 (m, 1H), 3.92-3.83 (m, 4H), 3.39-3.19 (m, 2H), 3.17-3.07 (m, 2H), 3.06-2.97 (m, 2H), 2.77-2.68 (m, 1H), 2.63-2.53 (m, 2H), 2.16-1.98 (m, 8H), 1.94-1.62 (m, 14H) ppm. LC-MS (ESI): m/z 1029.3 $[M+H]^+$.

Preparation of 6-(8-(benzo[d]thiazol-2-ylcarbamoyl)-3,4-dihydroisoquinolin-2(1H)-yl)-3-(1-(((1r,3r)-3-((6-((2-(2,6-dioxopiperidin-3-yl)-1,3-dioxoisoindolin-4-yl)amino) hexyl)carbamoyl)adamantan-1-yl)methyl)-5-methyl-1H-pyrazol-4-yl)picolinic acid (degrader #35). Following general method B, degrader #35 was obtained from 7b and 33 (9.1 mg, yield 43%). $^1$H NMR (600 MHz, $CDCl_3$) δ 10.58 (s, 11H), 7.97 (d, J=8.1 Hz, 1H), 7.83 (d, J=7.9 Hz, 11H), 7.57-7.52 (m, 2H), 7.49-7.41 (m, 2H), 7.37 (s, 1H), 7.36-7.31 (m, 1H), 7.24-7.20 (m, 1H), 7.16 (t, J=7.6 Hz, 1H), 7.06 (d, J=7.1 Hz, 11H), 7.01 (d, J=8.8 Hz, 11H), 6.78 (d, J=8.6 Hz, 11H), 6.56-6.47 (m, 1H), 6.04-5.99 (m, 11H), 5.13-5.00 (m, 2H), 4.87 (dd, J=12.4, 5.4 Hz, 1H), 3.87-3.75 (m, 4H), 3.30-3.18 (m, 2H), 3.15-2.95 (m, 4H), 2.89-2.66 (m, 3H), 2.14-1.94 (m, 8H), 1.62-1.54 (m, 12H), 1.38-1.26 (m, 6H) ppm. LC-MS (ESI): m/z 1057.5 $[M+H]^+$.

Preparation of 6-(8-(benzo[d]thiazol-2-ylcarbamoyl)-3,4-dihydroisoquinolin-2(1H)-yl)-3-(1-(((1r,3r)-3-((8-((2-(2,6-dioxopiperidin-3-yl)-1,3-dioxoisoindolin-4-yl)amino)octyl) carbamoyl)adamantan-1-yl)methyl)-5-methyl-1H-pyrazol-4-yl)picolinic acid (degrader #36). Following general method B, degrader #36 was obtained from 7c and 33 (9.5 mg, yield 44%). $^1$H NMR (600 MHz, $CDCl_3$) δ 11.22 (s, 1H), 8.06 (d, J=8.1 Hz, 1H), 7.86 (d, J=7.9 Hz, 1H), 7.60-7.52 (m, 3H), 7.50-7.45 (m, 1H), 7.39 (s, 1H), 7.38-7.34 (m, 1H), 7.13 (d, J=7.1 Hz, 2H), 7.07-6.98 (m, 2H), 6.88 (d, J=8.6 Hz, 11H), 6.55-6.47 (m, 11H), 6.11-6.05 (m, 11H), 5.13-5.00 (m, 2H), 4.93 (dd, J=12.6, 5.4 Hz, 1H), 3.95-3.80 (m, 4H), 3.29-3.12 (m, 4H), 3.05-2.74 (m, 5H), 2.15-1.96 (m, 8H), 1.69-1.51 (m, 12H), 1.37-1.26 (m, 10H). LC-MS (ESI): m/z 1085.5 $[M+H]^+$.

Preparation of 6-(8-(benzo[d]thiazol-2-ylcarbamoyl)-3,4-dihydroisoquinolin-2(1H)-yl)-3-(1-(((1r,3r)-3-((10-((2-(2,6-dioxopiperidin-3-yl)-1,3-dioxoisoindolin-4-yl)amino)decyl) carbamoyl)adamantan-1-yl)methyl)-5-methyl-1H-pyrazol-4-yl)picolinic acid (degrader #37). Following general method B, degrader #37 was obtained from 7g and 33 (5.6 mg, yield 25%). $^1$H NMR (600 MHz, $CDCl_3$) δ 11.28 (s, 1H), 8.09 (d, J=8.1 Hz, 1H), 7.88-7.82 (m, 1H), 7.60-7.51 (m, 3H), 7.49-7.45 (m, 1H), 7.38 (s, 1H), 7.37-7.32 (m, 1H), 7.15-7.09 (m, 2H), 7.03 (d, J=8.8 Hz, 1H), 6.96-6.87 (m, 2H), 6.50-6.42 (m, 1H), 6.13-6.06 (m, 1H), 5.17-4.97 (m, 2H), 4.93 (dd, J=12.6, 5.4 Hz, 1H), 3.95-3.81 (m, 4H), 3.27-3.16 (m, 4H), 3.05-2.73 (m, 5H), 2.15-1.94 (m, 8H), 1.61-1.51 (m, 12H), 1.34-1.22 (m, 14H) ppm. LC-MS (ESI): m/z 1113.9 $[M+H]^+$.

Preparation of 6-(8-(benzo[d]thiazol-2-ylcarbamoyl)-3,4-dihydroisoquinolin-2(1H)-yl)-3-(1-(((1r,3r)-3-((12-((2-(2,6-dioxopiperidin-3-yl)-1,3-dioxoisoindolin-4-yl)amino)dodecyl)carbamoyl)adamantan-1-yl)methyl)-5-methyl-1H-pyrazol-4-yl)picolinic acid (degrader #38). Following general method B, degrader #34 was obtained from 7 h and 33 (7.8 mg, yield 34%). $^1$H NMR (600 MHz, $CDCl_3$) δ 10.70 (s, 1H), 8.07 (d, J=8.1 Hz, 1H), 7.88 (d, J=8.0 Hz, 1H), 7.68 (d, J=7.8 Hz, 1H), 7.61-7.49 (m, 3H), 7.44 (s, 1H), 7.40 (t, J=7.6 Hz, 1H), 7.25 (d, J=7.5 Hz, 1H), 7.14 (d, J=7.0 Hz, 1H), 7.07-7.01 (m, 2H), 6.92 (d, J=8.6 Hz, 1H), 6.43 (t, J=5.7 Hz, 11H), 6.24-6.15 (m, 11H), 5.25-5.07 (m, 2H), 4.95 (dd, J=12.5, 5.4 Hz, 11H), 3.95-3.84 (m, 4H), 3.31-3.20 (m, 4H), 3.08 (t, J=6.2 Hz, 2H), 2.95-2.77 (m, 3H), 2.18-2.13 (m, 3H), 2.10 (s, 3H), 2.00-1.94 (m, 2H), 1.76-1.58 (m, 12H), 1.53-1.48 (m, 2H), 1.40-1.23 (m, 16H) ppm. LC-MS (ESI): m/z 1141.7 $[M+H]^+$.

Preparation of 6-(8-(benzo[d]thiazol-2-ylcarbamoyl)-3,4-dihydroisoquinolin-2(1H)-yl)-3-(1-(((1r,3r)-3-((2-(2-((2-(2,6-dioxopiperidin-3-yl)-1,3-dioxoisoindolin-4-yl)amino) ethoxy)ethyl)carbamoyl)adamantan-1-yl)methyl)-5-methyl-1H-pyrazol-4-yl)picolinic acid (degrader #39). Following general method B, degrader #39 was obtained from 7d and 33 (6.8 mg, yield 33%). $^1$H NMR (600 MHz, $CDCl_3$) δ 10.15 (s, 1H), 7.84 (d, J=7.9 Hz, 11H), 7.79 (d, J=8.2 Hz, 1H), 7.61 (d, J=7.6 Hz, 1H), 7.53 (d, J=8.7 Hz, 1H), 7.48-7.38 (m, 3H), 7.33 (t, J=7.4 Hz, 2H), 7.27-7.22 (m, 1H), 7.07 (d, J=7.1 Hz, 1H), 7.00 (d, J=8.8 Hz, 1H), 6.84 (d, J=8.5 Hz, 1H), 6.51-6.45 (m, 1H), 6.44-6.37 (m, 1H), 5.19-5.09 (m, 2H), 4.91 (dd, J=12.3, 5.4 Hz, 1H), 3.91-3.76 (m, 4H), 3.70-3.64 (m, 2H), 3.60-3.55 (m, 2H), 3.50-3.43 (m, 2H), 3.40-3.34 (m, 2H), 3.12-3.03 (m, 2H), 2.86-2.67 (m, 3H), 2.13-2.06 (m, 6H), 1.90-1.81 (m, 2H), 1.67-1.56 (m, 10H) ppm. LC-MS (ESI): m/z 1045.7 $[M+H]^+$.

Preparation of 6-(8-(benzo[d]thiazol-2-ylcarbamoyl)-3,4-dihydroisoquinolin-2(1H)-yl)-3-(1-(((1r,3r)-3-((2-(2-(2-(2-((2-(2,6-dioxopiperidin-3-yl)-1,3-dioxoisoindolin-4-yl)amino)ethoxy)ethoxy)ethoxy)ethyl)carbamoyl)adamantan-1-yl)methyl)-5-methyl-1H-pyrazol-4-yl)picolinic acid (degrader #40). Following general method B, degrader #40 was obtained from 7f and 33 (2.8 mg, yield 12%). $^1$H NMR (600 MHz, $CDCl_3$) δ 11.07 (s, 1H), 8.04 (d, J=8.1 Hz, 1H), 7.88-7.83 (m, 1H), 7.58 (d, J=7.6 Hz, 1H), 7.54-7.43 (m, 3H), 7.38 (s, 1H), 7.36-7.32 (m, 1H), 7.22 (d, J=7.6 Hz, 1H), 7.14-7.10 (m, 2H), 6.98 (d, J=8.8 Hz, 1H), 6.88 (d, J=8.6 Hz, 1H), 6.70-6.60 (m, 1H), 6.45-6.39 (m, 1H), 5.17-5.03 (m, 2H), 4.91 (dd, J=12.3, 5.4 Hz, 1H), 3.89 (t, J=6.2 Hz, 2H), 3.81 (s, 2H), 3.65-3.51 (m, 12H), 3.44-3.38 (m, 4H), 3.09-2.99 (m, 2H), 2.91-2.71 (m, 3H), 2.13-2.05 (m, 6H), 1.95-1.88 (m, 2H), 1.63-1.59 (m, 10H) ppm. LC-MS (ESI): m/z 1133.9 $[M+H]^+$.

Preparation of 6-(8-(benzo[d]thiazol-2-ylcarbamoyl)-3,4-dihydroisoquinolin-2(1H)-yl)-3-(1-(((1S,3r)-3-((3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropyl)carbamoyl)adamantan-1-yl)methyl)-5-methyl-1H-pyrazol-4-yl)picolinic acid (degrader #41). Following general method B, degrader #41 was obtained from 34a and 33 (8.0 mg, yield 33%). $^1$H NMR (600 MHz, $CDCl_3$+$CD_3OD$) δ8.65 (s, 1H), 7.90-7.85 (m, 1H), 7.74 (d, J=8.1 Hz, 1H), 7.62 (d, J=7.5 Hz, 1H), 7.51 (d, J=8.9 Hz, 1H), 7.45 (t, J=7.6 Hz, 1H), 7.42-7.28 (m, 10H), 7.12-7.05 (m, 1H), 7.01-6.96 (m, 1H), 5.14-4.98 (m, 3H), 4.79-4.69 (m, 1H), 4.61-4.45 (m, 2H), 3.93-3.08 (m, 10H), 2.52-2.46 (m, 4H), 2.27-2.07 (m, 8H), 1.58-1.32 (m, 15H), 1.00 (s, 9H) ppm. LC-MS (ESI): m/z 1200.7 $[M+H]^+$.

Preparation of 6-(8-(benzo[d]thiazol-2-ylcarbamoyl)-3,4-dihydroisoquinolin-2(1H)-yl)-3-(1-(((1S,3r)-3-((5-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)carbamoyl)adamantan-1-yl)methyl)-5-methyl-1H-pyrazol-4-yl)picolinic acid (degrader #42). Following general method B, degrader #42 was obtained from 34b and 33 (2.2 mg, yield 9.0%). $^1$H NMR (600 MHz, $CDCl_3$) δ 8.70 (s, 1H), 7.89 (d, J=8.0 Hz, 1H), 7.78 (d, J=8.0 Hz, 1H), 7.68 (d, J=7.7 Hz, 1H), 7.56 (d, J=8.7 Hz, 1H), 7.49 (t, J=7.6 Hz, 1H), 7.45-7.33 (m, 10H), 7.03 (d, J=8.8 Hz, 1H), 6.71-6.61 (m, 1H), 6.61-6.55 (m, 1H), 5.24-5.05 (m, 3H), 4.68-4.59 (m, 2H), 4.48-4.45 (m, 1H), 4.15-4.10 (m, 1H), 3.95-3.74 (m, 5H), 3.22-3.08 (m, 4H), 2.54-2.49 (m, 4H), 2.19-2.02 (m, 8H), 1.68-1.33 (m, 19H), 1.03 (s, 9H) ppm. LC-MS (ESI): m/z 1228.6 $[M+H]^+$.

Preparation of 6-(8-(benzo[d]thiazol-2-ylcarbamoyl)-3,4-dihydroisoquinolin-2(1H)-yl)-3-(1-(((1S,3r)-3-((7-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptyl)carbamoyl)adamantan-1-yl)methyl)-5-methyl-1H-pyrazol-4-yl)picolinic acid (degrader #43). Following general method, degrader #43 was obtained from 34c and 33 (1.0 mg, yield 4.0%). $^1$H NMR (600 MHz, $CDCl_3$) δ 8.71 (s, 1H), 7.90 (d, J=8.0 Hz, 1H), 7.82 (d, J=8.2 Hz, 1H), 7.67 (d, J=7.6 Hz, 1H), 7.58-7.49 (m, 2H), 7.48-7.35 (m, 9H), 7.31 (t, J=7.7 Hz, 1H), 6.99 (d, J=8.8 Hz, 1H), 6.66 (d, J=8.8 Hz, 1H), 6.46-6.39 (m, 1H), 5.19-5.04 (m, 3H), 4.62-4.51 (m, 2H), 4.48-4.43 (m, 1H), 4.12 (d, J=11.5 Hz, 1H), 3.91-3.71 (m, 5H), 3.26-3.06 (m, 4H), 2.51 (s, 3H), 2.48-2.43 (m, 1H), 2.37-1.88 (m, 8H), 1.70-1.46 (m, 19H), 1.19-1.12 (m, 4H), 1.04 (s, 9H) ppm. LC-MS (ESI): m/z 1256.6 $[M+H]^+$.

Example 10: Cell Viability Assay

Cancer cells from acute lymphoblastic leukemia (MOLT4) were incubated with increasing concentrations of compounds of Examples 1-9 for 48 h. Cell viability was measured by tetrazolium-based MTS assay. $5\times10^4$ to $1\times10^5$ suspension cells or $3\times10^3$ to $5\times10^3$ adherent cells were seeded and treated in 96-well plates for 48 h. The $EC_{50}$ values of individual agents were calculated with GraphPad Prism.

Example 11: Protein Degradation Assays in MOLT4 Cells

MOLT4 cells and human platelets can be incubated with increasing concentrations of test compounds for 16 h. The cells can be harvested and lysed in RIPA lysis buffer supplemented with protease and phosphatase inhibitor cocktails. An equal amount of protein (20 μg/lane) can be resolved on a pre-cast 4-20% SDS-PAGE gel. Proteins can be subsequently transferred to NOVEX PVDF membranes by electrophoresis. The membranes can be blocked in blocking buffer (5% non-fat dry milk in TBS-T), and can be incubated with primary antibodies (at optimized concentrations) overnight at 4° C. After washing in TBS-T, the membranes can be incubated with an appropriate HRP-conjugated secondary antibody for 1 h at room temperature. After extensive washing, the proteins of interest can be detected with ECL western blotting detection reagents and recorded with autoradiography (Pierce Biotech, Rockford, IL, USA). The primary antibodies for Bcl-xL (Cat #2762), Bcl-2 (Cat #2872), Mcl-1 (Cat #5453) and β-actin (Cat #4970) can be purchased from Cell Signaling technology. The relative band intensity can be measured using ImageJ software and normalized to b-actin. The $DC_{50}$ (concentration with 50% degradation) can be calculated using GraphPad Prism.

Compounds of the Invention Efficiently Kill MOLT-4 Cells

Table 1 demonstrates the antiproliferative effects for various compounds of Formula (I) in MOLT-4.

| Degrader # | $EC_{50}$ MOLT-4[a] |
|---|---|
| A1331852 | +++ |
| 1 | ++ |
| 2 | ++ |
| 3 | + |
| 4 | + |
| 5 | + |
| 6 | ++ |
| 7 | ++ |
| 8 | +++ |
| 9 | +++ |
| 10 | +++ |
| 11 | +++ |
| 12 | +++ |
| 13 | +++ |

-continued

| Degrader # | $EC_{50}$ MOLT-4[a] |
|---|---|
| 14 | +++ |
| 15 | ++ |
| 16 | ++ |
| 17 | ++ |
| 18 | ++ |
| 19 | ++ |
| 20 | ++ |
| 21 | + |
| 22 | ++ |
| 23 | ++ |
| 24 | + |
| 25 | + |
| 26 | ++ |
| 27 | ++ |
| 28 | +++ |
| 29 | +++ |
| 30 | +++ |
| 31 | +++ |
| 32 | +++ |
| 33 | +++ |
| 34 | ++ |
| 35 | ++ |
| 36 | +++ |
| 37 | ++ |
| 38 | ++ |
| 39 | ++ |
| 40 | ++ |
| 41 | NA |
| 42 | NA |
| 43 | + |

[a]Cellular activity: +++ ($EC_{50}$ < 10 nM), ++ ($EC_{50}$ between 10-100 nM), + ($EC_{50}$ between 100-1000 nM), NA ($EC_{50}$ > 1000 nM)

CLAUSES

1. A compound of Formula (I), or a pharmaceutically acceptable salt, hydrate, solvate, or prodrug thereof:

$Y\text{-}L_2\text{-}R\text{-}L_1\text{-}Y_2$ Formula (I);

wherein $L_1$ is independently

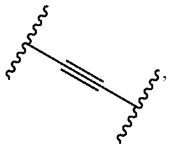,
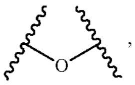,
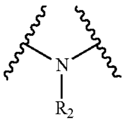,
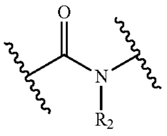,
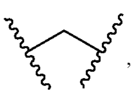,
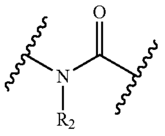,
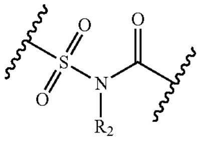,
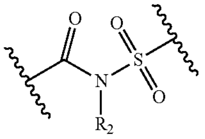, or absent;

R is independently optionally substituted $C_{1-50}$ alkylene or optionally substituted $C_{1-50}$ heteroalkylene wherein:

optionally one or more backbone carbon atoms of each instance of the optionally substituted alkylene or optionally substituted heteroalkylene are independently replaced with —C(═O)O—, —OC(═O)—, —NHC(═O)—, —C(═O)NH—, optionally substituted cycloalkylene, optionally substituted heterocycloalkylene, optionally substituted arylene, or optionally substituted heteroarylene; and optionally one or more backbone heteroatoms of each instance of the optionally substituted heteroalkylene are independently replaced with optionally substituted cycloalkylene, optionally substituted heterocycloalkylene, optionally substituted arylene, or optionally substituted heteroarylene;

$L_2$ is independently

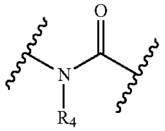,
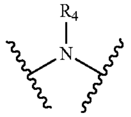,
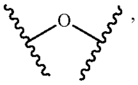,
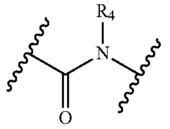,
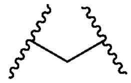,
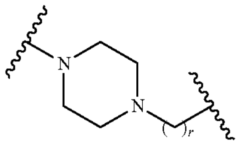,
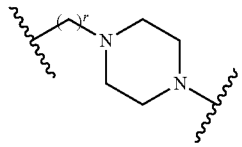,
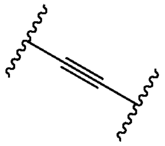, or
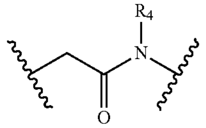;

Y is independently

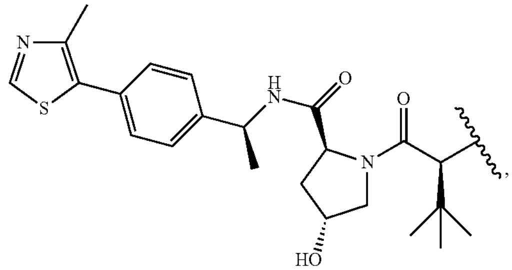,
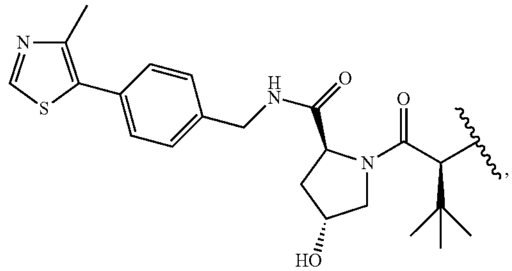,
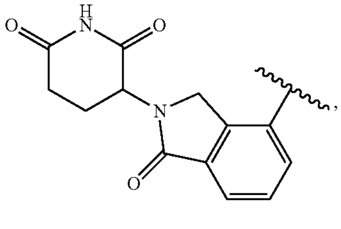,

-continued
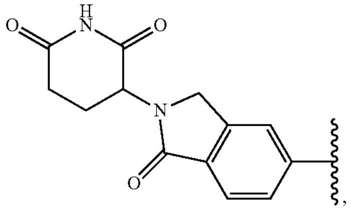
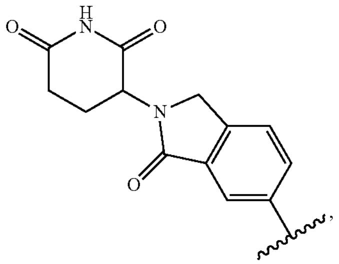
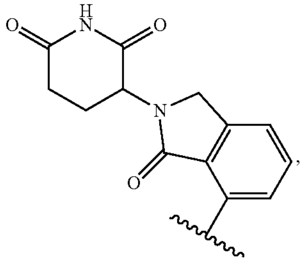
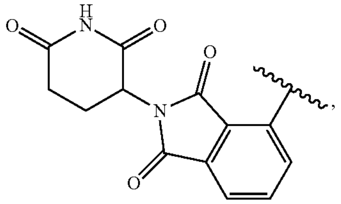
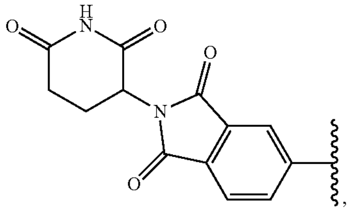
-continued
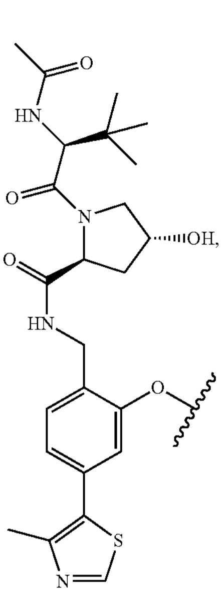
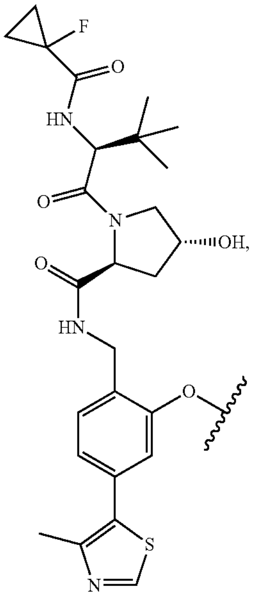
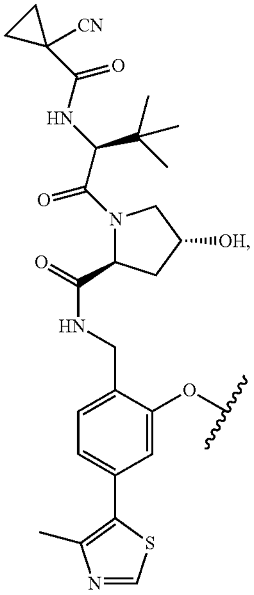
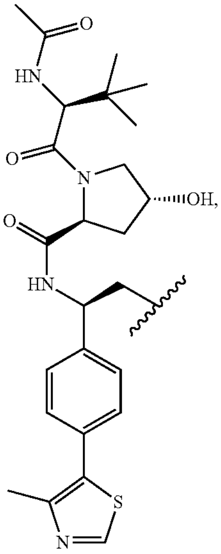

-continued
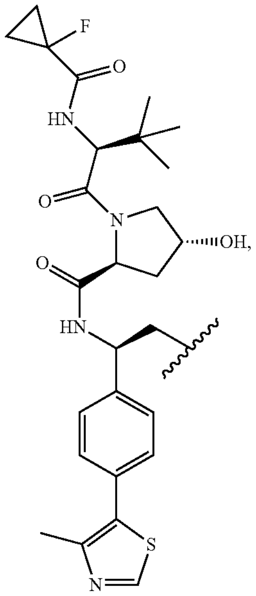
or
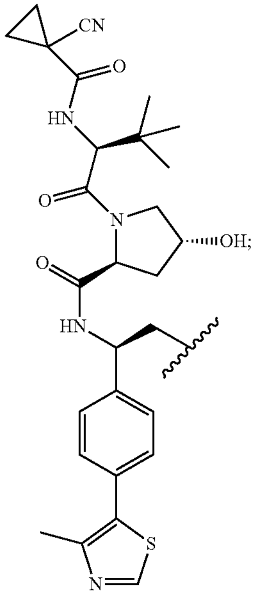
$Y_2$ is independently
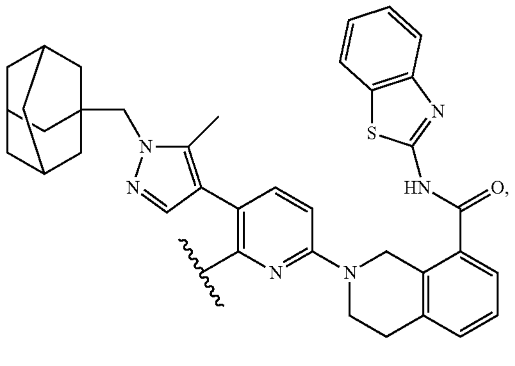
-continued
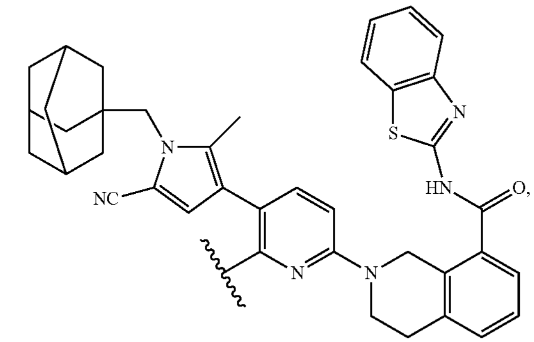
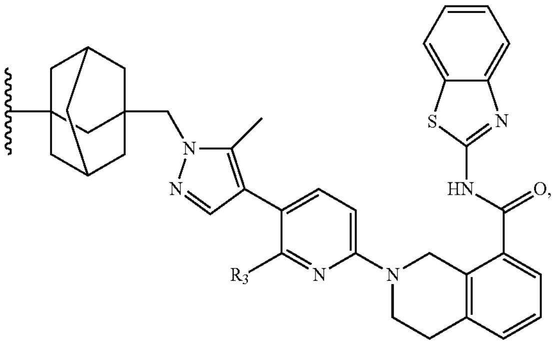
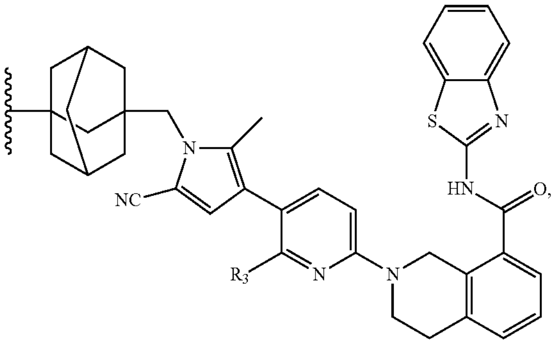
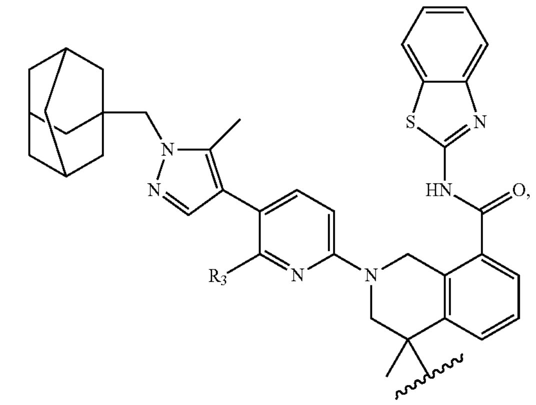

-continued
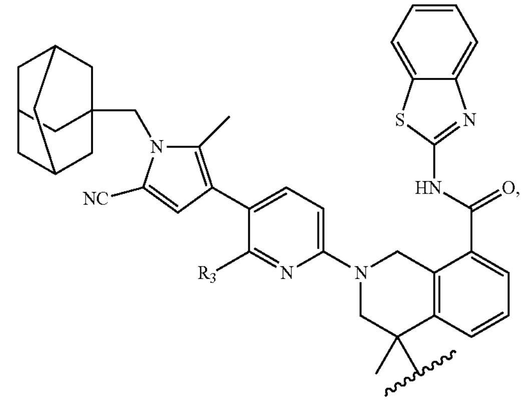
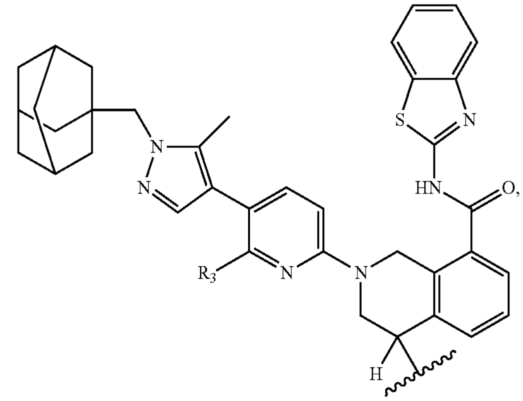
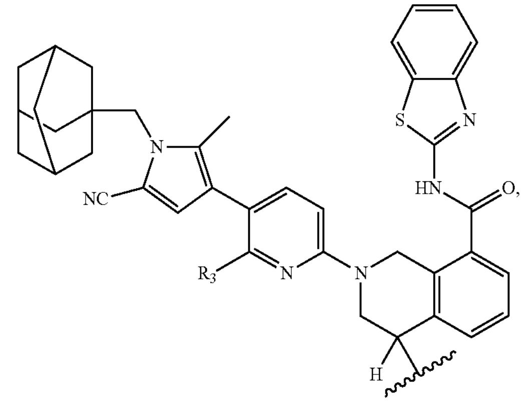
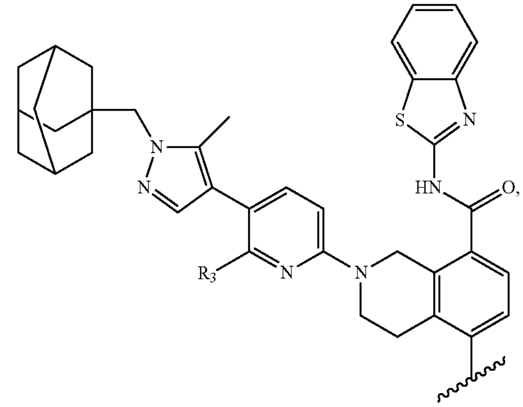
-continued
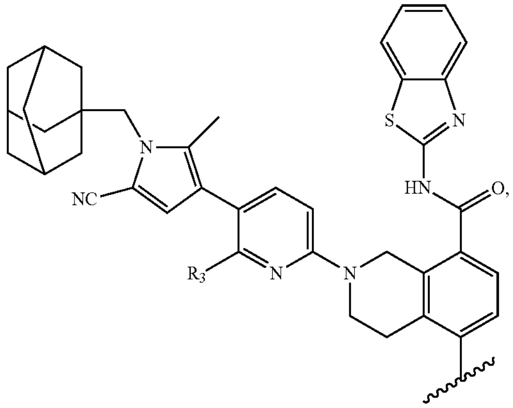
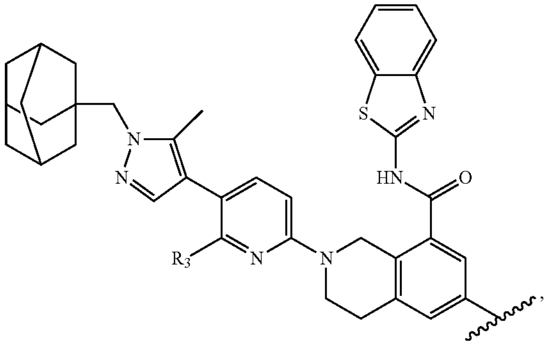
, or
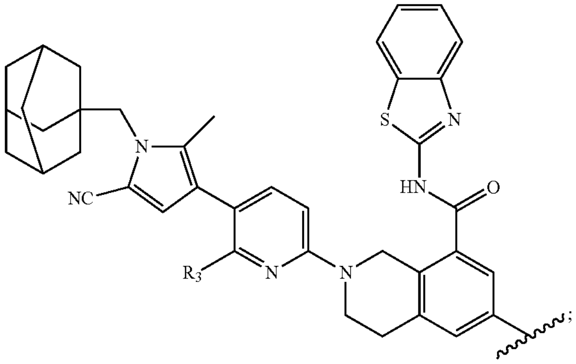
;
each $R_2$ is independently H, optionally substituted alkyl, or optionally substituted cycloalkyl;
each $R_3$ is hydrogen,
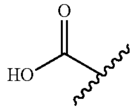
,
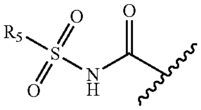
,
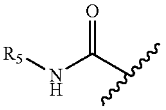
,
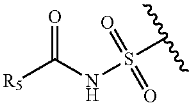
, or
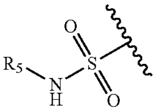
;
each $R_4$ is independently H, optionally substituted alkyl, or optionally substituted cycloalkyl;

each $R_5$ is independently H, optionally substituted alkyl, or optionally substituted cycloalkyl; and r is 0-10, inclusive.

2. The compound of clause 1, or a pharmaceutically acceptable salt, hydrate, solvate, or prodrug thereof, wherein R is

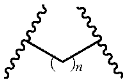 , 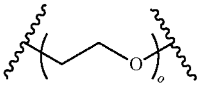 ,

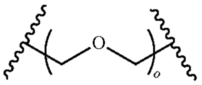 , 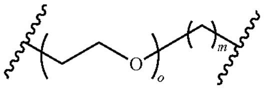 ,

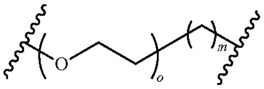 ,

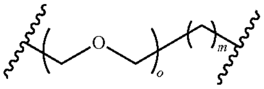 ,

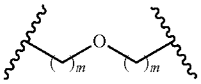 , 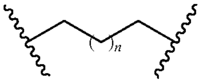 ,

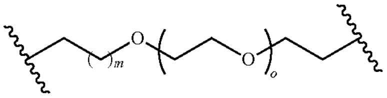 ,

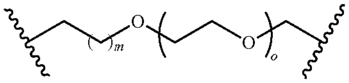 ,

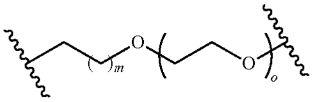 ,

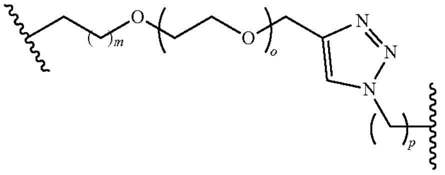 ,

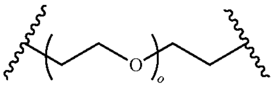 ,

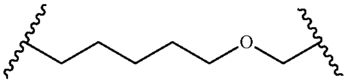 ,

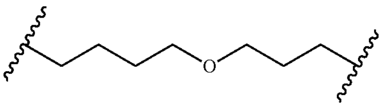 ,

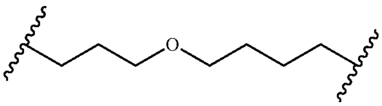 ,

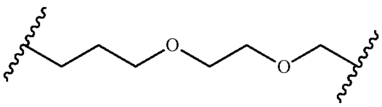 ,

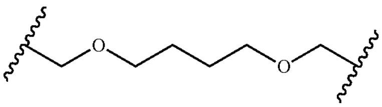 ,

-continued

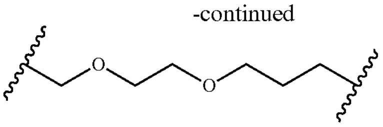 ,

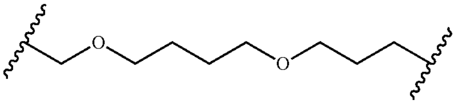 , or

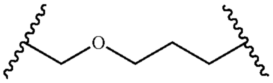 ;

and each m, n, o, and p is independently 0-10, inclusive.

3. The compound of clause 1 or 2, or a pharmaceutically acceptable salt, hydrate, solvate, or prodrug thereof, wherein $Y_2$ is

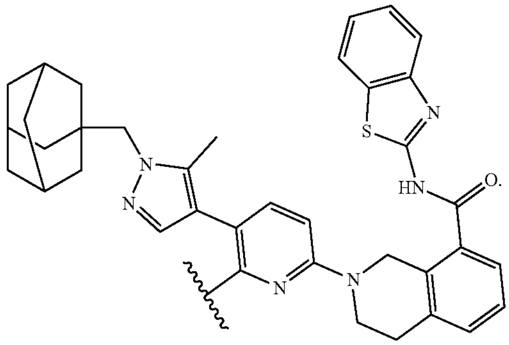 [SMILES: *c1nc(N2CCc3cccc(C(=O)Nc4nc5ccccc5s4)c3C2)ccc1-c1cnn(CC23CC4CC(CC(C4)C2)C3)c1C]

4. The compound of clause 3, or a pharmaceutically acceptable salt, hydrate, solvate, or prodrug thereof, wherein $L_1$ is

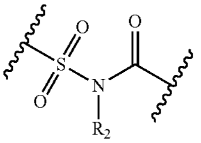 .

5. The compound of clause 3 or 4, or a pharmaceutically acceptable salt, hydrate, solvate, or prodrug thereof, wherein $L_2$ is

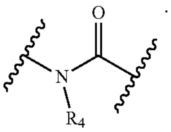 .

6. The compound of any one of clauses 3-5, or a pharmaceutically acceptable salt, hydrate, solvate, or prodrug thereof, wherein Y is

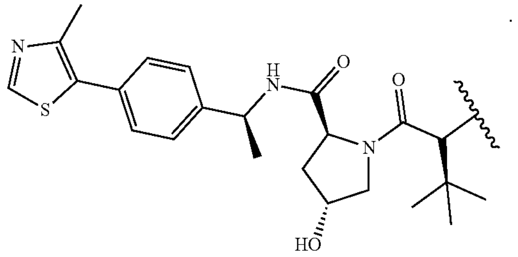

7. The compound of any one of clauses 3-6, or a pharmaceutically acceptable salt, hydrate, solvate, or prodrug thereof, wherein R is

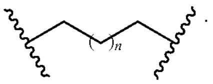

8. The compound of clause 7, or a pharmaceutically acceptable salt, hydrate, solvate, or prodrug thereof, wherein n is 1-9, inclusive.

9. The compound of clause 8, or a pharmaceutically acceptable salt, hydrate, solvate, or prodrug thereof, wherein n is 1-6, inclusive.

10. The compound of clause 3, or a pharmaceutically acceptable salt, hydrate, solvate, or prodrug thereof, wherein $L_1$ is

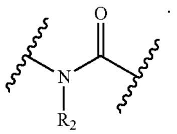

11. The compound of clause 10, or a pharmaceutically acceptable salt, hydrate, solvate, or prodrug thereof, wherein $L_2$ is

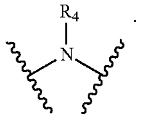

12. The compound of clause 10 or 11, or a pharmaceutically acceptable salt, hydrate, solvate, or prodrug thereof, wherein Y is

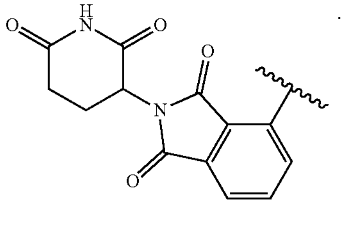 [SMILES: *c1cccc2c1C(=O)N(C1CCC(=O)NC1=O)C2=O]

13. The compound of any one of clauses 10-12, or a pharmaceutically acceptable salt, hydrate, solvate, or prodrug thereof, wherein R is

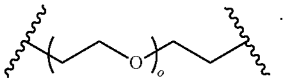

14. The compound of clause 13, or a pharmaceutically acceptable salt, hydrate, solvate, or prodrug thereof, wherein o is 0-9, inclusive.

15. The compound of clause 14, or a pharmaceutically acceptable salt, hydrate, solvate, or prodrug thereof, wherein o is 1-3, inclusive.

16. The compound of any one of clauses 10-12, or a pharmaceutically acceptable salt, hydrate, solvate, or prodrug thereof, wherein R is

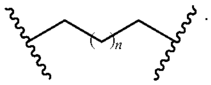

17. The compound of clause 16, or a pharmaceutically acceptable salt, rate, solvate, or prodrug thereof, wherein n is 0-9, inclusive.

18. The compound of clause 17, or a pharmaceutically acceptable salt, hydrate, solvate, or prodrug thereof, wherein n is 1-6, inclusive.

19. The compound of clause 17, or a pharmaceutically acceptable salt, hydrate, solvate, or prodrug thereof, wherein n is 1-3, inclusive.

20. The compound of clause 17, or a pharmaceutically acceptable salt, hydrate, solvate, or prodrug thereof, wherein n is 2.

21. The compound of clause 10, or a pharmaceutically acceptable salt, hydrate, solvate, or prodrug thereof, wherein Y is

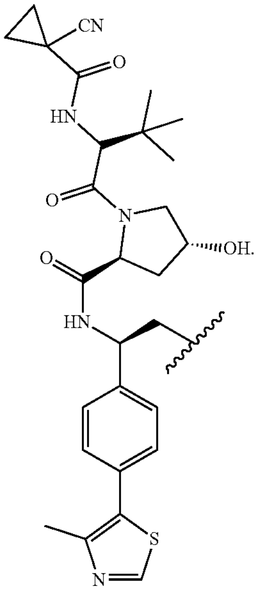

22. The compound of clause 10 or 21, or a pharmaceutically acceptable salt, hydrate, solvate, or prodrug thereof, wherein $L_2$ is

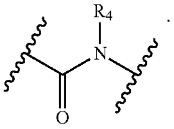

23. The compound of clause 21 or 22, or a pharmaceutically acceptable salt, hydrate, solvate, or prodrug thereof, wherein R is

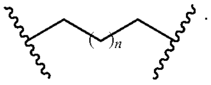

24. The compound of clause 23, or a pharmaceutically acceptable salt, hydrate, solvate, or prodrug thereof, wherein n is 0-6, inclusive.

25. The compound of clause 23, or a pharmaceutically acceptable salt, hydrate, solvate, or prodrug thereof, wherein n is 0-3, inclusive.

26. The compound of clause 23, or a pharmaceutically acceptable salt, hydrate, solvate, or prodrug thereof, wherein n is 2.

27. The compound of clause 1 or 2, or a pharmaceutically acceptable salt, hydrate, solvate, or prodrug thereof, wherein $L_1$ is

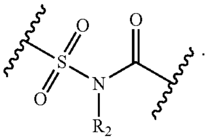

28. The compound of clause 27, or a pharmaceutically acceptable salt, hydrate, solvate, or prodrug thereof, wherein $L_2$ is

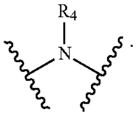

29. The compound of clause 27 or 28, or a pharmaceutically acceptable salt, hydrate, solvate, or prodrug thereof, wherein Y is

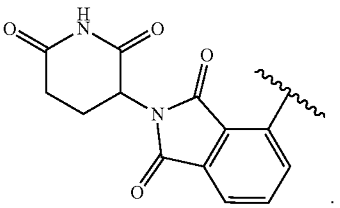 [SMILES: *c1cccc2c1C(=O)N(C1CCC(=O)NC1=O)C2=O]

30. The compound of any one of clauses 27-29, or a pharmaceutically acceptable salt, hydrate, solvate, or prodrug thereof, wherein $Y_2$ is

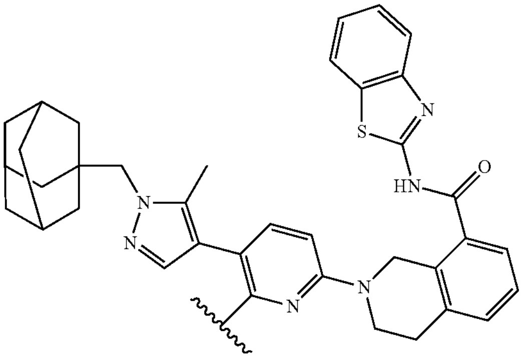

or

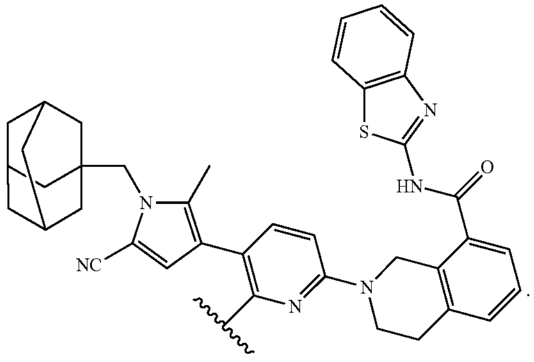

31. The compound of any one of clauses 27-30, or a pharmaceutically acceptable salt, hydrate, solvate, or prodrug thereof, wherein $Y_2$ is

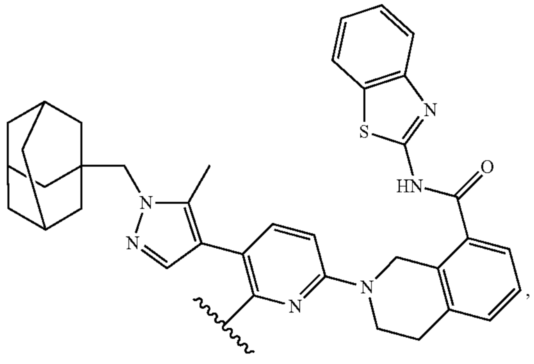 [SMILES: *c1nc(N2CCc3cccc(C(=O)Nc4nc5ccccc5s4)c3C2)ccc1-c1cnn(CC23CC4CC(CC(C4)C2)C3)c1C]

and R is

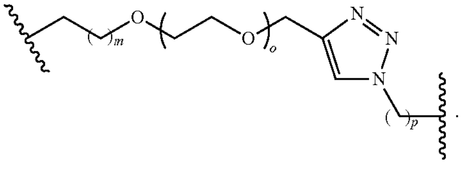

32. The compound of clause 31, or a pharmaceutically acceptable salt, hydrate, solvate, or prodrug thereof, wherein m is 1.

33. The compound of clause 31, or a pharmaceutically acceptable salt, hydrate, solvate, or prodrug thereof, wherein o is 1.

34. The compound of clause 31, or a pharmaceutically acceptable salt, hydrate, solvate, or prodrug thereof, wherein p is 1.

35. The compound of clause 31, or a pharmaceutically acceptable salt, hydrate, solvate, or prodrug thereof, wherein m is 1, o is 1, and p is 1.

36. The compound of any one of clauses 27-30, or a pharmaceutically acceptable salt, hydrate, solvate, or prodrug thereof, wherein $Y_2$ is

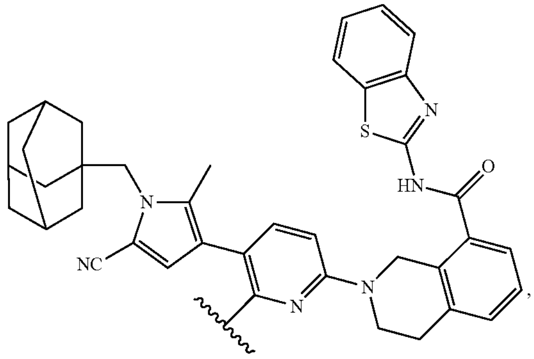 [SMILES: *c1nc(N2CCc3cccc(C(=O)Nc4nc5ccccc5s4)c3C2)ccc1-c1cc(C#N)n(CC23CC4CC(CC(C4)C2)C3)c1C]

, and R is

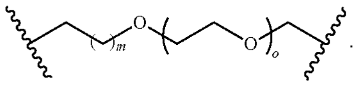

.

37. The compound of clause 36, or a pharmaceutically acceptable salt, hydrate, solvate, or prodrug thereof, wherein m is 1.

38. The compound of clause 36, or a pharmaceutically acceptable salt, hydrate, solvate, or prodrug thereof, wherein o is 1.

39. The compound of clause 36, or a pharmaceutically acceptable salt, hydrate, solvate, or prodrug thereof, wherein m is 1 and o is 1.

40. The compound of clause 1 or 2, or a pharmaceutically acceptable salt, hydrate, solvate, or prodrug thereof, wherein $L_2$ is

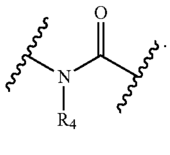

.

41. The compound of clause 40, or a pharmaceutically acceptable salt, hydrate, solvate, or prodrug thereof, wherein Y is

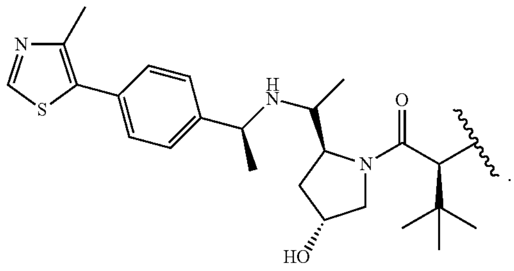 [SMILES: *[C@H](C(=O)N1C[C@H](O)C[C@H]1C(C)N[C@@H](C)c1ccc(-c2scnc2C)cc1)C(C)(C)C]

.

42. The compound of clause 40 or 41, or a pharmaceutically acceptable salt, hydrate, solvate, or prodrug thereof, wherein R is

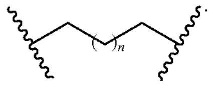

.

43. The compound of any of clauses 40-42, or a pharmaceutically acceptable salt, hydrate, solvate, or prodrug thereof, wherein n is 1-6, inclusive.

44. The compound of clause 43, or a pharmaceutically acceptable salt, hydrate, solvate, or prodrug thereof, wherein n is 5.

45. The compound of any one of clauses 40-44, or a pharmaceutically acceptable salt, hydrate, solvate, or prodrug thereof, wherein $Y_2$ is

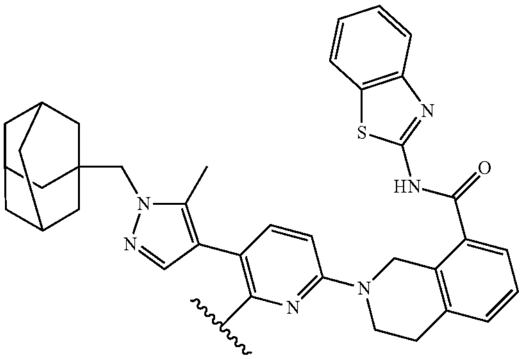

or

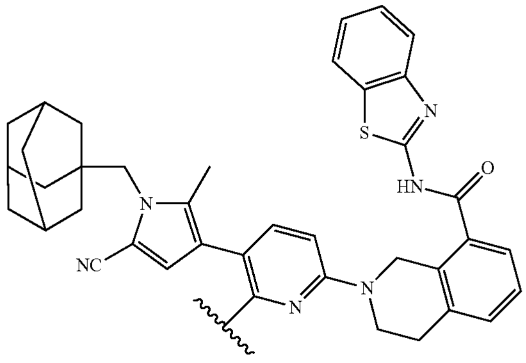

.

46. The compound of any one of clauses 1-45, or a pharmaceutically acceptable salt, hydrate, solvate, or prodrug thereof, wherein $L_1$ is

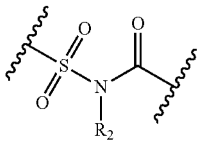
or
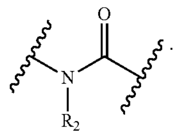
.
47. The compound of any one of clauses 40-45, or a pharmaceutically acceptable salt, hydrate, solvate, or prodrug thereof, wherein $L_1$ is:
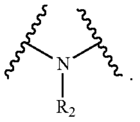
.
48. The compound of any one of clauses 1-47, or a pharmaceutically acceptable salt, hydrate, solvate, or prodrug thereof, wherein the compound is:
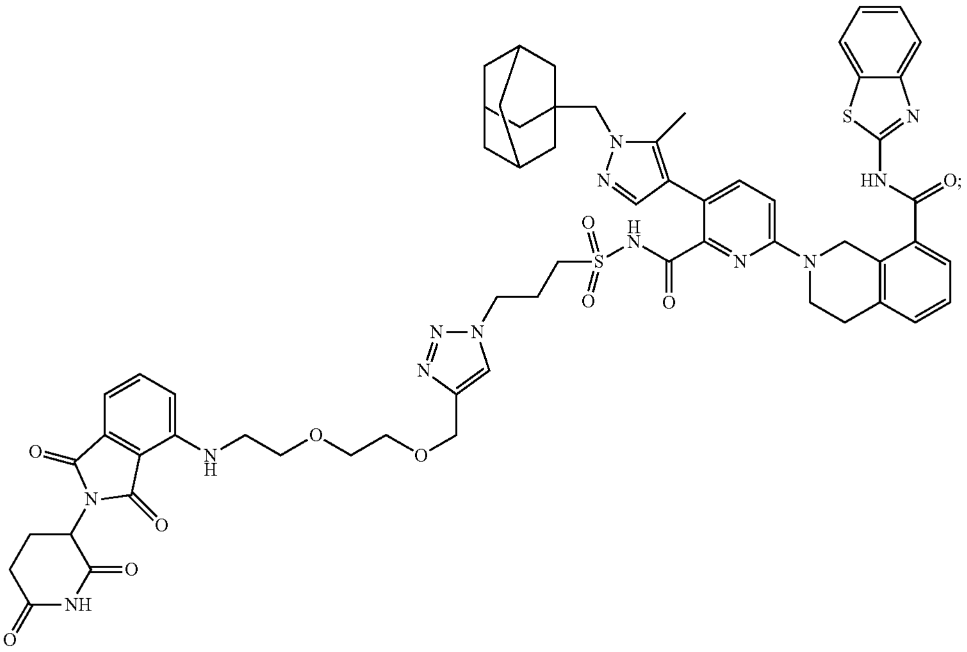
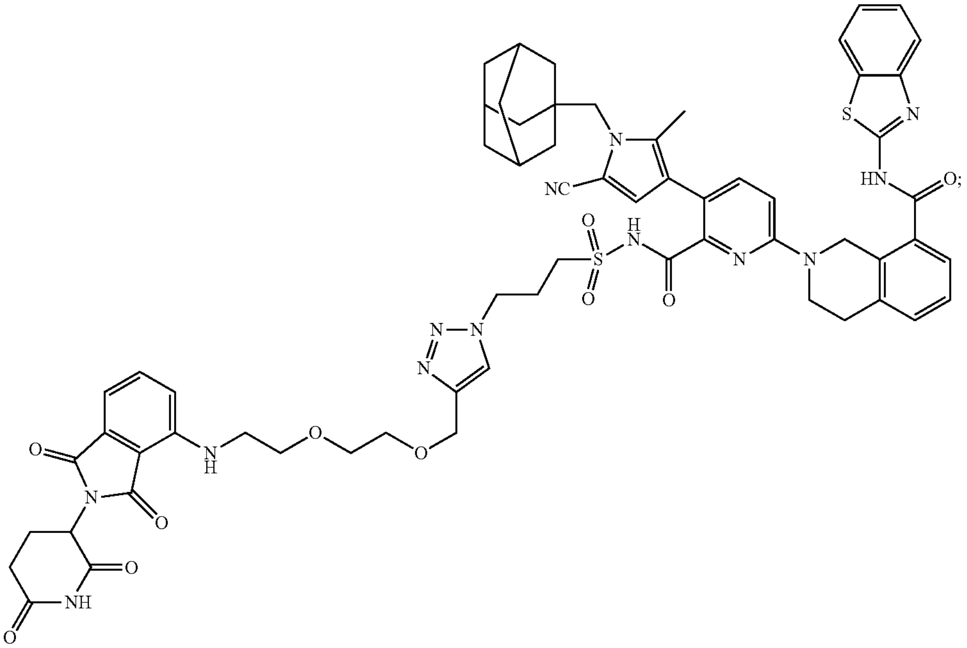

-continued
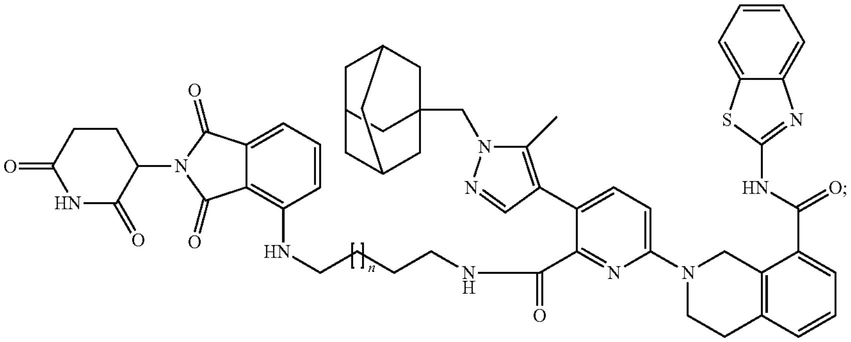
n = 1
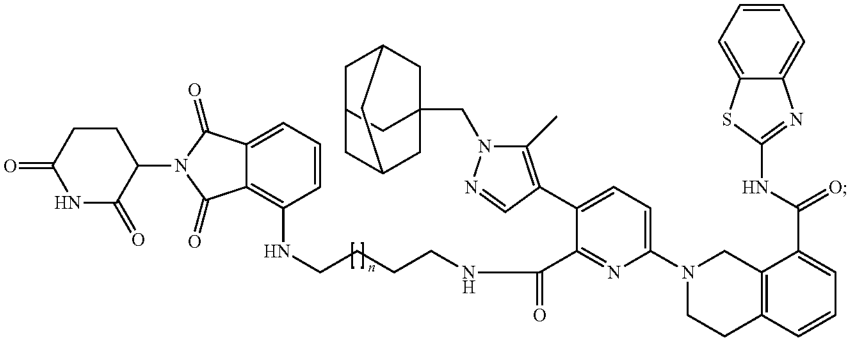
n = 3
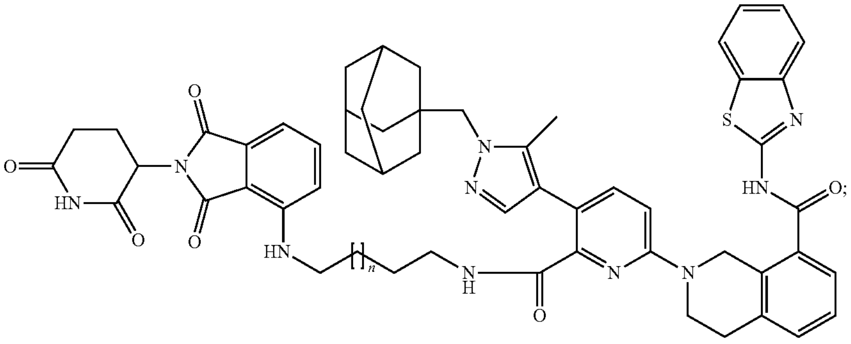
n = 5
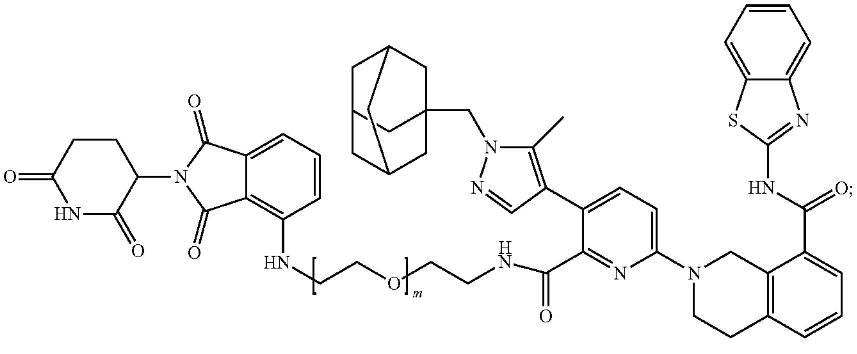
m = 1

-continued
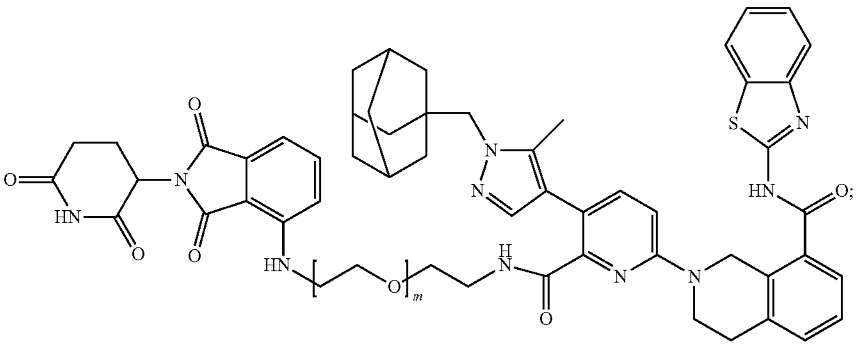
m = 2
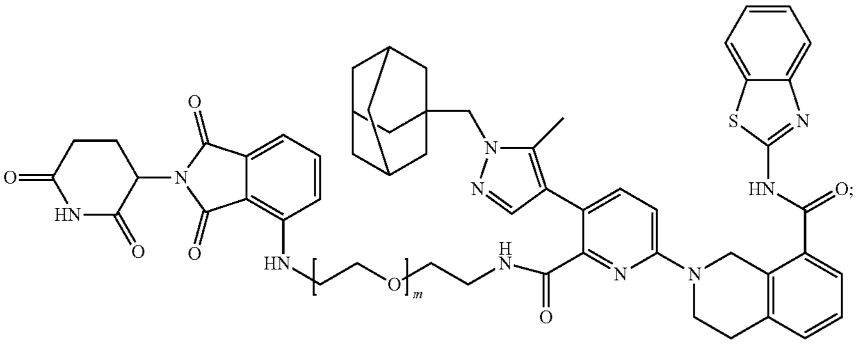
m = 3
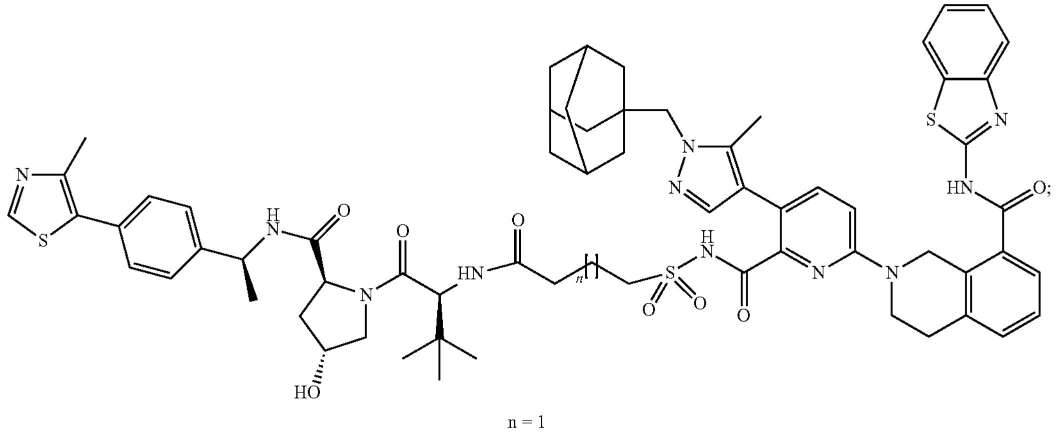
n = 1
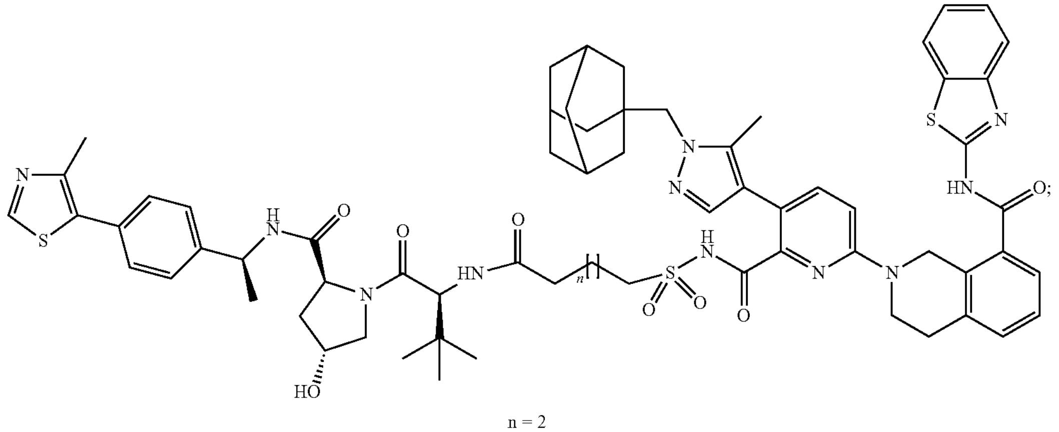
n = 2

-continued
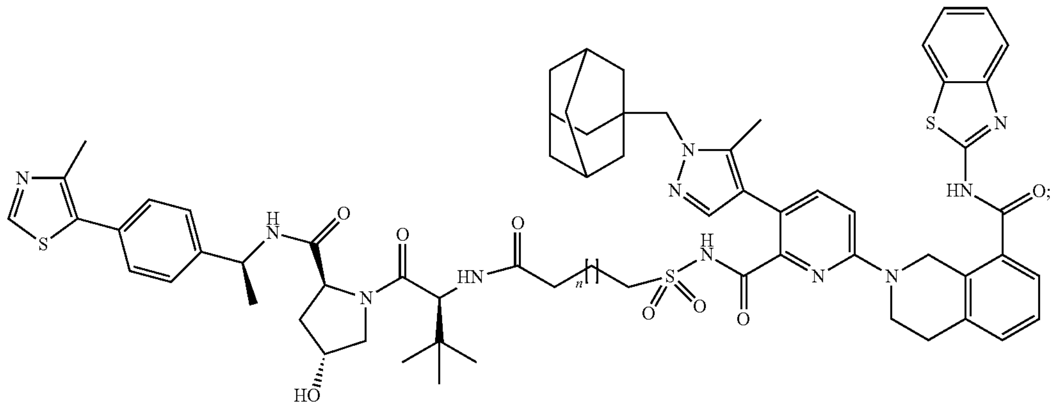
n = 3
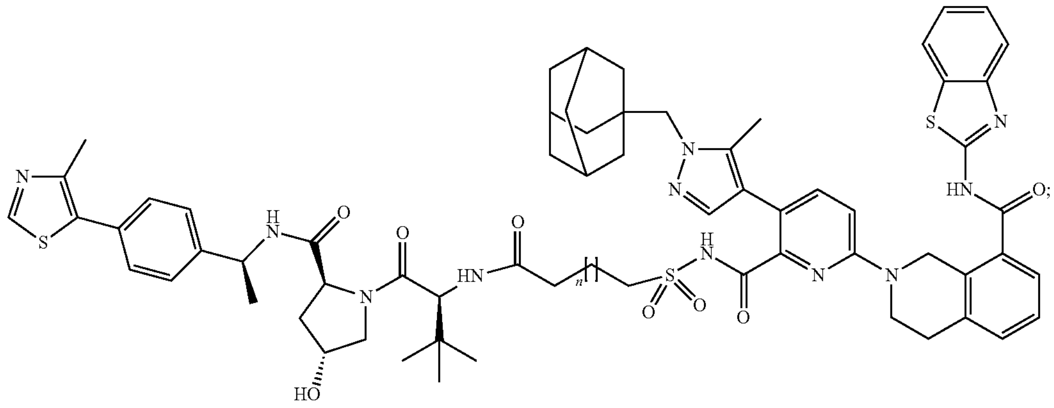
n = 4
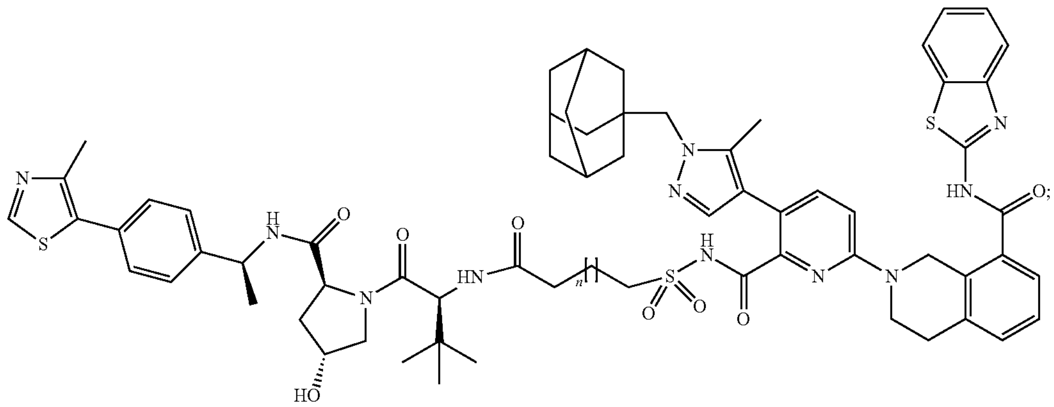
n = 5

-continued
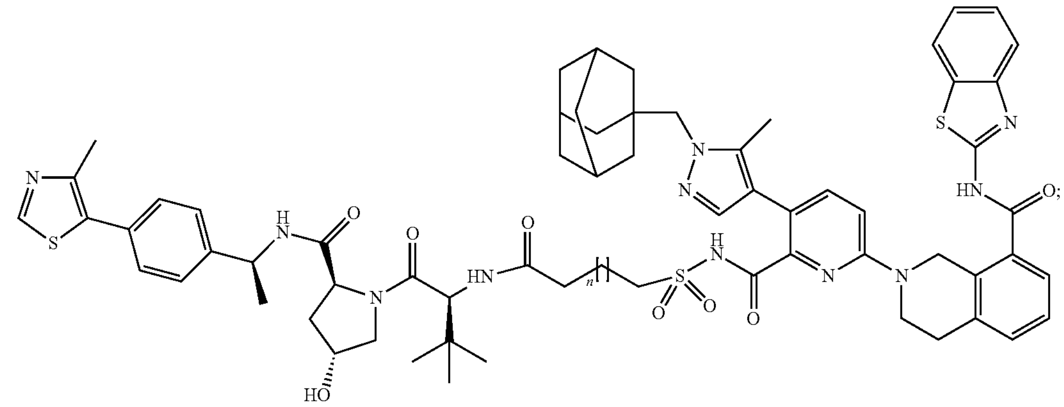
n = 6
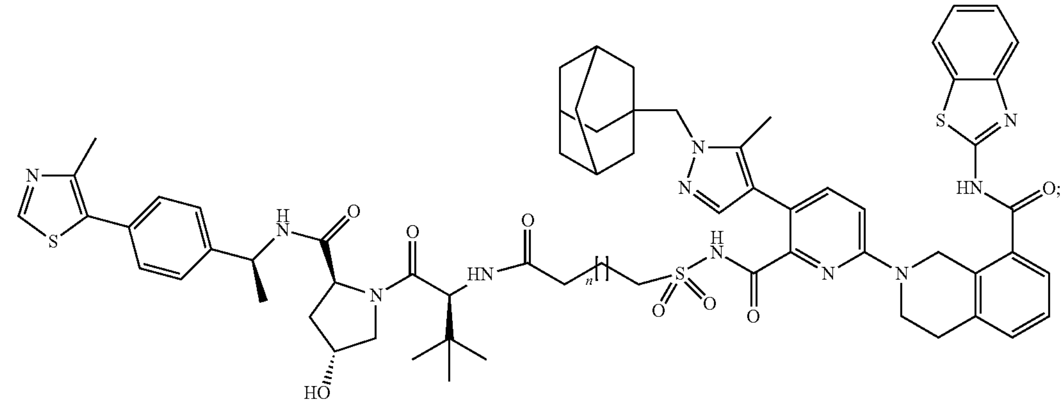
n = 7
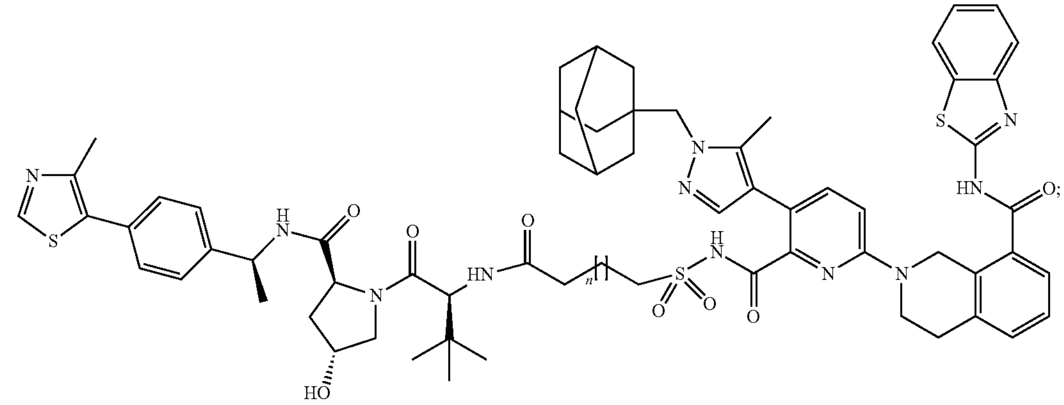
n = 8

-continued
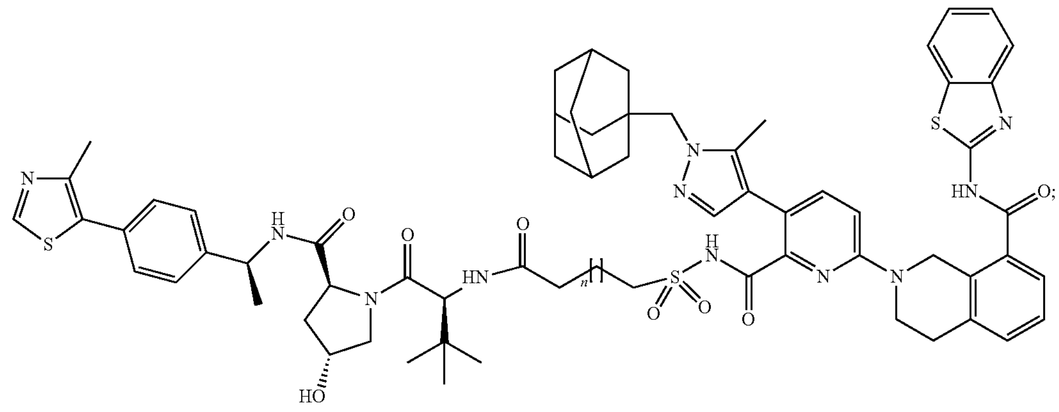
n = 9
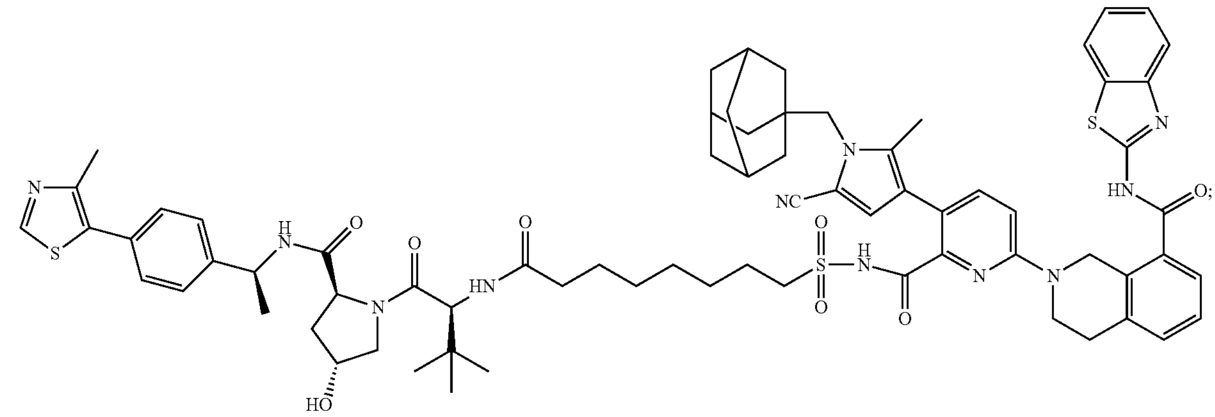
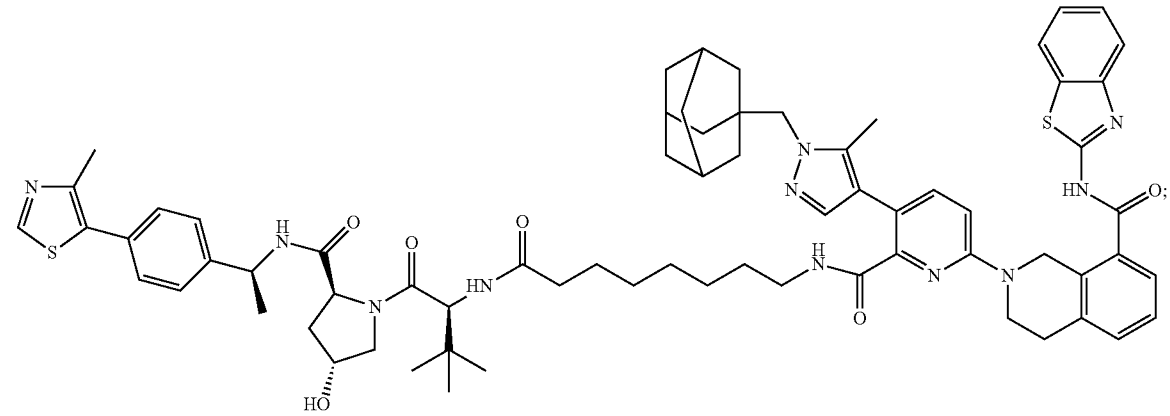

-continued
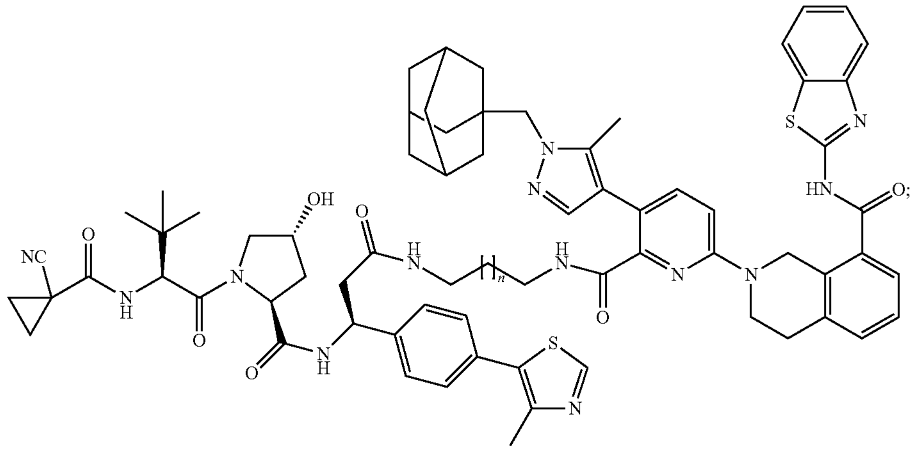
n = 0
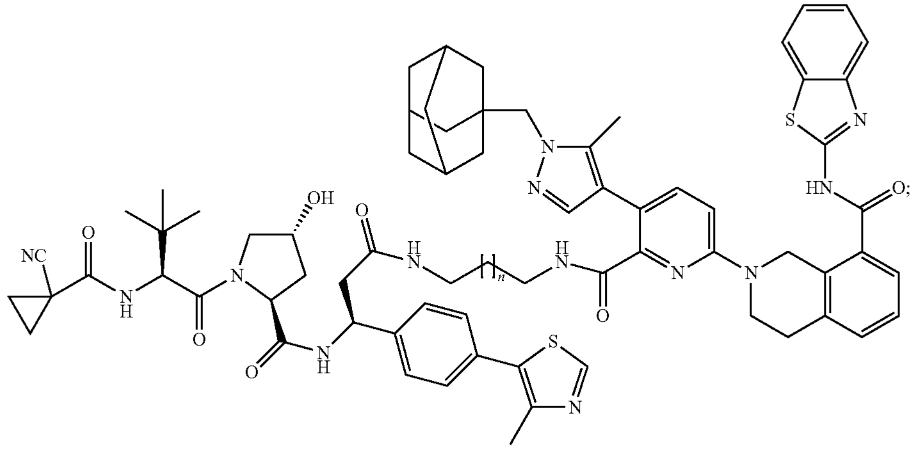
n = 1
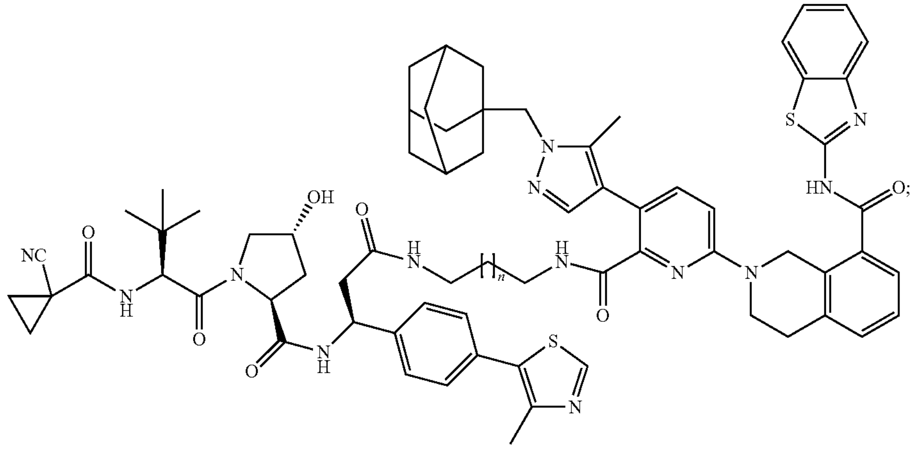
n = 2

-continued
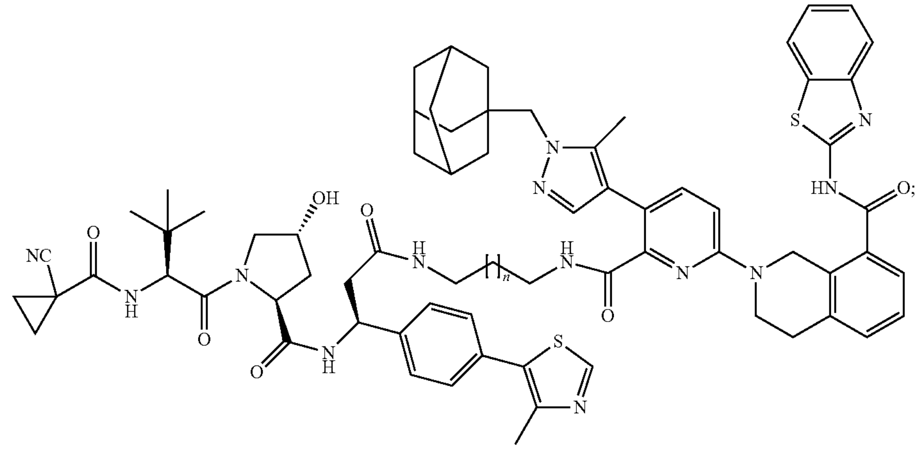
n = 3
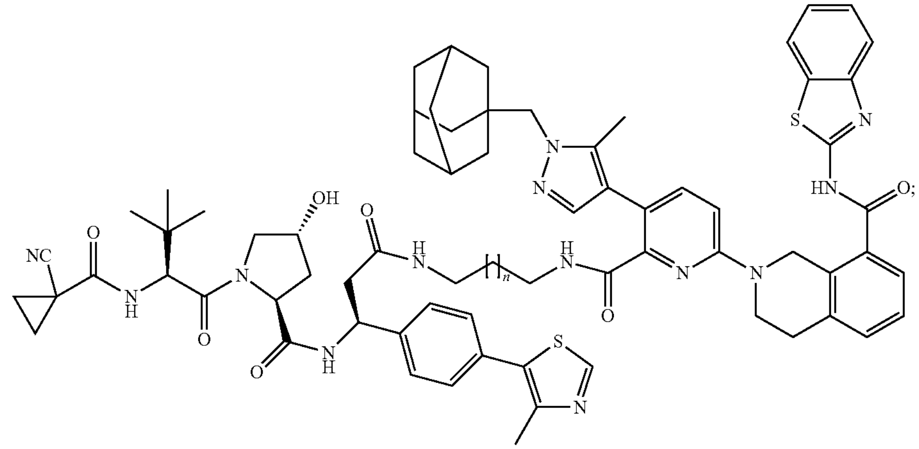
n = 4
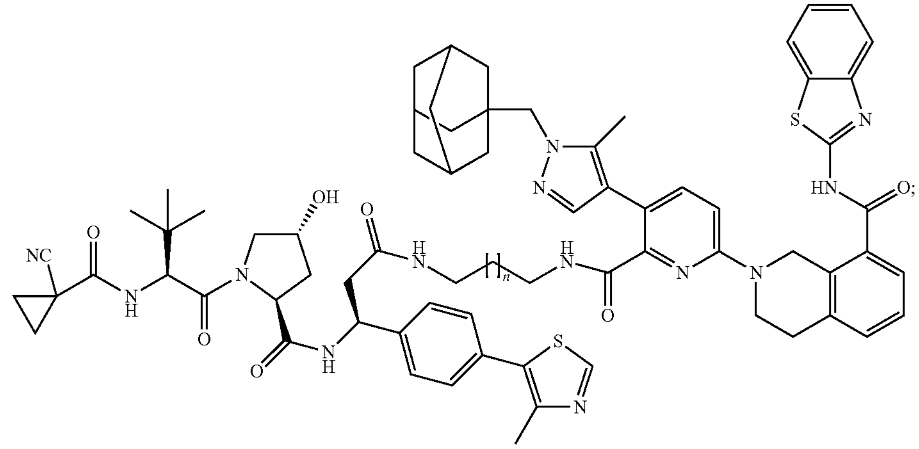
n = 6

-continued
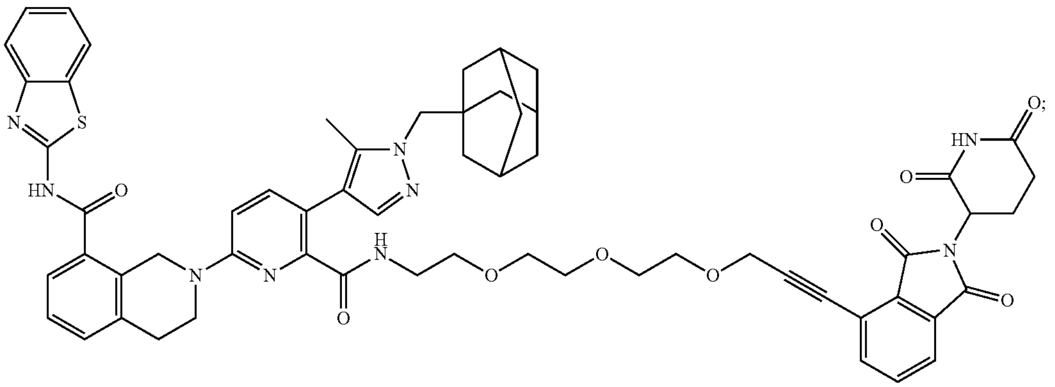
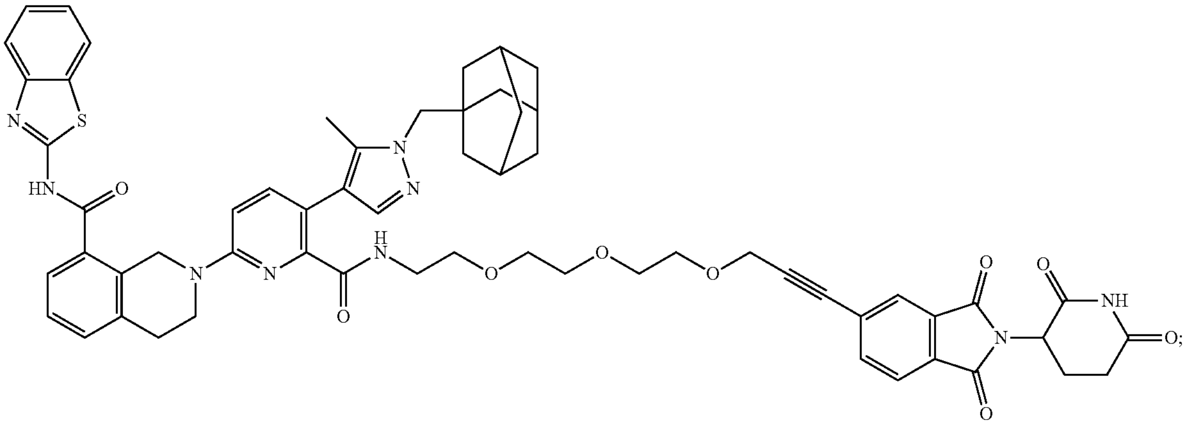
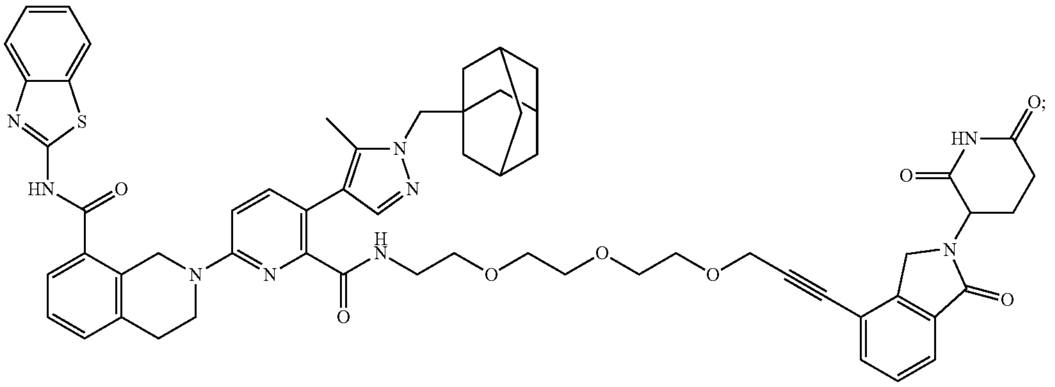
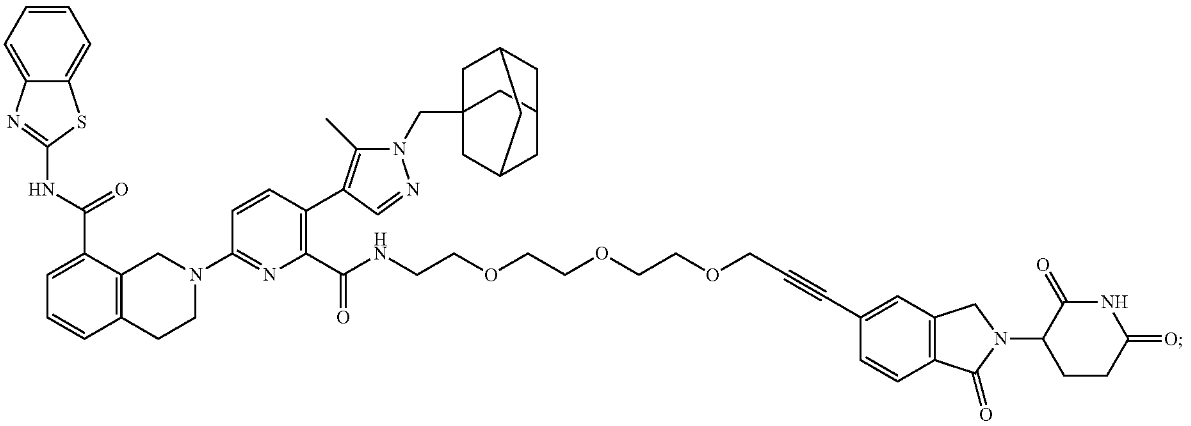

-continued
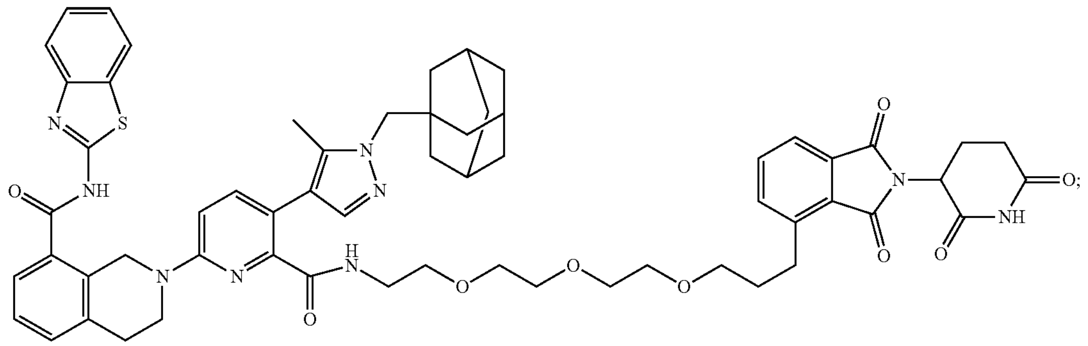
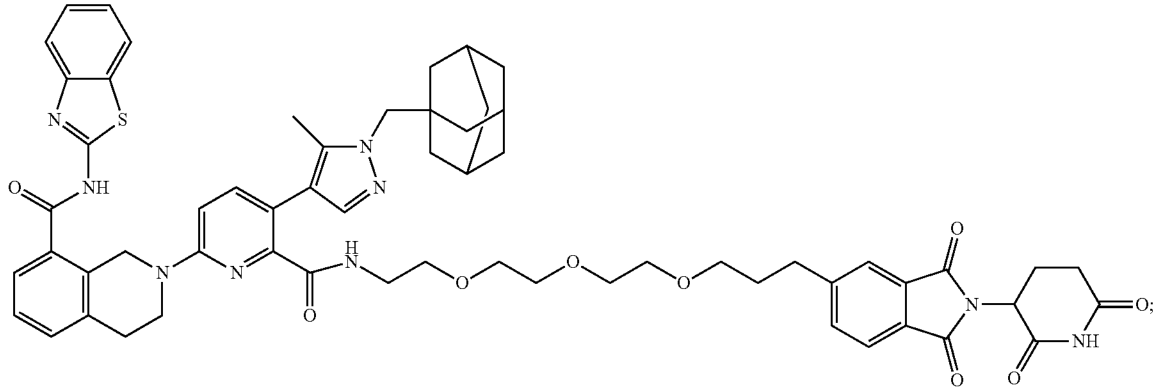
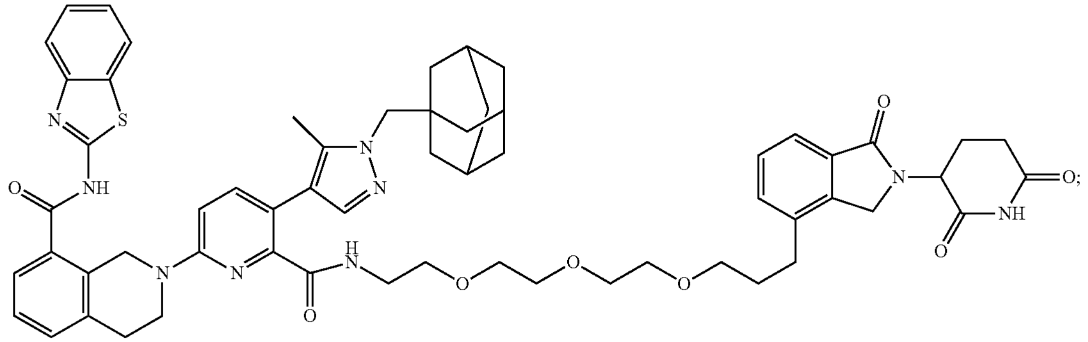
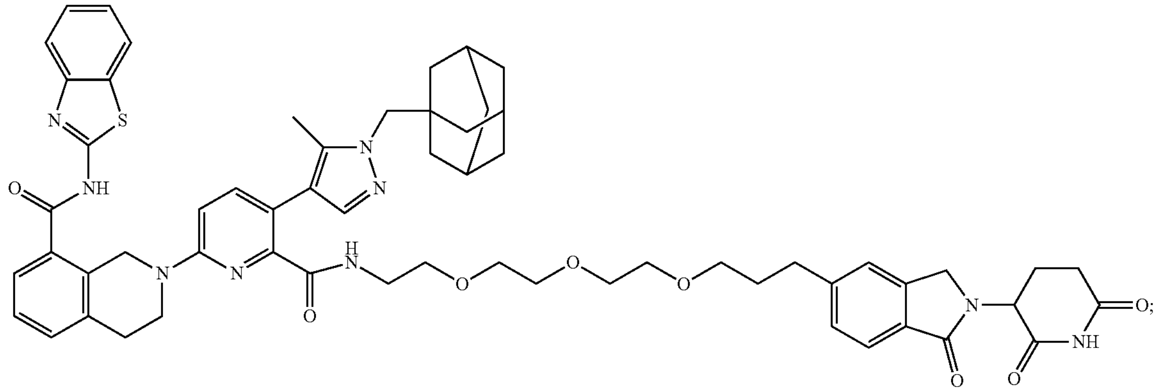

-continued
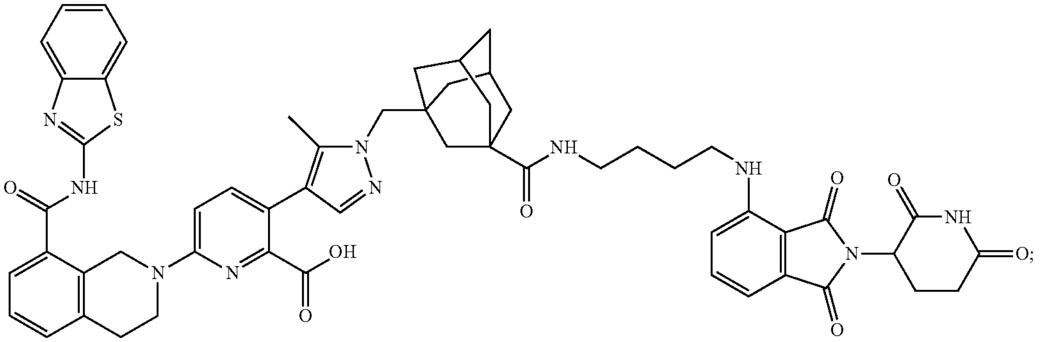
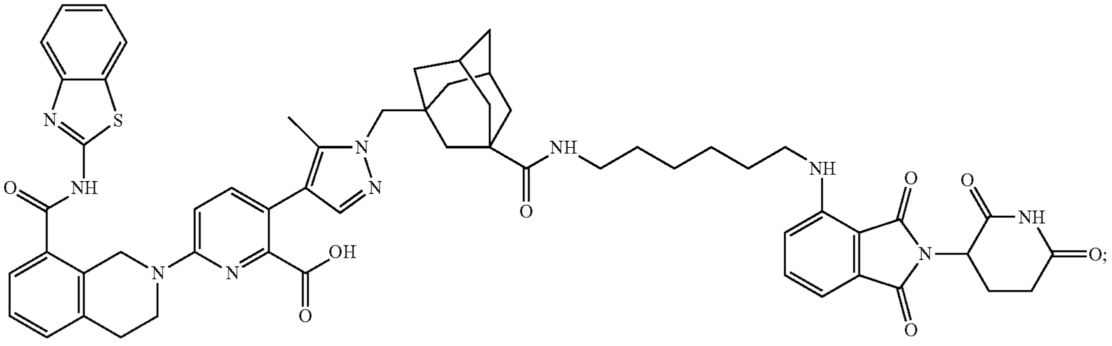
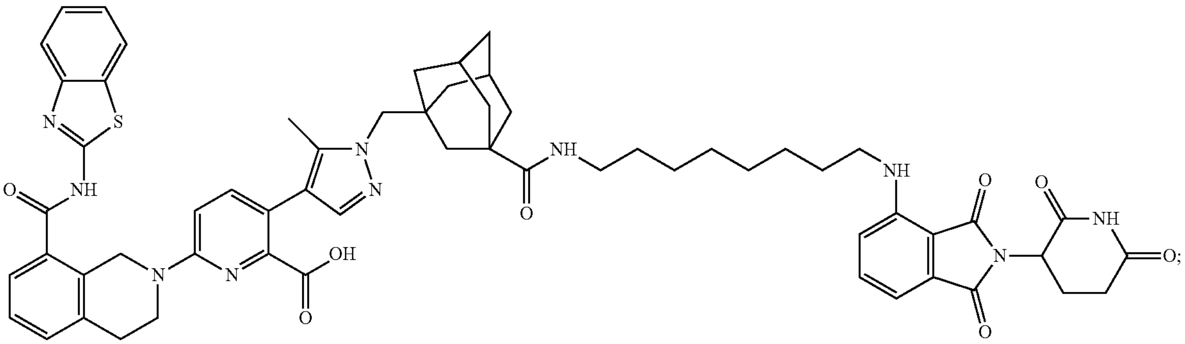
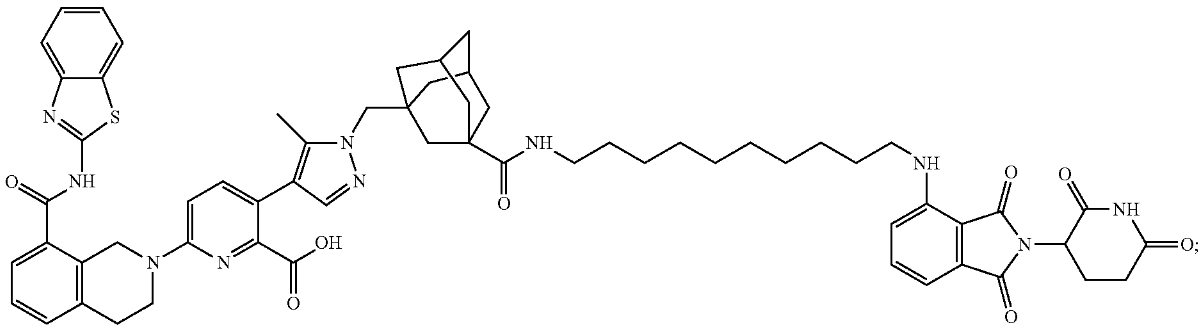
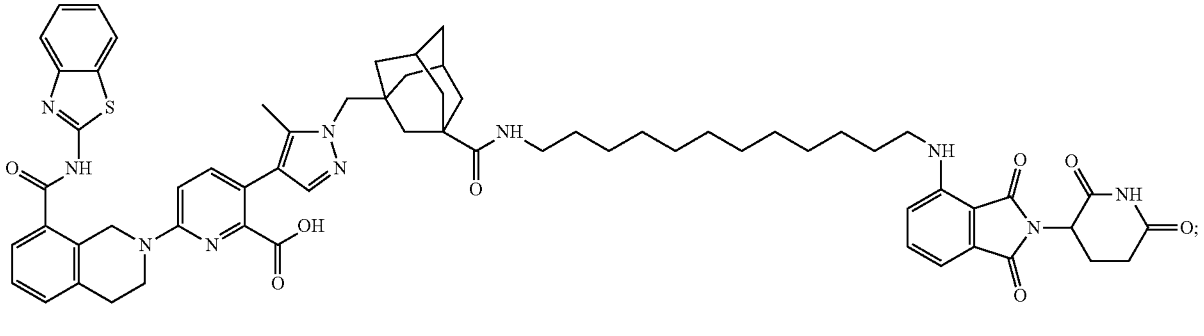

-continued
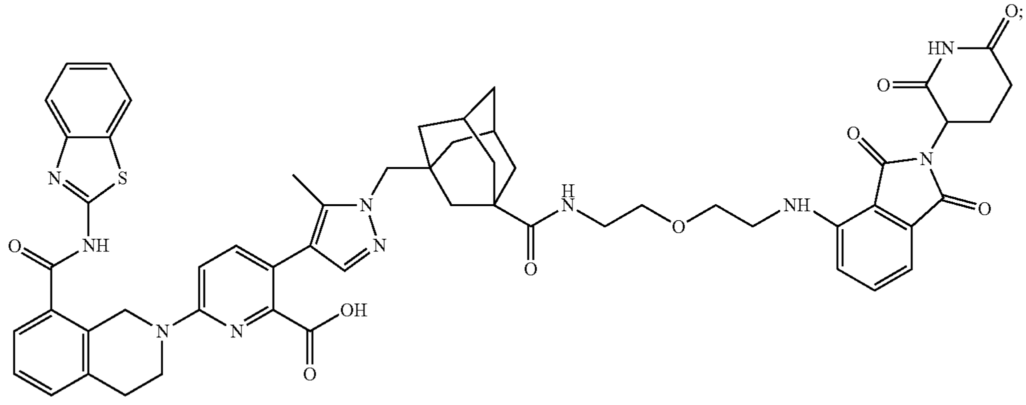
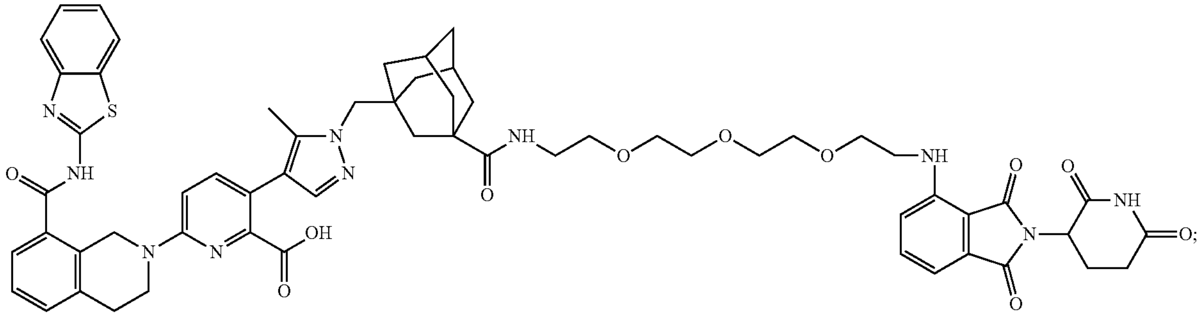
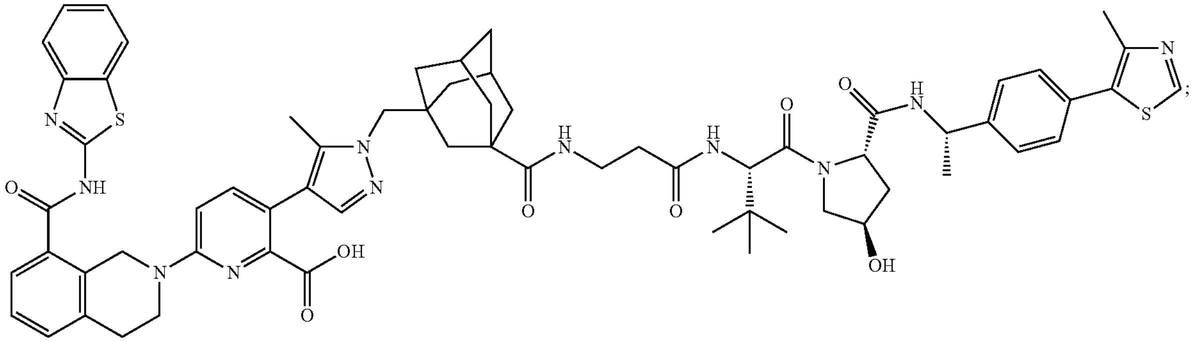
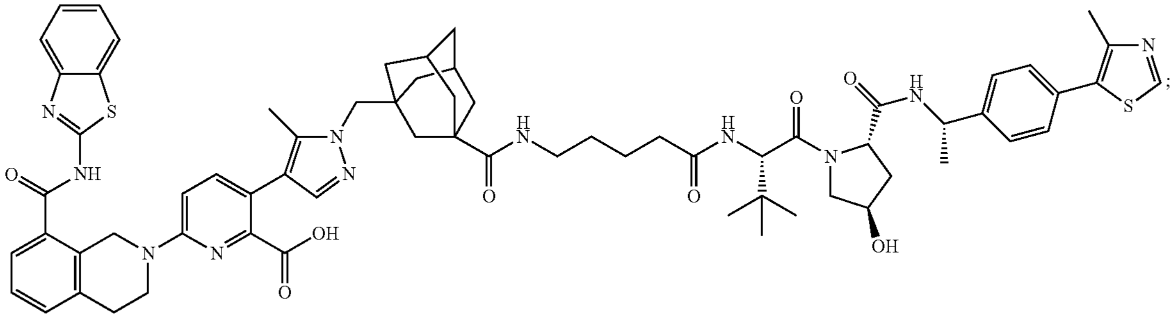
or
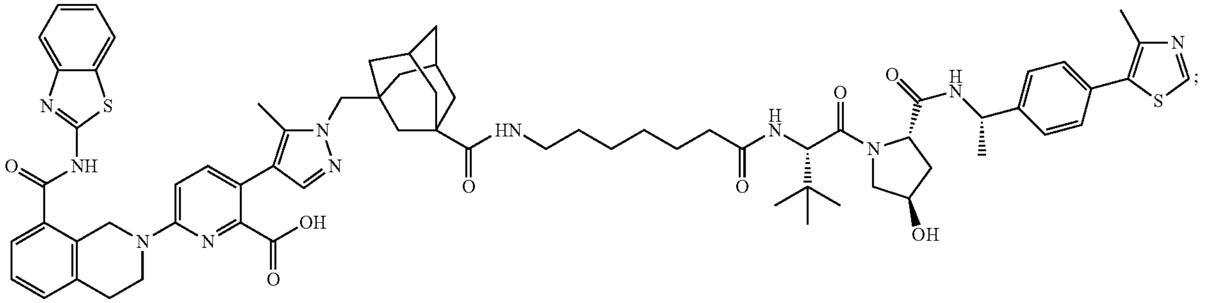

or a pharmaceutically acceptable salt, hydrate, solvate, or prodrug thereof.

49. A pharmaceutical composition comprising a compound of any one of clauses 1-48, or a pharmaceutically acceptable salt, hydrate, solvate, or prodrug thereof, and a pharmaceutically acceptable carrier.

50. The pharmaceutical composition of clause 49, further comprising an additional agent.

51. The pharmaceutical composition of clause 50, wherein the additional agent is an anti-cancer agent.

52. The pharmaceutical composition of clause 51, wherein the anti-cancer agent is an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

53. A method of degrading Bcl-2 proteins, the method comprising administering an effective amount of a compound of any one of clauses 1-48, or a pharmaceutically acceptable salt, hydrate, solvate, or prodrug thereof.

54. The method of clause 53, wherein the compound is administered in vitro.

55. The method of clause 53, wherein the compound is administered in vivo.

56. The method of clause 53, further comprising administering the compound to a subject.

57. A method of treating a disease or disorder in a subject in need thereof, the method comprising administering an effective amount of a compound of any one of clauses 1-48, or a pharmaceutically acceptable salt, hydrate, solvate, or prodrug thereof.

58. A method of treating a subject suffering from or susceptible to a disease or disorder, the method comprising administering an effective amount of a compound of any one of clauses 1-48, or a pharmaceutically acceptable salt, hydrate, solvate, or prodrug thereof.

59. The method of clause 57 or 58, wherein the disease is cancer.

60. The method of clause 59, wherein the cancer is a solid tumor.

61. The method of clause 59, wherein the cancer is chronic lymphocyctic leukemia.

62. The method of clause 57 or 58, wherein the subject is a mammal.

63. The method of clause 57 or 58, wherein the subject is a human.

64. A method of treating a Bcl-2-dependent (e.g., mediated) cancer in a subject in need thereof, the method comprising administering an effective amount of a compound of any one of clauses 1-48, or a pharmaceutically acceptable salt, hydrate, solvate, or prodrug thereof, wherein the platelet toxicity of the compound is less than that of other Bcl-2 inhibitors.

65. A method of treating a subject suffering from or susceptible to a Bcl-2-dependent (e.g., mediated) cancer, the method comprising administering an effective amount of a compound of any one of clauses 1-48, or a pharmaceutically acceptable salt, hydrate, solvate, or prodrug thereof, wherein the platelet toxicity of the compound is less than that of other Bcl-2 inhibitors.

66. The method of clause 64 or 65, wherein the Bcl-xL-dependent (e.g., mediated) cancer is acute lymphoblastic leukemia.

67. The method of clause 64 or 65, wherein the other Bcl-2 inhibitor is venetoclax or ABT-263.

68. A method of treating a Bcl-xL-dependent (e.g., mediated) cancer in a subject in need thereof, the method comprising administering an effective amount of a compound of any one of clauses 1-48, or a pharmaceutically acceptable salt thereof, wherein the ratio of human platelet toxicity ($IC_{50}$) to anticancer activity ($IC_{50}$) of the compound is greater than one.

69. A method of treating a subject suffering from or susceptible to a Bcl-xL-dependent (e.g., mediated) cancer, the method comprising administering an effective amount of a compound of any one of clauses 1-48, or a pharmaceutically acceptable salt thereof, wherein the ratio of human platelet toxicity ($IC_{50}$) to anticancer activity ($IC_{50}$) of the compound is greater than one.

70. The method of clause 68 or 69, wherein the Bcl-xL-dependent (e.g., mediated) cancer is acute lymphoblastic leukemia.

71. The method of clause 68 or 69, wherein the anticancer activity is measured in MOLT-4 cells.

72. The method of clause 68 or 69, wherein the ratio is greater than 2.5.

73. The method of clause 68 or 69, wherein the ratio is greater than 5.

74. The method of clause 68 or 69, wherein the ratio is greater than 10.

75. The method of clause 68 or 69, wherein the ratio is greater than 20.

76. The method of clause 68 or 69, wherein the ratio is greater than 40.

77. The compound of any one of clauses 1-48 or method of any one of clauses 49-79, wherein $R_3$ is

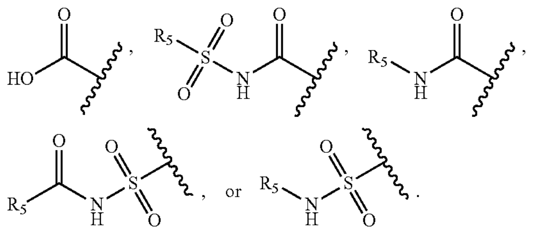

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A compound of Formula (I), or a pharmaceutically acceptable salt, hydrate, solvate, or prodrug thereof:

$$Y\text{-}L_2\text{-}R\text{-}L_1\text{-}Y_2 \qquad \text{Formula (I);}$$

wherein $L_1$ is independently

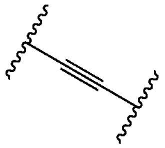, 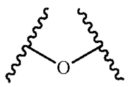, 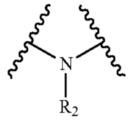,

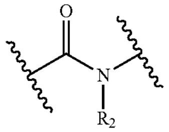, 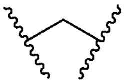, 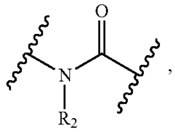,

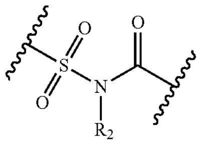, 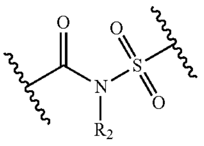, or absent;

R is independently optionally substituted $C_{1-50}$ alkylene or optionally substituted $C_{1-50}$ heteroalkylene wherein:

optionally one or more backbone carbon atoms of each instance of the optionally substituted alkylene or optionally substituted heteroalkylene are independently replaced with —C(═O)O—, —OC(═O)—, —NHC(═O)—, —C(═O)NH—, optionally substituted cycloalkylene, optionally substituted heterocycloalkylene, optionally substituted arylene, or optionally substituted heteroarylene; and optionally one or more backbone heteroatoms of each instance of the optionally substituted heteroalkylene are independently replaced with optionally substituted cycloalkylene, optionally substituted heterocycloalkylene, optionally substituted arylene, or optionally substituted heteroarylene;

$L_2$ is independently

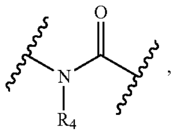, 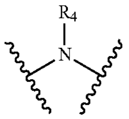, 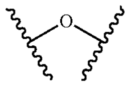,

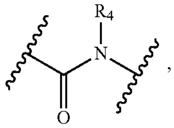, 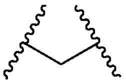,

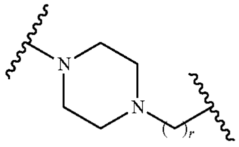, 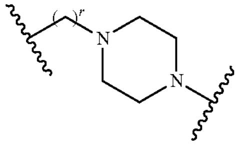,

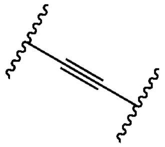, or 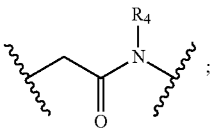;

Y is independently

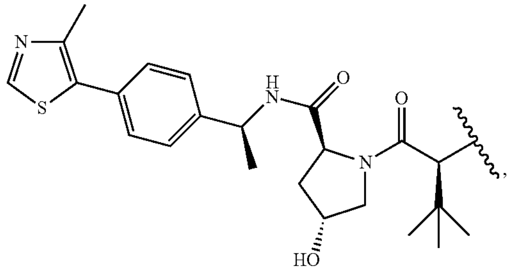,

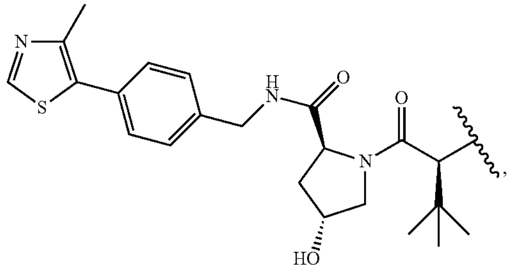,

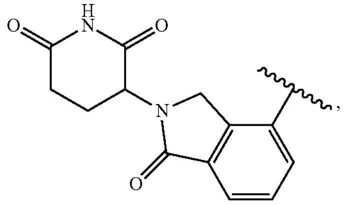,

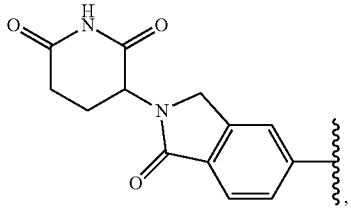,

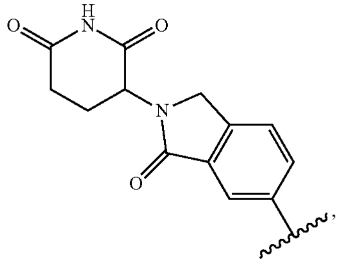,

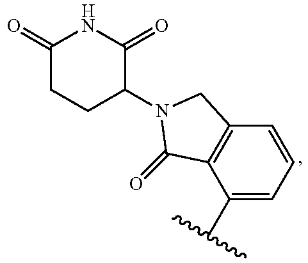,

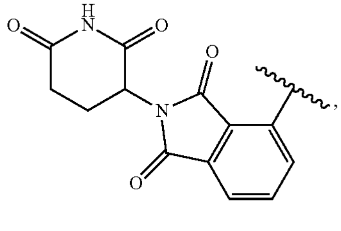,

-continued
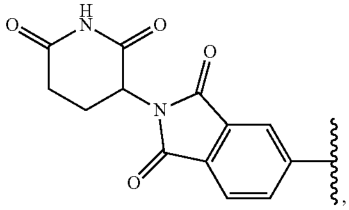
,
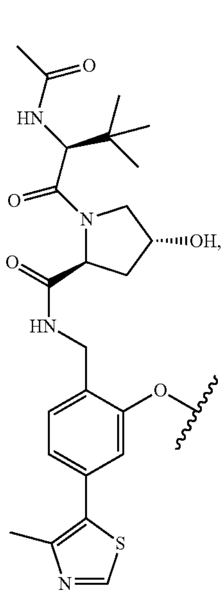
,
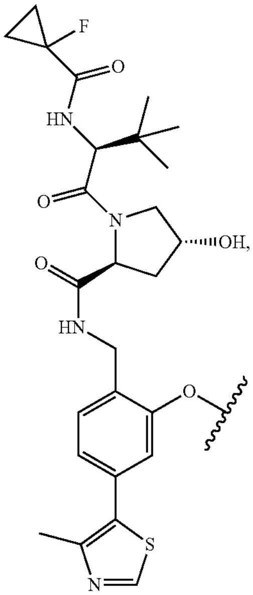
,
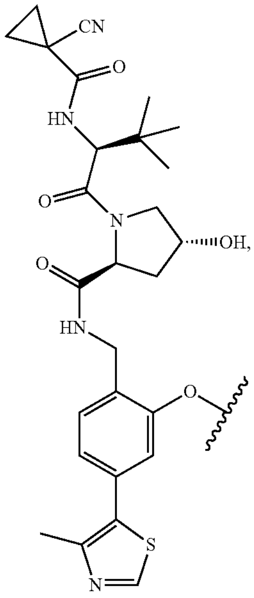
,
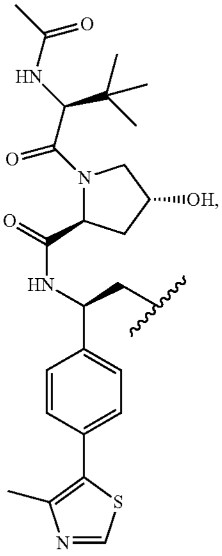
,
-continued
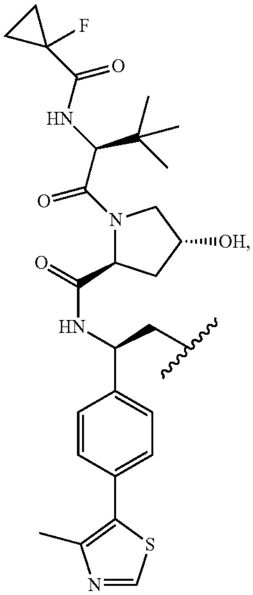
, or
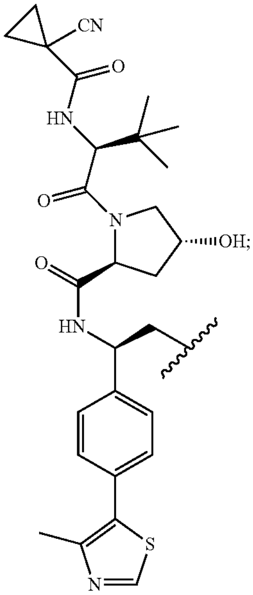
;
$Y_2$ is independently
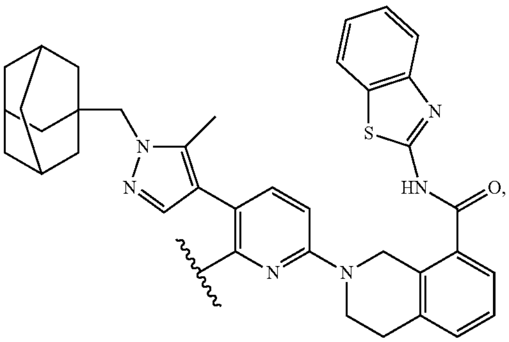
, -continued
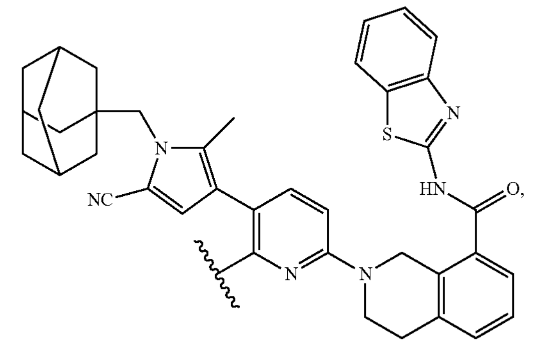
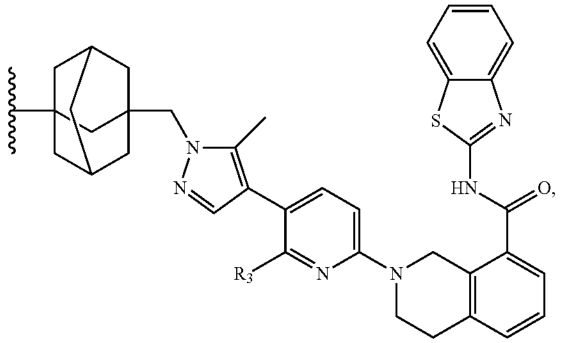
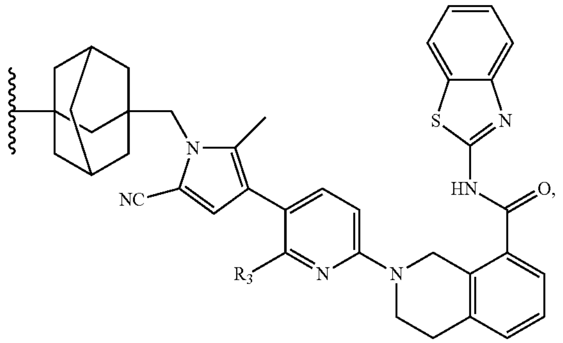
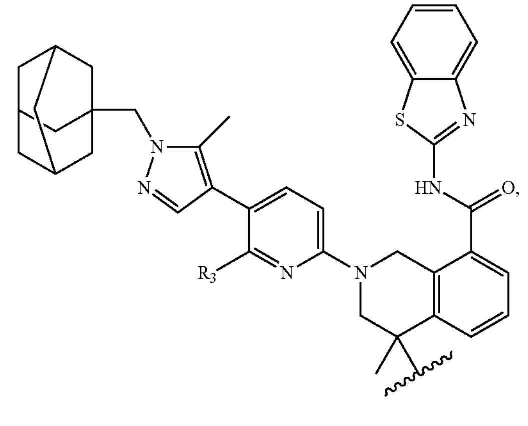
-continued
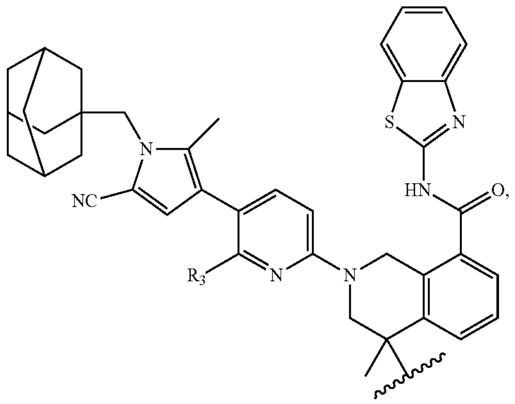
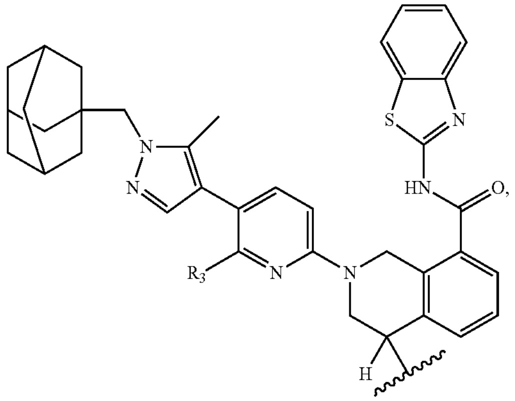
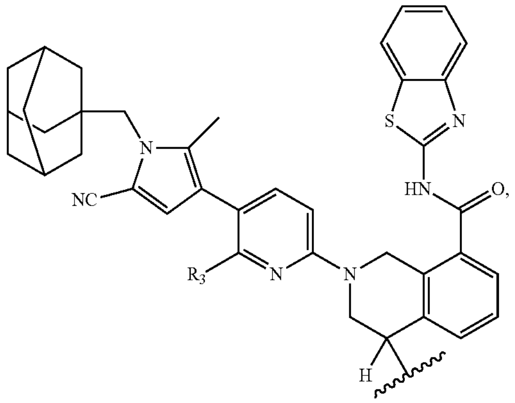
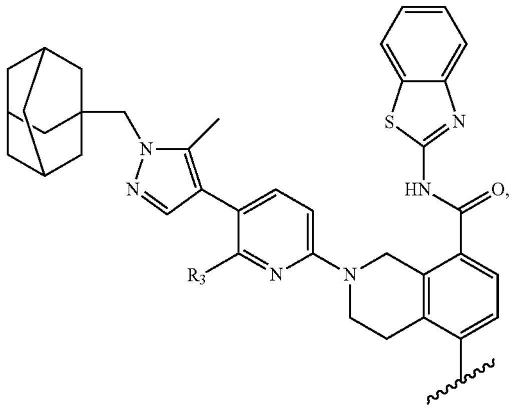

-continued

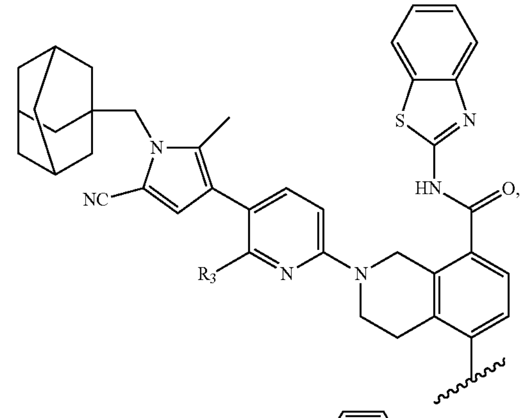

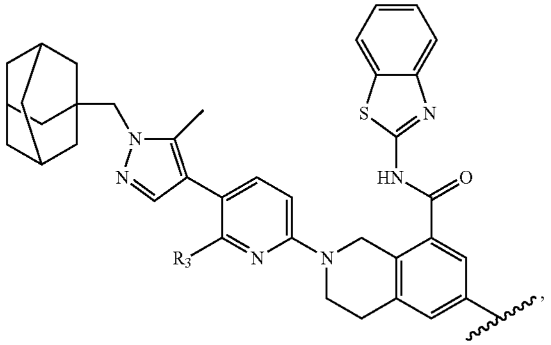

, or

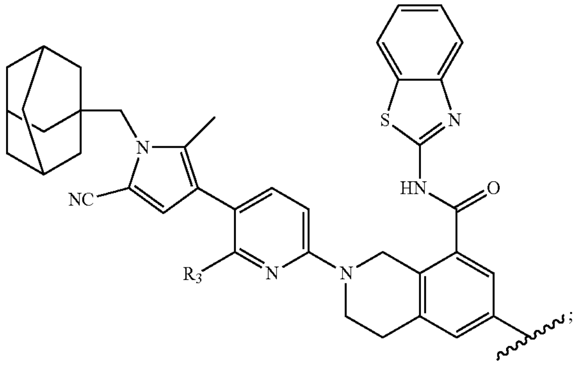

each $R_2$ is independently H, optionally substituted alkyl, or optionally substituted cycloalkyl;

each $R_3$ is hydrogen,

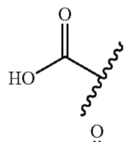 , 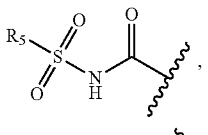 ,

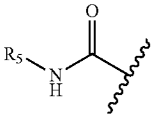 , 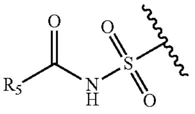 , or

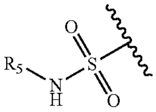 ;

each $R_4$ is independently H, optionally substituted alkyl, or optionally substituted cycloalkyl;

each $R_5$ is independently H, optionally substituted alkyl, or optionally substituted cycloalkyl; and r is 0-10, inclusive.

2. The compound of claim 1, or a pharmaceutically acceptable salt, hydrate, solvate, or prodrug thereof, wherein R is

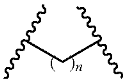 , 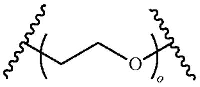 ,

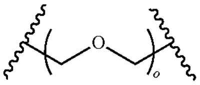 , 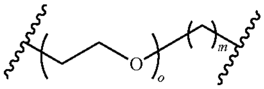 ,

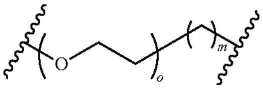 ,

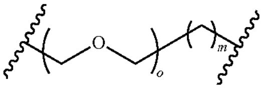 ,

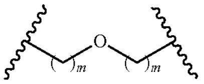 , 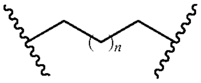 ,

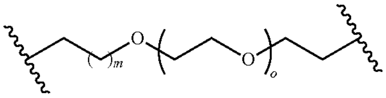 ,

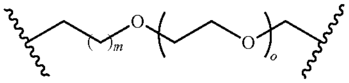 ,

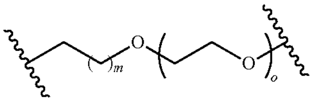 ,

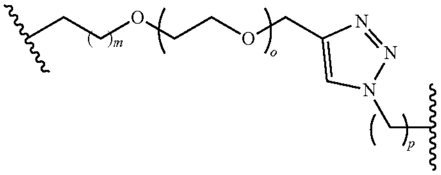 ,

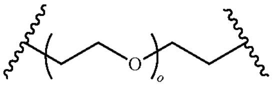 ,

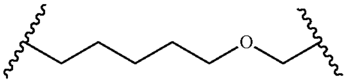 ,

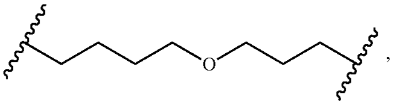 ,

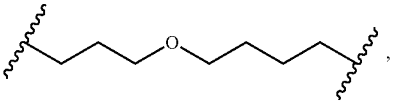 ,

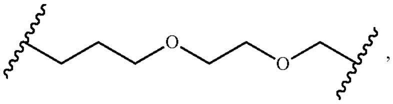 ,

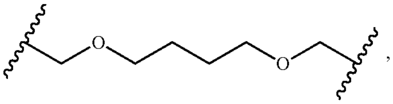 ,

-continued

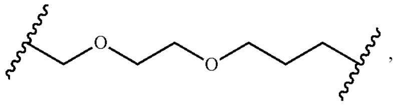

,

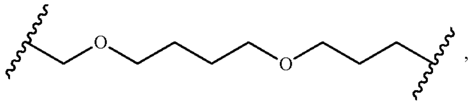

, or

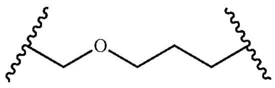

;

and each m, n, o, and p is independently 0-10, inclusive.

3. The compound of claim 1, or a pharmaceutically acceptable salt, hydrate, solvate, or prodrug thereof, wherein $Y_2$ is

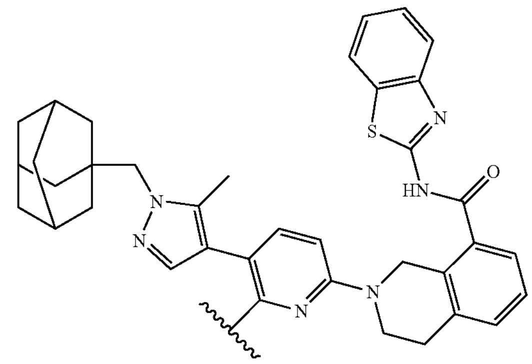

.

4. The compound of claim 3, or a pharmaceutically acceptable salt, hydrate, solvate, or prodrug thereof, wherein:

$L_1$ is

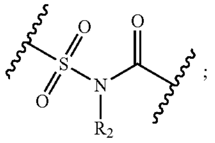

;

$L_2$ is

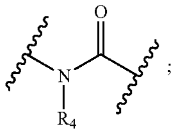

;

Y is

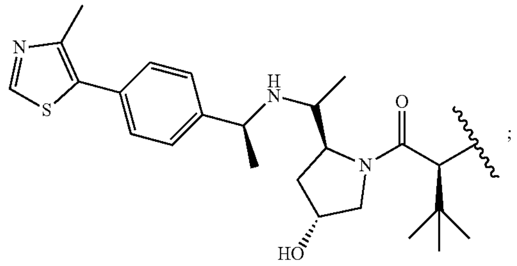 [SMILES: *[C@H](C(=O)N1C[C@H](O)C[C@H]1C(C)N[C@@H](C)c1ccc(-c2scnc2C)cc1)C(C)(C)C]

;

R is

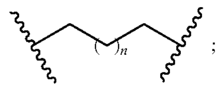

;

and n is 1-9, inclusive.

5. The compound of claim 3, or a pharmaceutically acceptable salt, hydrate, solvate, or prodrug thereof, wherein:

$L_1$ is

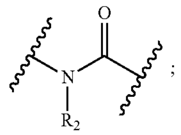

;

$L_2$ is

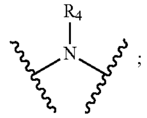

;

and

Y is

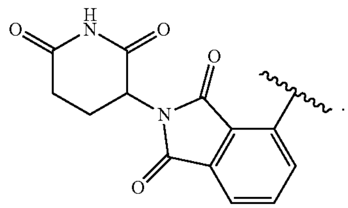 [SMILES: *c1cccc2c1C(=O)N(C1CCC(=O)NC1=O)C2=O]

.

6. The compound of claim 5, or a pharmaceutically acceptable salt, hydrate, solvate, or prodrug thereof, wherein R is

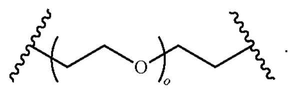

.

and o is 0-9, inclusive.

7. The compound of claim 5, or a pharmaceutically acceptable salt, hydrate, solvate, or prodrug thereof, wherein R is

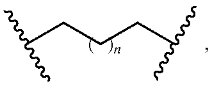

and n is 0-9, inclusive.

8. The compound of claim 3, or a pharmaceutically acceptable salt, hydrate, solvate, or prodrug thereof, wherein:

$L_1$ is

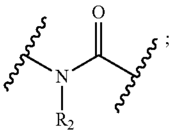

$L_2$ is

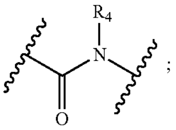

Y is

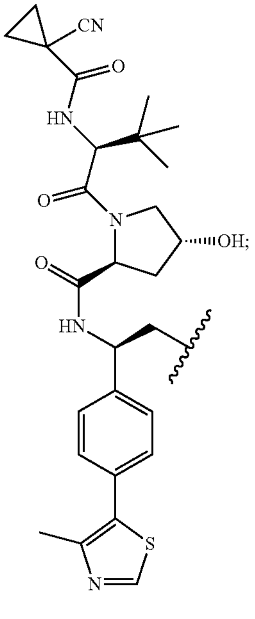

R is

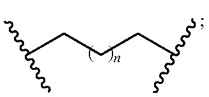

and n is 0-6, inclusive.

9. The compound of claim 1, or a pharmaceutically acceptable salt, hydrate, solvate, or prodrug thereof, wherein:

$L_1$ is

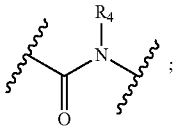

$L_2$ is

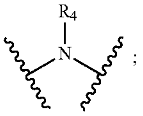

Y is

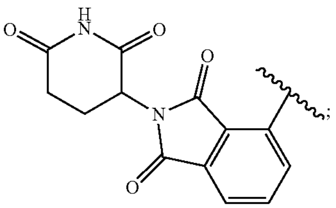 [SMILES: *c1cccc2c1C(=O)N(C1CCC(=O)NC1=O)C2=O]

and $Y_2$ is

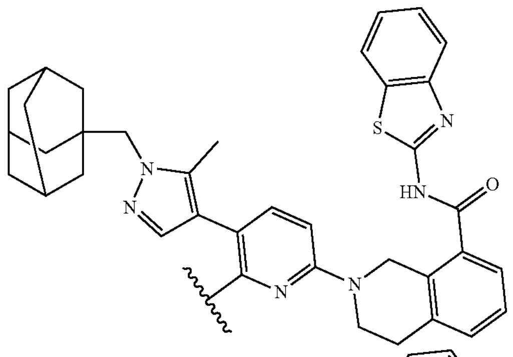

or

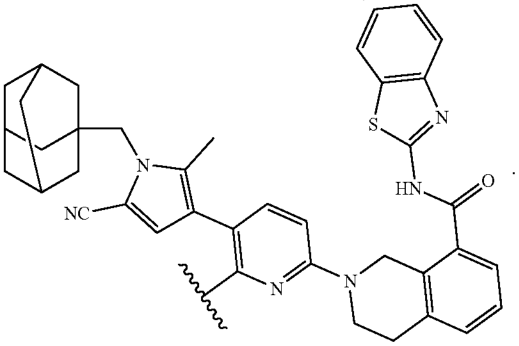 [SMILES: *c1nc(N2CCc3cccc(C(=O)Nc4nc5ccccc5s4)c3C2)ccc1-c1cc(C#N)n(CC23CC4CC(CC(C4)C2)C3)c1C ; ","]

10. The compound of claim 1, or a pharmaceutically acceptable salt, hydrate, solvate, or prodrug thereof, wherein $Y_2$ is

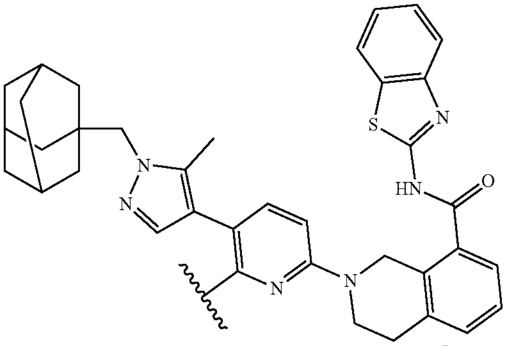

or

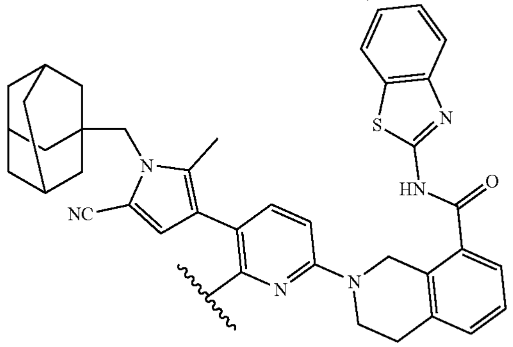

.

11. The compound of claim 9, or a pharmaceutically acceptable salt, hydrate, solvate, or prodrug thereof, wherein $Y_2$ is

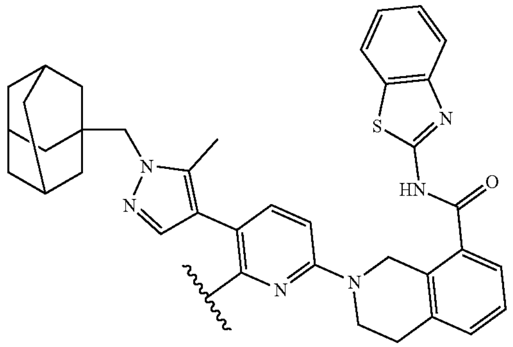

,

R is

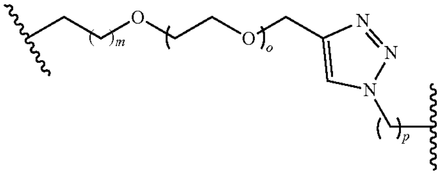

, m is 1, o is 1, and p is 1.

12. The compound of claim 9, or a pharmaceutically acceptable salt, hydrate, solvate, or prodrug thereof, wherein $Y_2$ is

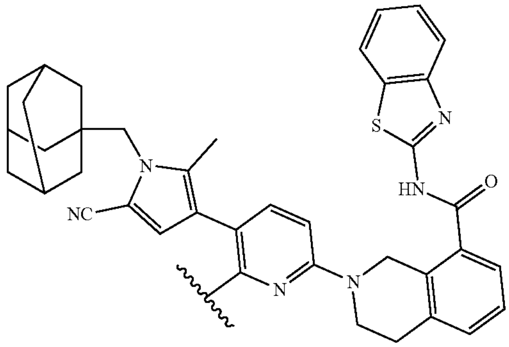

,

R is

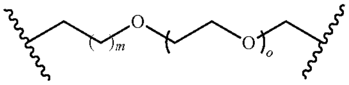

, m is 1, and o is 1.

13. The compound of claim 1, or a pharmaceutically acceptable salt, hydrate, solvate, or prodrug thereof, wherein:

$L_1$ is:

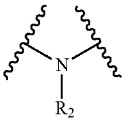

;

$L_2$ is

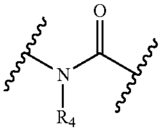

;

Y is

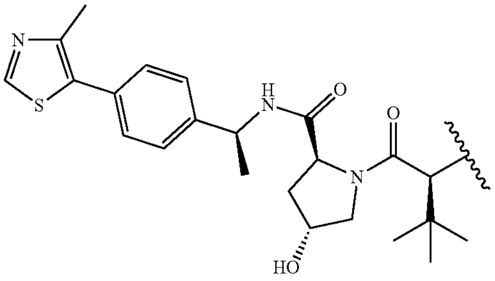

;

$Y_2$ is
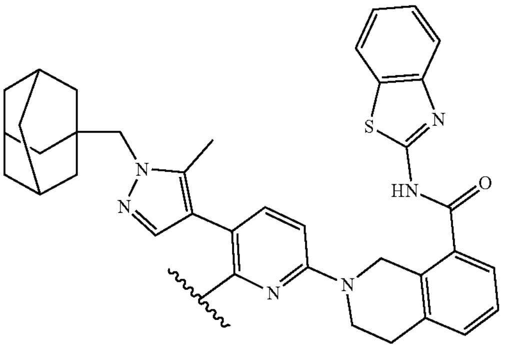
or
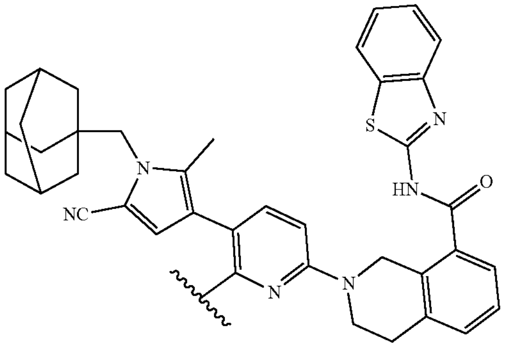
;
R is
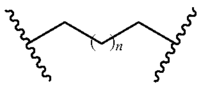
;
and
n is 1-6, inclusive.
14. The compound of claim 1, or a pharmaceutically acceptable salt, hydrate, solvate, or prodrug thereof, wherein $L_1$ is
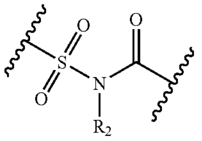
or
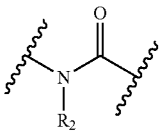
.
15. The compound of claim 1, or a pharmaceutically acceptable salt, hydrate, solvate, or prodrug thereof, wherein the compound is:
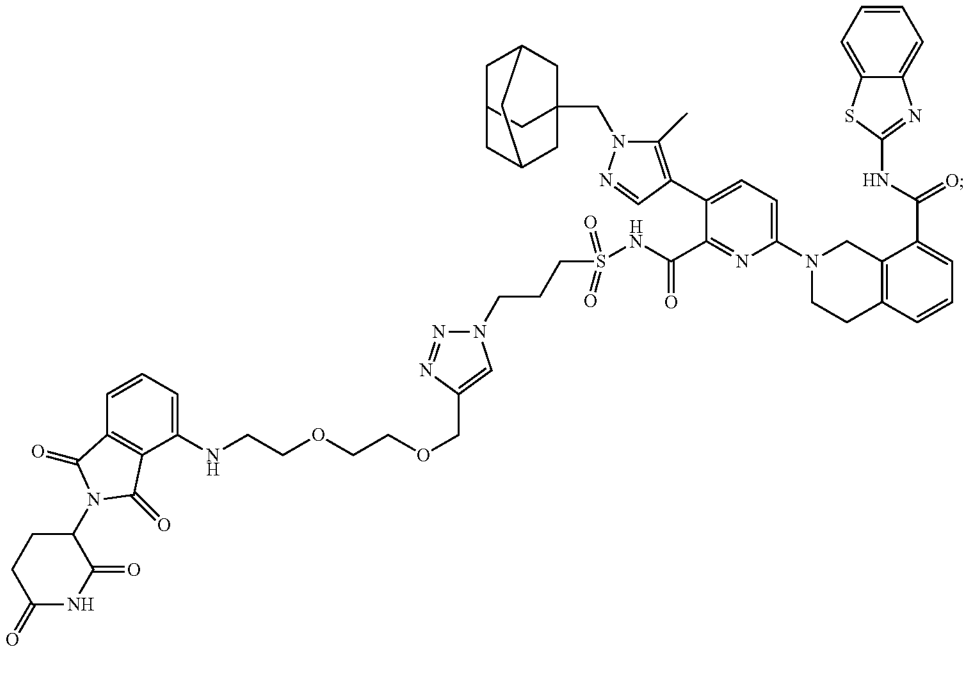

-continued
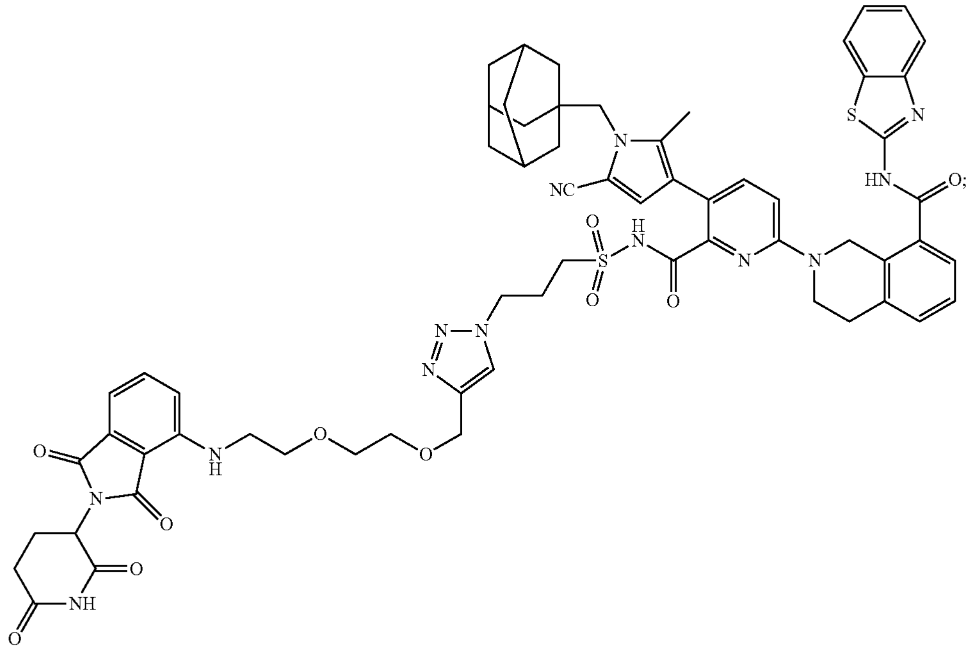
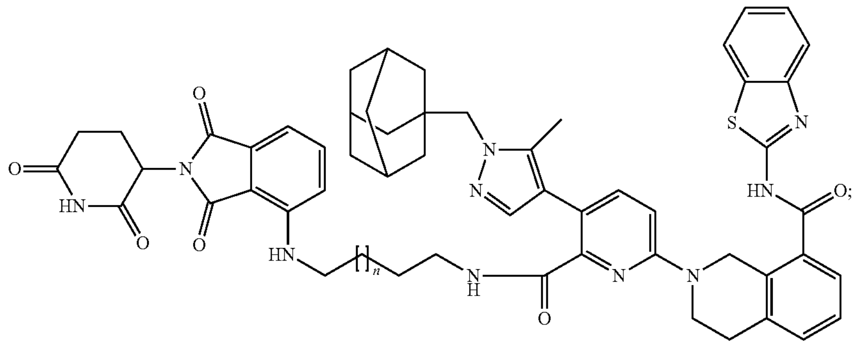
n = 1
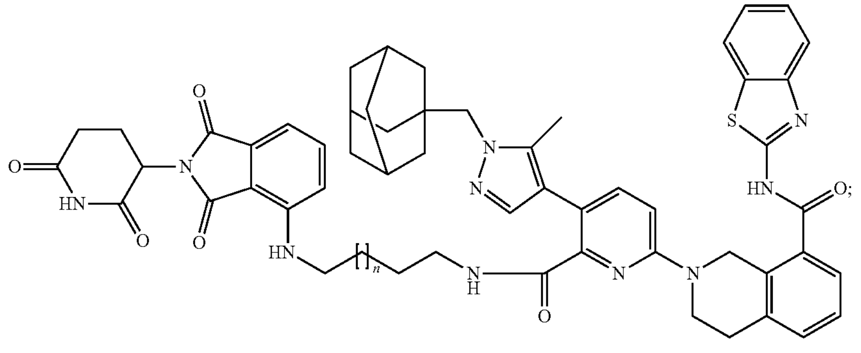
n = 3

-continued
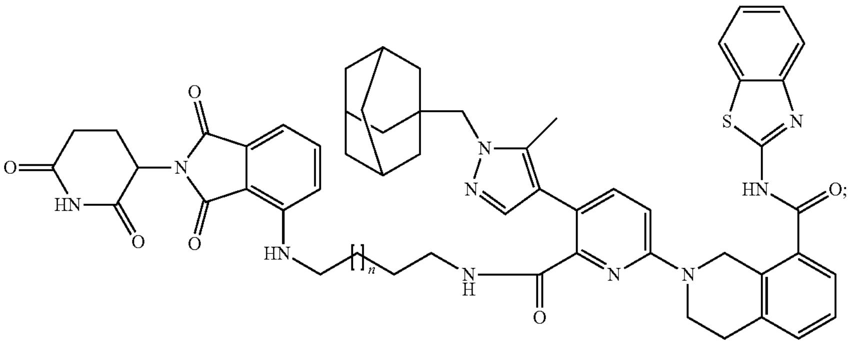
n = 5
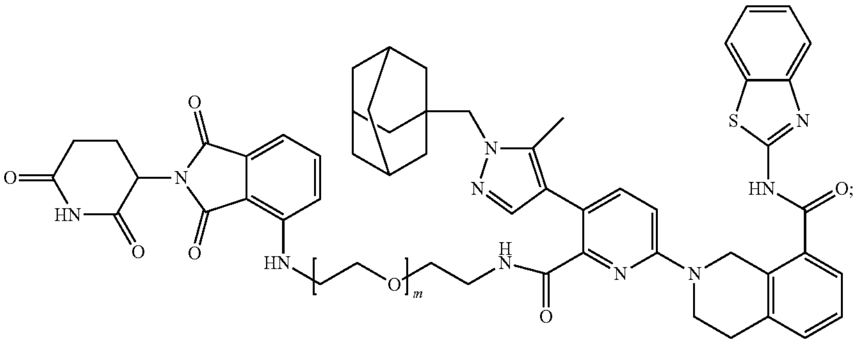
m = 1
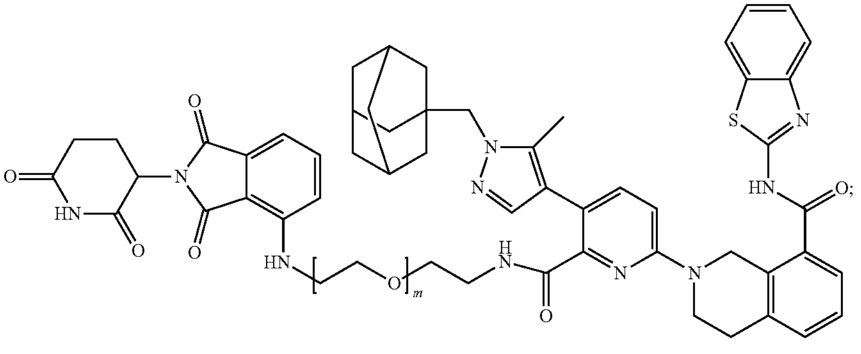
m = 2
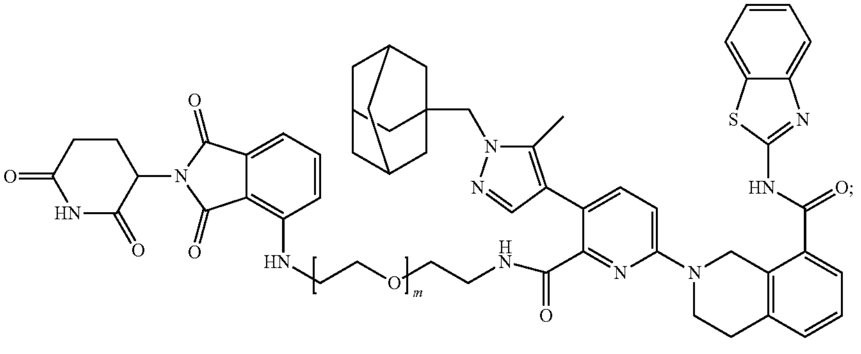
m = 3

-continued
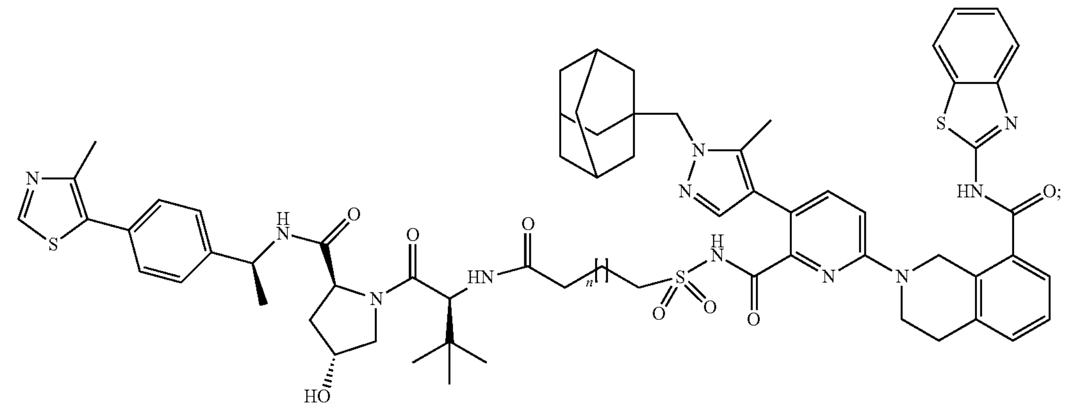
n = 1
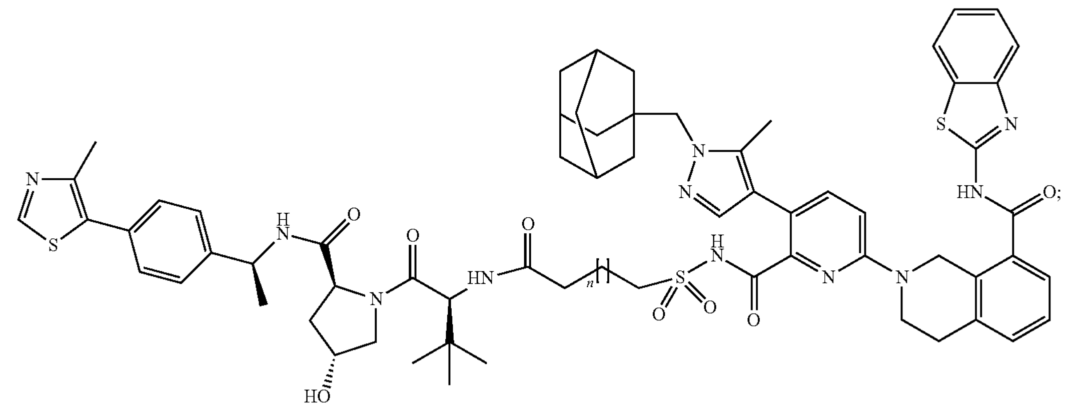
n = 2
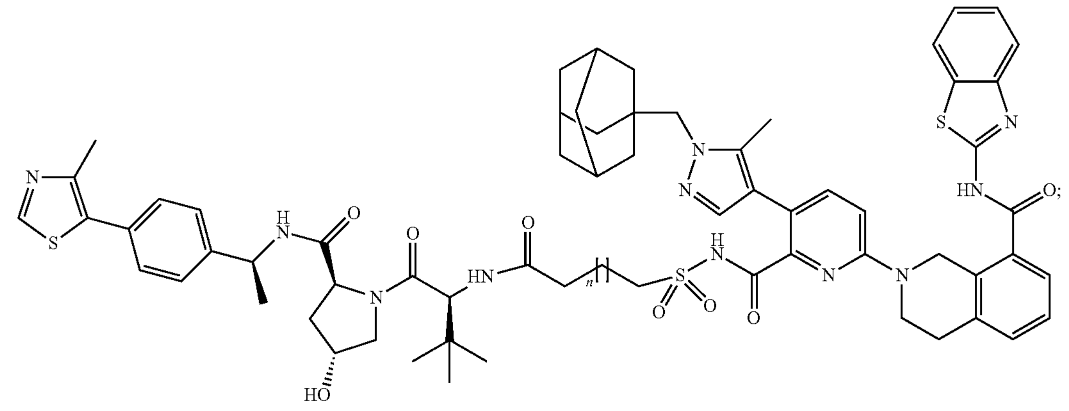
n = 3

-continued
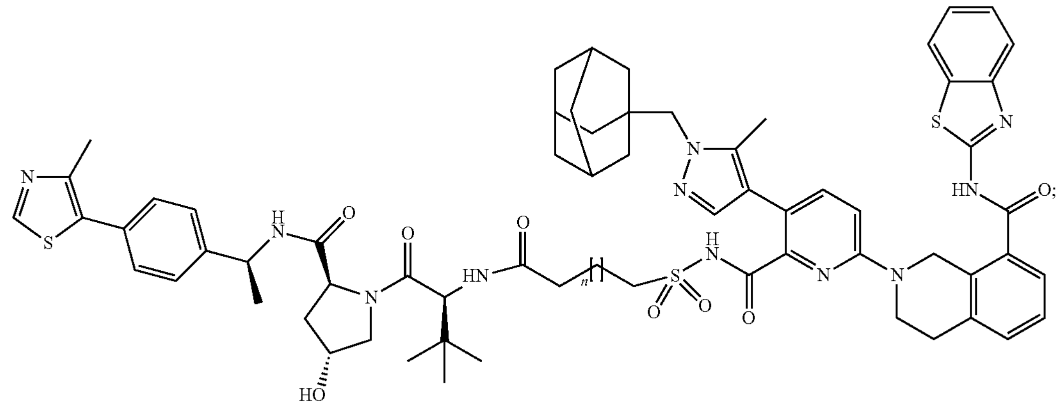
n = 4
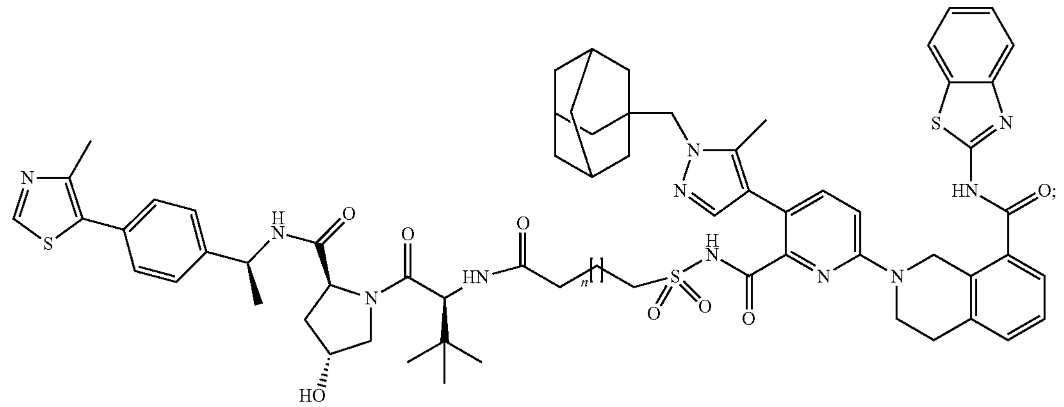
n = 5
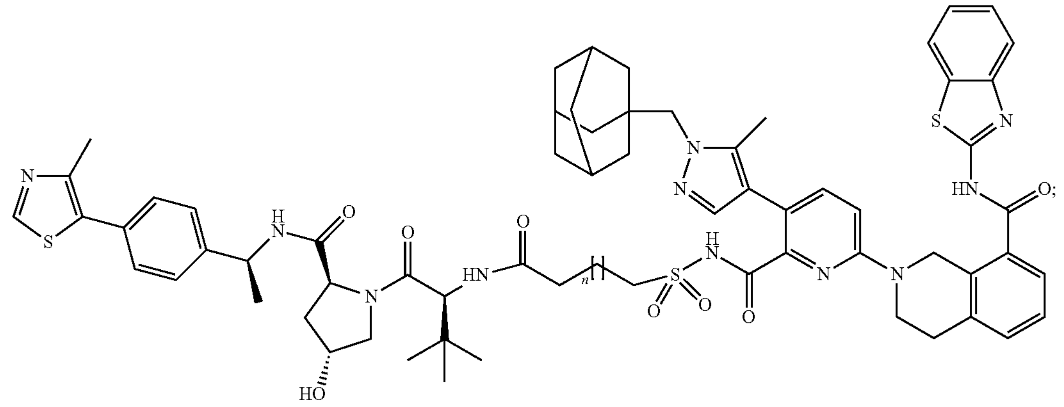
n = 6

-continued
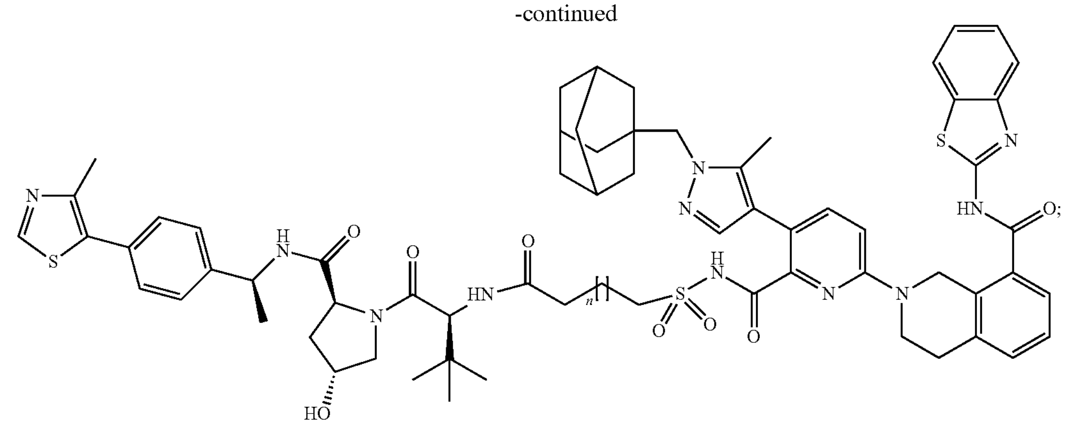
n = 7
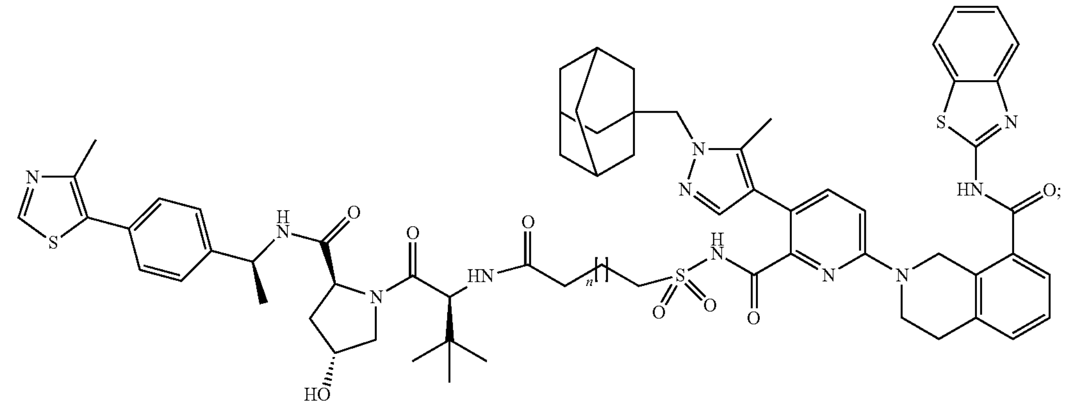
n = 8
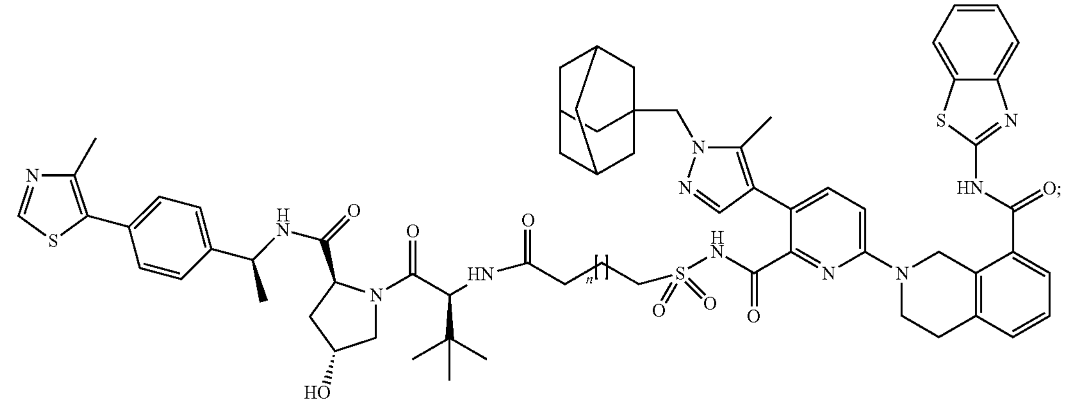
n = 9
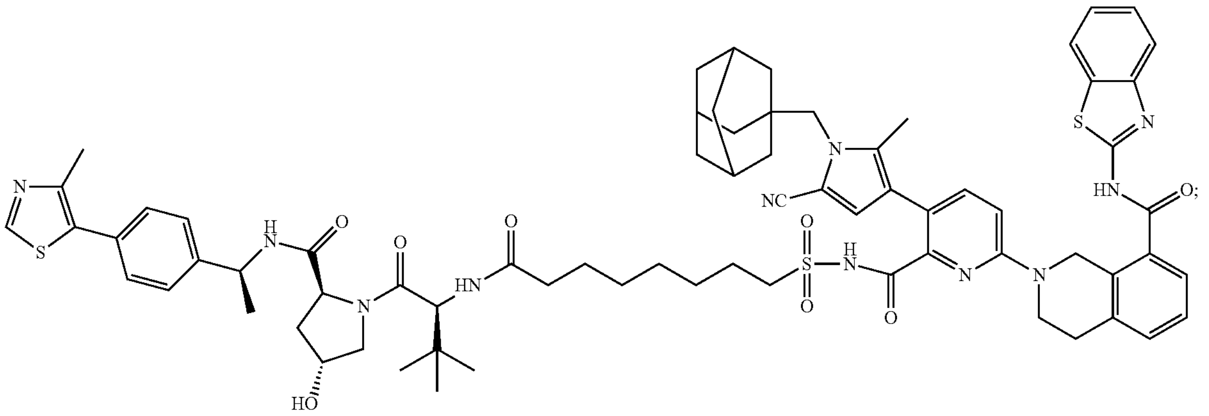

-continued
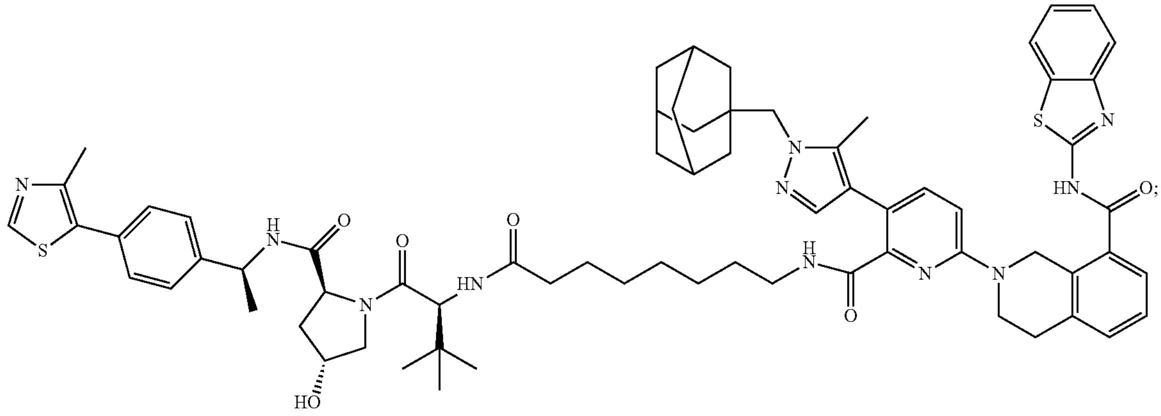
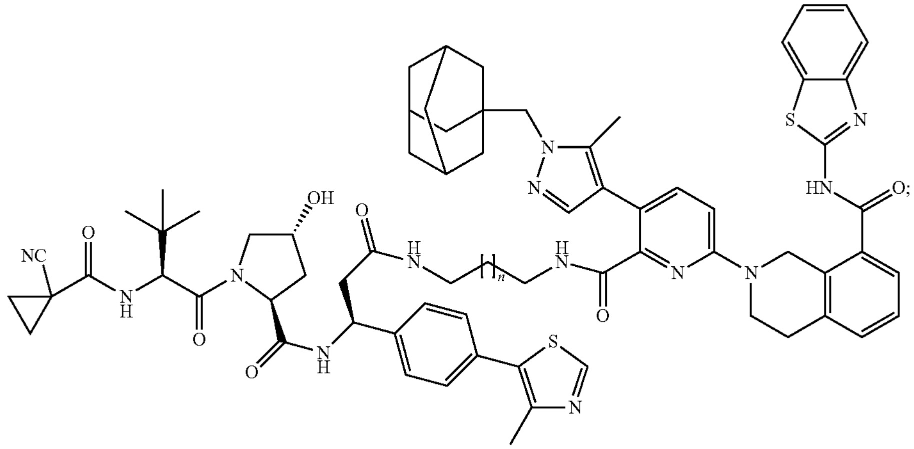
n = 0
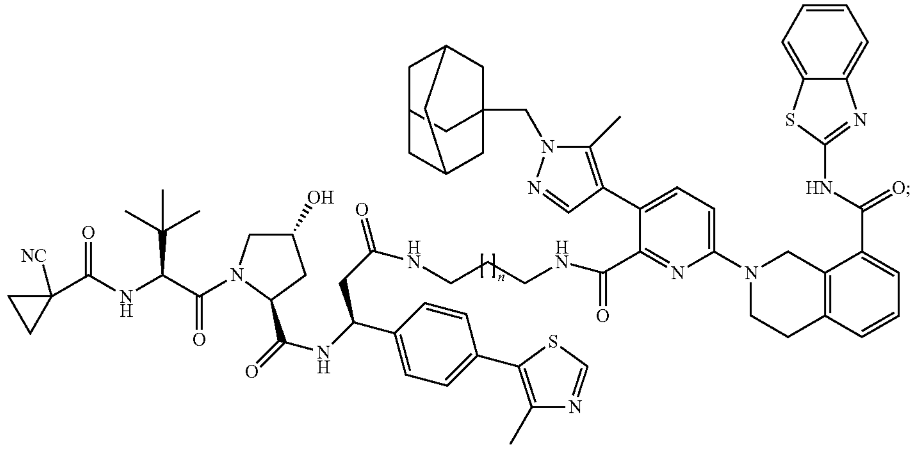
n = 1

-continued
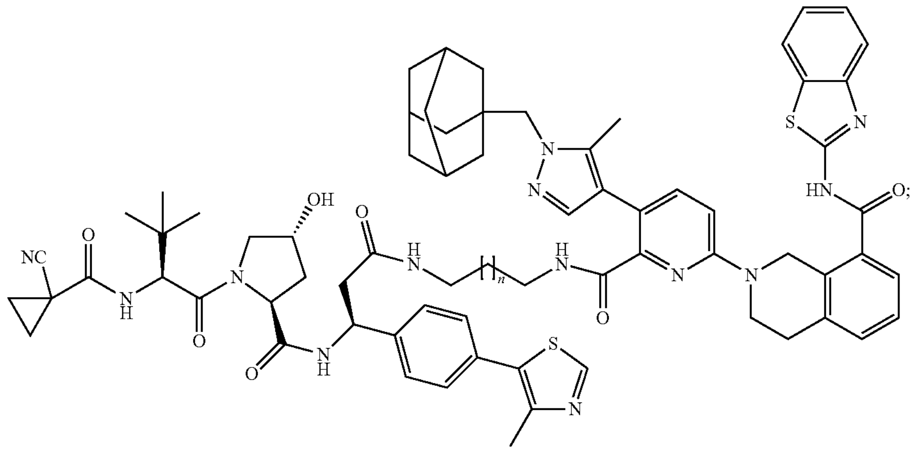
n = 2
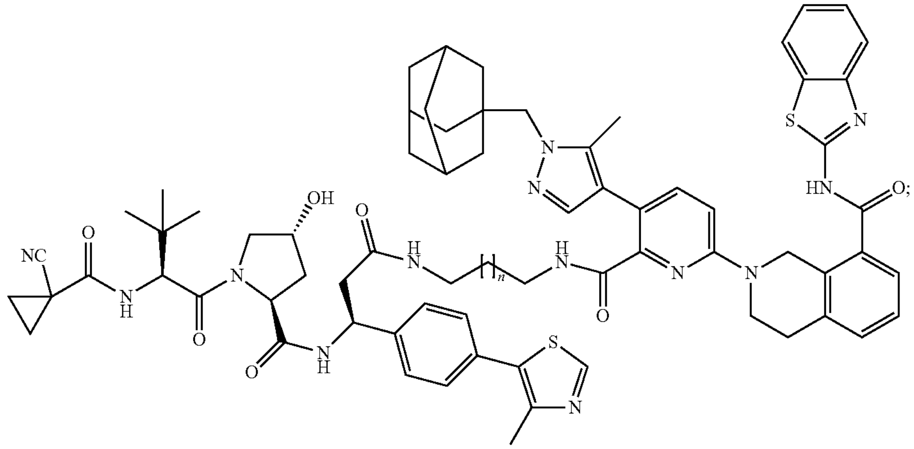
n = 3
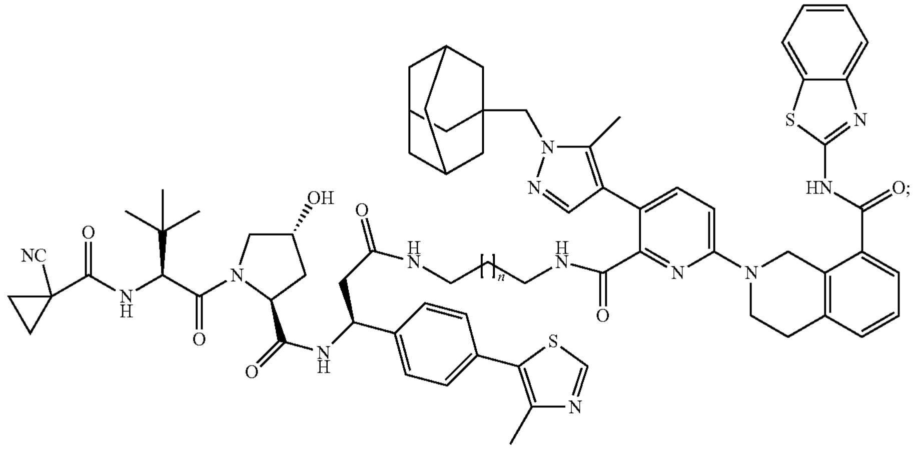
n = 4

-continued
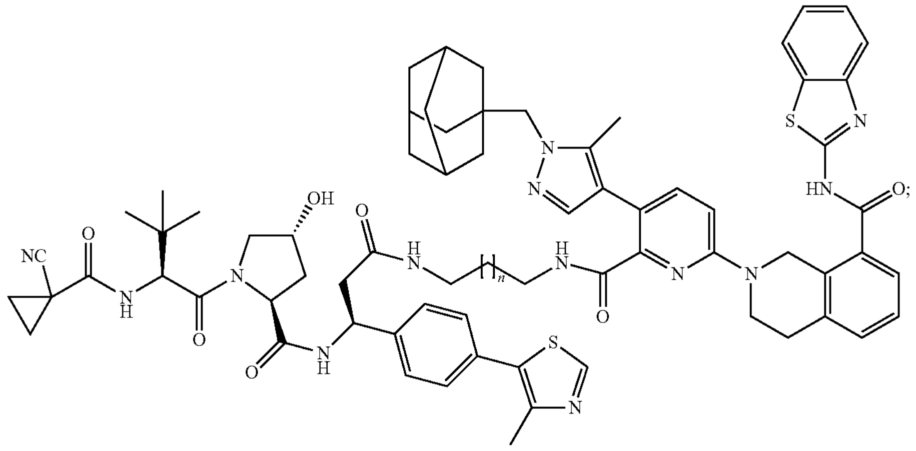
n = 6
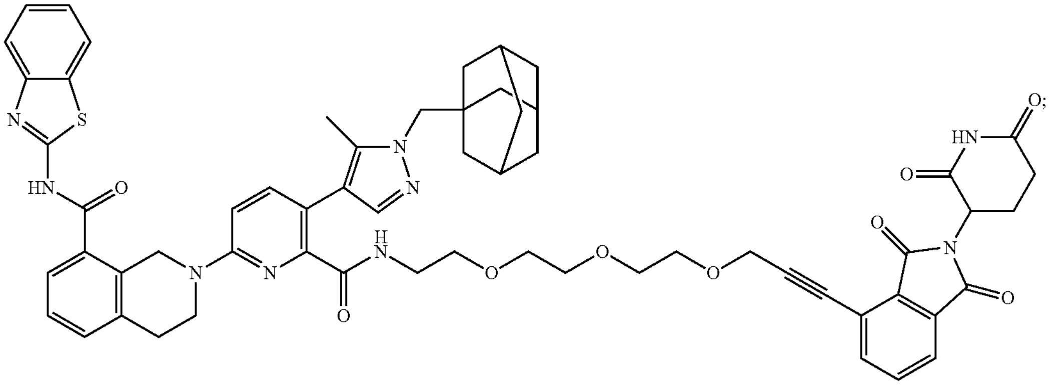
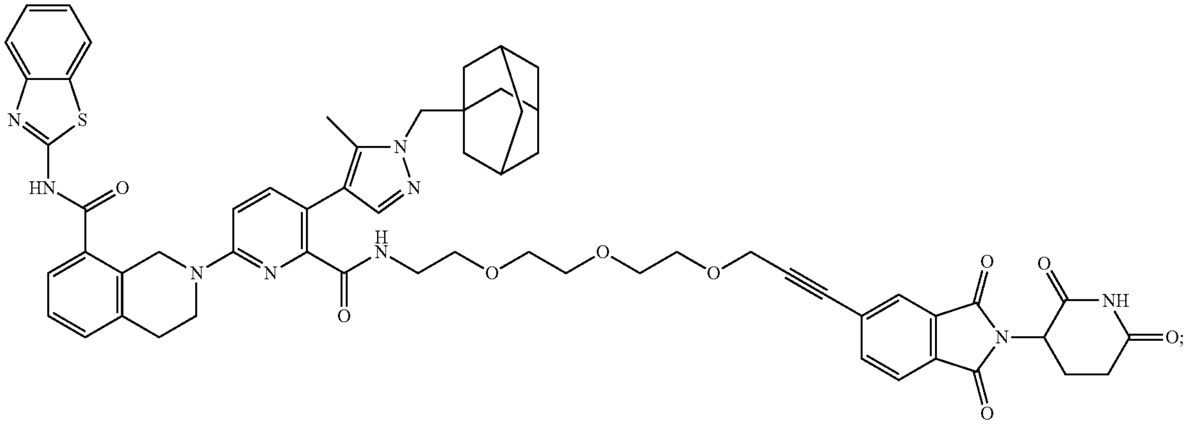
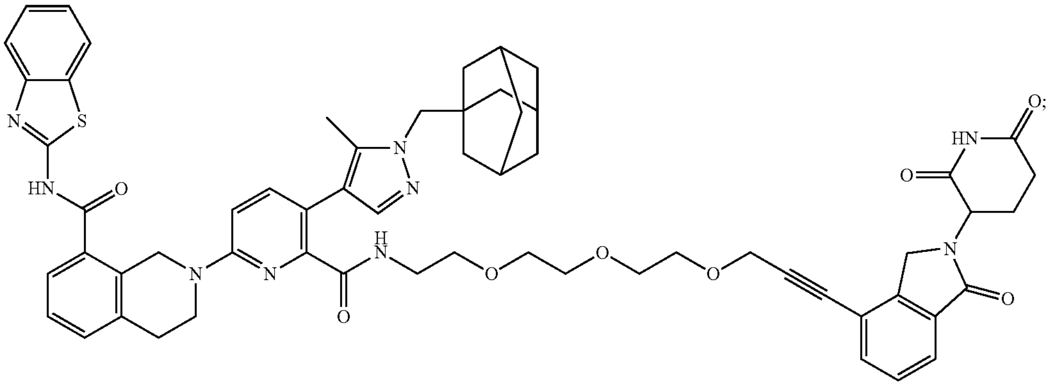

-continued
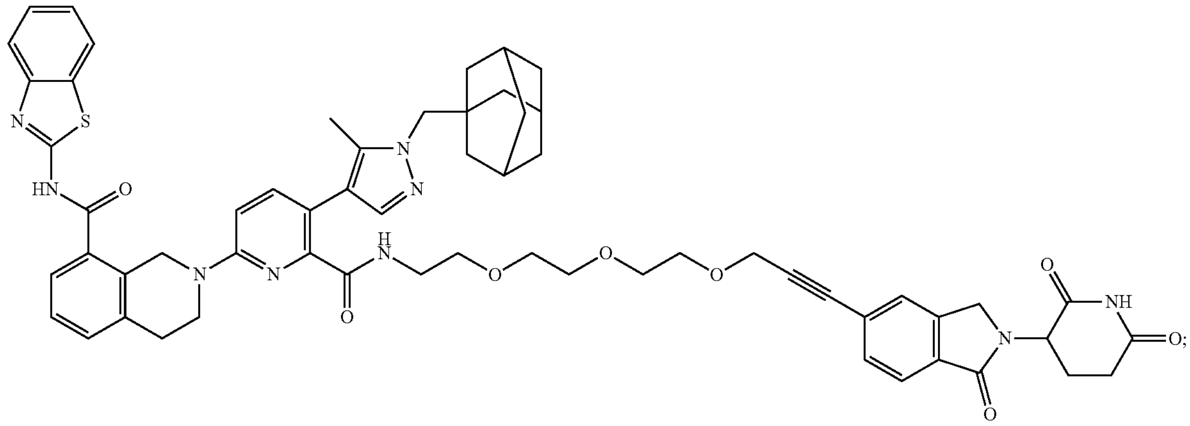
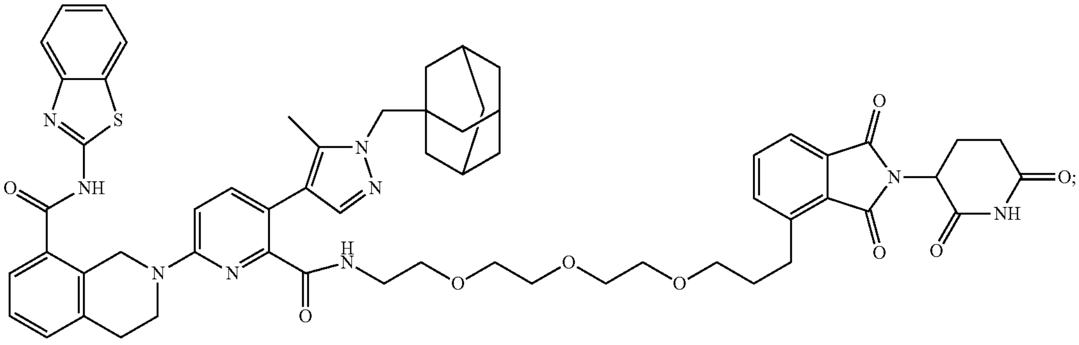
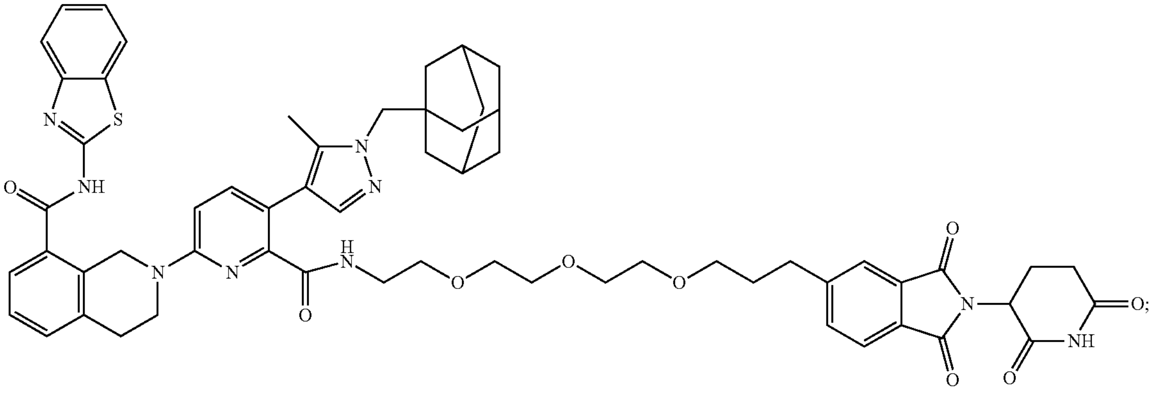
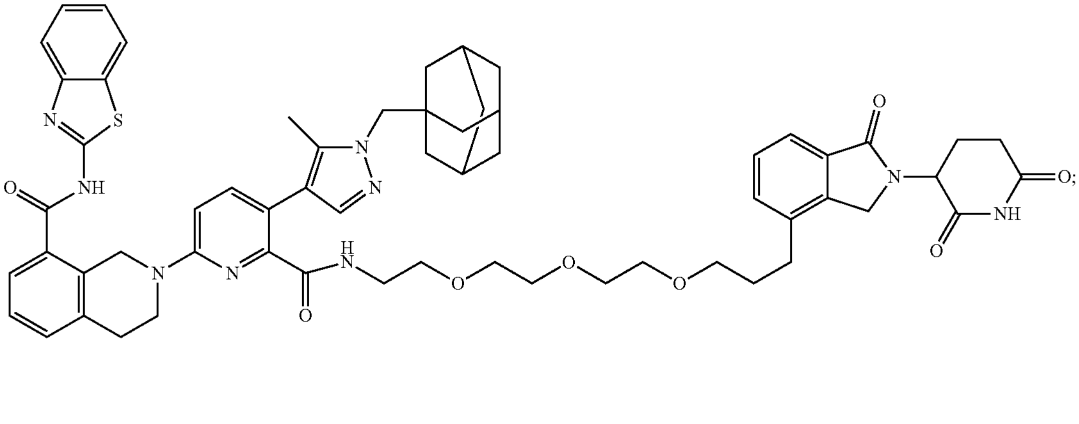

-continued
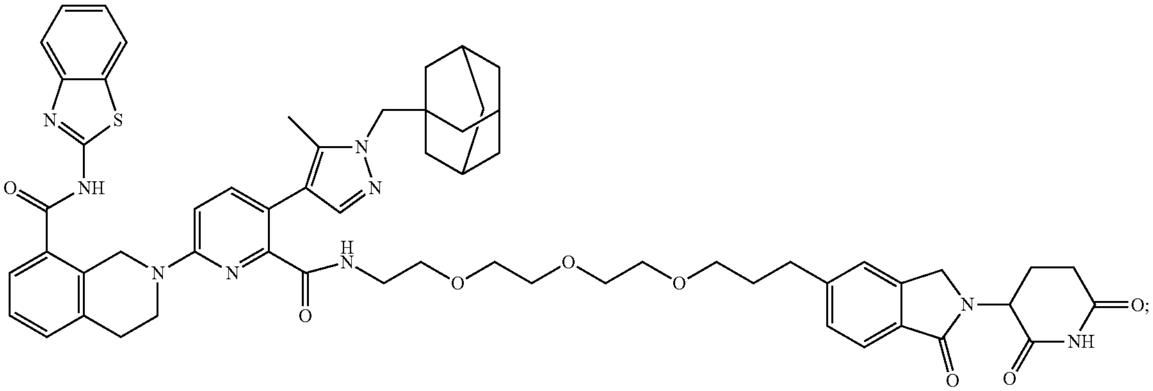
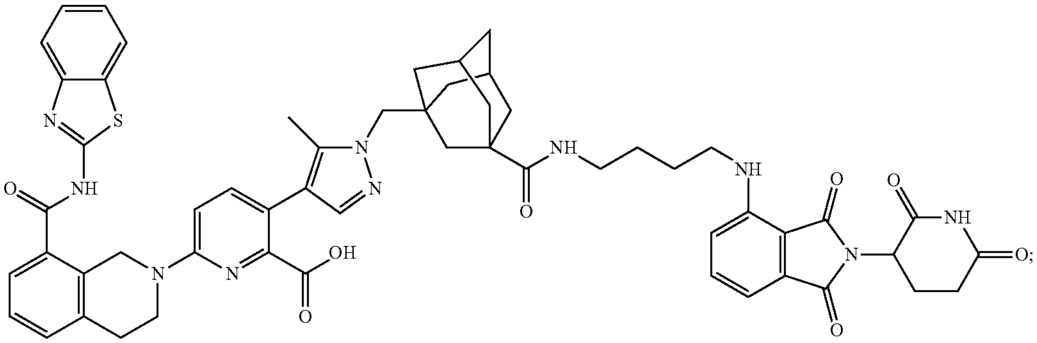
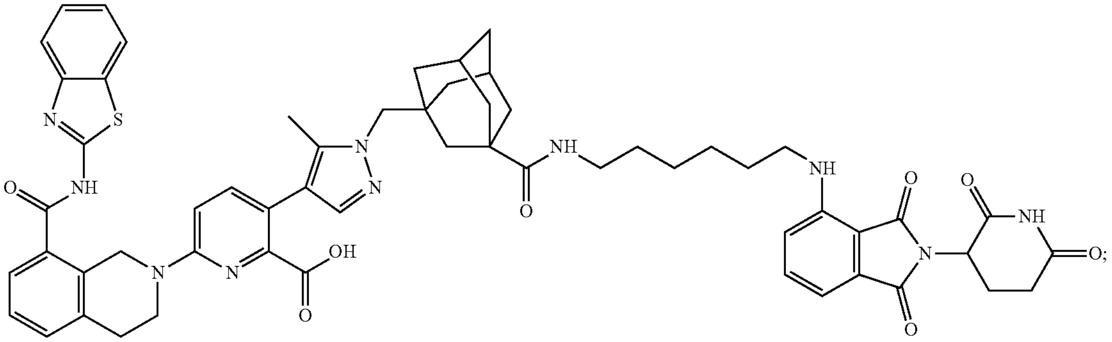
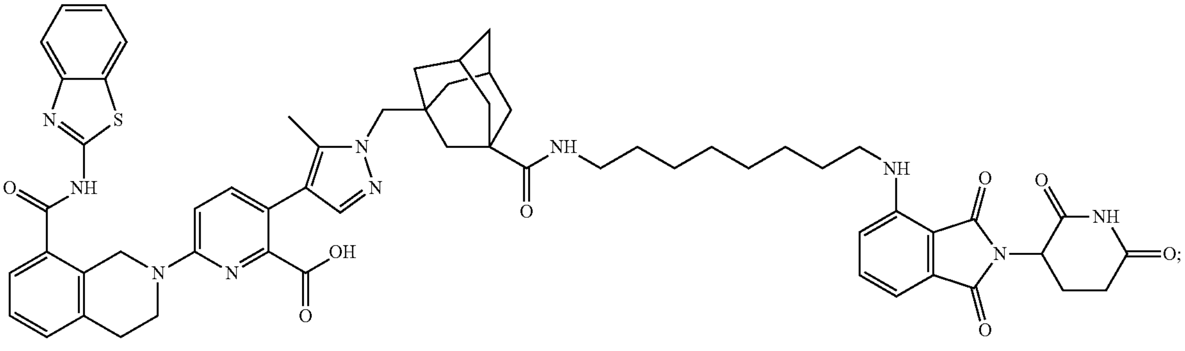

-continued
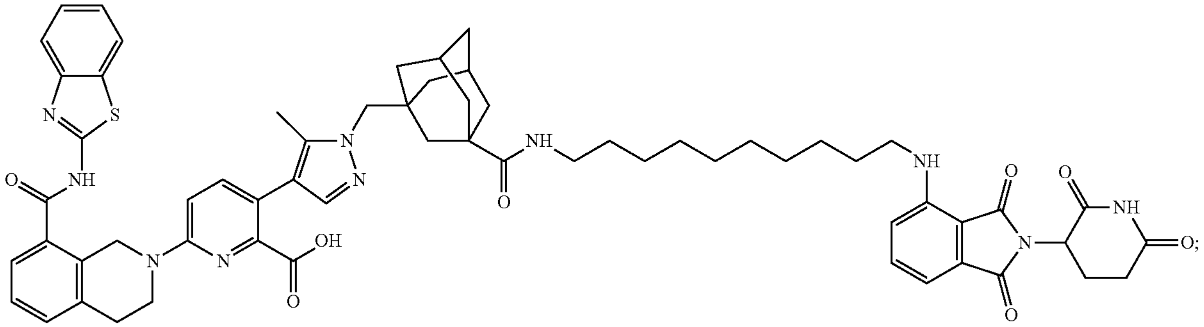
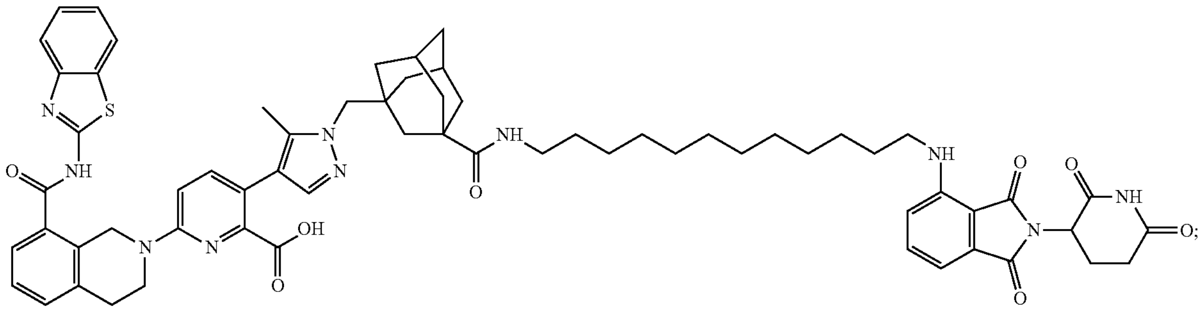
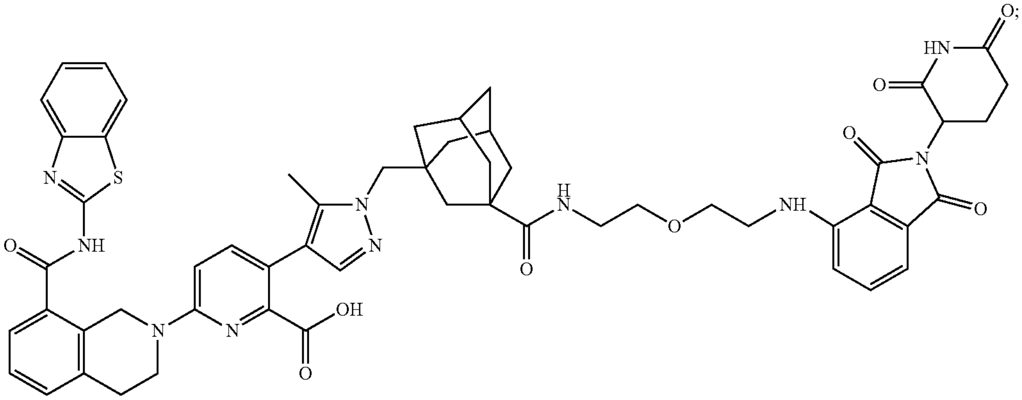
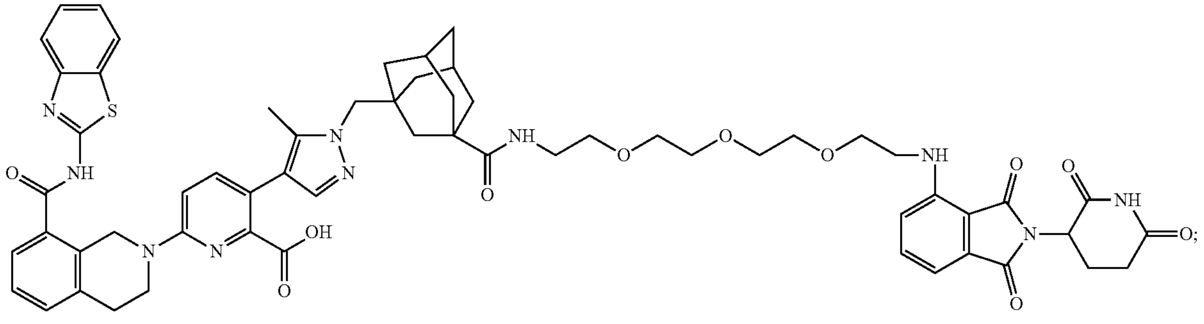
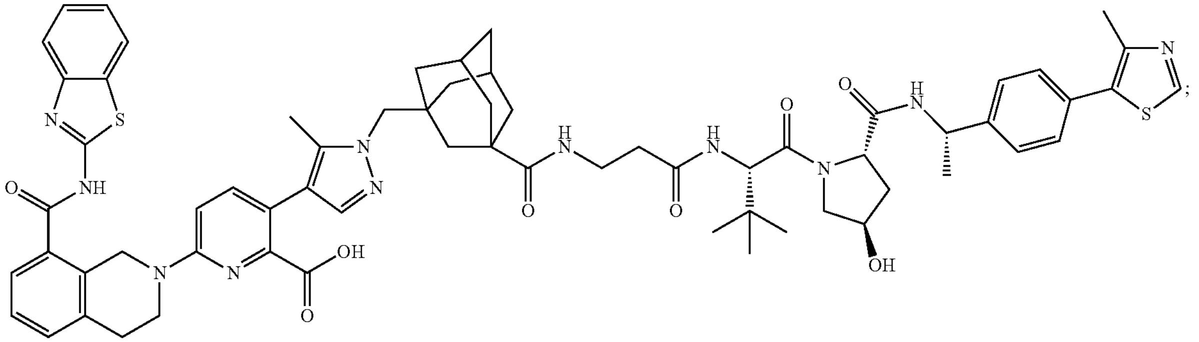

-continued

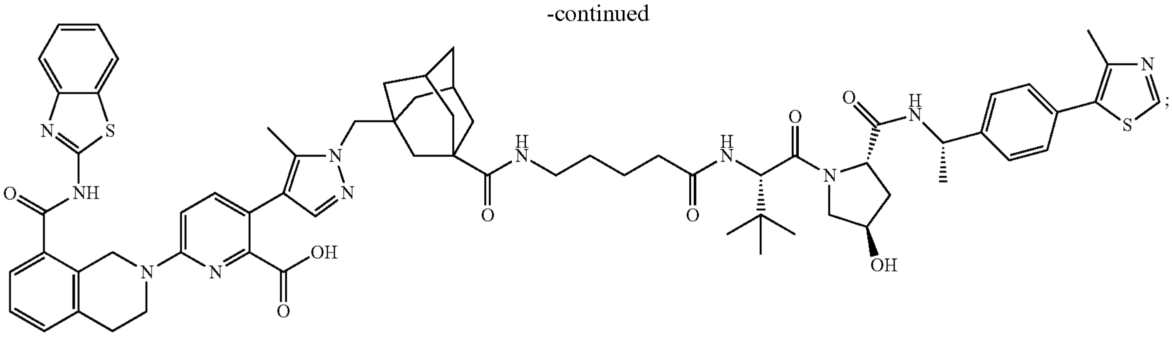

; or

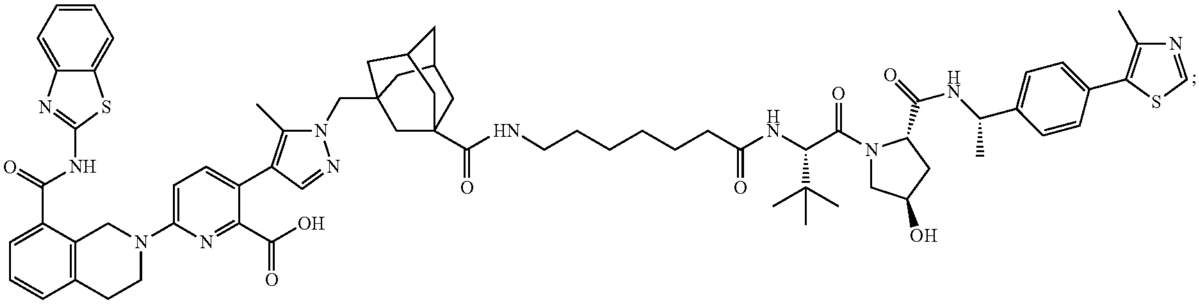

;

or a pharmaceutically acceptable salt, hydrate, solvate, or prodrug thereof.

16. A pharmaceutical composition comprising a compound of claim 1, or a pharmaceutically acceptable salt, hydrate, solvate, or prodrug thereof, and a pharmaceutically acceptable carrier.

17. A method of degrading Bcl-2 proteins, the method comprising administering an effective amount of a compound of claim 1, or a pharmaceutically acceptable salt, hydrate, solvate, or prodrug thereof.

18. A method of treating a disease or disorder in a subject in need thereof, the method comprising administering an effective amount of a compound of claim 1, or a pharmaceutically acceptable salt, hydrate, solvate or prodrug thereof, wherein the disease or disorder is a cancer.

19. A method of treating a Bcl-xL-dependent cancer in a subject in need thereof, the method comprising administering an effective amount of a compound of claim 1, or a pharmaceutically acceptable salt thereof, wherein the ratio of human platelet toxicity ($IC_{50}$) to anticancer activity ($IC_{50}$) of the compound is greater than one.

20. The compound of claim 1, or a pharmaceutically acceptable salt, hydrate, solvate, or prodrug thereof, wherein $L_1$ is:

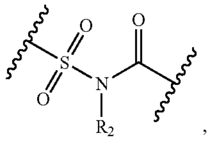

,

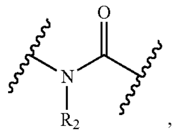

, or

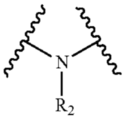

.

21. The compound of claim 1, or a pharmaceutically acceptable salt, hydrate, solvate, or prodrug thereof, wherein $L_2$ is

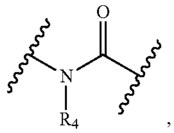

,

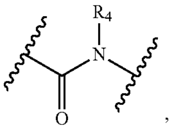

, or

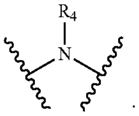

.

22. The compound of claim 1, or a pharmaceutically acceptable salt, hydrate, solvate, or prodrug thereof, wherein Y is

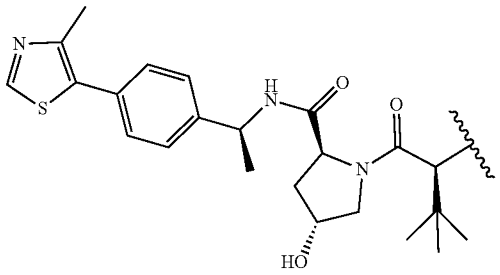

,

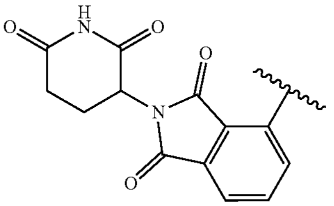

, or

-continued
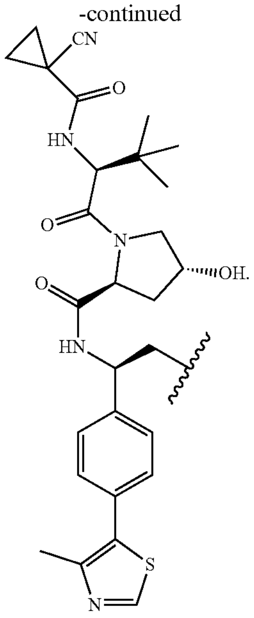
* * * * *